(12) United States Patent
Stavros

(10) Patent No.: US 11,172,900 B2
(45) Date of Patent: Nov. 16, 2021

(54) METHODS AND SYSTEMS TO DETERMINE CANCER MOLECULAR SUBTYPES BASED ON ULTRASOUND AND/OR OPTOACOUSTIC (OA/US) FEATURES

(71) Applicant: Seno Medical Instruments, Inc., San Antonio, TX (US)

(72) Inventor: Anthony Thomas Stavros, San Antonio, TX (US)

(73) Assignee: Seno Medical Instruments, Inc., San Antonio, TX (US)

( * ) Notice: Subject to any disclaimer, the term of this patent is extended or adjusted under 35 U.S.C. 154(b) by 105 days.

(21) Appl. No.: 16/554,961

(22) Filed: Aug. 29, 2019

(65) Prior Publication Data

US 2020/0069275 A1 Mar. 5, 2020

Related U.S. Application Data

(60) Provisional application No. 62/725,632, filed on Aug. 31, 2018.

(51) Int. Cl.
| | |
|---|---|
| *G06K 9/00* | (2006.01) |
| *A61B 6/00* | (2006.01) |
| *G06T 7/13* | (2017.01) |
| *G06T 7/246* | (2017.01) |
| *G06T 7/40* | (2017.01) |

(Continued)

(52) U.S. Cl.
CPC .............. *A61B 6/502* (2013.01); *A61B 6/03* (2013.01); *A61B 8/0825* (2013.01); *G06T 7/0014* (2013.01); *G06T 7/13* (2017.01); *G06T 7/251* (2017.01); *G06T 7/40* (2013.01);

(Continued)

(58) Field of Classification Search
CPC ......... A61B 6/502; A61B 6/03; A61B 8/0825; A61B 5/14542; A61B 2576/00; A61B 6/504; A61B 6/5247; A61B 8/5223; A61B 8/085; A61B 5/0095; G06T 7/13; G06T 7/251; G06T 7/40; G06T 7/97; G06T 7/62; G06T 7/0014; G06T 7/77; G06T 2207/10132; G06T 2207/30068

See application file for complete search history.

(56) References Cited

U.S. PATENT DOCUMENTS

| | | |
|---|---|---|
| 6,238,342 B1 | 5/2001 | Feleppa et al. |
| 2011/0245673 A1 | 10/2011 | Kamiyama |

(Continued)

OTHER PUBLICATIONS

International Preliminary Report on Patentability for corresponding Application No. PCT/US2019/048733 dated Mar. 11, 2021 (6 pages).

(Continued)

*Primary Examiner* — Amara Abdi
(74) *Attorney, Agent, or Firm* — The Small Patent Law Group LLC; Dean D. Small

(57) ABSTRACT

Methods, devices and systems are provided that utilize one or more processors in connection with, receiving OA/US feature scores in connection with OA/US images collected from a patient examination for a volume of interest. The methods, devices and systems apply the OA/US feature scores to a feature score to molecular subtype (FSMS) model. The methods, devices and systems determine, from the FSMS model, an indication of at least one of a molecular subtype or histologic grade of a pathology experienced by the patient.

39 Claims, 74 Drawing Sheets

(51) Int. Cl.
  *A61B 6/03* (2006.01)
  *G06T 7/00* (2017.01)
  *G06T 7/62* (2017.01)
  *A61B 8/08* (2006.01)
  *G06T 7/77* (2017.01)
(52) U.S. Cl.
  CPC .................. *G06T 7/62* (2017.01); *G06T 7/77* (2017.01); *G06T 7/97* (2017.01)

(56) References Cited

U.S. PATENT DOCUMENTS

| | | |
|---|---|---|
| 2012/0243757 A1 | 9/2012 | Funka-Lea |
| 2013/0030305 A1* | 1/2013 | Yu .................. A61B 5/0084 600/476 |
| 2016/0343132 A1* | 11/2016 | Stavros ................ G06K 9/6268 |
| 2017/0014108 A1* | 1/2017 | Mazurowski ......... G06T 7/0012 |
| 2017/0372117 A1 | 12/2017 | Bredno et al. |

OTHER PUBLICATIONS

Search Report and Written Opinion for corresponding PCT Application No. PCT/US2019/048733 dated Dec. 17, 2019 (9 pages).

* cited by examiner

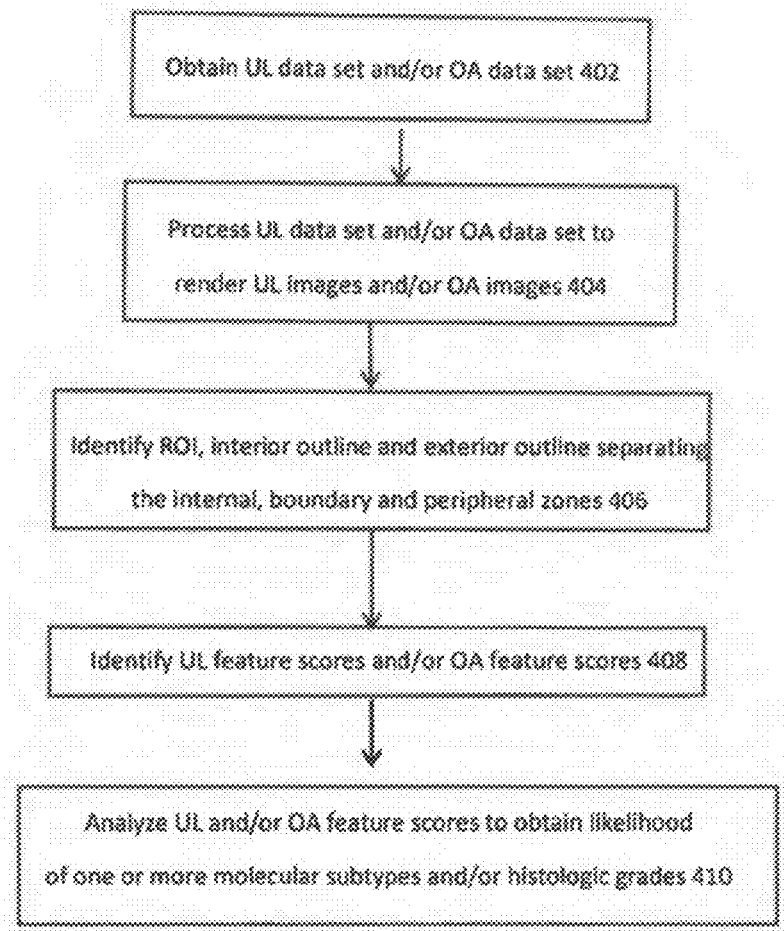

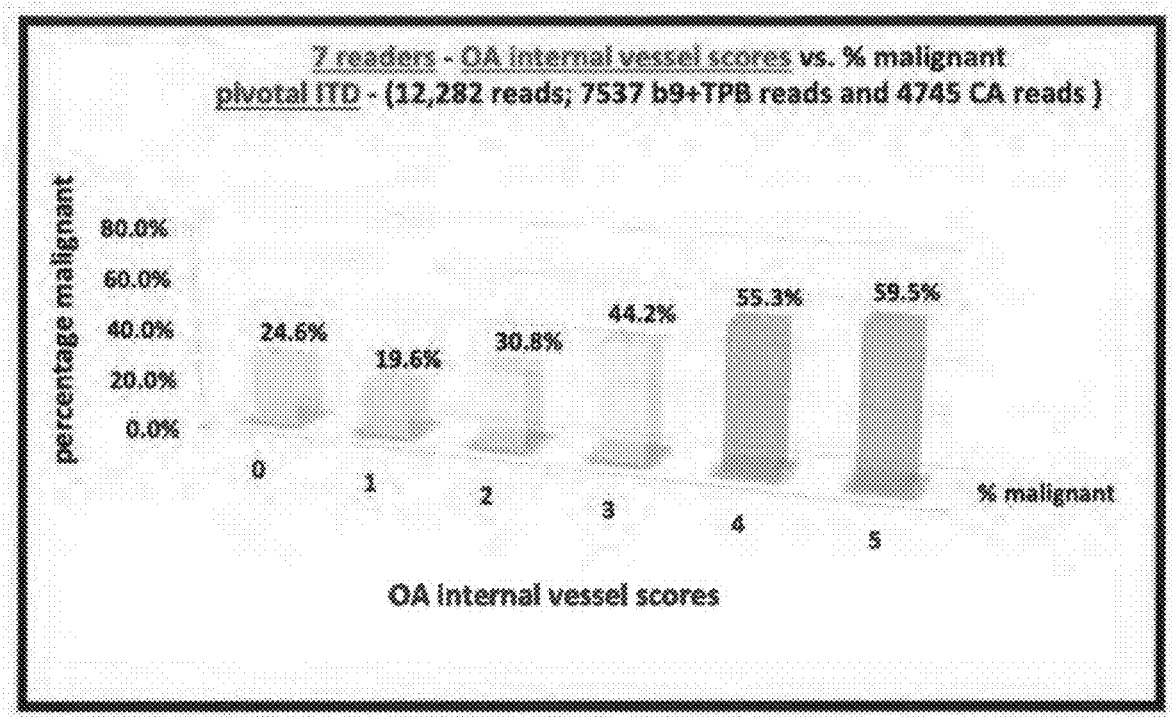

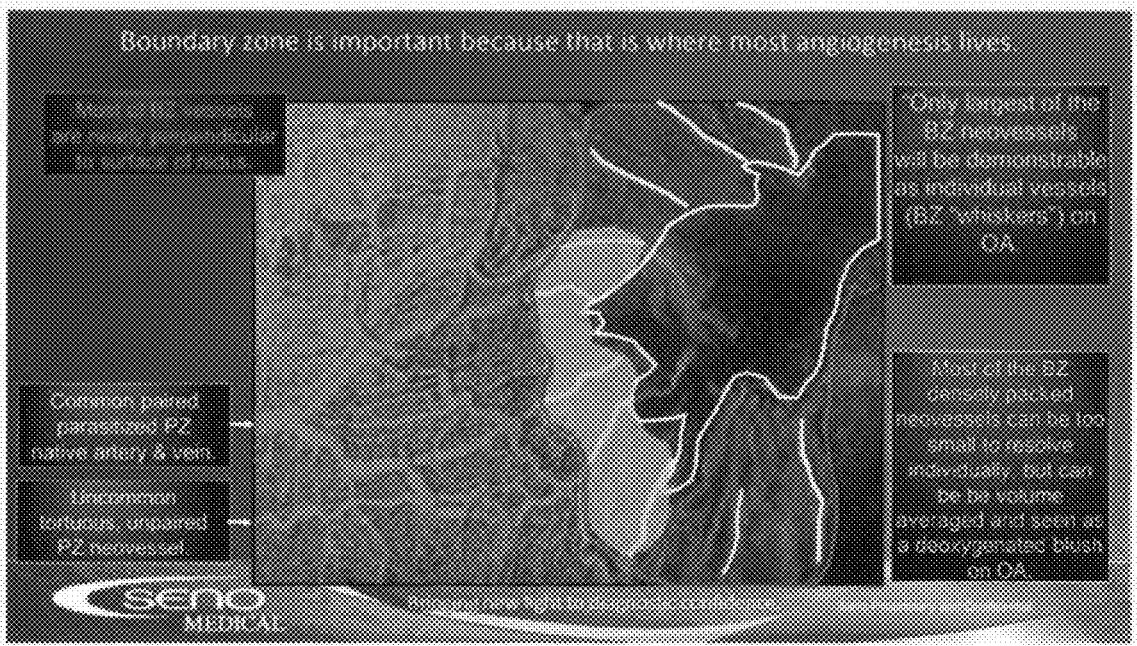

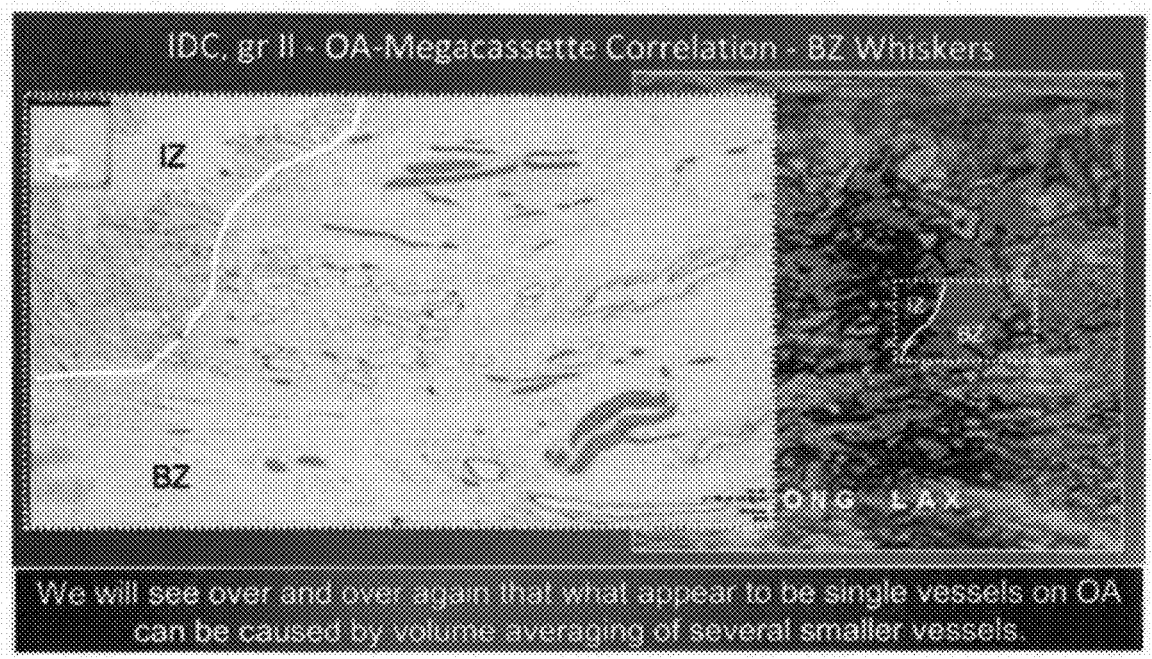
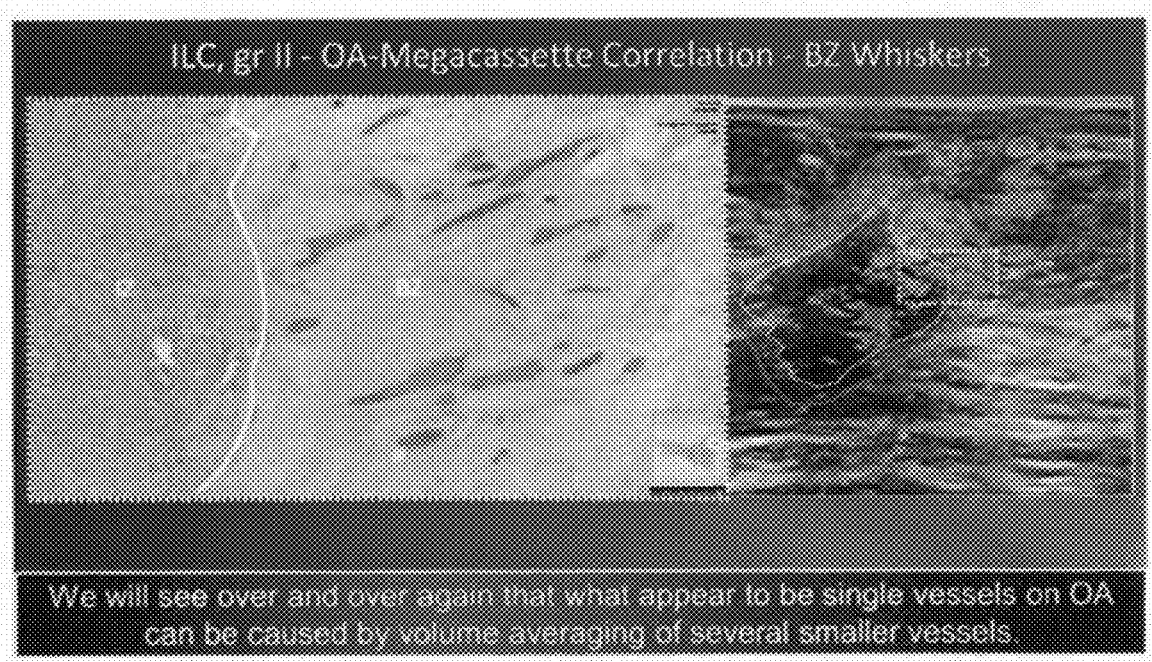

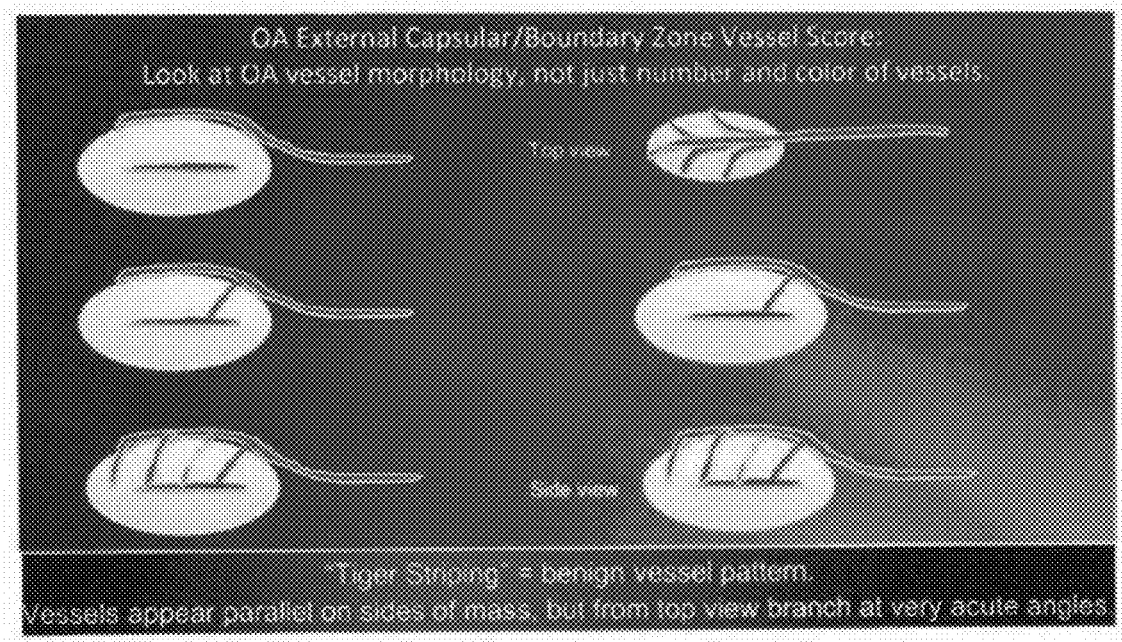

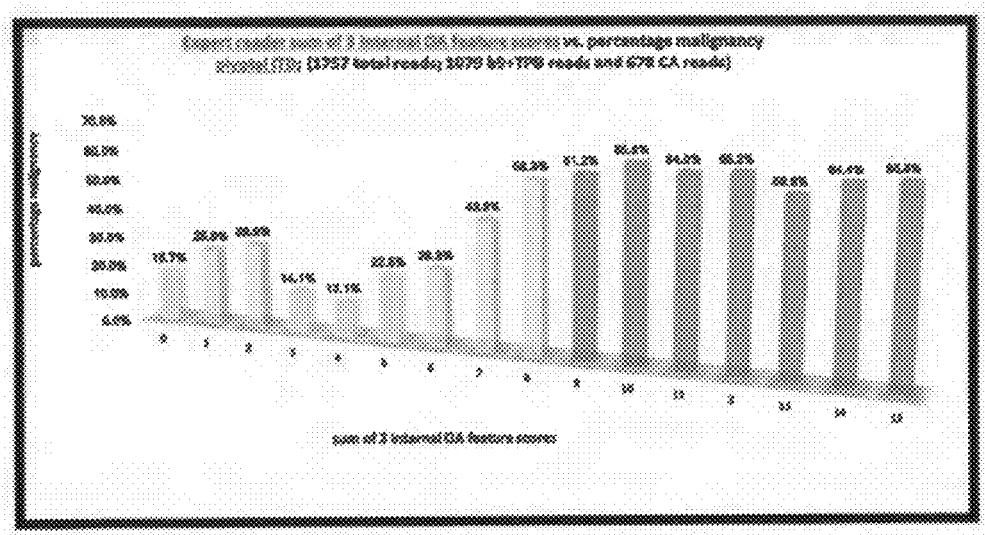
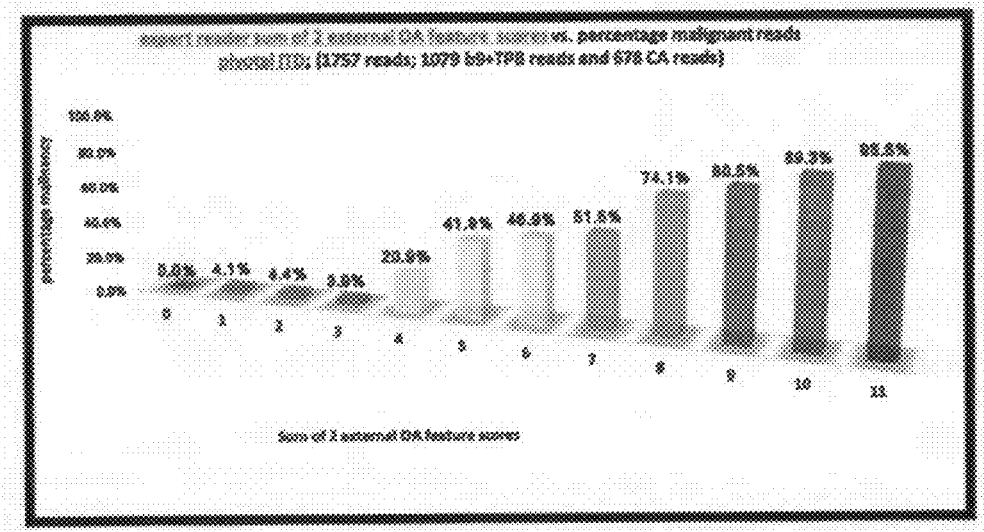

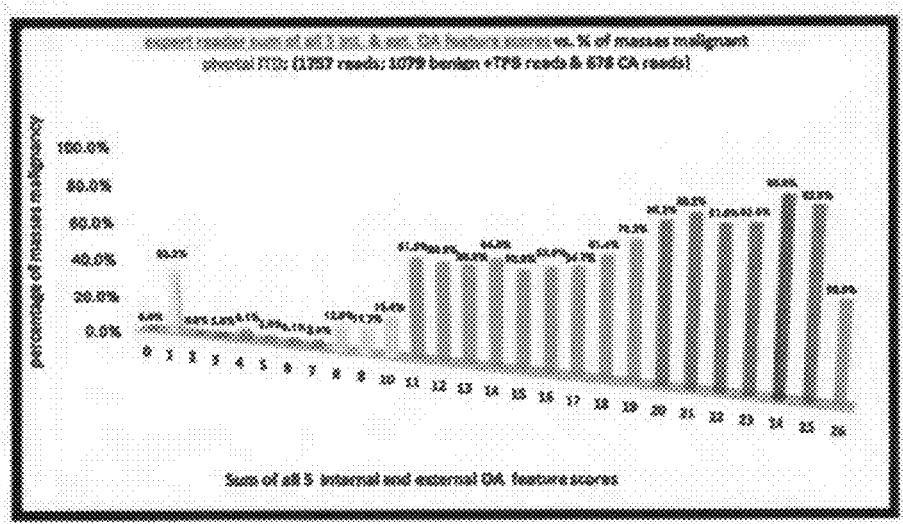

US Feature Score Correlations with KI-67

| US feature Score | Pearson correlation | p-value |
|---|---|---|
| Internal Shape Score | negative | 0.003 |
| Internal Echotexture Score | none | 0.445 |
| Internal Sound Transmission Score | negative | 0.10 |
| Internal Margin/BZ Score | negative | 0.002 |
| External Surrounding Tissue Score | negative | 0.10 |
| Sum of 3 Internal Feature Scores | negative | 0.02 |
| Sum of 2 external US Feature Scores | negative | 0.05 |
| Sum of All 5 US Feature Scores | negative | 0.01 |
| Ratio of Int Sum to Ext Sum | positive | 0.048 |
| Product of Sound x Surrounding Tissue | negative | <.10 |
| Product of Sound x Margin | negative | <.10 |

Figure 11F

| US Feature | Luminal A - Most Common US Feature | % in LUM A | TNBC - Most Common US Feature | % in TNBC |
|---|---|---|---|---|
| Shape | Irregular w/o angles non-parallel | 51.6% | Irregular w/o angles parallel | 51.6% |
| Echotexture | Isoechoic or mildly hypoechoic | 38.7% | Heterogeneous with microcalcifications | 29.0% |
| Sound Transmission | Partial Shadowing | 41.9% | Complete Enhancement | 61.3% |
| Boundary Zone | Thick echogenic halo | 51.6% | Thick echogenic halo | 64.5% |
| Peripheral Zone | Thin Spicules or thick Cooper's ligaments | 45.2% | Normal | 67.7% |

Figure 13B

| US Feature | Finding with large relative % differences | % in LUMA | % in TNBC |
|---|---|---|---|
| Shape | Oval shaped | 0.5% | 8.9% |
| Shape | Oval and round shape | 2.1% | 11.4% |
| Shape | Irregular w/o angles parallel | | |
| Shape | Irregular w/o angles non-parallel | | |
| Echotexture | Complex cystic and solid | 0.5% | 13.9% |
| Sound Transmission | Complete enhancement | 5.4% | 51.9% |
| Sound Transmission | Complete or partial enhancement | 11.1% | 62.0% |
| Sound Transmission | Complete, strong shadowing | 17.2% | 0.0% |
| Sound Transmission | Complete or partial shadowing | 65.0% | 16.5% |
| BZ | Complete or partial thin capsule | | |
| BZ | Indistinct | | |
| BZ | Short BZ spicules | 19.4% | 5.1% |
| PZ | Normal | | |
| PZ | Thickened Cooper's ligaments | | |

Figure 13C

METHODS AND SYSTEMS TO DETERMINE CANCER MOLECULAR SUBTYPES BASED ON ULTRASOUND AND/OR OPTOACOUSTIC (OA/US) FEATURES

REFERENCE TO RELATED APPLICATIONS

The present application claims priority to U.S. Provisional Application No. 62/725,632, which was filed on Aug. 31, 2018 and is incorporated herein by reference in its entirety.

BACKGROUND

Embodiments herein generally relate to opto-acoustic imaging and more specifically to methods and systems that correlate optoacoustic imaging-derived feature scoring and/or gray-scale ultrasound with molecular subtypes of malignancies.

Worldwide, breast cancer is the most commonly diagnosed cancer, and the second leading cause of cancer death in women. Although the death rate from breast cancer has significantly decreased in the last 20 years, breast cancer is still one of the major causes of morbidity and mortality in western women. One of the major challenges for its treatment is its heterogeneous nature, which determines the therapeutic options. The somatic genomic landscape of mutations largely influences breast cancer prognosis and therapeutic approach. Breast cancers with differing receptor expression and gene amplification profiles have different risk factors for incidence, therapeutic response, disease progression, and preferential organ sites of metastases. Four distinct main molecular subtypes of breast cancer are defined based on the presence of hormone receptors (Estrogen, and Progesterone) with or without human epidermal growth factor receptor 2 (HER2) protein overexpression- or extra copies of the HER2 gene: luminal A (ER+/HER2-negative); luminal B (ER+/HER2-negative, ki67>14%, or ER+/HER2+); HER-2 amplified (ER-negative, HER2+) and triple negative (TRN ER and PR-negative/HER2-negative). The presence of ER or PR receptors in invasive cancer are powerful indicators of the likelihood of benefit from anti-hormonal therapy. The c-erbB-2 (HER2/neu) proto-oncogene amplification is associated with increased tumor aggressiveness, increased rates of recurrence and in node positive patients, increased mortality. HER2/neu amplification status determined by Fluorescence In Situ Hybridization (FISH) identifies patients who may benefit from targeted anti-HER2 antibody therapy such as trastuzumab. These tissue prognostic markers, which largely guide management decisions and strongly correlate with patient outcomes are typically derived from tissue biopsies or surgical excision. However, breast cancer is a heterogeneous disease, and tissue biopsies may not be representative of the whole of breast tissue. Hence, extracting prognostic features from images of the whole tumor offers an opportunity to predict whole-tumor radiogenomics.

Ultrasound is used today in the evaluation of suspicious breast masses, and guiding biopsies. However, tissue architecture non-invasively assessed by breast ultrasound imaging does not provide enough prognostic information about cancers, and therefore has limited value to clinicians beyond the assessment of tumor size.

SUMMARY

In accordance with an embodiment, methods and systems are provided that utilize ultrasound and/or Optoacoustic imaging to identify and/or characterize breast cancer subtypes. Ultrasound and/or Optoacoustic images are obtained and assessed for features of interest. The ultrasound and/or Optoacoustic images include a set of images that illustrate Optoacoustic and/or ultrasound information alone or in combination in different manners. Different features may be apparent in different types of images. The features of interest are assigned scores indicative of the degree to which the feature of interest is present and/or pronounced in a corresponding type of image.

The methods and systems herein define models that correlate the features and feature scores to cancer molecular subtypes, including histologic grades. Methods and systems herein then utilize the models, in connection with analyzing new patient ultrasound and/or Optoacoustic image sets, to characterize and/or identify a particular subtype/grade of cancer for the corresponding patient.

In accordance with the embodiment herein, a method is provided comprising utilizing one or more processors in connection with, receiving OA/US feature scores in connection with OA/US images collected from a patient examination for a volume of interest; applying the OA/US feature scores to a feature score to molecular subtype (FSMS) model; determining, from the FSMS model, an indication of at least one of a molecular subtype or histologic grade of a pathology experienced by the patient.

In accordance with aspects herein, the pathology represents breast cancer and the molecular subtype represents one or more of Luminal A (LumA), Luminal B (LumB), Triple-negative (TRN) and HER2 amplified (HER2+). In accordance with aspects herein, the FSMS model distinguishes at least one of the following: A) between Luminal A and Luminal B molecular subtypes based on the OA/US features scores for at least two of: a) US internal zone sound transmission feature score; b) a sum of the US boundary and peripheral zone feature scores; or c) a sum of b), and a US internal zone shape feature score, US internal zone echotexture feature score, and the US internal zone sound transmission feature score; B) between Luminal A and TNBC molecular subtypes based on the OA/US features scores for at least two of: a) US internal zone sound transmission feature score; b) US boundary zone feature score; c) US peripheral zone feature score; d) a sum of US internal zone shape feature score, US internal zone echotexture feature score, and the US internal zone sound transmission feature score; e) a sum of the US boundary and peripheral zone feature scores; or f) a sum of d) and e); C) between Luminal A and HER2 molecular subtypes based on the OA/US features scores for at least two of: a) US internal zone sound transmission feature score; b) a sum of US internal zone shape feature score, US internal zone echotexture feature score, and the US internal zone sound transmission feature score; or c) a sum of b), and a US boundary zone feature score and peripheral zone feature score; or D) between Luminal B and TNBC molecular subtypes based on the OA/US features scores for at least two of: a) US internal zone sound transmission feature score; b) US peripheral zone feature score; c) a sum of US internal zone shape feature score, US internal zone echotexture feature score, and the US internal zone sound transmission feature score; or d) a sum of c), b) and a US boundary zone feature score.

In accordance with aspects herein, the OA/US feature scores include at least one of: a) multiple US feature scores only, and no OA feature scores; b) multiple OA feature scores only and no US feature scores; or c) at least one US feature score and at least one OA feature score.

In accordance with aspects herein, the FSMS model defines a correlation between one or more of the OA/US feature scores and at least one of one or more molecular subtypes or one or more histologic grades. In accordance with aspects herein, the FSMS model comprises a table associating pairs of molecular subtypes and the OA/US features scores, the table contains a correlation index indicative of an extent to which the corresponding OA/US feature scores differentiate between the corresponding pair of the molecular subtypes. In accordance with aspects herein, the OA/US feature scores include at least one of a US or OA boundary zone and at least one of a US or OA peripheral zone feature score. In accordance with aspects herein, the OA/US feature scores include at least one of a US or OA boundary zone feature score and at least one US/OA internal or peripheral feature score from the following: US internal zone shape feature score, US internal zone echotexture feature score, US internal zone sound transmission feature score, US peripheral zone feature score, OA internal deoxygenated blood feature score, OA internal total hemoglobin feature score, or OA peripheral zone feature score.

In accordance with aspects herein, at least one US or OA boundary zone feature score and at least one internal or peripheral US/OA feature score are scored applying at least one a)-j) hereafter:

a) the US internal zone shape feature score is assigned a value, each of which has a corresponding probability of malignancy, based on the following characteristics: Oval-shaped, parallel orientation, (wider than tall), >=2/1 ratio max width to AP dimension="flat" oval-shaped; Oval-shaped, parallel orientation, (wider than tall)<2/1 ratio width to AP="plump" oval-shaped; Round; Irregular without angles, parallel orientation; Irregular without angles, non-parallel orientation (taller-than-wide); or Irregular with angles, parallel or non-parallel (any angle of ≤90°);

b) the US internal zone echotexture feature score is assigned a value, each of which has a corresponding probability of malignancy, based on the following characteristics: Homogeneously hyperechoic (as hyperechoic as normal interlobular stromal fibrous tissue); Complex mixed cystic and solid; Homogeneously isoechoic or mildly hypoechoic; Heterogeneous without internal microcalcifications; Heterogeneous with internal microcalcifications; or Severely or markedly hypoechoic (compared to fat);

c) the US internal zone sound transmission feature score is assigned a value, each of which has a corresponding probability of malignancy, based on the following characteristics: Enhanced; Normal; Mixed normal and enhanced; Mixed enhanced and partial or weak shadowing; Mixed normal and partial or weak shadowing; or Complete and strong shadowing;

d) the US boundary zone feature score is assigned a value, each of which has a corresponding probability of malignancy, based on the following characteristics: Well circumscribed with complete thin hyperechoic capsule; Well-circumscribed with partial thin hyperechoic capsule; Thick well-defined capsule; Circumscribed, but without thin hyperechoic capsule; Indistinct margin; Thick ill-defined echogenic rim (halo) in boundary zone; or Frank short hypoechoic and/or hyperechoic spiculations within boundary zone;

e) the US peripheral zone feature score are assigned a value, each of which has a corresponding probability of malignancy, based on the following characteristics: Normal tissue; Critical angle phenomena (shadowing from adjacent structures); Enlarged surrounding ducts not containing microcalcifications (duct extension or branch pattern); Enlarged Surrounding ducts containing microcalcifications; Peripheral long hyperechoic spicules (or interrupted tissue plane); or Thickened spicules and/or Coopers ligaments and/or retracted or thick skin;

f) the OA internal vessel feature score is assigned a value, each of which has a corresponding probability of malignancy, based on the following characteristics: No internal vessels; Normal internal vessel(s) without branches, green or red; Normal internal vessel(s) with branches, green or red; Internal speckle—green ≥red in amount and red <background red; Internal speckle—red >green and IZ red >red in background; or Multiple internal red (deoxygenated) polymorphic vessels;

g) the OA internal total hemoglobin feature score is assigned a value, each of which has a corresponding probability of malignancy as noted, based on the following characteristics: No internal hemoglobin; Minimal internal hemoglobin <background; Minimal # internal discrete vessels <=background; Moderate # internal discrete vessels=background; Many large polymorphic internal vessels >background; or Many large polymorphic vessels almost fill lesion;

h) the OA internal deoxygenated blush feature score is assigned a value, corresponding to a probability of malignancy, based on the following characteristics: No internal vessels; Minimal internal speckle, all or mostly green; Mild internal speckle; Mild internal speckle; red ≥green, but red <bkgd red; Moderate internal speckle—red >green and red also >background red; or Internal red blush almost fills lesion;

i) the OA capsular/boundary zone vessel feature score is assigned a value, each of which has a corresponding probability of malignancy, based on the following characteristics: No capsular vessels; Normal capsular vessels without branches, parallel to capsule, not perpendicular, long, gently curved, and gradually tapered (green &/or red); Normal capsular vessels with normal tapering acutely angled branches, (green &/or red); Boundary zone speckle—green ≥red in amount and red <background red; Boundary zone speckle—red >green and red >background red; Multiple boundary zone neovessels—short red and/or green perpendicular "whiskers" or red enlarged tortuous vessels in "dot-dash" pattern; or Boundary zone deoxygenated blush (partial or complete); and j) the OA peripheral zone vessel feature score is assigned a value, each of which has a corresponding probability of malignancy, based on the following characteristics: No PZ vessels; Normal non-branching or branching non-radiating vessels in surrounding tissues; Cluster of enlarged, tortuous non-radiating vessels in PZ on one side of mass; One or two radiating PZ vessels on one side of mass; More than two radiating vessels on one side of mass; or 3 or more radiating vessels on more than one side of the mass.

The method further displays the indication as a collection of predictive results representative of probabilities of malignancy (POM) associated with a collection of the molecular subtypes and/or histologic grades.

In accordance with aspects herein, the method of receiving, applying and determining are performed in connection only with a US data set, US images and US feature scores. In accordance with aspects herein, the method receiving, applying and determining are performed in connection only with a OA data set, OA images and OA feature scores. In accordance with aspects herein, the receiving, applying and determining are performed in connection with a combination of a US data set, OA data set, US images, OA images, US feature scores, and OA feature scores. In accordance with aspects herein, the method identifies an interior outline of an internal zone for the region of interest, the interior outline separating the internal zone from a boundary zone, the interior outline is drawn between 0.5 and 1.0 mm inside of a margin of a hypoechoic nidus of the region of interest; and identifying an exterior outline separating the boundaries own from a peripheral zone. In accordance with aspects herein, scoring of the OA/US feature scores in a predetermined outside-to-inside order, that includes first requiring a user to assign one or more OA/US peripheral zone feature scores, second requiring a user to assign one or more OA/US boundary zone feature scores, third requiring a user to assign one or more OA/US internal zone feature scores. In accordance with aspects herein, memory is configured to store program instructions and a feature score to molecular subtype (FSMS) model, one or more processors that, when executing the program instructions, or configured to receive the OA/US feature scores comprised in connection with OA/US images collected from a patient examination for a volume of interest to apply the OA/US feature scores to the FSMS model to determine, from the FSMS model, an indication of at least one of a molecular subtype or histologic grade of a pathology experienced by the patient.

In accordance with aspects herein, the pathology represents breast cancer and the memory is configured to store molecular subtype represents one or more of Luminal A (LumA), Luminal B (LumB), Triple-negative (TRN) and HER2 amplified (HER2+). In accordance with aspects herein, the FSMS model distinguishes at least one of the following: A) between Luminal A and Luminal B molecular subtypes based on the OA/US features scores for at least two of: a) US internal zone sound transmission feature score; b) a sum of the US boundary and peripheral zone feature scores; or c) a sum of b), and a US internal zone shape feature score, US internal zone echotexture feature score, and the US internal zone sound transmission feature score; B) between Luminal A and TNBC molecular subtypes based on the OA/US features scores for at least two of: a) US internal zone sound transmission feature score; b) US boundary zone feature score; c) US peripheral zone feature score; d) a sum of US internal zone shape feature score, US internal zone echotexture feature score, and the US internal zone sound transmission feature score; e) a sum of the US boundary and peripheral zone feature scores; or f) a sum of d) and e); C) between Luminal A and HER2 molecular subtypes based on the OA/US features scores for at least two of: a) US internal zone sound transmission feature score; b) a sum of US internal zone shape feature score, US internal zone echotexture feature score, and the US internal zone sound transmission feature score; or c) a sum of b), and a US boundary zone feature score and peripheral zone feature score; or D) between Luminal B and TNBC molecular subtypes based on the OA/US features scores for at least two of: a) US internal zone sound transmission feature score; b) US peripheral zone feature score; c) a sum of US internal zone shape feature score, US internal zone echotexture feature score, and the US internal zone sound transmission feature score; or d) a sum of c), b) and a US boundary zone feature score.

In accordance with aspects herein, the OA/US feature scores include at least one of: a) multiple US feature scores only, and no OA feature scores; b) multiple OA feature scores only and no US feature scores; or c) at least one US feature score and at least one OA feature score. In accordance with aspects herein, a display is configured to present a probability of malignancy (POM) indicia in a manner and format representative of a collection of probabilities associated with a collection of at least one of the molecular subtypes or histologic grades.

In accordance with aspects herein, the display is configured to display the POM indicia to include at least one of a graph, alphanumeric characters, or color-coded scale, the POM indicia noting a central point/mean, and confidence intervals for the corresponding at least one of molecular subtypes or histologic grades. In accordance with aspects herein, the FSMS model comprises a table associating pairs of molecular subtypes and the OA/US features scores, the table contains a correlation index indicative of an extent to which the corresponding OA/US feature scores differentiate between the corresponding pair of the molecular subtypes. In accordance with aspects herein, the OA/US feature scores include at least one of a US or OA boundary zone and at least one of a US or OA peripheral zone feature score. In accordance with aspects herein, the OA/US feature scores include at least one of a US or OA boundary zone feature score and at least one US/OA internal or peripheral feature score from the following: US internal zone shape feature score, US internal zone echotexture feature score, US internal zone sound transmission feature score, US peripheral zone feature score, OA internal deoxygenated blood feature score, OA internal total hemoglobin feature score, or OA peripheral zone feature score.

BRIEF DESCRIPTION OF THE DRAWINGS

FIG. 4A illustrates a process for utilizing US and/or OA feature scores as biomarkers in accordance with embodiments herein.

FIG. 6C illustrates an example of a relation between positive predictive values and OA internal vessel feature scores.

FIG. 6J illustrates an example of the boundary zone where angiogenesis lives.

FIG. 7E illustrate an examples of vessel characteristics that may appear in the boundary zone and/or peripheral zone in connection with benign tumors and different types of malignancy molecular subtypes.

FIG. 7F illustrate an examples of vessel characteristics that may appear in the boundary zone and/or peripheral zone in connection with benign tumors and different types of malignancy molecular subtypes.

FIG. 7S illustrates examples of vessel morphology characteristics to be considered in connection with assigning a score for the capsular/BZ vessel feature.

FIG. 10B illustrates an example of a sum of the OA internal feature scores as compared to the POM. The graph of the POM versus the sum of the three OA internal stores shows that it is a good positive predictor of cancer, but by itself is not a good negative predictor of the apps of cancer.

FIG. 10C illustrates an example of a sum of the two OA external feature scores as compared to the POM.

FIG. 10D illustrates an example of a sum of the five OA feature scores as compared to the POM.

FIG. 11F illustrates a chart correlating different US feature scores with the Ki-67 molecular subtype, along with a related statistical P value based on a patient population of cases analyzed in connection here with.

FIG. 11-O illustrates a relation between masses having a nonparallel orientation (e.g. taller than wide) as a prognostic indicator.

FIG. 13B illustrates examples of the most common tumor gray scale ultrasound characteristics of luminal A versus TNBC molecular subtypes, along with a percentage estimate of the number of tumors with the corresponding molecular subtype that have the associated characteristic.

FIG. 13C illustrates US features other than the most common features that differ by molecular subtype between the luminal A and TNBC subtypes.

DETAILED DESCRIPTION OF THE INVENTION

Figure 1:
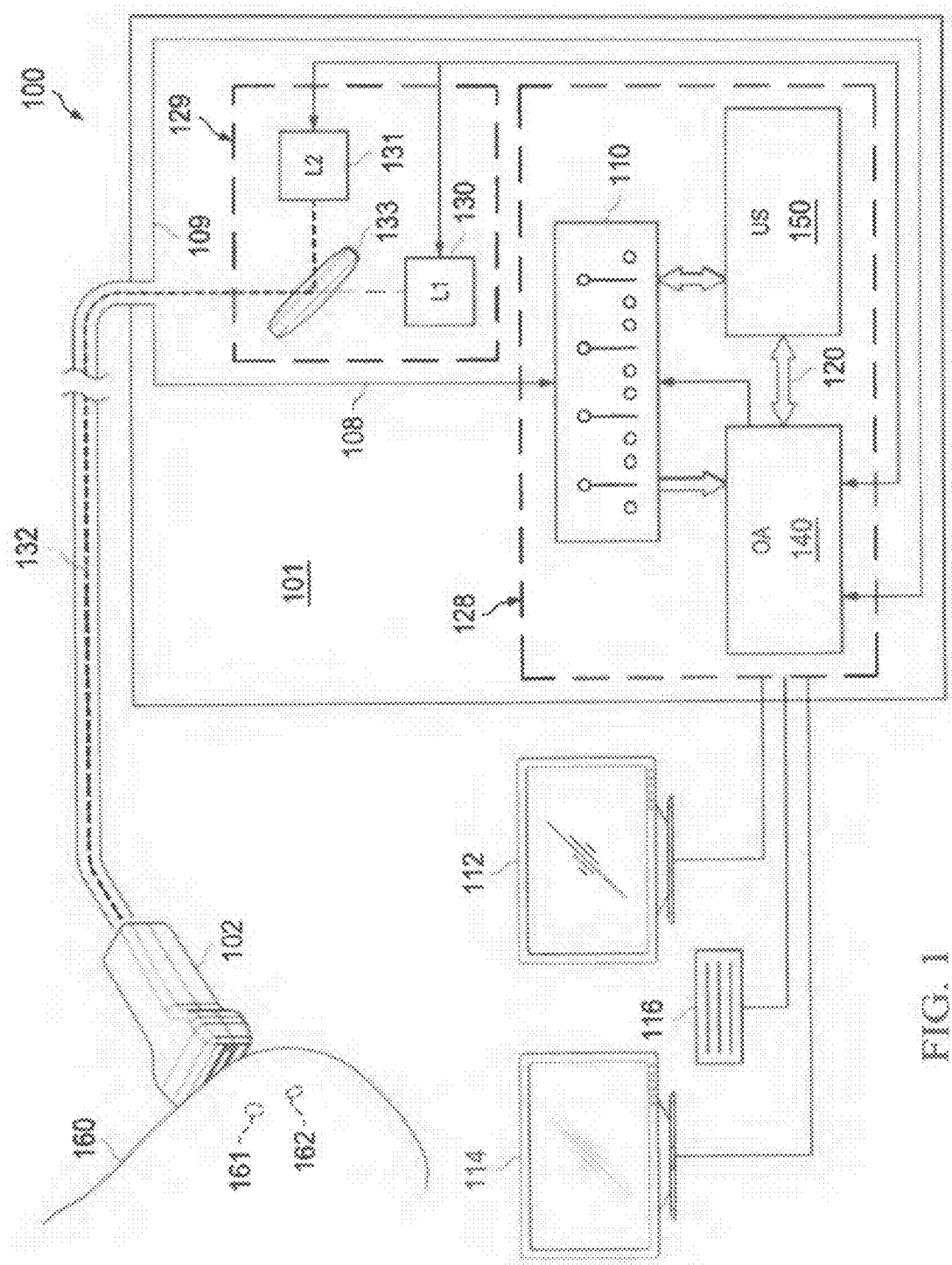
FIG. 1 shows a schematic block diagram illustrating an embodiment of a combined optoacoustic and ultrasound system that may be used as a platform for the methods and devices disclosed herein.

The following description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment; and, such references mean at least one.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments, but not other embodiments.

The systems and methods are described below with reference to, among other things, block diagrams, operational illustrations and algorithms of methods and devices to provide optoacoustic imaging with out-of-plane artifact suppression. It is understood that each block of the block diagrams, operational illustrations and algorithms and combinations of blocks in the block diagrams, operational illustrations and algorithms, can be implemented by means of analog or digital hardware and computer program instructions.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

These computer program instructions can be stored on computer-readable media and provided to a processor of a general purpose computer, special purpose computer, ASIC, or other programmable data processing apparatus, such that the instructions, which execute via the processor of the computer or other programmable data processing apparatus, implements the functions/acts specified in the block diagrams, operational block or blocks and or algorithms.

In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

Reference will now be made in more detail to various embodiments of the present invention, examples of which are illustrated in the accompanying Figures. As will be apparent to one of skill in the art, the data structures and processing steps described herein may be implemented in a variety of other ways without departing from the spirit of the disclosure and scope of the invention herein and should not be construed as being limited to the embodiments set forth herein. Rather, these embodiments are provided so that this disclosure will be thorough and complete, and will fully convey the concept of the disclosure to those skilled in the art.

Definitions

The term "AAB" shall mean acinar adenocarcinoma of the breast.

The term "ancillary feature score" shall mean a feature score assigned based on one or more features of interest within an ancillary image from an ancillary imaging modality, that does not include ultrasound imaging and does not include optoacoustic imaging.

The term "BI-RADS" shall mean Breast Imaging Reporting And Data System, and represents a method used by medical personnel to interpret and report in a standardized manner the results of mammography, ultrasound and MM used in breast cancer screening and diagnosis. By way of example, a BI-RADS 3 score may be indicative of a 2% or less probability of malignancy, a BI-RADS 4A score may be indicative of a probability of malignancy between 2% and less than or equal to 10%, a lower BI-RADS 4B score may be indicative of a probability of malignancy of greater than 10% and less than or equal to 25%, an upper BI-RADS 4B score may be indicative of a probability of malignancy of greater than 25%, a lower BI-RADS 4C score may be indicative of a probability of malignancy of less than or equal to 75%, and upper BI-RADS 4C score may be indicative of a probability of malignancy of greater than 75%, and a BI-RADS 5 score may be indicative of a probability of malignancy of greater than or equal to 95%.

The term "biomarker" shall mean an objective medical sign that is a measurable and quantifiable indicator of a physiologic or pathologic state of a mass, defined structure and/or living organism. The term biomarker shall include a defined characteristic that is measured as an indicator of normal biologic processes, genetic processes, or responses to an exposure or intervention, including therapeutic interventions. A biomarker may be derived from any substance, structure or process that can be measured in the body or its products and influence or predict the incidence or outcome of disease (e.g. positive predictive value of breast cancer). A biomarker is not a "symptom" which is a subjective perception of health or illness. Different types of biomarkers exist. For example, a diagnostic biomarker may be used for the detection or confirmation of a disease or condition and for identification of a specific disease subtype (e.g BI-RADS descriptors, ER, PR, and HER2 (also known as ERBB2) status). The diagnostic biomarker may represent a measurable and quantifiable indicator of whether to perform a biopsy or forgo a biopsy of a mass or other definable structure within a patient region of interest. As another example, a predictive biomarker may be used to identify individuals who are more likely to experience a favorable or unfavorable response to an intervention, medical product, or environmental exposure compared with individuals without the predictive biomarker. For example, the predictive biomarker may represent a possibility that mutations in BRCA genes are predictive of response to PA RP inhibitors in patients with advanced breast and ovarian cancer. As another example, the predictive biomarker may represent the likelihood that ER- and PR-positive breast cancers respond to endocrine therapy. As another example, the predictive biomarker may represent a possibility that dense breast tissue is predictive of decreased sensitivity of mammography for detecting noncalcified breast cancer. A predictive biomarker may indicate a percentage chance/probability of malignancy for a mass or other definable structure. As another example, a prognostic biomarker may reflect a likelihood of a clinical event, disease progression, or recurrence irrespective of an intervention (e.g TNM stage, tumor grade, tumor receptor status). The prognostic biomarker may be an indicator of a molecular subtype for a malignancy. As another example, a monitoring biomarker may be serially measured to assess a status of a disease or condition or to find evidence of exposure to, or effects of, a medical product or environmental agent. Monitoring biomarkers may focus on changes in a patients condition (e.g. tumor size and volume by imaging; prostate—specific antigen for monitoring of prostate cancer). The monitoring biomarker may provide an indicator of an effect a response to an exposure or intervention, including a therapeutic intervention or other treatment with respect to a malignancy.

The term "BZ" shall mean boundary zone.

The term "DAB" shall mean ductal adenocarcinoma of the breast.

The term "diagnostic imaging data set" shall mean a data set acquired by one or more of an ultrasound system, optoacoustic system, computed tomography (CT) system, magnetic resonance imaging (MRI) system, positron emission tomography (PET) system, single-photon emission computed tomography (SPECT) system, x-ray system, angiography system, fluoroscopy system and the like. The data set may represent the raw data acquired by the corresponding system and/or one or more images generated from processing (e.g. rendering) the corresponding data set.

The terms "feature" and "feature of interest" refer to features of an OA image, US image and feature combinations thereof. The non-OA features may be US features, MM features, X-ray features, CT features, PET features, SPECT features or another medical diagnostic imaging modality. Nonlimiting examples of OA features include 1) internal vascularity and de-oxygenation, 2) peri-tumoral boundary zone vascularity and deoxygenation, 3) internal deoxygenated blush, 4) internal total blood, 5) external peri-tumoral radiating vessels, and 6) interfering artifact. Non-limiting examples of ultrasound features include 1) US Shape Score, 2) US Internal Texture, 3) US Sound Transmission, 4) US Capsular or Boundary Zone, 5) US Peripheral Zone, 6) Patient Age, 7) Mammogram-BIRADS, 8) Lesion Size (cm), and 9) Lesion Posterior Depth (cm). Additional and alternative features are described in U.S. Pat. No. 9,398,893, to Anthony Thomas Stavros et al., titled "system and method for diagnostic vector classification support", filed Mar. 11, 2014 as application Ser. No. 14/205,005, and issuing Jul. 26, 2016 (hereafter the Stavros '893 Patent), the complete and total subject matter of which is expressly incorporated herein by reference in its entirety.

The term "feature score" refers to a grade, rating, ranking or other evaluation information that is descriptive of one or more characteristics of a feature in an OA image and/or non-OA image. Non-limiting examples of feature scores include i) a numeric value along a range of numeric values, ii) a dimension measured from an OA or non-OA image, and/or iii) a word, phrase, or sentence describing a characteristic of the feature.

The term "horizontal", when used to refer to a direction within a US or OA image, shall mean a direction perpendicular to a scanning direction of an ultrasound transmission/reception and/or optoacoustic transmission/reception.

The term "IZ" shall mean internal zone.

The term "imaging biomarker" shall mean a biomarker that is present in, or derived from, an imaging data set and can be measured and quantified, from the imaging data set, to determine an indicator of a physiologic or pathologic state of the mass, defined structure and/or living organism within a region of interest, for which the imaging data set is obtained. An imaging biomarker represents a diagnostic, not a therapeutic, by providing useful information to guide therapy. An imaging biomarker may be semi-quantitative and may be an ordinal score in which the risk of a certain outcome increases with increasing ordinal score. Imaging procedures indirectly affect an outcome and utilize surrogate endpoints for accuracy (e.g. sensitivity, specificity, PPV, NPV, ROC, AUC). The endpoints are measurable and reproducible. Imaging biomarkers may not have a desired level of sensitivity or specificity to be utilized individually in isolation. However, select combinations of different imaging biomarkers will cumulatively provide a desired level of sensitivity and specificity. While embodiments herein describe certain combinations of different imaging biomarkers as applied utilizing ultrasound and/or Optoacoustic imaging of breast masses, it is recognized that the subject matter herein is not limited to the particular combinations of imaging biomarkers, nor the ultrasound and/or Optoacoustic imaging modalities, nor breast imaging. Instead, principals described herein may be applied to additional and alternative combinations of imaging biomarkers, additional and alternative imaging modalities, as well as other anatomical regions. Nonlimiting examples of descriptors for an imaging biomarker applicable to characterizing a mass as benign or malignant include margin, shape and orientation of the mass.

The term "LOM" shall mean likelihood or probability of malignancy.

The term "non-OA image" refers to any medical diagnostic image, other than an OA image, captured by one or more medical imaging modalities. A non-OA image constitutes an image that is captured based on an imaging principle that does not utilize transmission of optical light in two distinct frequency ranges to cause a volume of interest to generate acoustic signals. Non-limiting examples of non-OA images include ultrasound (US) images (transmissive and/or reflective), MRI images, X-ray images, CT images, PET images, and SPECT images. When the non-OA image is a US image, the US image may be captured by a US imaging system that is integrated with, coupled to or entirely separate from, an OA imaging system.

The term "NPV" shall mean negative predictive value.

The term "OA feature score" shall mean a feature score assigned based on one or more features of interest within an OA image.

The term "observation" refers to one or more OA images (alone or in combination with one or more non-OA images) that are collected from a patient during an OA examination. The observation may also include diagnostic information entered by a clinician, such as OA feature scores and/or non-OA feature scores.

The terms "optoacoustic image" and "OA image" refer to an image captured by an optoacoustic imaging system that utilizes transmit light at one or more frequencies into a volume of interest and receives an ultrasound data set that is processed and converted into an OA image.

The term "PPV" shall mean positive predictive value.

The term "PZ" shall mean peripheral zone.

The term "ROC AUC" shall mean receiver operator characteristics area under the curve.

The terms "obtain" or "obtaining", as used in connection with data, signals, information and the like, includes at least one of i) accessing memory of various systems or devices (e.g. a diagnostic imaging system, PACS workstation, medical network workstation, desktop computer, laptop computer, tablet device, smart phone or remote server) where the data, signals, information, etc. are stored, ii) receiving the data, signals, information, etc. over a wireless communications link between the various systems and devices, and/or iii) receiving the data, signals, information, etc. at a remote server over a network connection. The obtaining operation, when from the perspective of a diagnostic imaging system, may include collecting new imaging data in real time, and/or accessing memory to read stored data, signals, information, etc. from memory within the diagnostic imaging system. The obtaining operation, when from the perspective of a local non-imaging device (e.g. PACS workstation, medical network workstation, desktop computer, laptop computer, tablet device, smart phone), includes receiving the data, signals, information, etc. at a transceiver of the local non-imaging device where the data, signals, information, etc. are transmitted from the diagnostic imaging system and/or a remote server. The obtaining operation may be from the perspective of a remote server, such as when receiving the data, signals, information, etc. at a network interface from a local non-imaging device and/or directly from a diagnostic imaging system. The remote server may also obtain the data, signals, information, etc. from local memory and/or from other memory, such as within a cloud storage environment and/or from the memory of a workstation or clinician external programmer.

The terms "receive" and "receiving" when used in connection with OA/US feature scores and/or OA/US images, includes at least one of i) collecting OA/US data sets in real time from a diagnostic imaging system, while performing a patient scan; ii) receiving inputs, such as OA/US feature scores entered by medical personnel; iii) receiving an automatic output of a machine learning classifier that automatically assigns OA/US feature scores; iv) receiving the data, signals, information, etc. over a wired or wireless communications link between the various systems and devices, and/or iii) receiving the data, signals, information, etc. at a remote server over a network connection.

The term "TDLU" shall mean a terminal duct lobular unit.

The term "UL feature score" shall mean a feature score assigned based on one or more features of interest within an ultrasound only image.

The terms "US" and "UL" are used interchangeably to refer to ultrasound only, and not optoacoustics.

The terms "OA/US", "OA/UL", "OA/US" and "UL/OA" shall mean ultrasound and/or optoacoustic and shall include ultrasound only, optoacoustic only, or a combination of ultrasound and optoacoustic. For example, a OA/US data set (or US/OA data set) may include 1) only a US data set, with no OA data, 2) an OA data set, with no US data, or e) a US data set and an OA data set. As another example, a OA/US feature score (or US/OA feature score) may include 1) only a US feature score, with no OA feature score, 2) an OA feature score, with no US feature score, or 3) a US feature score and an OA feature score. As another example, a OA/US image (or US/OA image) may include 1) only a US image, with no OA image, 2) an OA image, with no US image, or 3) a US image and an OA image.

The term "vertical", when used to refer to a direction within a US or OA image, shall mean a direction parallel to a scanning direction of an ultrasound transmission/reception and/or opotoacoustic transmission/reception.

Overview and Trial Results

A retrospective review of 653 invasive breast cancers was undertaken. The patients underwent pre-biopsy OA/US scans using an Imagio™ breast imaging system as part of a prospective multi-institutional study between December 2012 and September 2015. A group of medical professionals (Board certified radiologists and breast imaging subspecialist, referred to herein as "readers") reviewed the OA images, US images and combined OA/US images generated from the OA/US scans. The readers reviewed the OA, US and combined images in a "blind" manner. For example, among other things, the readers did not have knowledge of the patients type of cancer and/or the complete medical history of the patients. The reads were also blinded to mammographic findings and histologic results. The readers analyzed the OA, US and combined images to identify regions of interest and to analyze the ROIs in connection with a predefined set of OA feature and US features. For example, the features included various internal OA (OAINT) features and external OA (OAEXT) features (collectively "OA/US features") in connection with one or more ROI. The readers assigned scores (e.g., 0-6) to each OA/US feature.

The ER+ cancers had significantly higher OA-EXT ($p=0.0004$), with lower OA-INT ($p<0.05$), and RInt/Ext ($p<0.0001$) compared to ER-negative ones. Of 532 patients with available pathologic molecular subtype, 186(35.0%) were LumA, 244(45.9%) LumB, 79(14.8%) TNBC and 23(4.3%) were HER2+. OA-EXT was lower in TNBC compared to LumA ($p<0.0001$), whereas OA-INT were lower in LumA compared to TRN($p=0.031$). The mean RInt/Ext was significantly higher in TNBC (1.7, SD±0.7) compared to LumB (1.3, SD±0.5) and LuminalA (1.2, SD±0.5) subtypes ($p<0.0001$), but not significantly different from HER2 (1.5, SD±0.6). RInt/Ext helped distinguish LumA vs LumB (p=0.04), LumA vs HER2+(p=0.02), LumA vs TNBC (p<0.0001), LumB vs TNBC (p<0.0001).

In accordance with new and unique aspects herein, a prospective multi-institutional trial enrolled women 18 years or older with no current or prior history of ipsilateral breast cancer who presented either with a palpable mass or with a breast mass assessed at US as suspicious (BI-RADS 4-5) or probably benign (BI-RADS 3, <2% probability of malignancy) between Dec. 21, 2012, and Sep. 9, 2015. The institutional review board of each participating institution approved this HIPAA-compliant prospective multi-institutional study performed at 16 sites. Women that met the inclusion criteria underwent OA/US first, followed by core needle biopsy and/or surgical excisional biopsy within the next 45 days. Patients whose biopsy revealed invasive breast cancer constituted the population for the current study. Various portions of the data presented herein may be based in whole or in part on the results of this trial.

All patients were scanned with an Imagio™ breast imaging system (Seno Medical Instruments, San Antonio, Tex.), using a handheld duplex probe that functions both as a stand-alone grayscale US transducer and as a duplex optoacoustic imaging device prior to biopsy. The grayscale US transducers wideband 128-element linear array can emit and receive a range of frequencies from 4 MHz to 16 MHz at a 20 dB power point. The optoacoustic imaging device contained within the same duplex probe emits short pulses of laser light at two wavelengths-a shorter wavelength of 757 nm absorbed primarily by deoxygenated hemoglobin, and a longer wavelength of 1064 nm absorbed primarily by oxygenated hemoglobin. Site investigator radiologists or technologists who received didactic and initial hands-on training on the OA/US device performed OA/US scans in all sites. A standard, predefined imaging protocol was followed at all participating sites. Images were sent for central analysis and submitted for the reader study.

Seven dedicated breast imagers with 18-34 years of experience in breast imaging served as independent readers. Readers were blinded to clinical presentation, mammography or any other type of imaging or their reports and pathology. The readers only had access to imaging obtained with the OA/US device, including device grayscale ultrasound and OA color maps. Readers evaluated OA/US images and scored internal (OA-INT) and external (OA=EXT) OA features within the tumor interior on a pre-defined numeric scale: the number of individually resolved vessels and their relative degree of deoxygenation (OA vessel score), volume-averaged vessels too small to resolve individually (OA blush score), and amount of hemoglobin (OA hemoglobin score). The two external scores reflect the amount and relative oxygenation of hemoglobin as well as vessel morphology within the tumor boundary zone (OA boundary zone score) and periphery (OA peripheral score) using previously published scoring scale.

Patient age and tumor size was derived using registered case report forms. An independent central pathologist (F.L.T.) with more than 30 years of experience in breast pathology, blinded to the imaging features, reviewed all pathology reports and, at his discretion, had the option to request and review histologic specimen slides to determine the final diagnosis. Immunohistochemical data was derived from pre-treatment excision or core biopsy specimens in women who underwent neoadjuvant chemotherapy, and from final surgical specimens if treated with upfront surgery. Tumors were considered ER+ if ≥1% of tumor nuclei stained positive, according to national guidelines. HER2 by Fluorescence In Situ Hybridization (FISH) was performed on ImmunoHistoChemistry (IHC) 2+ lesions (Ventana INFORM HER2 DNA probe staining). The 2+ cases were considered HER2+ if the HER2/Chr17 ratio by FISH was equal to or greater than 2.0. Ki-67 testing was performed using the MIB1 antibody clone (DAKO, Agilent Technologies, Glostrup, Denmark) and results were expressed as percent nuclear staining. Molecular classes were defined as Luminal A (ER+ and/or PR+, Ki67<14%), Luminal B (ER+ and Ki67≥14% or PR negative, or ER+ and HER2+ regardless of Ki67), HER2+(ER and PR−, HER2 amplified), and Triple Receptor Negative (TRN, ER−, PR−, HER2-) based on published criteria (ref).

Results

Of 2055 masses that underwent pre-biopsy OA/US in 1972 women, 653 in 629 women showed invasive cancer at final pathology, constituting the study population. Mean patient age was 57.9 years (SD±12.6 yrs, range 18-88 yrs), and median tumor size was 1.7 cm (SD±1.03 cm, range 0.1-9.0 cm).

Ki67 index was available in 519 cancers. Pearson correlation test showed increasing Ki67 correlated with the sum of all three internal OA feature scores: OA hemoglobin score (p=0.0004), OA Internal blush score (p=0.02), OA vessel score (p=0.002) and total OA-INT (p=0.001) scores. Increasing Ki67 correlated with decreasing external OA peripheral zone scores (p=0.009), and the sum of the external OA feature scores (total OA-EXT, p=0.03), while correlation with decreasing external boundary zone score did not reach statistical significance (p=0.13). Increasing $R_{Int/Ext}$ (ratio of total internal to total external OA feature scores) correlated significantly with increasing Ki67 labeling index (p<0.0001).

Five hundred and thirty seven cancers (82.2%) were ER+, 111 (17%) ER-negative, and ER was unavailable in 5(0.8%). ER+ cancers had significantly higher OA-EXT (p=0.0004), with lower OA-INT (p=0.014), and RInt/Ext (p<0.0001) compared to ER-negative ones (Table 2). ER-negative cancers had higher OA hemoglobin scores—indicating a higher total Internal hemoglobin concentration (p=0.005)—and higher OA internal vessel score (p=0.002). None of the OA/US features were significantly different in HER2+ versus HER2-negative cancers (p=0.22-0.78, Table 2).

Fluorescence In Situ Hybridization (FISH) was unavailable in 29 (18.5%) cancers with IHC 2+ score, which were excluded from the molecular subtype analysis. Of the remaining 532 cancers with available pathologic molecular subtype, 186 (35.0%) were Luminal A, 244(45.9%) Luminal B, 79(14.8%) TNBC and 23(4.3%) were HER2 amplified. All external features of TNBC were significantly lower compared to Luminal A [OA external boundary zone p<0.0001; OA external peripheral vessels p<0.0001, total external score p<0.0001) whereas OA internal vessels (p<0.05) and total internal OA (p<0.05)] were significantly higher. The mean RInt/Ext was significantly higher in TNBC (1.7, SD±0.7) compared to Luminal B (1.3, SD±0.5) and Luminal A (1.2, SD±0.5) subtypes (p<0.0001), but not significantly different from HER2 amplified cancers (1.5, SD±0.6).

Figure 2:
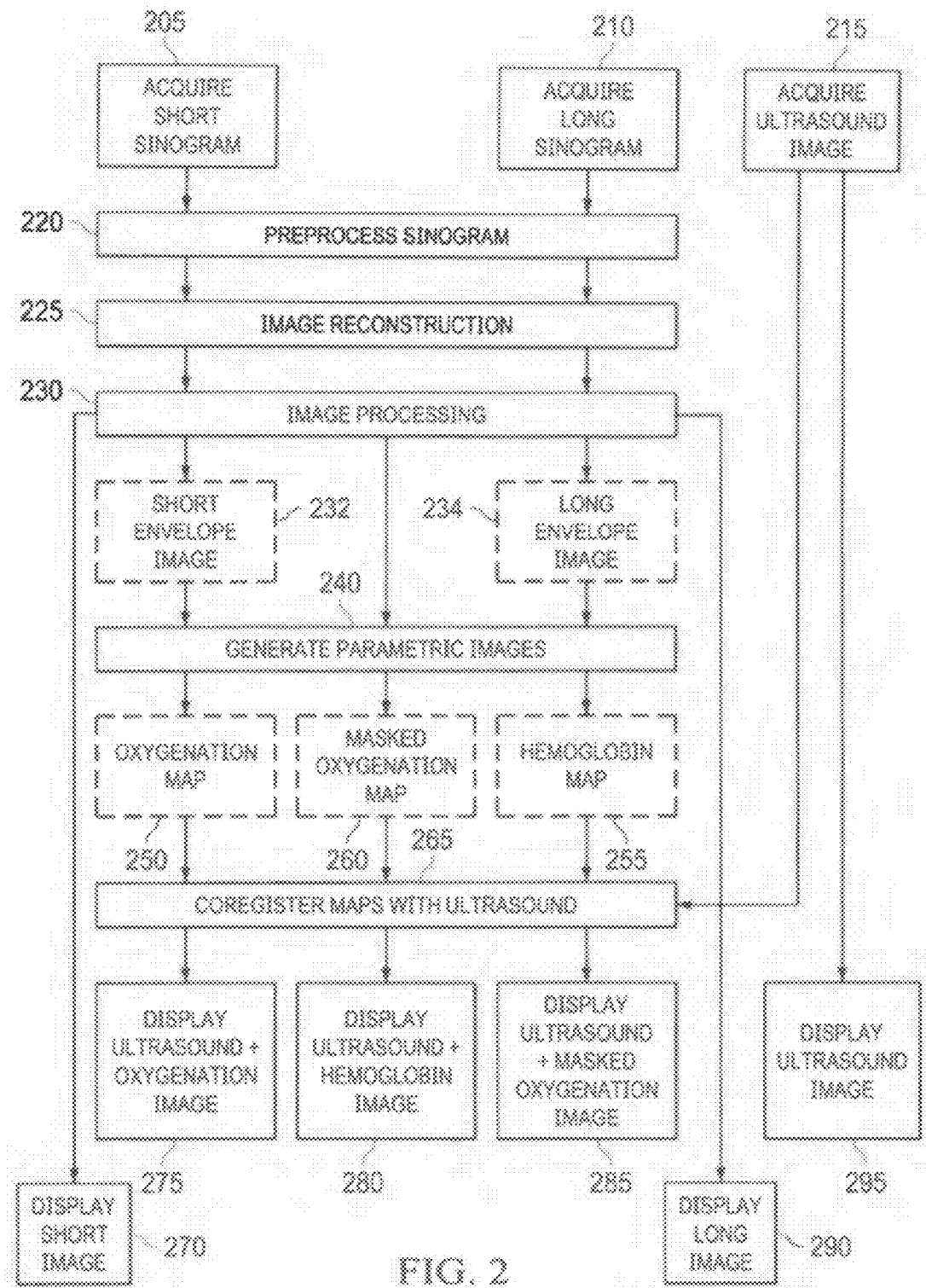
FIG. 2 shows a schematic block diagram illustrating hardware components of the system.

Receiver operating characteristic (ROC) curve analysis was performed to test the sensitivity and specificity of each OA feature. The Rint/ext had significantly higher diagnostic performance [Area Under the Curve (AUC)=0.78, SD±, 95% CI 0.71, 0.84, p<0.0001] with an optimal sensitivity of 81%, specificity of 64% in distinguishing TNBC from Luminal A cancer (FIG. 2). The AUC of the remaining OA/US parameters remained below diagnostic threshold (range, 0.3-0.6). The optimal sensitivity/specificity cut off for differentiating Luminal A from HER2 amplified cancers was 94% and 44% respectively, with AUC of $R_{Int/Ext}$ 0.70 (SD±0.54, 95% CI 0.60, 0.81; p=0.001), and the remaining features' AUC ranging between 0.3-0.6. Similarly, Rint/ext showed a significantly better performance (p<0.0001) than the remaining OA/US features (AUC=0.72, SD±0.03, 95% CI 0.67, 0.78) in distinguishing TNBC from other molecular subtypes (AUC range, 0.34-0.56) with an optimal sensitivity/specificity of 81% and 55%, respectively (FIG. 4). Luminal B vs TNBC showed an AUC=0.7 (SD±0.03, 95% CI 0.63, 0.76 p<0.0001).

In distinguishing Luminal A from other molecular subtypes, Rint/ext performed significantly better [AUC=0.69 (SD±0.02), 95% CI 0.60, 0.70, p<0.0001] than other features alone. None of the OA/US features showed significant diagnostic performance to distinguish Luminal B [AUC range, 0.47-0.5] or HER2 amplified [AUC range, 0.4-0.6] cancers from other molecular subtypes In accordance with embodiments herein, models have been developed that enable identification of cancer molecular subtypes based on distinct OA/US characteristics. In our study, luminal A cancers had significantly higher OA-EXT score compared to other molecular subtypes, and TNBC cancers showed significantly higher OA-INT and lower OA-EXT, resulting in the ability to distinguish these cancers using OA features. Our study is the first to analyze in vivo differences in tumor-related vascular structures in human breast cancer. The ability to observe intratumoral and peripheral vascular structures as well as hemoglobin oxygenation status non-invasively will likely allow a better understanding of breast cancer microenvironment. Our findings suggest that each breast cancer molecular subtype exhibits differing microvessel distribution profiles. We found that while TNBC (RINT/EXT=1.7) are more likely to have internal vessels rich in deoxygenated hemoglobin, luminal A tumors were internal vessel-poor, but had highly prominent external microvessels (RINT/EXT=1.2) (p<0.0001). The increased microvascular proliferation rate in basal-like (TNBC) breast cancers compared to luminal A cancers was previously reported. In general, breast cancers that show prognostically adverse characteristics, such as with ER-negative status have higher proportions of anoxic and hypoxic areas. Our findings of higher OA hemoglobin and internal vessel scores in ER-negative tumors parallel these differences in their microenvironment from ER+ cancers. Using the study device, these unfavorable features that suggest poor prognosis can be co-registered with standard B-mode ultrasound images at the time of real-time clinical practice. In real life application, correlating OA/US features with available tumor molecular subtypes can help determine tumor heterogeneity in discordant cases and guide in sampling relevant sections of the tumor, helping clinical management decisions. Additionally, it has been found that, even in patients who did not undergo neoadjuvant chemotherapy, tumor cell receptor information (ER, PR, HER2, Ki-67) varies between core biopsy and surgical excisional biopsy 15-20% of the time, owing to internal tumor heterogeneity. While it is currently recommended that receptor data be obtained both on core biopsy specimens and again on the surgical excisional specimen, recommendations for repeating receptor data on the surgical specimen are frequently not followed. OA biomarkers that are discordant with receptor biomarkers obtained at core biopsy, could suggest the absolute need to repeat receptor biomarkers on the surgical specimen. Furthermore, since TNBC are significantly less likely to metastasize to the ipsilateral lymph nodes compared to other subtypes, predicting the correct molecular subtype prior to needle biopsy can help determine the need to further evaluate the ipsilateral axilla at the time of real-time ultrasound. Longer term, microvascular structures demonstrated by OA/US are ideal imaging targets to monitor response to neoadjuvant anti-angiogenic therapy.

Previous work investigating differing imaging phenotypes associated with breast cancer molecular subtypes found distinct mammographic and sonographic features associated with HER2-positive and triple-negative cancers, while the MRI features of triple-negative cancers stood out from other subtypes. Unlike MM, which uses gadolinium contrast, OA/US uses a unique noninvasive technology that does not involve contrast or radiation and allows quantifying vascularization independent of temporal resolution within breast cancers. Since hemoglobin is a dominant absorber of light in tissue, it provides a method not only to resolve blood vessels without exogenous labels, but also to characterize the oxygenation saturation inside those vessels because oxyhemoglobin and deoxyhemoglobin display significantly different optical absorption spectra. Our finding of increased OA hemoglobin scores within TNBC compared to other subtypes are in keeping with gene sequencing studies that showed increased hypoxia within TNBC compared to other molecular subtypes. Furthermore, methods and systems herein are capable of obtained gray scale ultrasound data sets alone as well as duplex OA/US data sets, and thus the system can analyze sonographic and OA features together, with the possibility that using both ultrasound and OA biomarker data together will be complementary, rather than just additive.

We found that increasing ki67 strongly correlated with increasing OA hemoglobin score (p=0.0004), overall OA internal score (p<0.001) and with decreasing total external score ($OA_{EXT}$, p=0.03). Ki67 is a breast cancer proliferation index which is known to have prognostic significance independent of other prognostic factors. Our findings support the hypothesis that tumors with a higher proliferation rate, have higher rates of internal hypoxia, causing neo-angiogenesis to lag behind tumor growth. The resulting inadequate nutrient and oxygen supply causes activation of the hypoxia pathway, facilitating aggressive growth and early metastatic spread.

The diagnostic performance of OA/US features was best in distinguishing TNBC (AUC=0.72), and Luminal A (AUC=0.69) from other molecular subtypes, while none of the OA/US features helped distinguish Luminal B or HER2-amplified cancers from other molecular profiles. While these findings limit the practical application of OA/US features to help profile these subtypes using imaging alone, they parallel the observed overlapping outcomes and survival rates between luminal B and HER2-amplified cancers. Furthermore, combining ultrasound biomarkers with OA biomarkers may yet help better distinguish luminal B and HER2 amplified subtypes from other subtypes.

System and Method for Presenting Optoacoustic Data

Optoacoustic imaging (OA) is an imaging technique that uses pulsed laser light to illuminate the tissue, then resolves the optoacoustic waves generated by transient thermoelastic expansion following the absorption of the incident laser pulses by multiple absorbers such as hemoglobin, and deoxyhemoglobin. Optoacoustic systems using linear-array ultrasound (US) transducers leverage the advantage of using internal tissue contrast to add functional value to anatomical gray-scale US imaging. Prior clinical trials showed that when used as in combination with US, OA features of breast masses has the potential to help better differentiate malignant from benign masses, significantly decreasing false positive US assessments, with potential downstream effect of reducing unnecessary biopsies. In breast cancer, hypoxia mainly occurs because of the cancers outgrowth of existing vasculature and leads to adaptive responses that result in therapy response and tumor progression. The importance of hypoxia in breast tumor microenvironment as a significant indicator of poor prognosis has been well recognized in recent years. Imaging of hemoglobin concentration and its oxygenation status co-registered with the tumor image in real time may help better characterize breast cancers prognostically and assist clinical management decisions. Therefore, we undertook this study to investigate whether imaging-derived OA/US features correlate with breast cancer molecular subtypes determined by tissue immunohistochemistry.

All references, including publications, patent applications and patents, cited herein are hereby incorporated by reference to the same extent as if each reference were individually and specifically indicated to be incorporated by reference and were set forth in its entirety herein. Embodiments herein may be implemented in connection with one or more of the systems and methods described in one or more of the following patents, publications and/or published applications, all of which are expressly incorporated herein by reference in their entireties:

U.S. Pat. No. 7,999,161, titled "Laser-Activated Nanothermolysis Of Cells" filed Jul. 23, 2007; U.S. Pat. No. 9,289,191, titled "System and method for Acquiring Optoacoustic Data and Producing Parametric Maps Thereof", and filed Jun. 13, 2012; U.S. Pat. No. 9,517,055, titled "System And Method For Acquiring Optoacoustic Data And Producing Parametric Maps Using Subband Acoustic Compensation" filed Nov. 25, 2013; U.S. Pat. No. 9,724,072, titled "System And Method For Mixed Modality Acoustic Sampling" filed Dec. 13, 2013; U.S. Pat. No. 9,456,805, titled "System And Method For Acquiring Optoacoustic Data And Producing Parametric Maps Using Interframe Persistent Artifact Removal" filed Dec. 19, 2013; U.S. Publication 2016/0199037, titled "System And Method For Acquiring Optoacoustic Data And Producing Parametric Maps thereof" filed Mar. 22, 2016; U.S. Publication 2017/0035388, titled "System And Method For Mixed Modality Acoustic Sampling" filed Oct. 18, 2016; U.S. Pat. No. 9,792,686, titled "System And Method For Acquiring Optoacoustic Data And Producing Parametric Maps Using Subband Acoustic Compensation" filed Nov. 17, 2016; U.S. Publication 2017/0296151, titled "System And Method For Mixed Modality Acoustic Sampling" filed Jun. 30, 2017; U.S. Publication 2013/0109950, titled "Handheld Optoacoustic Probe" filed Nov. 2, 2011; U.S. Publication 2016/0296121, titled "Handheld Optoacoustic Probe" filed May 2, 2016; U.S. Pat. No. 8,686,335, titled "System And Method For Adjusting The Light Output Of An Optoacoustic Imaging System" filed Dec. 31, 2011; U.S. Pat. No. 9,528,936, titled "System And Method For Adjusting The Light Output Of An Optoacoustic Imaging System" filed Mar. 31, 2014; U.S. Publication 2017/0108429, titled "System And Method For Adjusting The Light Output Of An Optoacoustic Imaging System" filed Dec. 27, 2016; U.S. Pat. No. 9,330,452, titled "Statistical Mapping In An Optoacoustic Imaging System" filed Mar. 11, 2013; U.S. Pat. No. 9,836,838, titled "Statistical Mapping In An Optoacoustic Imaging System" filed May 3, 2016; U.S. Publication 2018/0061050, titled "Statistical Mapping In An Optoacoustic Imaging System" filed Nov. 6, 2017; U.S. Pat. No. 9,610,043, titled "System And Method For Producing Parametric Maps Of Optoacoustic Data" filed Jun. 13, 2012; U.S. Publication 2017/0100040, titled "System And Method For Producing Parametric Maps Of Optoacoustic Data" filed Dec. 21, 2016; U.S. Publication 2013/0338501, titled "System And Method For Storing Data Associated With The Operation Of A Dual Modality Optoacoustic/Ultrasound System" filed Jun. 13, 2012; U.S. Publication 2013/0338475, titled "Optoacoustic Imaging System With Fiber Optic Cable" filed Jun. 13, 2012; U.S. Publication 2014/0194723, titled "Multi-Layer Coating For Optoacoustic Probe" filed Jan. 13, 2014; U.S. Publication 2017/0150890, titled "Optoacoustic Probe With Multi-Layer Coating" filed Jan. 31, 2017; U.S. Pat. No. 9,615,750, titled "Methods And Compositions For Carrier Agents And Clearing Agents Used In Optoacoustic Imaging Systems" filed Jun. 14, 2012; U.S. Publication 2013/0116538, titled "Optoacoustic Imaging Systems And Methods With Enhanced Safety" filed Oct. 19, 2012; U.S. Publication 2015/0297090, titled "Optoacoustic Imaging Systems And Methods With Enhanced Safety" filed Jan. 23, 2015; U.S. Publication 2013/0289381, titled "Dual Modality Imaging System For Coregistered Functional And Anatomical Mapping" filed Nov. 2, 2012; U.S. Pat. No. 9,757,092, titled "Method For Dual Modality Optoacoustic Imaging" filed Nov. 2, 2012; U.S. Publication 2014/0039293, titled "Optoacoustic Imaging System Having Handheld Probe Utilizing Optically Reflective Material" filed Jan. 22, 2013; U.S. Publication 2017/0014101, titled "Dual Modality Imaging System For Coregistered Functional And Anatomical Mapping" filed Sep. 27, 2016; U.S. Publication 2013/0303875, titled "System And Method For Dynamically Varying The Angle Of Light Transmission In An Optoacoustic Imaging System" filed Nov. 2, 2012; U.S. Pat. No. 9,445,785, titled "System And Method For Normalizing Range In An Optoacoustic Imaging System" filed Dec. 21, 2012; U.S. Pat. No. 9,282,899, titled "System And Method For Detecting Anomalous Channel In An Optoacoustic Imaging System" filed Dec. 21, 2012; U.S. Publication 2014/0005544, titled "System And Method For Providing Selective Channel Sensitivity In An Optoacoustic Imaging System" filed Dec. 21, 2012; U.S. Publication 2016/0317034, titled "System And Method For Providing Selective Channel Sensitivity In An Optoacoustic Imaging System" filed Jul. 11, 2016; U.S. Pat. No. 9,445,786, titled "Interframe Energy Normalization In An Optoacoustic Imaging System" filed Jan. 22, 2013; U.S. Publication 2017/0000354, titled "Interframe Energy Normalization In An Optoacoustic Imaging System" filed Sep. 19, 2016; U.S. Publication 2014/0206978, titled "Probe With Optoacoustic Isolator" filed Jan. 22, 2013; U.S. Pat. No. 9,743,839, titled "Playback Mode In An Optoacoustic Imaging System" filed Mar. 15, 2013; U.S. Publication 2017/0332916, titled "Playback Mode In An Optoacoustic Imaging System" filed Jul. 27, 2017; U.S. Pat. No. 9,398,893, titled "System And Method For Diagnostic Vector Classification Support" filed Mar. 11, 2014; U.S. Pat. No. 10,026,170, titled "System And Method For Diagnostic Vector Classification Support" filed Jul. 19, 2016; U.S. application Ser. No. 16/022,138, titled "System And Method For Diagnostic Vector Classification Support" filed Jun. 28, 2018; U.S. Pat. No. 9,730,587, titled "Diagnostic Simulator" filed Mar. 15, 2013; U.S. Publication 2017/0332915, titled "Diagnostic Simulator" filed Jul. 27, 2017; U.S. Pat. No. 8,823,928, titled "Light Output Calibration In An Optoacoustic System" filed Mar. 15, 2013; U.S. Pat. No. 9,163,980, titled "Light Output Calibration In An Optoacoustic System" filed Jul. 11, 2014; U.S. Pat. No. 9,814,394, titled "Noise Suppression In An Optoacoustic System" filed Mar. 15, 2013; U.S. Publication 2018/0078144, titled "Noise Suppression In An Optoacoustic System" filed Nov. 13, 2017; U.S. Pat. No. 9,733,119, titled "Optoacoustic Component Utilization Tracking" filed Mar. 15, 2013; U.S. Publication 2017/0322071, titled "Optoacoustic Component Utilization Tracking" filed Jul. 27, 2017; U.S. Publication 2015/0101411, titled "Systems And Methods For Component Separation In Medical Imaging" filed Oct. 13, 2014; U.S. Publication 2015/0305628, titled "Probe Adapted To Control Blood Flow Through Vessels During Imaging And Method Of Use Of Same" filed Feb. 27, 2015; U.S. Publication 2016/0187481, titled "Opto-Acoustic Imaging System With Detection Of Relative Orientation Of Light Source And Acoustic Receiver Using Acoustic Waves" filed Oct. 30, 2015;

Siegel R L, Miller K D, Jemal A. Cancer statistics, 2018. C A Cancer J Clin 2018; 67:7-30. doi:10.3322/caac.21387; Polyak K. "Heterogeneity in breast cancer". J Clin Invest 2011; 121:3786-3788. doi:10.1172/JCI60534; Perou C M, Sorlie T, Eisen M B, van de Rijn M, Jeffrey S S, Rees C A, et al. "Molecular portraits of human breast tumours". Nature 2000; 406:747-52. doi: 10.1038/35021093; Sorlie T, Perou C M, Tibshirani R, Aas T, Geisler S, Johnsen H, et al. "Gene expression patterns of breast carcinomas distinguish tumor sub-classes with clinical implications". Proc Natl Acad Sci USA. 2001; 98:10869-74. doi: 10.1073/pnas.191367098; Russnes H G, Lingjærde O C, Børresen-Dale A L, Caldas C. "Breast Cancer Molecular Stratification: From Intrinsic Subtypes to Integrative Clusters". Am J Pathol. 2017; 187:2152-2162. doi: 10.1016/j.ajpath.2017.04.022.; Kim Y J, Kim J S, Kim I A. "Molecular subtype predicts incidence and prognosis of brain metastasis from breast cancer in SEER database". J Cancer Res Clin Oncol. 2018; 144:1803-1816. doi: 10.1007/s00432-018-2697-2.; Clarke M. "Meta-analyses of adjuvant therapies for women with early breast cancer: the Early Breast Cancer Trialists' Collaborative Group overview". Ann Oncol. 2006; 10:59-62. doi:10.1093/annonc/md1238.; "Early Breast Cancer Trialists' Collaborative Group (EBCTCG). Effects of chemotherapy and hormonal therapy for early breast cancer on recurrence and 15-year survival: an overview of the randomised trials". Lancet. 2005; 365:1687-717. Doi: 10.1016/S0140-6736(05)66544-0.; Loibl S, GianniL. "HER2-positive breast cancer". Lancet. 2017 17; 389:2415-2429. doi: 10.1016/S0140-6736 (16)32417-5. 'Pinker K, Chin J, Melsaether A N, Morris E A, Moy L. "Precision Medicine and Radiogenomics in Breast Cancer: New Approaches toward Diagnosis and Treatment". Radiology. 2018; 287:732-747. doi:10.1148/radiol.2018172171.; Chen J, Wang Z, Lv Q, Du Z, Tan Q, Zhang D, et al. "Comparison of Core Needle Biopsy and Excision Specimens for the Accurate Evaluation of Breast Cancer Molecular Markers: a Report of 1003 Cases". Pathol Oncol Res. 2017; 23:769-775. doi: 10.1007/s12253-017-0187-5.; Valluru K S, Wilson K E, Willmann J K. "Photoacoustic Imaging in Oncology: Translational Preclinical and Early Clinical Experience". Radiology 2016; 280:332-349. doi: 10.1148/radiol.16151414.; Schellenberg M W, Hunt H K. "Hand-held optoacoustic imaging: A review. Photoacoustics". 2018 6; 11:14-27. doi: 10.1016/j.pacs.2018.07.001.; Neuschler E I, Butler R, Young C A, Barke L D, Bertrand M L, Bohm-Velez M, et al. "A Pivotal Study of Optoacoustic Imaging to Diagnose Benign and Malignant Breast Masses: A New Evaluation Tool for Radiologists". Radiology. 2018; 287:398-412. doi: 10.1148/radiol.2017172228.; Neuschler E I, Lavin P T, Tucker F L, Barke L D, Bertrand M L, Bohm-Velez M, et al. Downgrading and Upgrading Gray-Scale Ultrasound B I-RADS "Categories of Benign and Malignant Masses With Optoacoustics: A Pilot Study". Am J Roentgenol. 2018; 211:689-700. doi: 10.2214/AJR.17.18436.; Menezes G L G, Pijnappel R M, Meeuwis C, Bisschops R, Veltman J, Lavin P T, van de Vijver M J, Mann R M. "Downgrading of Breast Masses Suspicious for Cancer by Using Optoacoustic Breast Imaging". Radiology. 2018; 288:355-365. doi: 10.1148/radiol.2018170500.; Lundgren K, Holm C, Landberg G. "Cell Mol Life Sci. Hypoxia and breast cancer: prognostic and therapeutic implications". 2007; 64:3233-3247. doi: 10.1007/s00018-007-7390-6; Vleugel M. M., Greijer A. E., Shvarts A., et al: "Differential prognostic impact of hypoxia induced and diffuse HIF-1alpha expression in invasive breast cancer". J Clin Pathol 2005; 58:172-177. DOI: 10.1136/jcp.2004.019885; van der Groep P, Bouter A, Menko F H, van der Wall E, van Diest P J. "High frequency of HIF-1alpha overexpression in BRCA1 related breast cancer Breast Cancer Res Treat". 2008; 111:475-80. doi: 10.1007/s10549-007-9817-z; Gilkes D M, Semenza G L. "Role of hypoxia-inducible factors in breast cancer metastasis". Future Oncol. 2013; 9:1623-1636. doi: 10.2217/fon.13.92.; Kraby M R, Kruger K, Opdahl S, Vatten L J, Akslen L A, Bofin A M. "Microvascular proliferation in luminal A and basal-like breast cancer subtypes". J Clin Pathol. 2015; 68:891-897. doi: 10.1136/jclinpath-2015-203037.; Lin N U, Vanderplas A, Hughes M E, Theriault R L, Edge S B, Wong Y N, et al. Cancer 2012; 118:5463-5472. doi: 10.1002/cncr.27581.; Ugras S, Stempel M, Patil S, Morrow M. "Estrogen receptor, progesterone receptor, and HER2 status predict lymphovascular invasion and lymph node involvement". Ann Surg Oncol. 2014; 21:3780-3786. doi: 10.1245/s10434-014-3851-y.; Yang W T, Dryden M, Broglio K, Gilcrease M, Dawood S, Dempsey P J, et al. "Mammographic features of triple receptor-negative primary breast cancers in young premenopausal women". Breast Cancer Res Treat. 2008; 111:405-410. doi: 10.1007/s10549-007-9810-6; Wang Y, Ikeda D M, Narasimhan B, et al. "Estrogen receptor-negative invasive breast cancer: imaging features of tumors with and without human epidermal growth factor receptor type 2 overexpression". Radiology 2008; 246:367-375. doi: 10.1148/radiol.2462070169; Uematsu T, Kasami M, Yuen S. "Triple-negative breast cancer: correlation between M R imaging and pathologic findings". Radiology 2009; 250:638-647.; Dogan B E, Gonzalez-Angulo A M, Gilcrease M, Dryden M J, Yang W T. "Multimodality imaging of triple receptor-negative tumors with mammography, ultrasound, and MRI". AJR Am J Roentgenol. 2010; 194:1160-1166. doi:10.2214/AJR.09.2355.; Wang C, Wei W, Santiago L, Whitman G, Dogan B. "Can imaging kinetic parameters of dynamic contrast-enhanced magnetic resonance imaging be valuable in predicting clinicopathological prognostic factors of invasive breast cancer?" Acta Radiol. 2018; 59:813-821. doi: 10.1177/0284185117740746.; Huuse E M, Moestue S A, Lindholm E M, Bathen T F, Nalwoga H, Kruger K et al. "In vivo M M and histopathological assessment of tumor microenvironment in luminal-like and basal-like breast cancer xenografts". J Magn Reson Imaging. 2012; 35:1098-1107. doi: 10.1002/jmri.23507.; Ye I C, Fertig E J, DiGiacomo J W, Considine M, Godet I, Gilkes D M. "Molecular Portrait of Hypoxia in Breast Cancer: A Prognostic Signature and Novel HIF-regulated Genes". Mol Cancer Res. 2018 Jul. 23. pii: molcanres.0345.2018 doi: 10.1158/1541-7786.MCR-18-0345.; Viale G, Giobbie-Hurder A, Regan M M, Coates A S, Mastropasqua M G, Dell'Orto P, et al. "Breast International Group Trial 1-98: Prognostic and predictive value of centrally reviewed Ki67 labeling index in postmenopausal women with endocrine-responsive breast cancer: results from Breast International Group Trial 1-98 comparing adjuvant tamoxifen with letrozole" J Clin Oncol 2008; 26:5569-5575. doi: 10.1200/JCO.2008.17.0829.; Parker J S, Mullins M, Cheang M C, et al. "Supervised risk predictor of breast cancer based on intrinsic subtypes". J Clin Oncol. 2009; 27:1160-1167. doi: 10.1200/ JCO.2008.18.1370.; Prat A, Pineda E, Adamo B, et al. "Clinical implications of the intrinsic molecular subtypes of breast cancer". Breast. 2015; 24 Suppl 2:S26-35. doi: 10.1016/j.breast.2015.07.008.;

Optoacoustic/ultrasound imaging systems as described below visualize thin tissue slices noninvasively through skin at a tissue site. The term "tissue site" broadly refers to locations or targets of animal and human tissues and organs such as, for example, breast tissue. A tissue site may contain a variety of different "tissue structures" that may include, for example, tumors, blood vessels, tissue layers, and components of blood. As described below, a sinogram may contain a sample recording of acoustic activity occurring over a period of time in response to one or more light events impinging on the tissue site. The acoustic activity captured in the sinogram may include an optoacoustic response, i.e., the acoustic signal that is created as a result of the electromagnetic energy being absorbed by materials within the tissue site such as, for example, various tissue structures that absorb the electromagnetic energy. These optical signals result from the release of thermo-elastic stress confinement within the tissue structures in response to the light events.

Turning to FIG. 1, and as described generally below under the heading Optoacoustic System and Method is a device 100, including a probe 102 connected via a light path 132 and an electrical path 108 to a system chassis 101. Within the system chassis 101 is housed a light subsystem 129 and a computing subsystem 128. The computing subsystem 128 includes one or more computing components for, among other things, optoacoustic control and analysis. In an embodiment, through the sampling of transducers in the probe 102, the device 100 can obtain data received in response to: stimulation caused by pulsed light sources 130, 131 (i.e., the optoacoustic return signal); and to stimulation caused by acoustic output of the ultrasound transducer elements.

In an embodiment, to obtain an optoacoustic return signal corresponding to a single light event occurring in a volume of tissue, the transducers in the probe 102 can be sampled for a period of time after the light event. In an embodiment, the transducers in the probe 102 can be sampled for a period of time after the light event approximately equal to the time it would take sound to travel a desired distance in the tissue. In an embodiment, the desired distance may be at least one centimeter. In an embodiment, the desired distance may be at least two centimeters. In an embodiment, the period of sampling would correspond to the amount of time it would take sound to travel at least one, but not more than 15 centimeters in tissue. The sampling rate should be sufficient to obtain sufficient information in the optoacoustic return signal. In an embodiment, the sampling rate is above 20 megahertz (MHz), in another embodiment, the sampling rate is above about 30 MHz.

As discussed further below, in an embodiment, the device 100 comprises at least two light sources 130, 131 operating at different light wavelengths. In an embodiment, with two light sources 130, 131 operating at different light wavelengths, the optoacoustic return signal from one light event and from each of the light sources can be used in the method and system for presenting the optoacoustic data. In an embodiment, the device 100 comprises a single light source that may be operated at different wavelengths, such as a tunable laser that can change wavelengths quickly enough for use as described herein. In an embodiment, the device 100 comprises at least two light sources 130, 131, each being capable of tuning to a plurality of different wavelengths. In an embodiment, the device 100 comprises one light source 130 operating a one light wavelength, and at least one additional light source 131 capable of being tuned to a plurality of different wavelengths.

As used herein, the term sinogram refers to sampled data or processed sampled data corresponding to a single light event. The term sinogram is also used at times to refer to an image presented by using the original or filtered sampled data as gray scale or color data, wherein there is a correspondence between the samples in the data and the voxels in the image. In an embodiment, using optoacoustic return signals from two different light events, each corresponding to a different wavelength of light, the term short sinogram refers to the sinogram corresponding to the shorter wavelength of light generating a light event, and the term long sinogram refers to the sinogram corresponding to the longer wavelength of light generating a light event. Because more than two different wavelengths may be used, the use of the terms short and long wavelength are intended to embody the extended context of a system with an arbitrary number of wavelengths.

In an embodiment, as discussed in more detail below, sinograms are processed to produce an envelope image. As used herein the term short envelope image refers to an envelope image corresponding to the short sinogram, and the term long envelope image refers to an envelope image corresponding to the long sinogram. In an embodiment, the short sinogram and long sinogram are each processed separately to produce a short envelope image and a long envelope image, respectively. The short and long envelope images are then used together to generate parametric images. From the parametric images, maps can be created of oxygenation, hemoglobin and masked oxygenation. These maps can be co-registered data representing an ultrasound image of substantially the same volume, and can thereafter produce one or more of an oxygenation image, a hemoglobin image and a masked oxygenation image. In an embodiment, the oxygenation image, hemoglobin image and masked oxygenation image reflect information about the composition of the volume of tissue. The terms parametric map and parametric image are in some instances used interchangeably. The use of the term map generally relates to the correspondence between the image and a volume. Parametric maps may be represented in numerous ways, including, for example, as a single-channel (i.e., grayscale) representation, as a color (i.e., RGB) representation, or as a color with transparency (RGBA) representation. Parametric maps may be used to convey qualitative or quantitative information about one or more parameters. A parametric map or parametric image may be represented in computer memory or presented as a displayed representation, thus, as used herein, the term "image" or "map" do not necessarily imply a visual representation.

Generally in each of the following steps for processing the sinogram, the processing is performed on the time domain signal. In a preferred embodiment (and as discussed below) the probe 102 includes an acoustic lens that enables the sinogram data to be more focused on what is on the plane below that of the transducers—the image plane. In an embodiment, the probe comprises an acoustic lens having a focal length of between 10 and 40 millimeters. In an illustrative embodiment, the probe comprises an acoustic lens having a focal length of 20 millimeters. In an embodiment, the probe may comprise an acoustic lens having a focal length that can be zoomed in or out, in hardware, or in software.

Turning to FIG. 2, an overview of an example process is shown, beginning with the acquisition of three sets of data, namely, a short sinogram (step 205), a long sinogram (step 210) and an ultrasound image (step 215), and processing the data to produce up to six separate images that may be useful in viewing various aspects of that acquired data. In an example embodiment, the three sets of acquired data may be acquired using a probe 102 (FIG. 1). For the purposes of illustration herein, it may be presumed that probe 102 movement is minimal, if any, between the acquisition of the three sets of data in steps 205, 210 and 215. In an example embodiment, a reasonable frame rate (e.g., 10 Hz), coupled with a reasonably steady hand used in handholding the probe may yield the three data sets having substantially minimal movement occurring there-between. It should be noted that the process described herein is not limited to being used with the three identified data sets. Use of additional data sets, such as, for example, data sets from additional wavelengths of light, may be used to further improve the resulting images.

As will be discussed in more detail below, the short and long sinogram data are preprocessed (step 220) in one or more separate manners to reduce or compensate for undesired data in the sinogram, including characteristics of the measuring instrument (e.g., the probe) or the light used, characteristics of the volume (i.e., the tissue), characteristics of the interaction between the volume and the probe or light, external stimuli, or other sources. After the preprocessing, separate short and long images are reconstructed (step 225). In an embodiment, separate real and imaginary components of complex short and long images result from the reconstruction step. In an embodiment, the processing (step 230) of the reconstructed images is performed. The processing (step 230) may remove additional artifacts that can be identified in the reconstructed images, and in any event creates a short envelope image (232) and a long envelope image (234). In an embodiment, the short and long envelope images (232, 234) are used to generate parametric images (step 240) process. The generated parametric images (step 240) process outputs an oxygenation map (250), a hemoglobin map (255) and a masked oxygenation map (260). In an embodiment, any or all of the three maps are coregistered with and overlaid on an ultrasound image (step 265). A display can be provided for display of one or more of the displayable images displayed in steps 270, 275, 280, 285, 290 and 295. In an embodiment, a group of two or more of the images may be displayed on the same screen, and may be commonly scaled and sized. In an embodiment, the group of all six images may be displayed on the same screen, and may be commonly scaled and sized. In an embodiment, the system performing processing on the optoacoustic data, and/or the system displaying the optoacoustic output—which may, but need not be the same as the system acquiring the sinogram—would provide the operator the ability to vary parameters used in processing, when processing or viewing optoacoustic images. In an embodiment, the system performing processing on the optoacoustic data, and/or the system displaying the optoacoustic output would provide the operator the ability to switch on and off, and potentially vary the order of, the processing steps used to process the optoacoustic images.

Returning to FIG. 1, generally, device 100 provides an optoacoustic system that may also be employed as multimodality, combined optoacoustic and ultrasound system. In an embodiment, the device 100 includes a probe 102 connected via a light path 132 and an electrical path 108 to a system chassis 101. Within the system chassis 101 is housed a light subsystem 129 and a computing subsystem 128. The computing subsystem 128 includes one or more computing components for ultrasound control and analysis and optoacoustic control and analysis; these components may be separate, or integrated. In an embodiment, the computing subsystem comprises a relay system 110, an optoacoustic processing and overlay system 140 and an ultrasound instrument 150. In an embodiment, the light subsystem 129 is capable of producing pulses of light of at least two different wavelengths. In an embodiment, the light subsystem 129 outputs should be capable of producing short pulses of light in each of those wavelengths, e.g., a pulse lasting less than about 100 ns, and potentially as short as about 5 ns. As will be apparent to one of ordinary skill in the art from this disclosure, the inventions disclosed herein may also be practiced using pulsed light comprising pulses lasting greater than 100 ns. In an embodiment, the light subsystem 129 includes two separate light sources 130, 131. The output of the light subsystem 129 is delivered to the probe 102 via the light path 132. In an embodiment, the light sources 130, 131 are lasers producing light in the infrared, near-infrared, and/or visible spectrum. In an embodiment, light source 130 and light source 131 each produce light at a different wavelength in the infrared or near-infrared spectrum. In an embodiment, the light path 132 used to deliver light from the light subsystem 129 to the probe 102 is a fiber optic bundle comprising multiple strands of optical fiber. In an embodiment, the light path 132 comprises sufficient optical fibers of sufficient size (diameter) to carry a short, high powered pulse of light to the distal end of the light path 132. In an embodiment, the total pulse energy carried over the light path 132 may be on the order of one or more millijoules. In an embodiment, the total energy per light pulse delivered from the light path 132 is less than about 100 millijoules. In an embodiment, the total energy per light pulse carried over the light path 132 is in the range of about 50-90 millijoules, and the light path 132 comprises between about 1,000 and 2,000 optical fibers of between about 100 and 300 microns each. In an embodiment, a single fiber can be used as the light path 132. In such embodiment, the fiber may be 1000-1500 microns in diameter. Of course, the diameter of such single fiber may be smaller, e.g., 400 microns. Given the required total pulse energy carried over the fiber, one skilled in the art can calculate the diameter required of the fiber accordingly.

In an illustrative embodiment, the light subsystem 129 may use Nd:YAG and Alexandrite lasers as its two light sources 130, 131, although other types or wavelengths, and additional lights, may also be used. Light sources 130, 131 should be capable of producing a short pulse of light, e.g., a pulse lasting less than about 100 ns, and more preferably around 5 ns. In an embodiment, the two light sources 130, 131 can be separately triggered. In an embodiment, the light output by the light sources 130, 131 may be projected onto the same light path 132 through the use of an optical element 133 that generally permits one light 130 to pass through from a first side to a second side, while reflecting one light source 131 that strikes the second side. The use of optical element 133 or a similar element permits the alignment of the output of two light sources 130, 131 such as lasers onto proximal end of the light path 132. In an embodiment, optical elements 133 can align the light output from more than two lasers, for example, through the use of multiple optical elements 133. In an embodiment, multiple light systems and light paths may be employed, with the light of each light system being carried on separate fibers or fiber groups that may be intermingled and/or randomized (discussed further below) and/or grouped at their distal ends. Intermingled, as used in this context, refers to the mapping of the fibers in the light path such that fibers are generally distributed in a relatively even manner in the distal groupings. Thus, a plurality of adjacent fibers on the proximal end of the light path would generally be about evenly divided in groupings on the distal end. As an illustrative example, where there are two distal groupings, any arbitrary selection of a sufficient group of adjacent fibers on the proximal end should be about evenly split between the two distal groupings. The randomization, intermingling and/or grouping need not take place at any specific location on the light path 132. In other words, for example, the division of a fiber cable from one proximal group to two distal groups can occur at any point along the light path 132, or along substantially the entire length of the light path 132. Similarly, the randomization and/or intermingling need not take place along the entire length of the light path, but rather, for example, may take along a the distance of, e.g., a few centimeters or more near either end of the light path, or anywhere else along the light path 132. Randomizing fibers between one end and the other end of a light path prevents a local anomaly affecting an adjacent group of the fibers on the input from affecting a significant adjacent group of the fibers on the output. Intermingling fibers between one end and the other end of a light path prevents a local anomaly affecting an adjacent group of the fibers on the input from disproportionately affecting one group or subgroup of fibers on the output.

Where the light path terminates in multiple groupings (or subgroupings) of fibers, the distal ends of the groupings (or subgroupings) may be fused, or lapped and polished, or just secured together (removable or otherwise). In an embodiment, the distal end of the light path is formed into a plurality of groups that are spaced in such a manner so as to permit light to emit on each side of the transducer array. In an embodiment, the distal end of the light path is formed into a plurality of groups that are spaced in such a manner so as to permit light to emit around the entire transducer array. In an embodiment, the distal end of the light path is formed into two or more groups, and the two or more groups subdivided into subgroups that are separately secured by a light bar guide, which light bar guide may be associated with the group. In an embodiment, optical elements 133 can consist of optical elements that are used to measure the light energy to determine energy per light pulse.

Although the total energy per light pulse carried over the light path 132 is in the order of tens of millijoules, because the pulse of light sources 130, 131 is so short, the peak power output over the light path 132 is frequently approaching or in the megawatt range. Accordingly, the output of light sources 130, 131 has the capacity to cause the optical fibers and/or the cladding on the optical fibers to burn, discolor or otherwise degrade. Such degraded optical fibers and/or cladding, whether burnt, discolored, or otherwise, can exacerbate the problem as they begin to transmit less light power and cause more heating. Accordingly, in an embodiment, sufficient number and size optical fibers are present in the light path 132 to permit handling of the peak power loads and avoid fiber burnout. To accommodate higher peak power, a larger fiber bundle can be used. It will be apparent to a person of skill in the art that the peak power capacity of a fiber bundle can be increased by increasing the number of optical fibers, or the diameter of optical fibers, or both. Notably, however, as the dimension of the fiber bundle increases, the weight and flexibility of the light path 132 may become less desirable. Moreover, when using more optical fibers, or optical fibers of a larger diameter, the output of light subsystem 129 must be delivered to the light path 132 across the wider diameter of the larger bundle. In an embodiment, regardless of the ultimate size of the proximal end of light path 132, the output of light subsystem 129 should be distributed sufficiently across its cross section to prevent burn out failures when operating in expected peak power ranges.

In an embodiment, the fibers of the proximal end of the light path 132 may be fused to form a fused entry point to the light path 132 for the output of light subsystem 129. In an embodiment, the fiber ends can be fused by applying heat. In an embodiment, a fused end may be surrounded with a metal ring. In an embodiment, a fused end may be surrounded with a stainless steel ring. Once the proximal end of light path 132 has been fused, it will resist burnout at substantially higher peak power. For example, using a fused end light path 132 may permit carriage of three, four or even five times as much peak power. The ability to carry substantially higher peak power in a given light path 132 permits use of a more flexible and lighter fiber optic bundle to carry the same peak power as an un-fused light path 132. Thus, in an embodiment, where a ½" (12.7 mm) fiber optic bundle may have been required in an un-fused bundle of optical fibers forming a light path, a ¼" (6.35 mm) fiber optic bundle with a fused proximal end may be used to carry the same peak power. A ¼" (6.35 mm) fiber optic bundle with a fused proximal end is approximately ¼ of the weight and much more flexible than a ½" (12.7 mm) fiber optic bundle. Moreover, fusing of the proximal end of light path 132 may produce an even smaller fused area to illuminate using light source 132 as the fusing removes the inter-fiber spaces that would have existed in the bundled end of the round-cross-section optical fibers. Accordingly, one or more of the following advantages may be attained by fusing the proximal end of the optical fibers comprising the light path 132: reduced weight of the light path; increased flexibility of the light path; reduced failure; increased reliability; higher peak power capacity.

In an embodiment, the proximal end of the light path 132 may be separated into separate groups for separate light sources 130, 131 in a light source 132, and light output by the light sources 130, 131 may be projected onto different proximal groups of the light path 132. More than two separate lights may be used, and the proximal end of the light path 132 may be separated into at least one group for each light. Each group of fibers at the proximal end of the light path 132 may be fused together to form a fused entry point to the light path 132 for the light with which it is associated. In an embodiment, the fibers of a light path having multiple groups on the proximal and are intermingled with respect to the groups or subgroups on the proximal ends. In an embodiment, the fibers of a light path having multiple groups on the proximal and are randomized with respect to the groups or subgroups on the proximal ends. In an embodiment, a light path is provided with a fused proximal end (input) and at least two groups on its distal end (outputs), the fibers being intermingled and randomized, thus preventing a local anomaly affecting adjacent fibers at the input of the light path from: (i) causing an anomaly affecting a substantial number of adjacent fibers on an output; and (ii) disproportionately affecting one of the outputs. In an embodiment, a light path is provided with at least two groups on its proximal end (inputs) and at least two groups on its distal end (outputs), the fibers being intermingled and randomized, thus preventing a local anomaly affecting adjacent fibers at an input of the light path from: (i) causing an anomaly affecting a substantial number of adjacent fibers on an output; and (ii) disproportionately affecting one of the outputs. In an embodiment, a light path is provided with at least two fused groups on its proximal end (inputs) and at least two fused groups on its distal end (outputs), the fibers being intermingled and randomized, thus preventing a local anomaly affecting adjacent fibers at an input of the light path from: (i) causing an anomaly affecting a substantial number of adjacent fibers on an output; and (ii) disproportionately affecting one of the outputs.

In an embodiment, optical fiber of the type that may be used in light path 132 includes a transparent core surrounded by a transparent cladding material with a lower index of refraction. The core may be made from any transparent material, although excellent results have been observed using pure glass (i.e., silica). In an embodiment, where a bundle of optical fibers are to be fused, the cladding may be removed in the area to be fused. In an embodiment, the cladding may be removed using a chemical process. For example, for some cladding, hot sulfuric acid or acetone may be used. The removal of cladding prior to fusing reduces the chance of particles of the cladding material becoming embedded in the fused end; as such particles may interfere with the light transmission across light path 132. In an embodiment, the light output by the light sources 130, 131 is sent towards a fused optical fiber bundle at the proximal end of light path 132 via a light path, which may include optical element 133, internal to the light subsystem 129. In an embodiment, light subsystem 129 is a laser system capable of outputting laser light pulses, at one or more wavelengths, onto light path 132. In an embodiment, light path 132 is a fiber optic bundle having a fused end proximal to the light subsystem 129. In an embodiment, the device 100 also comprises an electrical path 108 running to and/or from the probe 102 to the system chassis 101. In an embodiment, electrical path 108 runs to and/or from the probe 102 to a relay system 110 within the system chassis 101. The electrical path 108 may run near, alongside or coaxially with the light path 132 from the probe 102 toward their respective connections on the system chassis 101. In an embodiment, the electrical path 108 comprises a plurality of separate coaxial wires. In an embodiment, the electrical path 108 is run in a common jacket with at least a portion of the light path 132. Running electrical path 108 in a common jacket with at least a portion of the light path 132 reduces the number of cables running from the system chassis 101 to the probe 102. Running electrical path 108 in a common jacket with at least a portion of the light path 132 may minimize the diameter and weight of, and increase the durability of, the combined cables (i.e., light path 132 and electrical path 108) running from the system chassis 101 to the probe 102. One or more displays 112, 114, which may be touch screen displays, are provided for displaying images and all or portions of the device 100 user interface. One or more other user input devices (not shown) such as a keyboard, mouse and various other input devices (e.g., dials and switches) may be provided for receiving input from an operator. As an option, power and control path(s) 109 carry power to the probe 102 and control signals between the probe 102 and the computing subsystem 128.

Figure 3:
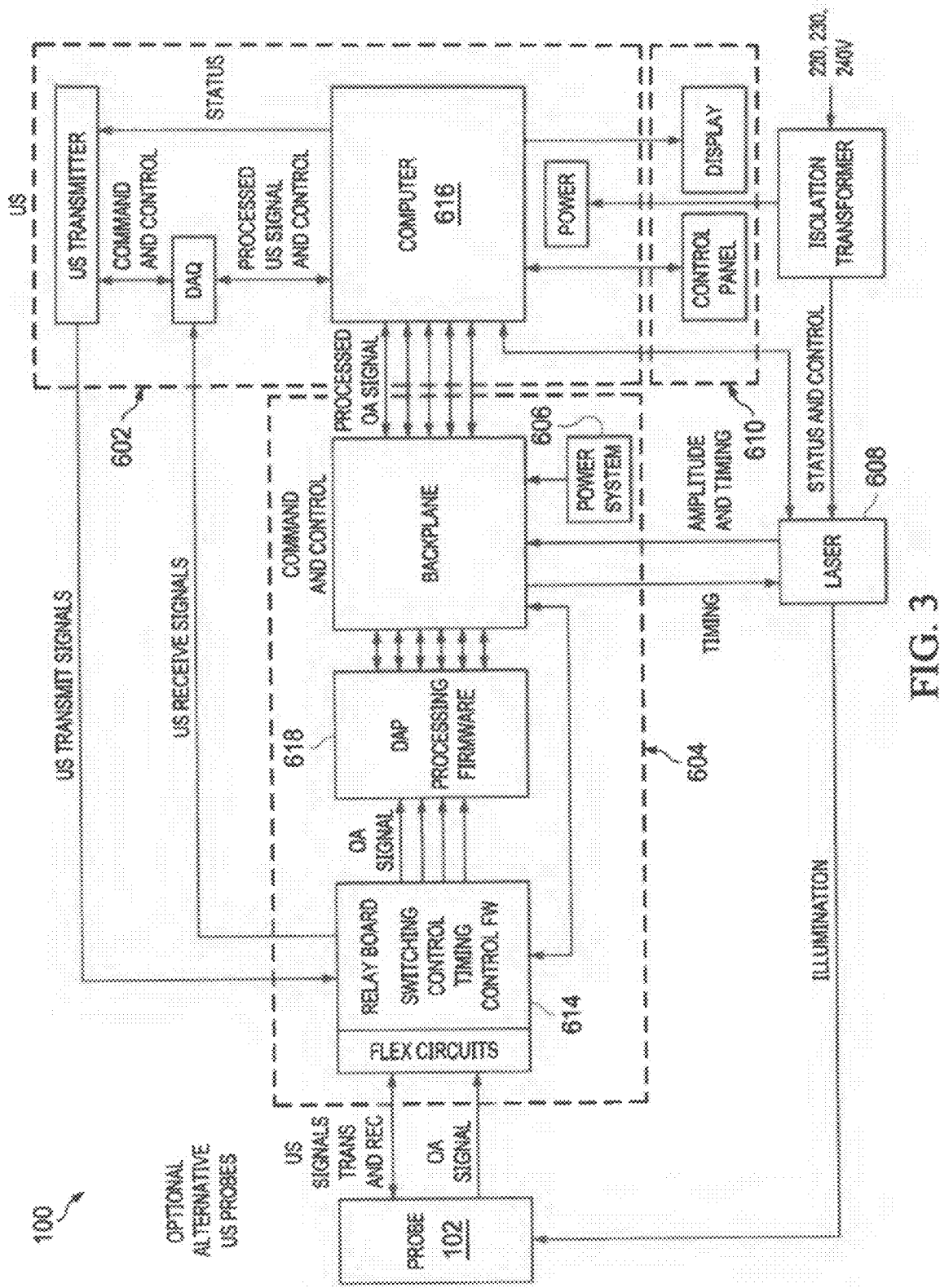
FIG. 3 illustrates a block diagram of an embodiment of the system, formed in accordance with embodiments herein.

FIG. 3 illustrates a block diagram of an embodiment of the system, formed in accordance with embodiments herein. In an embodiment, device 100 provides an integrated system consisting of the following subsystems: ultrasound subsystem 602, optoacoustic electronics subsystem 604, power supply subsystem 606, probe 102 and illumination/laser subsystem 608, which may be housed in one console, and the control and display subsystem 610 that can be attached to a console. The ultrasound subsystem 602, the optoacoustic electronics subsystem 604 and the control & display subsystem 610 will be referred to hereinafter collectively as the UOA.

The ultrasound subsystem 602 may be, e.g., a fully functional stand-alone ultrasound system. The ultrasound subsystem 602 includes an ultrasound transmitter 612 that outputs an ultrasound signal that is used to stimulate tissue. The ultrasound transmitter 612 provides its output to a relay board 614 in the optoacoustic electronics subsystem 604 which switches the ultrasound signal to the probe 102. The ultrasound subsystem further includes a data acquisition board, or DAQ, that receives ultrasound signals from the relay board 614 and processes them for transmission to and further processing by a computer 616. The computer 616 provides signal processing, user interface, and command and control functionality through software. The computer 616 includes one or more computer-readable medium for storage of programming as well as data generated by the system. The computer-readable medium may be in the form of volatile and/or non-volatile RAM, ROM, solid state drive, optical media, magnetic media (e.g., hard drive) or other storage device. The memory and storage may be integrated into or physically separate from the remaining components of the computer. The computer 616 further receives and transmits command and control signals to the DAQ for control of the data acquisition process and the ultrasound transmitter.

The optoacoustic electronics subsystem 604 includes a relay board 614 that provides switching functionality for alternately switching received ultrasound signals to the DAQ of the ultrasound subsystem 602 and received optoacoustic signals to a digital acquisition and processing (DAP) board 618. The relay board 614 includes firmware for both switching control and timing control. In an embodiment, flex circuits that form ultrasound transducers for both transmitting and receiving ultrasound signals are integrated into the relay board 614. The DAP 618 receives and processes the OA signal and outputs processed OA signals to the computer 616. The computer 616 provides command and control signals via a backplane to the DAP 618 and the relay board 614, and provides timing signals via the backplane to the illumination/laser subsystem 608.

FIG. 4A illustrates a process for utilizing US and/or OA feature scores as biomarkers in accordance with embodiments herein. The operations of FIG. 4A may be implemented by one or more processors of a US imaging system, an OA imaging system, a picture archive computing system (PACS), a network server (e.g. within a medical network), a workstation provided at a doctor's office or other medical facility, as well as other types of computing devices utilized by medical personnel (e.g. desktop computer, laptop computer, tablet device, smart phone). The operations of FIG. 4A may be divided between different physical systems, such that a portion of the operations are implemented by a first one of the example devices or systems described herein, while another portion of the operations are implemented by a second one of the example devices or systems described herein. At 402, one or more processors of the system obtain a US data set and/or an OA data set. The US data set and/or OA data set may represent one or more corresponding individual imaging frames/slices, and/or corresponding volumetric data sets. The US data set and/or OA data set may be obtained from a single or multiple diagnostic imaging sessions prior to or in real time during the remainder of the operations of FIG. 4A. The US data set and/or OA data set may be attained from a single common imaging system and/or from multiple separate imaging systems. For example, during one clinical visit, a US data set may be obtained for the patient utilizing an ultrasound only imaging system. During a separate second clinical visit, and OA data set may be obtained for the patient utilizing an OA imaging system. Additionally or alternatively, the US data set and OA data set may be obtained by a single imaging system having the capability to perform a US imaging session and to separately perform an OA imaging session.

Figure 4B:
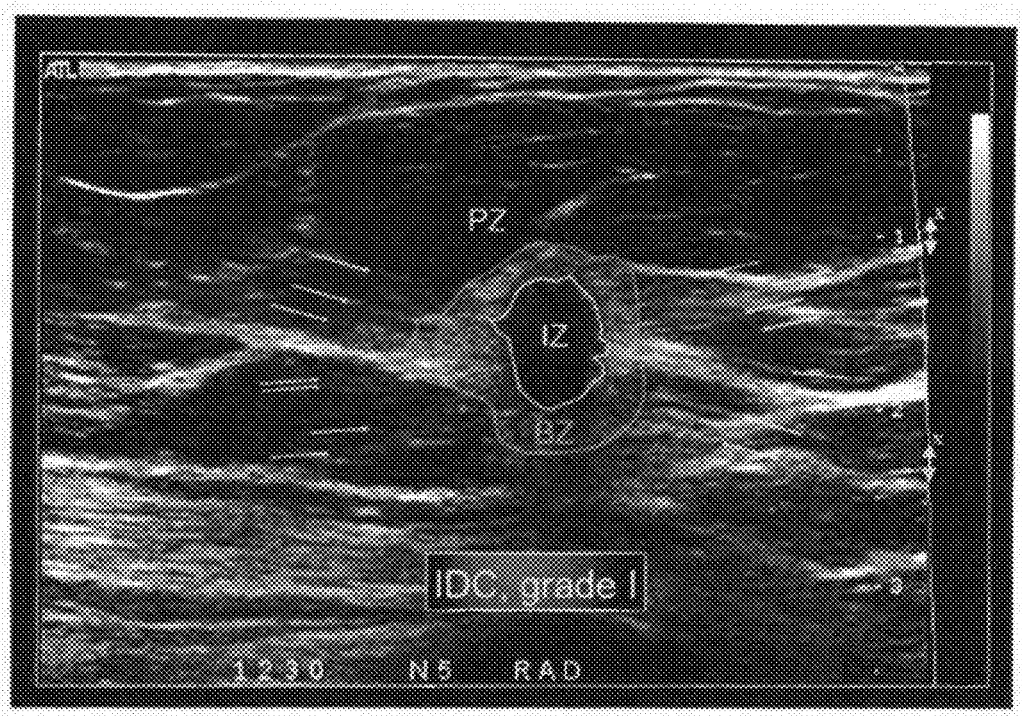
FIG. 4B illustrates an example of a US image displayed in accordance with an embodiment herein.

At 404, the one or more processors analyze the US data set and/or OA data set to render one or more US images and/or OA images. One or more of the US images and/or OA images are displayed on a display of the system to one or more medical personnel. At 406, one or more ROIs are identified from the US images and/or OA images. Additionally, an interior outline is identified that separates the internal zone from the boundary zone and an exterior outline is identified that separates the boundaries own from the peripheral zone. FIG. 4B illustrates an example of a US image displayed in accordance with an embodiment herein. The US image includes an ROI that includes an internal zone 420 that is surrounded by an interior outline 422. The interior outline 422 separates the internal zone 420 from a boundary zone 424. An exterior outline 426 separates the boundary zone 424 from the peripheral zone 428. The internal zone 420 represents a hypoechoic central nidus, while the boundary zone 424 may represent a thin hyperechoic capsule or thick echogenic rim (e.g. halo). The peripheral zone 428 is outside of the boundary zone 424. The peripheral zone 428 may include, among other things, hyperechoic spicules, hyperechoic thickened collateral ligaments (CLs), and the like (as generally indicated by the arrows in the regions 430, 432. The identification of 406 may be implemented in various manners, such as described in U.S. Pat. No. 9,398, 893, titled "System And Method For Diagnostic Vector Classification Support", issue date Jul. 26, 2016. The identification at 406 may be performed by medical personnel while viewing the images. For example, the medical personnel may utilize various tools within a user interface to designate the interior and exterior outlines (e.g. a mouse, trackball, stylus and touch screen, and the like). Optionally, the identification at 406 may be performed entirely automatically by the one or more processors of the system, such as based on image recognition algorithms, deep learning algorithms and the like. As a further option, at 406, the user may input an initial determination for the position and shapes of the interior and exterior boundaries, in response to which the one or more processors may automatically generate recommendations for adjustments in the interior and exterior boundaries. As a further option, at 406, the one or more processors may automatically generate the initial recommendation for the position and shapes of the interior and exterior boundaries. The user may be then afforded the opportunity to adjust the position and/or shape of the interior and exterior boundaries. For example, the user interface may be configured to allow the user to click on points along a boundary of interest and dragging the boundary to a new position. As another example, the user interface may be configured to allow the user to draw new segments within the interior and exterior boundaries that are then tied to the original automated recommendation.

Figures 5A, 5B:
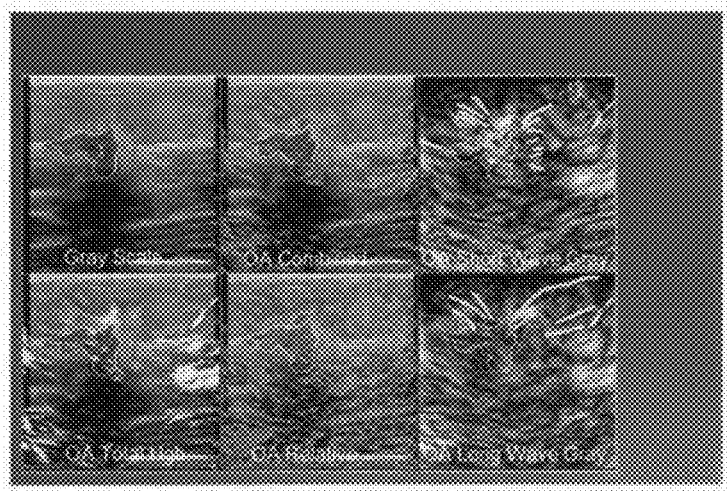
FIG. 5A illustrates an example of a set of images that may be co-displayed while medical personnel are assigning the various US feature scores and/or OA feature scores.
FIG. 5B illustrates the interior outline drawn in a manner to avoid mistakenly assigning boundary zone regions to the internal zone which will otherwise lead to underestimation of the POM.
Figure 5C:
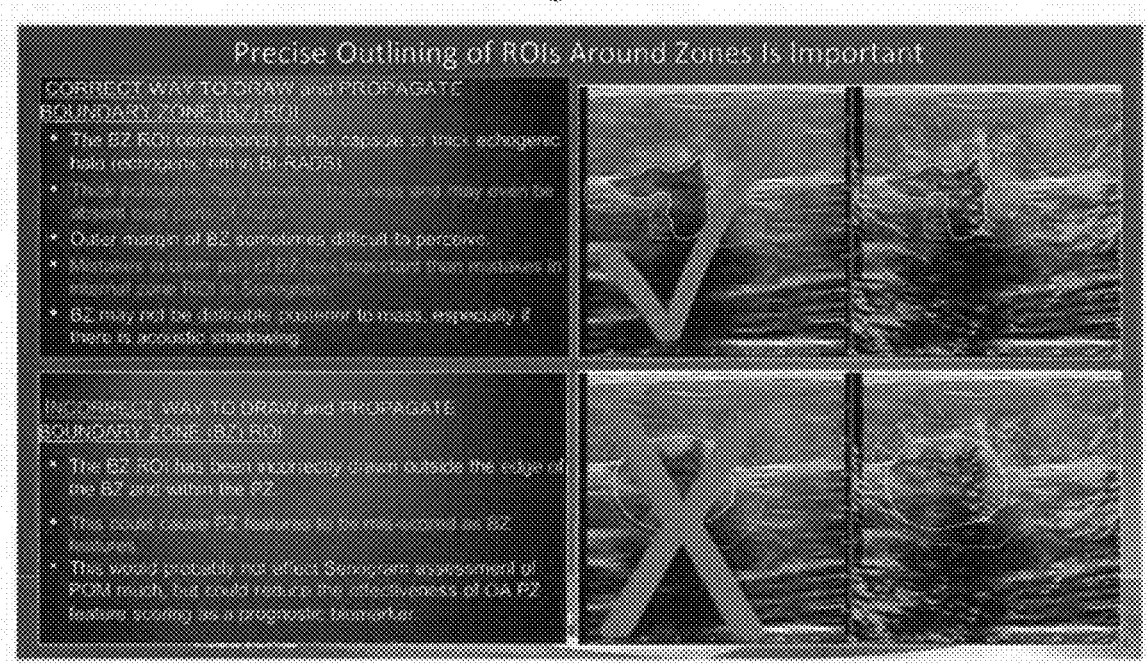
FIG. 5C illustrates additional examples of correctly and incorrectly drawn exterior outlines to separate the boundary zone from the peripheral zone.
Figure 5D:
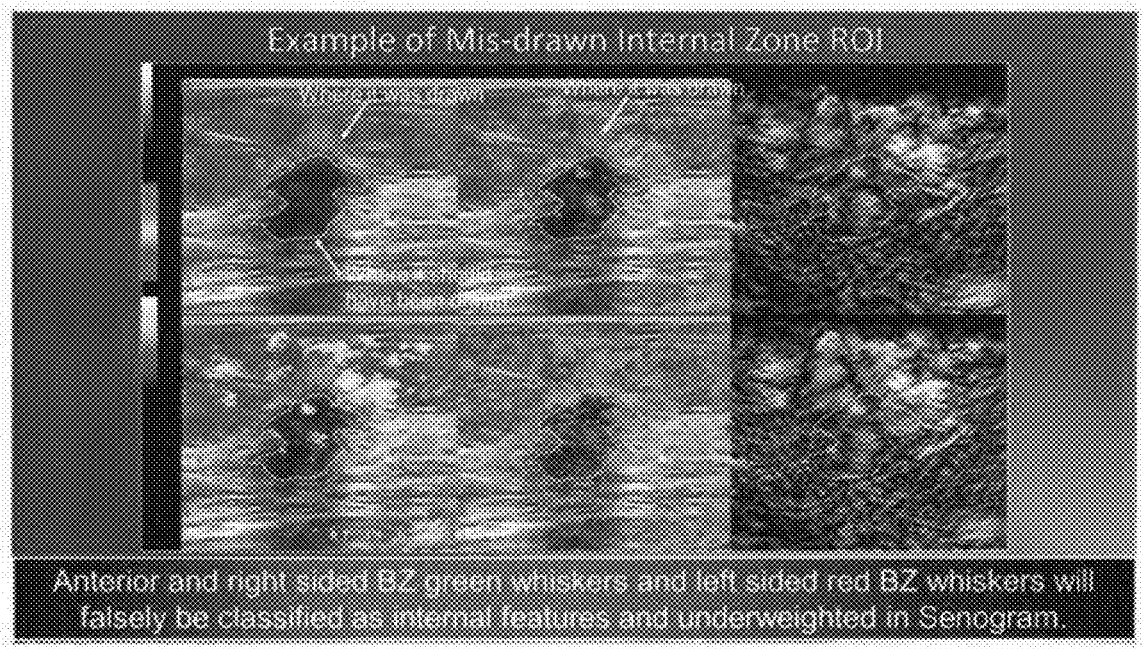
FIG. 5D illustrates another example of a mis-drawn interior outline around the internal zone.

In accordance with new and unique aspects herein, the operations of FIG. 4A may be performed only in connection with US data, US images, and US feature scores, to determine indications of molecular subtypes and/or histologic grades for a pathology based only on ultrasound. In accordance with new and unique aspects herein, the operations of FIG. 4A may be performed only in connection with OA data, away images, and OA feature scores, to determine indications of molecular subtypes and/or histologic grades for a pathology based only on optoacoustics. In accordance with new and unique aspects herein, techniques have been identified to precisely outline the ROI with the interior outline. FIGS. 5B-5D illustrate examples in connection with correctly identifying the interior outline of the internal zone for the ROI. For example, the interior outline is drawn between 0.5 and 1.0 mm inside of the margin of the hypoechoic nidus. FIG. 5B illustrates (in the upper left and upper right panels) the interior outline drawn in a manner to avoid mistakenly assigning boundary zone regions to the internal zone which will otherwise lead to underestimation of the POM. FIG. 5B also illustrates (in the lower left and lower right panels) an improperly drawn interior outline that includes a portion of the boundary zone within the internal zone. The lower panels of FIG. 5B incorrectly include areas outside of the hypoechoic central nidus edge, whereas the interior outline should have been drawn 0-1 mm inside of the hypoechoic central nidus edge. Incorrectly drawing the interior outline introduces the potential that a powerful boundary feature characteristic could be mis-scored as an internal feature characteristic, and/or assigning a more powerful suspicious boundary zone finding to the internal zone which could result in underestimation of the POM.

FIG. 5C illustrates additional examples of correctly and incorrectly drawn exterior outlines to separate the boundary zone from the peripheral zone. The exterior outline for the boundary zone should be drawn to correspond to the thin capsule or thick echogenic halo. The thick echogenic halo varies in thickness and at times may be absent over parts of the mass. The border for the boundary zone may not be definable in the area posterior to the mass, such as when there is acoustic shadowing. The upper left and right panels in FIG. 5C illustrate a correctly drawn exterior outline to separate the boundary and peripheral zones. The lower left and right panels illustrate and incorrectly drawn exterior outline. In the lower panels, the exterior outline has been drawn outside of the edge of the boundary zone which will cause peripheral zone features to be mis-scored as boundary zone features, which could affect an assessment of the POM and reduce and effectiveness of NOA peripheral zone feature score is a prognostic biomarker.

FIG. 5D illustrates another example of a mis-drawn interior outline around the internal zone. In the example of FIG. 5D, by drawing the interior outline to include part of the boundary zone, anterior and right-sided boundary zone "whiskers" and left-sided boundary zone "whiskers" will be falsely classified as internal features and under weighted in the calculation of the POM.

Figure 5E:
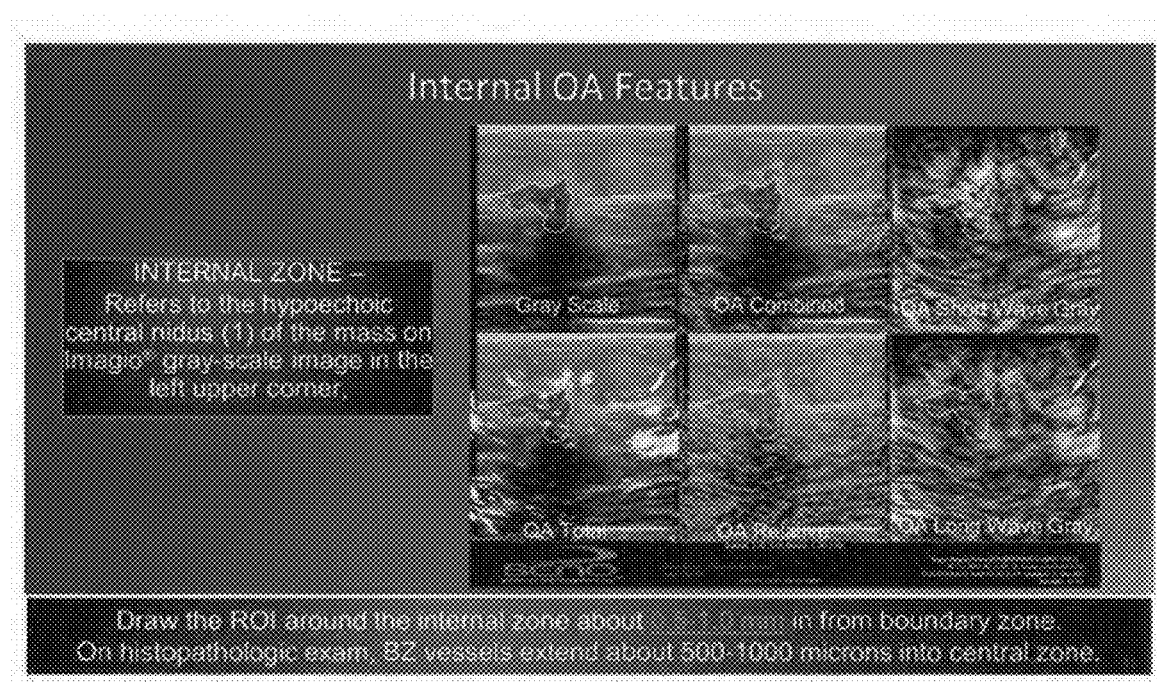
FIG. 5E an example of a 6-on-1 display presenting gray scale ultrasound in the left upper corner and 5 co-registered images/maps in the other 5 frames, yielding a total of six types of information used when scoring OA features.

FIG. 5E an example of a 6-on-1 display presenting gray scale ultrasound in the left upper corner and 5 co-registered images/maps in the other 5 frames, yielding a total of six types of information used when scoring OA features. An interior outline is drawn around the internal zone in the left upper gray scale ultrasound image, and then propagated to a co-registered location in the 5 different OA images/maps. The interior outline is drawn approximately 0.5 1.0 mm in from the boundary zone because boundary zone vessels may extend 500 1000 μm into the internal zone. At 408, the one or more processors, automatically or with input through a user interface by one or more medical personnel, obtain an identification of one or more US feature scores for corresponding US features within the US images. Examples are described below in connection with identifying internal US feature scores, external US feature scores, sums of internal and external feature scores and ratios there between. Additionally or alternatively, the one or more processors, automatically or with input through a user interface by one or more medical personnel, obtain an identification of one or more OA feature scores for corresponding OA features within the OA images. Examples are described below in connection with identifying internal OA feature scores, external OA feature scores, sums of internal and external feature scores and ratios there between. Various US feature scores and/or OA feature scores may be assigned in connection with the three zones, namely the internal zone, boundary zone and peripheral zone.

In accordance with new and unique aspects herein, the machine learning classifiers or other models described herein analyze US/OA images based on the characteristics of the feature scores described herein to automatically determine feature scores for two or more of the features described herein. The automatic determination of the feature scores may be performed in real time during an examination of the patient, such as when implementing the machine learning classifier or other model in the software operating on the diagnostic imaging system. Additionally or alternatively, a separate computing device may be connected through a wired or wireless connection to a diagnostic imaging system. The diagnostic imaging system may provide US/OA raw data and/or rendered US/OA images to the separate computing system in real time while examining a patient and while the US/OA data is collected. During the patient examination, in real time, the separate computing device may apply one or more of the machine learning classifiers or other models described herein to analyze the US/OA images based on the characteristics of the feature scores described herein to automatically determine feature scores for two or more of the features described herein.

In accordance with new and unique aspects herein, when scoring features is performed manually by medical personnel, the one or more processors may manage scoring of the OA/US feature scores to be assigned to the respective zones in a predetermined order, namely an "outside-to-inside" order. One or more processors of a computing device (e.g. diagnostic imaging system, PACS workstation, medical workstation, desktop computer, laptop computer, tablet device, smart phone or remote server) manage scoring of the OA/US feature scores in a predetermined outside-to-inside order, that includes first requiring a user to assign one or more OA/US peripheral zone feature scores, second requiring a user to assign one or more OA/US boundary zone feature scores, third requiring a user to assign one or more OA/US internal zone feature scores. For example, the system may limit the users ability to assign feature scores in a manner that the OA/US feature scores must first be assigned to the peripheral zone before the user is afforded an input window to assign feature scores for another zone. The system may limit the users score entry options by first only presenting one or more score entry windows and/or OA/US images associated with OA/US peripheral zone feature scores. Next, the system may limit the users score entry options by next only presenting one or more score entry windows and/or OA/US images associated with OA/US boundary zone feature scores. Next, the system may limit the users score entry options by only presenting one or more score entry windows and/or OA/US images associated with OA/US internal zone feature scores. While limiting entry of new data to the next zone in the series of zones working from the outside to inside, the user may be allowed to review prior data entries and prior OA/US images, but may be prevented from changing a previously entered feature score. For example, while scoring the OA/US internal zone feature scores, the user may be allowed to review the images associated with the peripheral zone and boundary zone, but may be blocked from changing scores for peripheral and boundary zone features. Once the OA/US feature scores are completed for the peripheral zone, the system may then present a window that allows the user to enter OA/US feature scores for the boundary zone. The system may limit the users ability to assign feature scores such that the feature scores for the boundary zone must be completed second before the user is afforded an input window to assign feature scores for the peripheral zone. Once the OA/US feature scores are completed for the boundary zone, the system then presents a window that allows user to enter the OA/US feature scores for the peripheral zone. By way of example, it may be desirable to require a particular order for feature scoring from outside to inside, because medical personnel are not accustomed to looking at external features. Many key features of OA/US images are hyperechoic features (appearing in the boundary zone), but traditionally medical personnel may be accustomed to looking only for hypoechoic features (appearing in the internal zone). Also, external boundary zone features are more robust and distinguishing benign from malignant masses and more robust at assessing POM and BI-RADS categories. Further, requiring scoring to follow an outside to inside order may further prevent the risk of placing excessive importance on the hypoechoic features of the internal zone, which may otherwise lead to false scoring of boundary zone features and/or peripheral zone features. Before scoring features, it may be desirable to find the images best useful for scoring, such as by looking at still images and/or surveying multiple video suites. Once the preferred still images and/or individual frame from a video sweep is identified, the interior outline surrounding internal zone ROI is drawn. Next, the exterior outline surrounding the boundary zone is drawn. After the interior and exterior outlines are drawn, a series of scoring windows are presented to the medical personnel. In accordance with at least certain embodiments, the order in which scoring is performed begins by scoring features of the peripheral zone, followed by features of the boundary zone, followed by features of the interior zone.

Figure 10A:
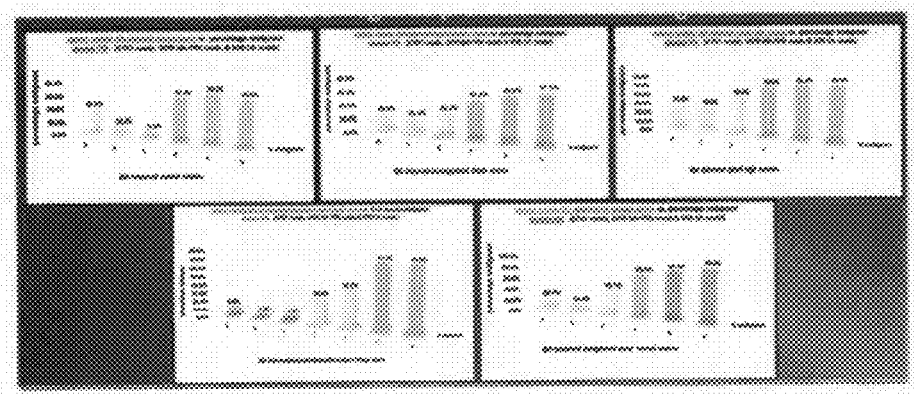
FIG. 10A illustrates an example of individual feature scores derived in connection with an analysis of a number of subjects.

At 410, the one or more processors analyze the US feature scores and/or the OA feature scores to obtain one or more probabilities that a region of interest in the US image(s) and/or OA images(s) corresponds to one or more particular molecular subtypes. As part of the analysis, the one or more processors may calculate an unweighted sum of the three OA internal feature scores, namely an unweighted sum of the OA internal vessel score, OA internal deoxygenated blood score and OA internal total hemoglobin score. FIG. 10A illustrates an example of individual feature scores derived in connection with an analysis of a number of subjects. Each individual feature score includes a plot for each score value (e.g. 0-6 or 0-5), along with a percentage of malignancy. FIG. 10B illustrates an example of a sum of the OA internal feature scores as compared to the POM. The graph of the POM versus the sum of the three OA internal stores shows that it is a good positive predictor of cancer, but by itself is not a good negative predictor of the apps of cancer. It shows that the sum of the three internal OA scores should be considered in connection with one or more boundary and/or peripheral scores that have lower POMs at lower score values in order to exclude cancers. At 410, the one or more processors also calculate an unweighted sum of the two OA external feature scores. The unweighted sum is for the OA external capsular/boundary zone vessel score and OA external peripheral zone radiating vessel score. FIG. 10C illustrates an example of a sum of the two OA external feature scores as compared to the POM. The graph of the POM versus the sum of the OA external scores shows that it is a very, very good positive predictor of cancer and by itself is also a very good negative predictor of the absence of malignancy. In accordance with new and unique aspects herein, it has been surprisingly recognized that the sum of the two external OA scores could function as both a positive and a negative predictor for cancer alone without any other feature scores. FIG. 10D illustrates an example of a sum of the five OA feature scores as compared to the POM. The graph of FIG. 10D illustrates that the sum of the five OA feature scores exhibits a superior positive predictor of cancer and a superior negative predictor of the absence of malignancy. In accordance with new and unique aspects herein, it has been recognized that the sum of all five OA feature scores provides a preferred PPV and NPV, as compared to using only the sum of the three internal feature scores or the sum of the two external feature scores alone. In accordance with at least some embodiments, the one or more processors at 410 may automatically utilize one or more feature score(s)-to-molecular subtype (FSMS) models as a basis to generate probabilities that a particular mass corresponds to certain molecular subtypes and/or histologic grades. The FSMS model defines a correlation between one or more of the OA/US feature scores and at least one of one or more molecular subtypes or one or more histologic grades.

Figure 13A:
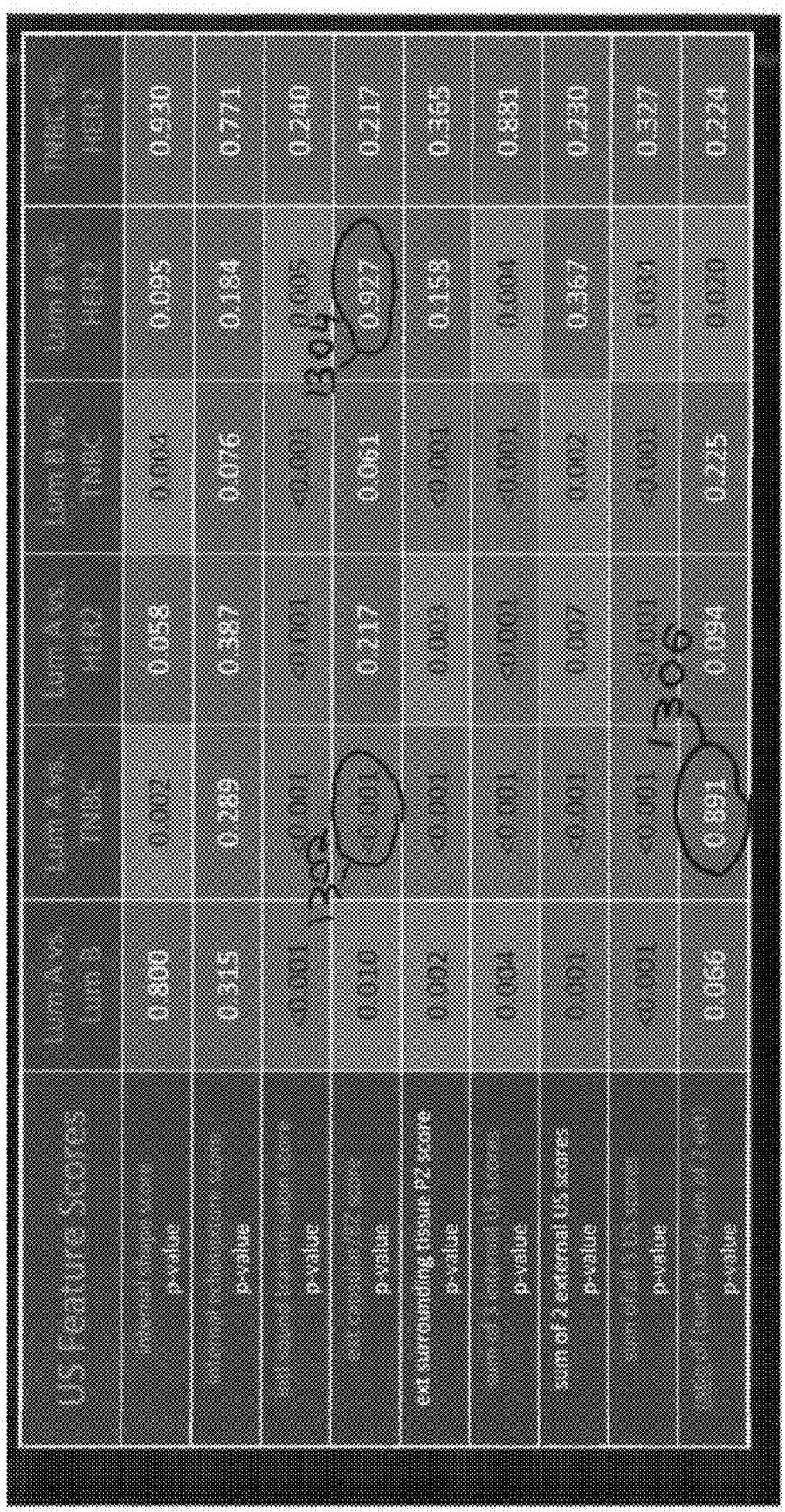
FIG. 13A illustrates a FSMS model in the form of an FSMS table setting forth the potential correlation between various US feature scores and different molecular subtypes.

FIG. 13A illustrates a FSMS model in the form of an FSMS table setting forth the potential correlation between various US feature scores and different molecular subtypes. The FSMS model may be implemented as a look up table, as part of a flowchart, regression equations, machine learning model, or otherwise. The table lists various internal US features (e.g. internal shape, internal echotexture, internal sound transmission) and external features (capsular/boundary zone, peripheral zone). In addition, individual and summed internal and external feature scores may be combined in various different ways that represent "feature engineering" or "data engineering". For example, the sum of the three internal feature scores may be utilized, as well as the sum of the two external feature scores. Further, the sum of all five feature scores may be used, as well as a ratio of various feature scores. For example, one ratio may be represented by the sum of the three internal features divided by the sum of the two external features. It is recognized that the examples in FIG. 13A are not limiting and additional and alternative mathematical combinations of the internal and external feature scores may be utilized, as well as the addition of further feature scores. It is also recognized that aspects herein may utilize scores that are not only based on ultrasound, but instead may include OA feature scores, as well as feature scores from other diagnostic imaging modalities.

The columns of the FSMS table in FIG. 13A correspond to comparisons of various molecular subtype pairs. For example, the molecular subtype pairs include luminal A versus luminal B, luminal A versus TNBC, luminal A versus HER-2, luminal B versus TNBC, luminal capital B versus HER-2, and TNBC versus HER-2. Additionally or alternatively, the comparison of subtype pairs may be more specific, such as comparing a select histologic grade for 1 molecular subtype (e.g. luminal A grade I) with a same or different holistic grade for another molecular subtype (luminal B grade I). Additionally or alternatively, the comparison may be between different histologic grades for a single molecular subtype (e.g. luminal A grade III versus luminal A grade I).

Each of the cells in the FSMS table contains a correlation index indicative of an extent to which the corresponding feature score differentiates between the molecular subtypes within the corresponding pair. In the present example, the correlation index is indicated as a statistical value, such as a p-value, although it is recognized that other types of information may be used as the correlation index in connection with each pair of molecular subtypes and feature score. By way of example, the correlation index 1302 (denoted as p-value=0.001) indicates a very high degree of statistical correlation between changes in the US capsular/boundary zone feature score and the distinction between the luminal A subtype and TNBC subtype. As an example, when the US capsular/boundary zone feature score is high, the probability is also high that the tumor is a luminal A subtype, and not a TNBC subtype. As another example, the correlation index 1304 (p=0.927) indicates that a change in the US capsular/boundary zone feature score has very poor correlation to any distinction between the luminal B molecular subtype versus the HER-2 subtype. As another example, correlation index 1306 (p=0.891) indicates that a change in the ratio of the sum of the three internal US feature scores to the sum of the two external US feature scores has a very poor correlation to any distinction between luminal A subtype and the TNBC subtype. During operation, once an OA/US data set has been assigned a set of corresponding feature scores, the feature scores may be analyzed utilizing the FSMS table. For example, the process may identify the feature scores having higher values or values above a predetermined threshold (greater than 2, greater than 3). The correlation indices associated with the features having the higher feature scores may then identified and based thereon a distinction made between the various pairs of molecular subtypes. Continuing with the example of FIG. 13A, as a nonlimiting example, the US sound transmission feature score may be high, the peripheral zone feature score is high, the echotexture feature score is low and the boundary zone feature score is low, which may result in a determination that the molecular subtype has a higher probability of being a luminal B, and a lower probability of being a TNBC.

FIG. 13B illustrates examples of the most common tumor gray scale ultrasound characteristics of luminal A versus TNBC molecular subtypes, along with a percentage estimate of the number of tumors with the corresponding molecular subtype that have the associated characteristic. For example, based on the cases analyzed in connection here with, the luminal A molecular subtype had a shape that is irregular without angles and is nonparallel in approximately 51.6% of the luminal A cases. The luminal A subtype exhibits a texture that is isoechoic or mildly hypoechoic (up in approximately 30.1% of the study cases), exhibits partial shadowing in sound transmission (in approximately 43% of the study cases), exhibits thick echogenic halo in the boundary zone, and exhibits then spicules or thick Coopers ligaments in the peripheral zone. When viewing a malignant tumor of the TN BC subtype, it exhibits and a regular shape without angles, but is parallel in the internal zone, is heterogeneous with microcalcifications in the internal zone, exhibits complete enhancement in sound transmission in the internal zone, has a thick echogenic halo in the boundary zone, and exhibits normal tissue in the peripheral zone.

Figure 13D:
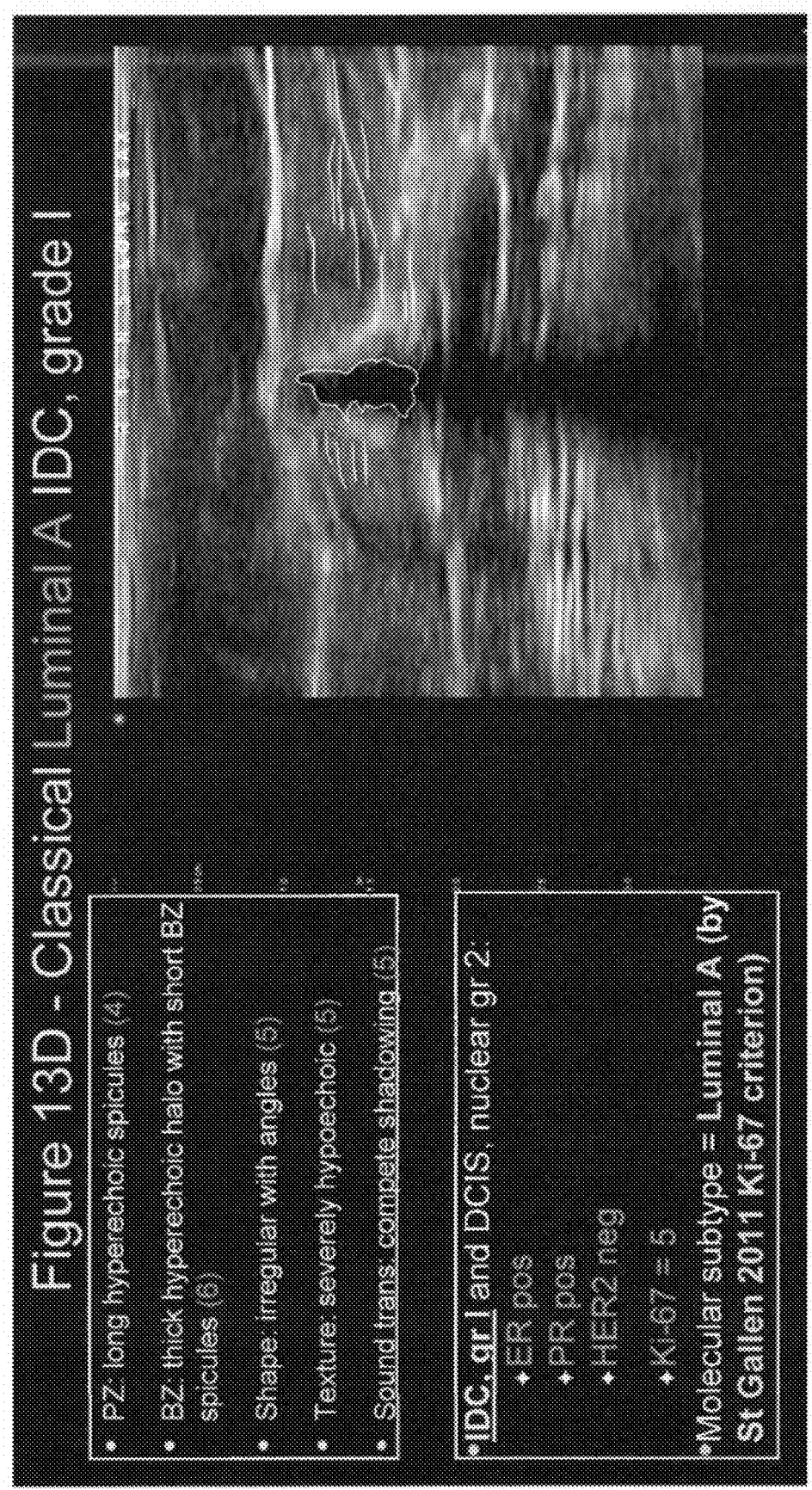
FIG. 13D illustrates a classical luminal A invasive ductal carcinoma having grade I, along with characteristics associated with the US features and representative scores to be assigned in connection with each feature.
Figure 13E:
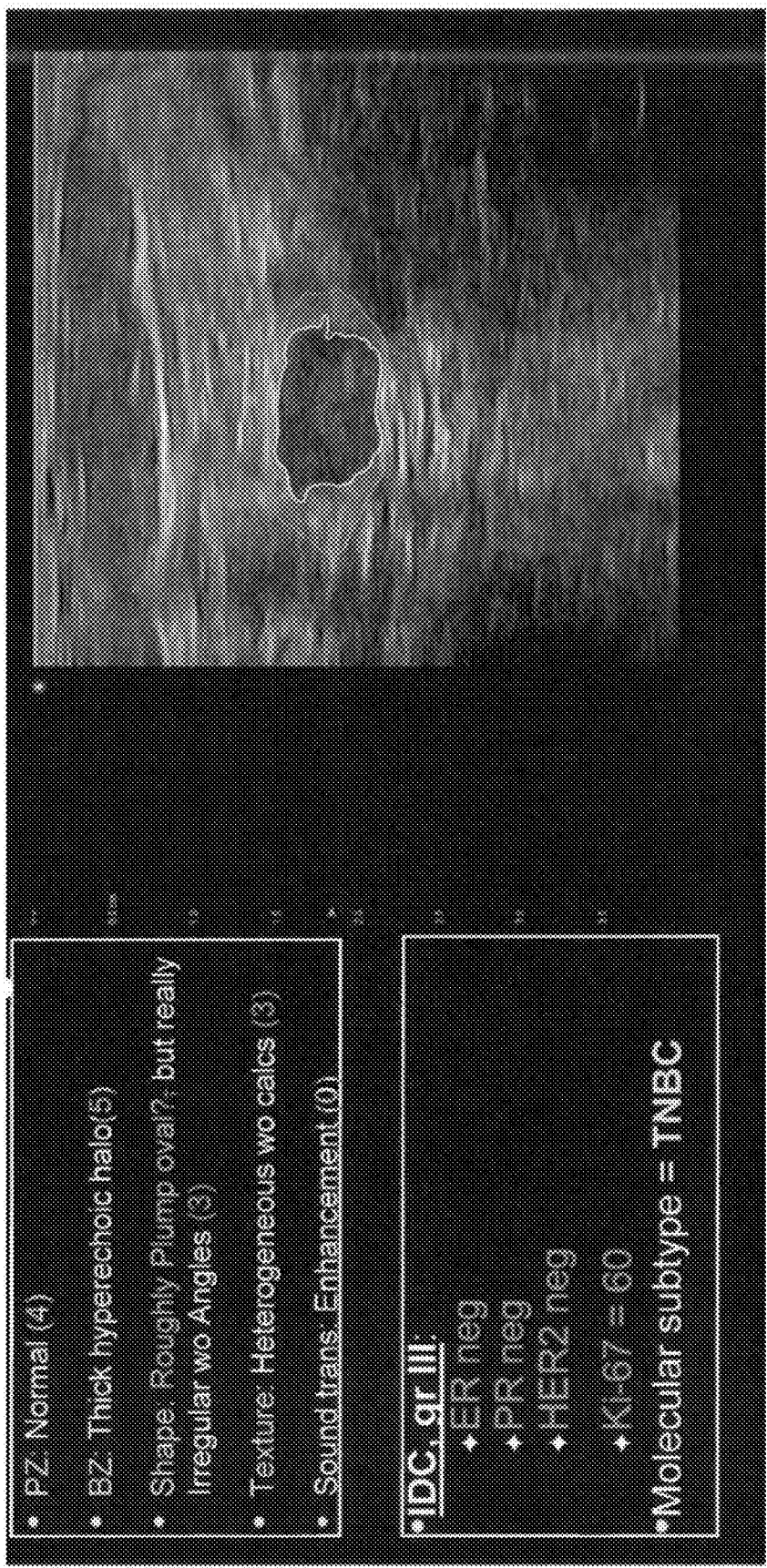
FIG. 13E illustrates a classical TNBC carcinoma having grade III, along with characteristics associated with the US features and representative scores to be assigned in connection with each feature.
Figure 13F:
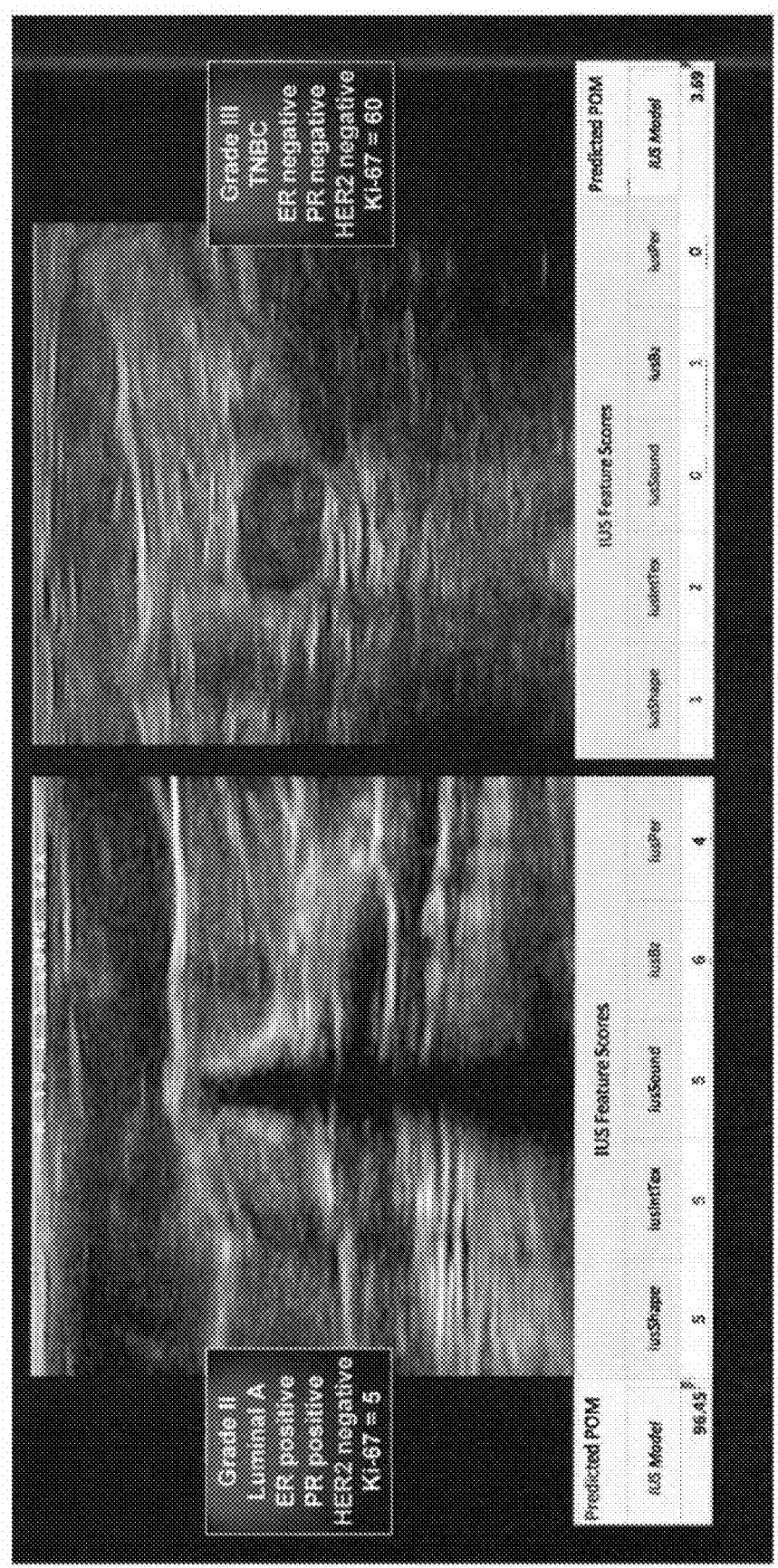
FIG. 13F illustrates a comparison between two images, one corresponding to a luminal A, grade II (left panel) and one corresponding to a TNBC, grade III (right panel).
Figure 13G:
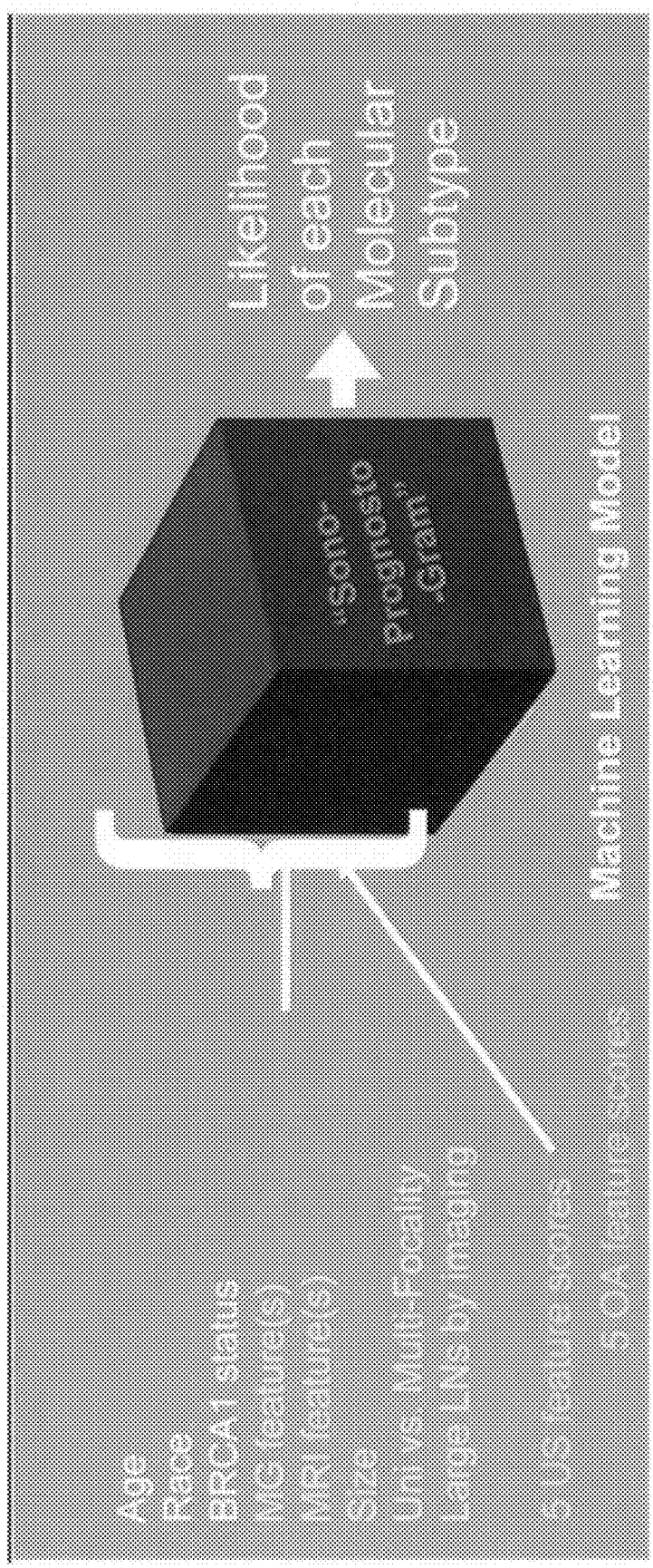
FIG. 13G illustrates an example of various inputs that may be applied to a machine learning model that generates a probability of malignancy for one or more molecular subtypes.
Figure 13H:
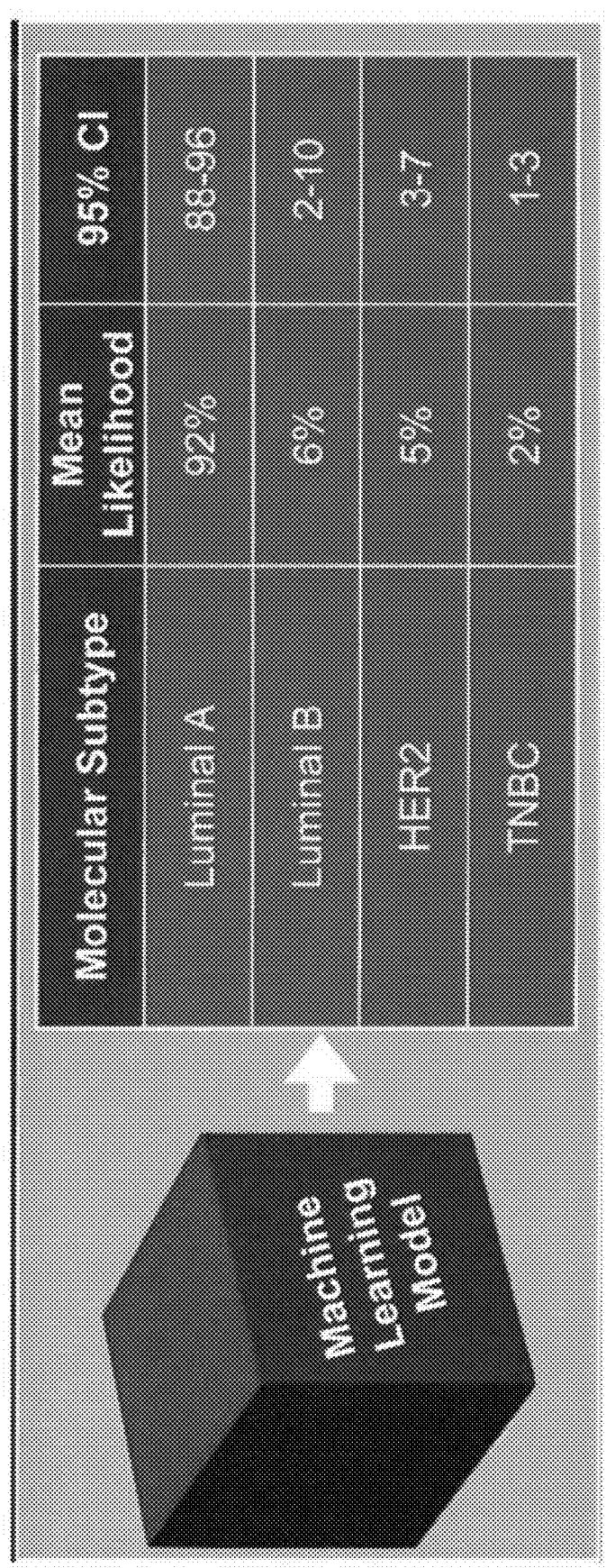
FIG. 13H illustrates an example of the output that may be generated by the machine learning model.

FIG. 13C illustrates US features other than the most common features that differ by molecular subtype between the luminal A and TNBC subtypes. While none of these features is the most common feature in Luminal A or TNBC molecular subtypes, there are significant differences in these features between LumA and TNBC subtypes that could be useful in distinguishing between these molecular subtypes. Those features that are shown in yellow and bold font exhibit a 3-fold or greater difference in the incidence of that feature between Lum A and TNBC subtypes. For example, oval-shape and complex cystic and solid echotexture are so rare in Lum A tumors (0.5%) that presence of either would virtually exclude a tumor being of the Lum A subtype. On the other hand, complete strong shadowing was never seen in a TNBC tumor, so its presence excludes a tumor being TNBC. Additionally or alternatively, using all of these minor features together with major features, using one or more processors in various different computing methods that could include regression equations or machine learning, may provide superior distinction between molecular subtypes than can any individual features alone. FIG. 13D illustrates a classical luminal A invasive ductal carcinoma having grade I, along with characteristics associated with the US features and representative scores to be assigned in connection with each feature. FIG. 13D also illustrates values for the receptor statuses and proteins indicative of the luminal A subtype, namely ER positive, PR positive, HER-2 negative, KI-67=5. FIG. 13E illustrates a classical TNBC carcinoma having grade III, along with characteristics associated with the US features and representative scores to be assigned in connection with each feature. FIG. 13E also illustrates values for the receptor statuses and proteins indicative of the TNBC subtype, namely ER negative, PR negative HER-2 negative, KI-67=60. FIG. 13F illustrates a comparison between two images, one corresponding to a luminal A, grade II (left panel) and one corresponding to a TNBC, grade III (right panel). FIG. 13F also illustrates examples of US feature scores that may be assigned to each of the internal and external features associated with the corresponding tumors as well as regression equation output of percentage POM for each of the two molecular subtypes. FIG. 13G illustrates an example of various inputs that may be applied to a machine learning model that generates a probability of malignancy for one or more molecular subtypes. For example, the various inputs may include the US and OA feature scores, as well as other patient specific information (e.g. age, race), and other diagnostic imaging information (MG features, MM features, size, unifocal versus multifocal, LN size, etc.). The machine learning model receives the various inputs, including the OA/US feature scores, and generates a POM for one, all or a portion of the molecular subtypes. Once the probabilities of the molecular subtypes and/or histologic grades are determined, the results may be output in various forms. For example, the output may be displayed on a graphical user interface to one or more medical personnel, recorded in a report, conveyed to a remote location for present or future review and the like. FIG. 13H illustrates an example of the output that may be generated by the machine learning model. For example, the machine learning model may output, in connection with each molecular subtype, a mean likelihood, as well as upper and lower CI boundaries.

Figure 13I:
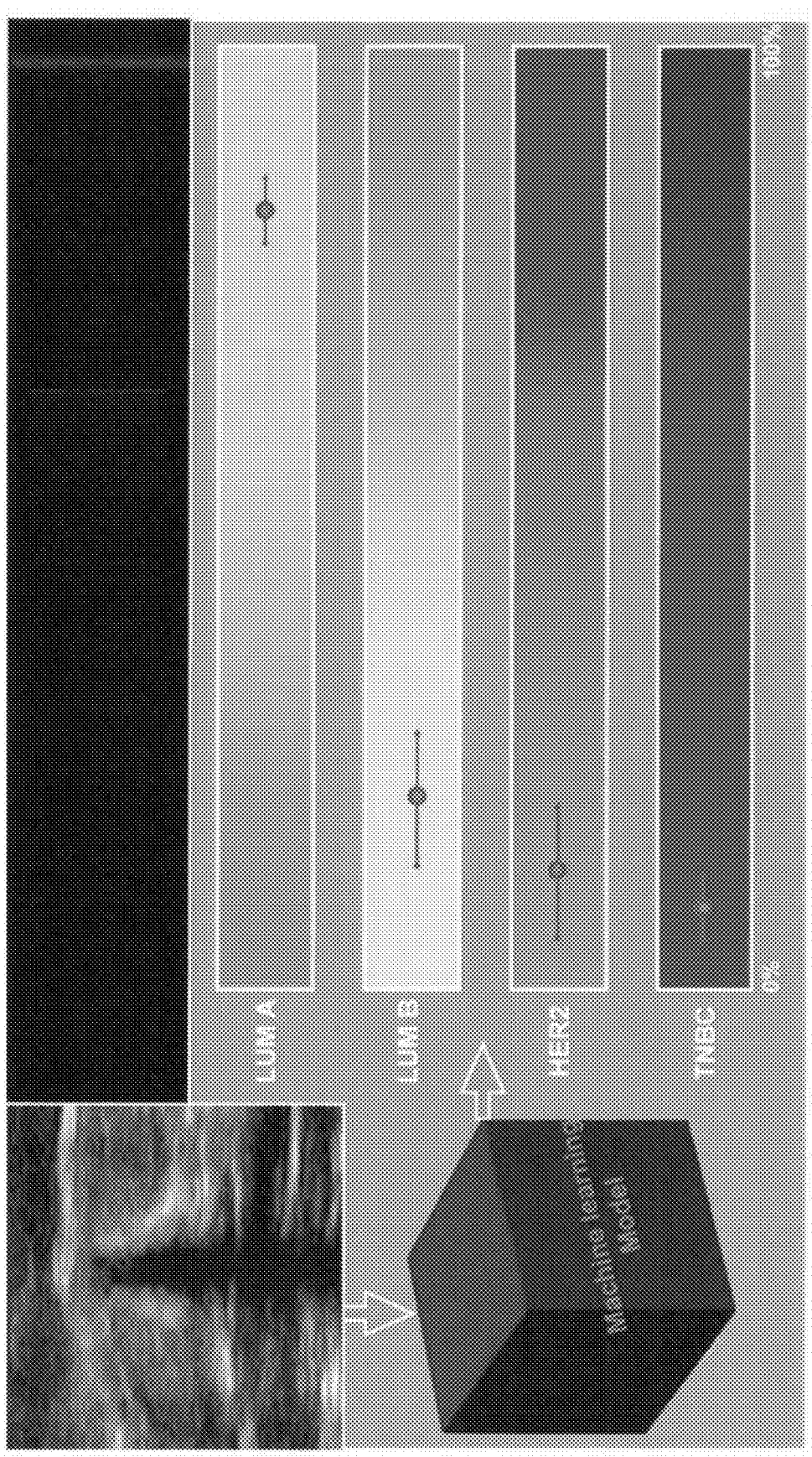
FIG. 13I illustrates another example of a format for the output indicia of the machine learning model.

FIG. 13I illustrates another example of a format for the output indicia of the machine learning model. The indicia are displayed in a manner and format representative of a collection of probabilities associated with a collection of the molecular subtypes. For example, the output may illustrate a POM indicia in connection with each molecular subtype or a collection of the molecular subtypes. The POM indicia may represent a bar graph associated with each molecular subtype, with an indicator on the graph denoting a central point/mean, and confidence intervals for the corresponding POM. In the example of FIG. 13I, a high POM exists that the tumor has the luminal A subtype, while low POMs exist that the tumor is a luminal B, HER-2 or TNBC subtype. Additionally or alternatively, the POM indicia may represent a graph, alphanumeric characters, a color-coded scale, and the like. The POM indicia in FIG. 13I represent examples of resultant predictive results may be displayed in accordance with embodiments herein. Embodiments for calculating resultant predictive results are described herein, such as in connection with machine learning classifier's (e.g. FIGS. 16 and 17). Each resultant predictive result corresponds to a different molecular subtype and/or histologic grade. An individual predictive result may be presented along a color-coded scale, representing a probability of malignancy scale for the molecular subtype and/or histologic grade, where the scale extends from a 0% (e.g. 0% probability of malignancy) at a start to 100% (e.g. 100% probability of malignancy) at an end. The color-coded scale may include color shades that transition, such as between a green zone at, the yellow zone, and orange zone and a red zone, where the colors merge between the zones. The predictive result includes a POM for each denoted molecular subtype and/or histologic grade, which may correspond to the classification probability determined by the master composite model and/or the positive predictive value determined by the PPV mapping function. The predictive result may also include a prediction interval extending on either side of the LOM.

Figure 13J:
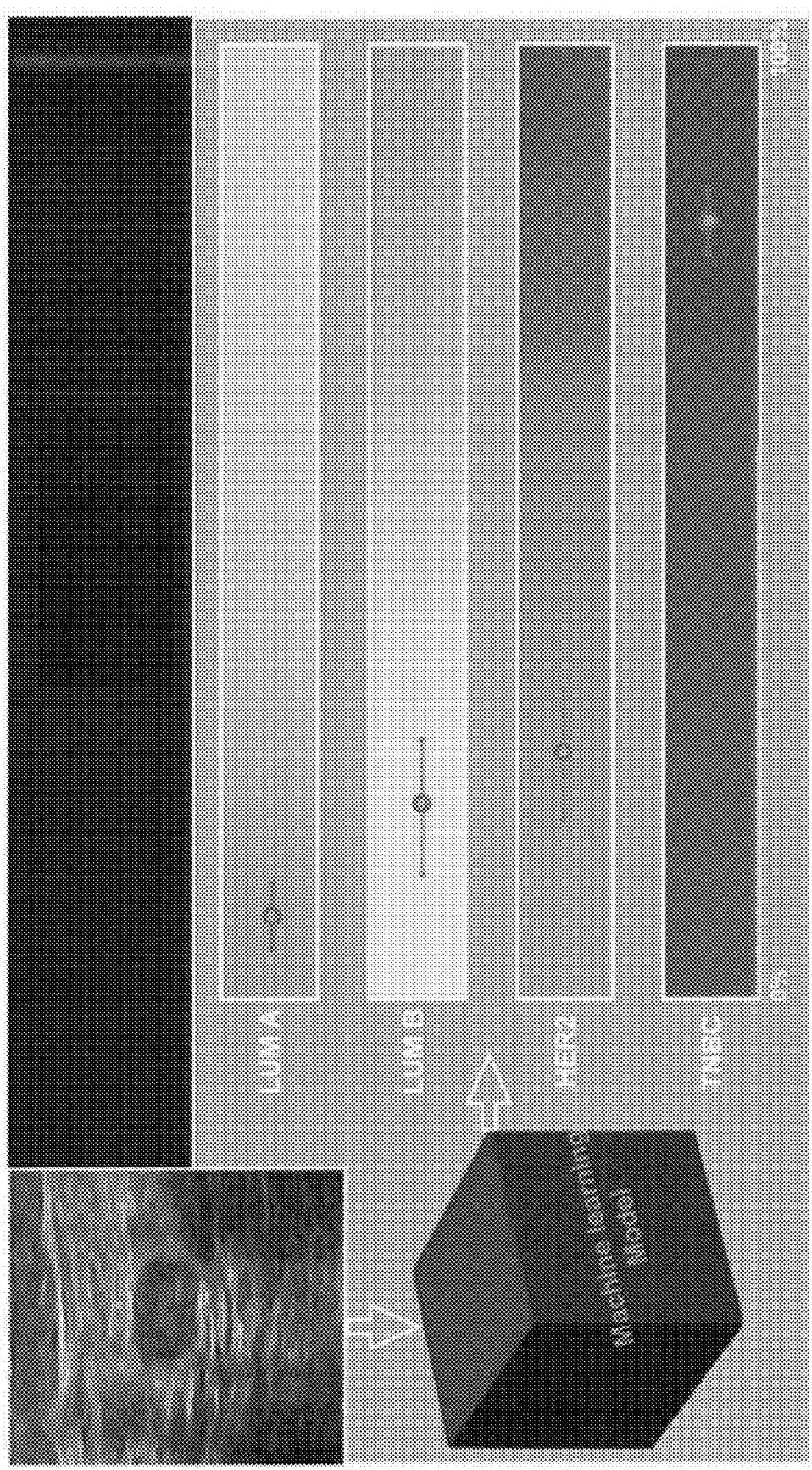
FIG. 13J illustrates another example of an output of the machine learning model.
Figure 13K:
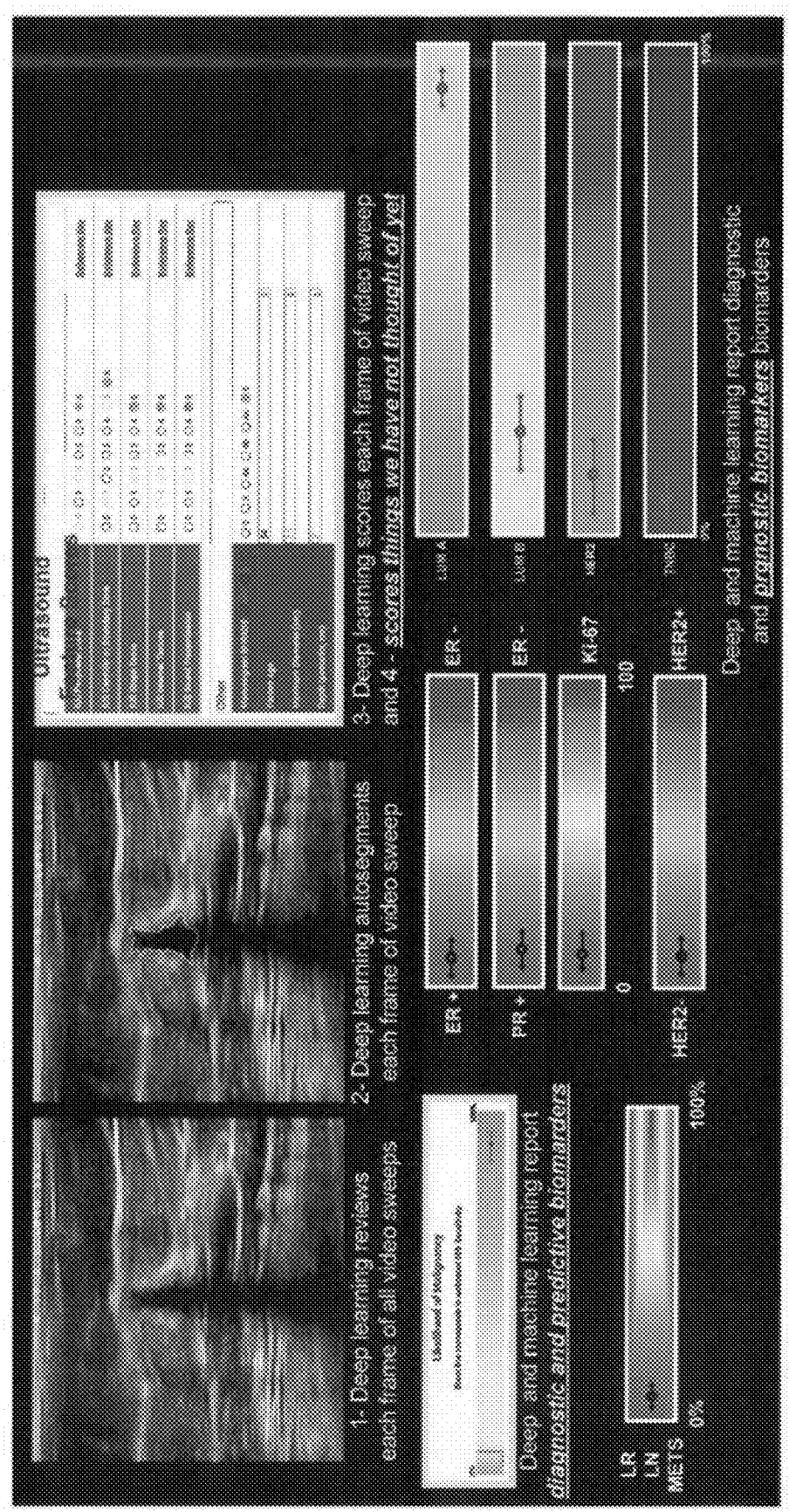
FIG. 13K illustrates an example where scoring 5 US and 5 OA features could lead to many different outputs from machine learning.

FIG. 13J illustrates another example of an output of the machine learning model. For example, the output may illustrate POM indicia in connection with each molecular subtype. In the example of FIG. 13J, a high probability exists that the tumor has the TNBC subtype, while low probabilities exist that the tumor is Luminal A, luminal B, or HER-2. FIG. 13K illustrates an example where scoring 5 US and 5 OA features could lead to many different outputs simultaneously from machine learning: 1) POM with 90% confidence intervals; 2) Mean likelihood with confidence intervals of ER positivity or negativity, 3) mean likelihood with confidence intervals of PR positivity or negativity, 4) mean likelihood of HER2 positivity 5) predicted Ki67 with confidence interval; 6) mean likelihood with confidence intervals of histologic grade; 7) mean likelihood with confidence intervals of each molecular subtype; and mean likelihood of lymph node metastases.

Next, a more detailed discussion of examples of OA and US features is provided, along with a more discussion of how the OA and US features may be scored and then used to identify molecular subtypes and/or histologic grades.

Feature Scores

Next, the discussion turns to certain feature scores that are assigned in connection with three different zones, namely the internal zone, boundary zone and peripheral zone. Certain feature scores are assigned in connection with US features, while other feature scores are assigned in connection with OA features.

In accordance with new and unique aspects herein, a number of feature scores have been identified and are described hereafter. The feature scores include a group of US feature scores and a group of OA feature scores that may be used separately or in combination to identify biomarkers, a POM for a mass, molecular subtypes for a malignant mass histologic grades for the mass. It is recognized that not all of the US feature scores and not all of the OA feature scores are necessarily utilized in each and every embodiment. Instead, a subset of the US feature scores may be utilized in combination with all or a subset of the OA feature scores. Similarly, a subset of the OA feature scores may be utilized in combination with all or a subset of the US feature scores. Different combinations of the US and OA feature scores may be utilized for different purposes, such as whether in connection with diagnostic biomarkers, prognostic biomarkers, predictive biomarkers, or monitoring biomarkers. As another example of a purpose, different combinations of the OA/US feature scores may be utilized when attempting to downgrade or upgrade a BI-RADS classification of a tumor. Further, different combinations of the OA/US feature scores may be utilized when attempting to identify particular molecular subtypes for a malignant mass. Based on the identified molecular subtype, different types of treatments may be identified that are better suited to particular molecular subtypes.

Shape US Feature Score

Conventional BI-RADS scoring of US images is based on examination of the internal zone, without regard for a margin category. The margin represents the transition between the outer surface (margin) of the inner zone and the surrounding tissues. However, in accordance with new and unique aspects herein, the old margin category is removed and a new boundary zone is defined in a manner that exhibits features, that have heretofore never been scored, but provide important information concerning an aggressiveness of a mass or other structure of interest. The boundary zone represents an extra layer that lies between the margin and the peripheral zone. In a malignant mass that has both invasive and in situ components, genetics of the invasiveness and the in situ epithelial cells are substantially identical to each other. The items that distinguish the invasive from the in situ parts of the malignant mass represent the epigenetic microenvironment and intercell signaling. Intercell signaling occurs between malignant cells and tumor associated stromal cells (e.g. tumor associated fibroblast, tumor associated endothelial cells, tumor associated lipocytes). Intercell signaling also occurs between malignant epithelial cells and tumor associated immune cells (e.g. tumor associated lymphocytes, tumor associated macrophages). Also, intercell signaling occurs between tumor associated immune cells and tumor associated stromal cells. As such, the internal zone and its margins reflect the genetics of the tumor, the site of origin, and the resistance of tissues to tumor growth. The boundary zone, and the appearance of how the internal zone transitions into the perioperal zone is largely a reflection of the epigenetics of the tumor and a manifestation of its aggressiveness.

Embodiments herein recognize and take advantage of the differences between internal hypoechoic central nidus and the newly defined boundary zone. The internal center nidus (internal zone) defines a shape but does not define an aggressiveness for a malignancy. The shape reflects the genetics of the malignancy, site origin of the malignancy (TDLU versus duct versus stroma), resistance of surrounding tissues to growth of the malignancy. However, the appearance of the newly defined boundary zone defines the aggressiveness of the malignancy. The boundary zone appearance reflects epigenetics of the malignancy, how the cancer interacts with surroundings stroma, and how effectively the malignancy usurps the host stromal and immune apparatus. The foregoing differences between the internal zone and boundary zone are not accounted for through conventional BI-RADS scoring systems that do recognize a boundary zone and not score features of the newly defined boundary zone.

Existing BI-RADS scoring features are utilized as a partial subset of a new scoring system that adds new features and feature scoring criteria, mixes and matches new and old features and feature scoring criteria. In addition, embodiments herein place the various features in a unique order, namely in an order of increasing PPV. Optionally, the feature scoring may include one or more of the features described in connection with lesion classification in U.S. Pat. No. 9,398,893.

A unique and novel aspect herein is the combination of the shape and orientation features into a single shape ordinal feature score for the internal zone. Nonlimiting examples of the internal zone shape include oval, round or irregular, while examples of the orientation include parallel or non-parallel. Shape and orientation represent strong predictors of a risk of malignancy. For example, the shape feature score may be assigned an ordinal value between 1-5 based on whether the shape is oval, round, irregular, parallel or nonparallel.

A unique and novel aspect herein adds, to the shape feature score, an angular characteristic (e.g. irregular with angles) and a microlobulated characteristic (irregular without angles). Previously, angularity and microlobulation characteristics were not considered when scoring the internal zone shape, but instead, if considered at all, were only considered in connection with analyzing a margin category. A new and unique aspect of at least some embodiments herein represents the addition of the angular and microlobulation characteristics to the determination of what value to be assigned to the internal zone shape feature score. Previously, the value for the internal zone shape feature score was not based on the angular and microlobulation characteristics.

The improvement, of adding the angular and microlobulation characteristics to the IZ shape feature score, is due in part to recognition that an oval and microlobulated mass may be roughly oval in shape, but is not strictly oval in shape. Instead, the oval microlobulated mass is irregular without angles, and thus the microlobulation represents a characteristic of shape, not a margin characteristic. Further, the foregoing improvement is due in part to the recognition that an oval shape combined with angles may be roughly an oval shape but is not strictly an oval shape. Instead, the oval angulated mass represents a shape that is irregular with angles and thus the angles are a shape characteristic, not a margin characteristic. By way of example, the US internal zone shape feature score may be assigned an integer value between 0-5, each of which has a corresponding probability of malignancy as noted, such as based on the following:

0=Oval-shaped, parallel orientation, (wider than tall), $>=2/1$ ratio max width to AP dimension="flat" oval-shaped (BR 4A, >2%—<=10% POM)
1=Oval-shaped, parallel orientation, (wider than tall)<2/1 ratio width to AP="plump" oval-shaped (BR 4A, >2%—<=10% POM)
2=Round (lower BR 4B, <=25% POM)
3=Irregular without angles, parallel orientation (upper BR 4B, >25% POM)
4=Irregular without angles, non-parallel orientation (taller-than-wide) (lower BR 4C, <=75% POM)
5=Irregular with angles, parallel or non-parallel (any angle of ≤90°) (lower BR 4C, <=75% POM)

Figure 4C:
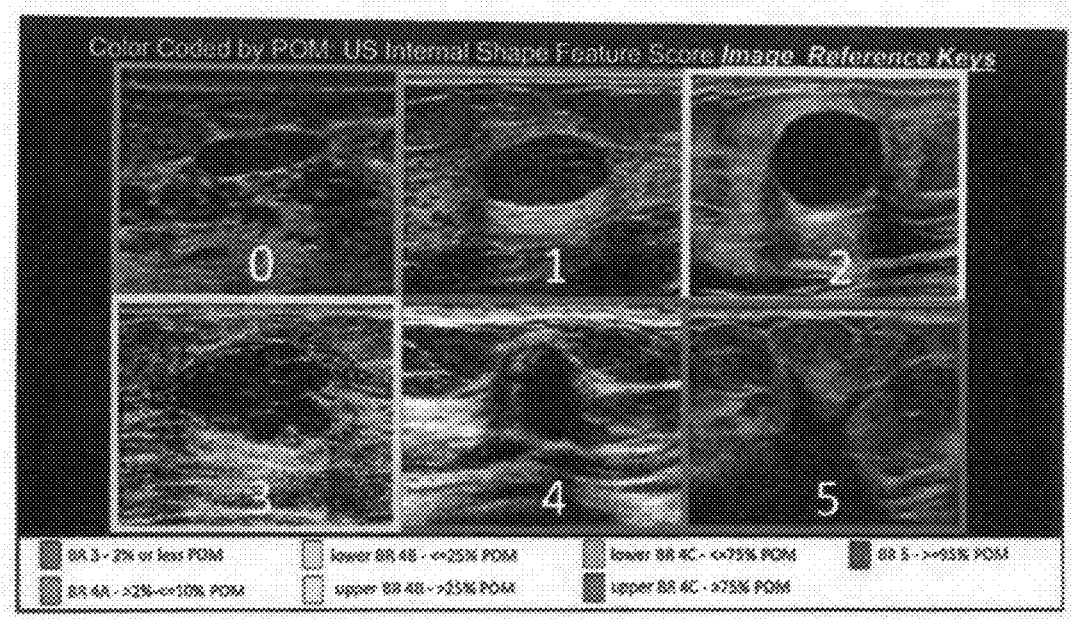
FIG. 4C illustrates an example of an image key for images with different internal zone shapes that warrant corresponding different internal zone feature scores.

The foregoing internal zone shape scores are assigned in connection with the hypoechoic central nidus, and are not based on the shape or orientation of the boundary zone. FIG. 4C illustrates an example of an image key for images with different internal zone shapes that warrant corresponding different internal zone feature scores 0-5. The lower margin of FIG. 4C illustrates corresponding probabilities of malignancy associated with the internal zone shape feature scores (assuming no other feature scoring information).

Figure 4D:
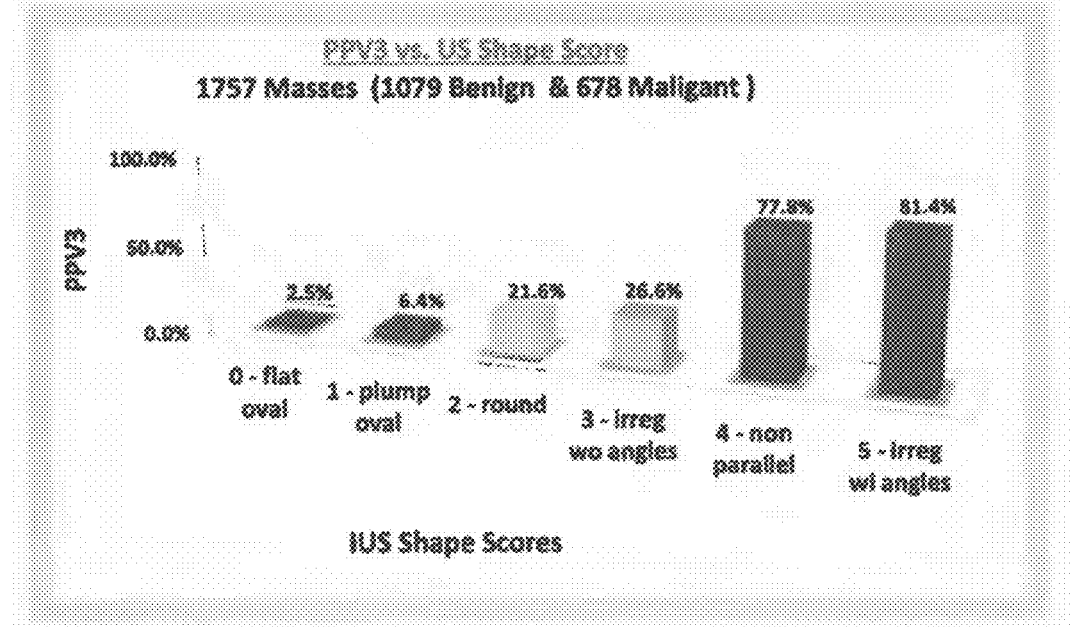
FIG. 4D illustrates an example of a relation between positive predictive values and feature scores for the internal zone shape.

FIG. 4D illustrates an example of a relation between positive predictive values and feature scores for the internal zone shape. The PPV rises continuously with increasing feature score. In accordance with new and unique aspects herein, it is recognize that a single feature score cannot provide both a good positive predictor and a good negative predictor. An interior zone that is severely hypoechoic and heterogeneous with microcalcifications provides a good positive predictor of CA (e.g., a high BI-RADS 4C score). However, the hyperechoic characteristic is not a good enough negative predictor to be used alone when it does not achieve a PPV of less than or equal to 2%.

In accordance with aspects herein, to assign a feature score associated with an oval shape, a mass should be either truly oval in shape or microlobulated. When distinguishing between masses that have a flat oval or a plump oval shape, a predetermined cut off may be utilized. For example, a flat oval shape may be defined as shapes having a predetermined horizontal/vertical diameter ratio (e.g. >+2/1 max/AP diameter ratio), whereas plump oval shapes have a ratio of less than two. Embodiments herein measure each mass from multiple directions in OA/US images oriented along different axes to calculate the ratio of the horizontal and vertical diameters. Masses having an approximately oval shape, but should be classified as irregular, usually exhibit an irregular shape along the sides of the mass (relative to the vertical direction), within the coronal plane, where resistance to invasion is lower or lowest. Masses having an approximately oval shape or irregular in shape, and not oval, and should not be classified as oval shapes. Instead, such masses should be classified as irregular with angles. Irregular shapes with angles have a much higher risk of malignancy then irregular shapes without angles. Angles occur where resistance to invasion is lowest and tend to occur where 1) a mass intersects the bases of Coopers ligaments, and/or 2) along sides of the mass between the coronally oriented tissue planes. Nonparallel orientations exhibit a higher risk than do irregular shapes without angles, but exhibit a lower risk than irregular shapes with angles. And orientation of a mass may be heterogeneous with part of the mass being oriented nonparallel and part of the mass oriented parallel. Masses that are not partially nonparallel and orientation should be classified as nonparallel (e.g. taller than wide) in orientation.

In accordance with unique and novel aspects herein it has been recognized that the internal zone shape feature score should account for irregular shapes with angles. Invasive cancers tend to form angles where they invade surrounding tissue where resistance to invasion is lowest. For example, resistance to invasion is low in fat areas, where the anterior mammary fascia is absent, in the bases of Coopers ligaments, and between collagen fibers, which are roughly oriented in a coronal or slanted coronal plane. The coronal plane may be best viewed in 3-D/4D OA/US reconstructions. Surrogates for 3-D reconstructions may include short axis video sweeps and close examination of the sides of masses in the coronal plane. Masses may have limited numbers of angles and thus the process may examine the whole mass into orthogonal planes, and/or overweight the presence of angles when most of the mass shape is not angular.

Internal Zone EchoTexture US Feature Score

Next, the discussion turns to an IZ echotexture US feature score assigned in connection with the internal zone. The IZ echotexture US feature score may be assigned a lesser weight in connection with a negative predictive value, as compared to the internal zone shape feature score. The IZ echotexture US feature score is assigned a value based on various echo pattern characteristics exhibited by the internal zone of a mass, such as whether the echo pattern is anechoic, hyperechoic, complex cystic and solid, hypoechoic, isoechoic or heterogeneous. Previously, there was no distinction in the level/degree of the hypoechoic characteristic, but instead the analysis merely determined whether a mass was hypoechoic or not hypoechoic.

A unique and novel aspect herein adds, to the echotexture shape feature score, a distinction between first and second classes of the hypoechoic characteristic, namely mildly hypoechoic and markedly hypoechoic. Masses with an IZ that has the first/mildly hypoechoic characteristic is indicative of a lower risk of malignancy, similar to masses exhibiting and isoechoic characteristic. Masses with an IZ that has the second/severely hypoechoic characteristic exhibit a much higher risk of malignancy as compared to the first/mildly hypoechoic characteristic. The hyperechoic and hypoechoic characteristics are considered relative to fat echogenicity.

In the prior BI-RADS rating system, the hyperechoic characteristic could include a mixture of hypoechoic and hyperechoic characteristics which is highly undesirable. Mixing hypoechoic and hyperechoic characteristics formed a heterogeneous hyperechogenicity. Including heterogeneously hyperechogenicity substantially destroys the negative predictive value of the echotexture shape feature score. Instead, a unique and novel aspect herein recognizes that, in order to have good negative predictive value, the hyperechoic characteristic should be defined to be homogeneously as echogenic as normal inter-lobular stromal fiber tissue and contain no isoechoic nor hypoechoic areas larger than normal ducts or lobules. Thus, embodiments herein enforce a rigid distinction between the hypoechoic characteristic and hyperechoic characteristic went assigning a value to the echotexture feature score. Furthermore, in BI-RADS editions 4 and 5, no distinction was made between different degrees of hypoechogenicity. This adversely affects the predictive value of hypoechogenicity. Stavros et al. in 1995 showed that mild hypoechogenicity had has no predictive usefulness and carried the same relatively low risk of malignancy as did isoechogenicity. On the other had, Stavros et al. showed that marked hypoechogenicity compared to that of fat carried a very high risk of malignancy. In the this internal echotexture scoring system, severe or marked hypoechogenicity is distinguished from mild hypoechogenicity or isoechogenicity. Marked hypoechogenicity carries a much higher risk of malignancy (69.6%) than did mild hypoechogenicity or isoechogenicity (25.5%).

Masses that exhibit a purely severely hyperechoic characteristic carry close to a 100% negative predictive value. The severely hypoechoic characteristic is a strong predictor of malignancy in a tumor. The mildly hypoechoic and iso-echoic characteristics are not as strongly of positive predictors as the severely hyperechoic characteristic. A heterogeneous internal echotexture can be seen in benign masses, but more commonly in malignant masses due to polyclonal nature, areas of necrosis and hemorrhage, areas of fibrosis and unresolved microcalcifications. Microcalcifications in a mass increase the risk of the mass being malignant.

By way of example, the US internal zone echotexture feature score may be assigned an integer value between 0-5, each of which has a corresponding probability of malignancy as noted, such as based on the following:

0=Homogeneously hyperechoic (as hyperechoic as normal interlobular stromal fibrous tissue) (lower BR 4B, <25% POM)

1=Complex mixed cystic and solid (lower BR 4B, <25% POM)

2=Homogeneously isoechoic or mildly hypoechoic (upper BR 4B, >25% POM)

3=Heterogeneous without internal microcalcifications (upper BR 4B, >25% POM)

4=Heterogeneous with internal microcalcifications (lower BR 4C, <=75% POM)

5=Severely or markedly hypoechoic (compared to fat) (lower BR 4C, <=75% POM)

Figure 4E:
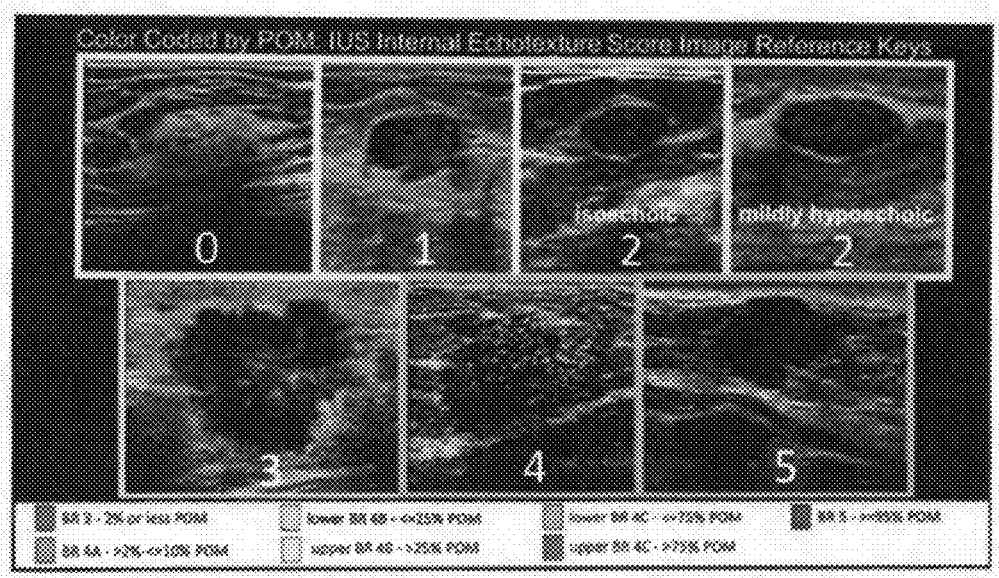
FIG. 4E illustrates an example of an image key for images with different internal zone echotexture patterns that warrant corresponding different internal zone feature scores.
Figure 4F:
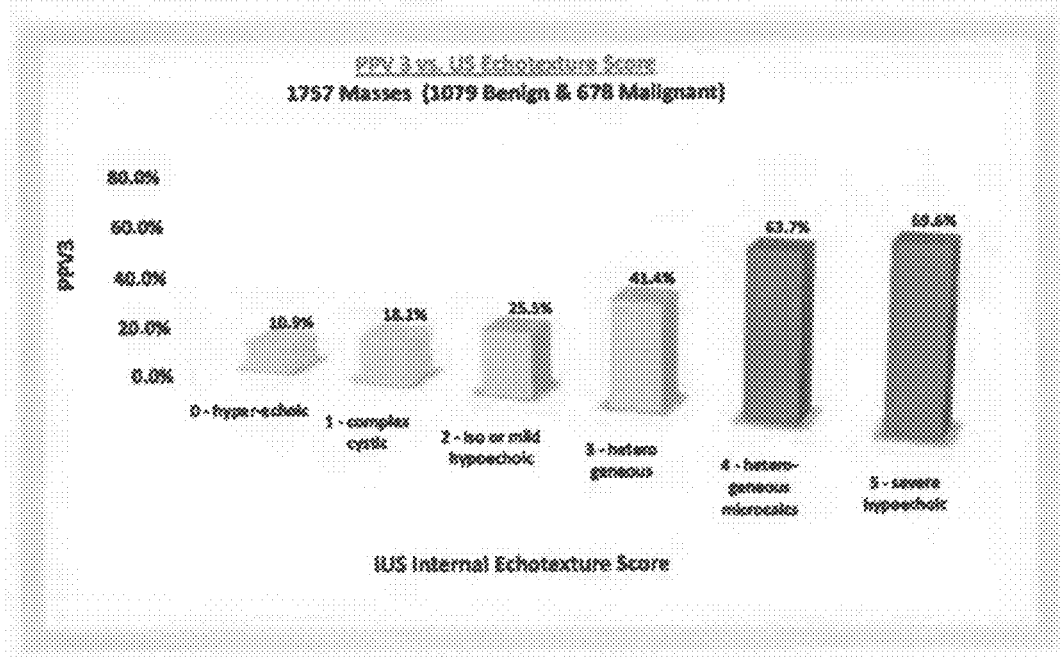
FIG. 4F illustrates an example of a relation between positive predictive values and feature scores for the internal zone echotexture.

FIG. 4E illustrates an example of an image key for images with different internal zone echotexture patterns that warrant corresponding different internal zone feature scores 0-5. The lower margin of FIG. 4E illustrates corresponding probabilities of malignancy associated with the internal zone echotexture feature scores (assuming no other feature scoring information). FIG. 4F illustrates an example of a relation between positive predictive values and feature scores for the internal zone echotexture. The PPV rises continuously with increasing feature score. In accordance with new and unique aspects herein, it is recognize that a single feature score cannot provide both a good positive predictor and a good negative predictor. Masses that exhibit the severely hypoechoic or heterogeneous microcalcification characteristics represent good positive predictors of malignancy (e.g. BI-RADS 4C).

When utilizing the conventional BI-RADS scoring system, masses that exhibit the hyperechoic characteristic do not afford good negative predictive values because of sub optimal definitions in the BI-RADS scoring system. The BI-RADS scoring system defines hyperechoic as having increased echogenicity 1) relative to fat "or" 2) equal to fibroglandular tissue.

In accordance with unique and novel aspects herein, it has been recognized that the foregoing definition of hyperechoic is too broad by covering the alternative factors 1) and 2), thereby resulting in the hyperechoic characteristic not affording good negative predictive values. The unduly broad definition in the conventional BI-RADS scoring system allows the hyperechoic characteristic to be defined as having heterogeneous echotexture which destroys the NPV value. Instead, in accordance with aspects herein, the hyperechoic characteristic should be (and is) defined as having increased echogenicity 1) relative to fat "and" 2) equal to fibroglandular tissue. Also, the conventional BI-RADS scoring system did not distinguish between markedly and mildly hypoechogenicity, where as unique and novel aspects herein recognize and take advantage of the differences therebetween.

By redefining the definition to include both of the foregoing factors 1) and 2), and not simply either of the foregoing factors, new and unique aspects herein render the hyperechoic characteristic to have very low PPV, but very high in PV. Heterogeneous internal zone echotexture is more common in malignant masses, as compared to benign masses because of 1) polyclonal nature of cancer, and/or 2) central fibrosis, and/or 3) central necrosis, and/or 4) central microcalcifications. However, heterogeneous internal zone echotexture may be found in some benign conditions, such as 1) internal fibrocystic changes, and/or 2) sub nodules of different ages and biologic activity, and/or 3) internal microcalcifications.

Sound Transmission US Feature Score

Next, the discussion turns to an IZ sound transmission US feature score assigned in connection with the internal zone (e.g. posterior acoustic features). The posterior acoustic features category, in the prior BI-RADS rating system, included the following characteristics: no posterior acoustic features, enhancement, shadowing or a combined pattern. In the prior BI-RADS rating system, the combined pattern represented one/binary characteristic, such that a mass either included a combined pattern or did not include a combined pattern.

In accordance with new and unique aspects herein, the combined pattern characteristic is broken into three subcategories, namely 1) partial enhancement with partial normal sound transmission, 2) partial enhancement with partial shadowing, and 3) partial shadowing with partial normal sound transmission. A significant percentage of malignant masses do not cast acoustic shadows and have normal or enhanced sound transmission. Thus, while a finding such as shadowing can be a good positive predictor of malignancy, in accordance with aspects herein, it is not expected that any of the posterior acoustic features would exhibit good negative predictive values of an absence of malignancy.

When determining a distinction between an enhanced sound transmission characteristic versus a normal sound transmission characteristic, the following points should be considered. Many solid masses with enhanced sound transmission are misdiagnosed complicated system, potentially accounting for the low percentage of malignancies with enhanced sound transmissions. Young, active plump oval FAs tend to have enhanced sound transmission as well. Mixed sound transmission in ACR BI-RADS can be any combination. Mixed sound transmission with partial shadowing is more concerning then mixed sound transmission with enhanced sound transmission. Thus, a new and unique aspect herein separates mixed sound transmission into different groups depending whether or not there is partial shadowing. Because malignant masses may be internally heterogeneous, only part of a malignant mass may exhibit shadowing.

By way of example, the US internal zone sound transmission feature score may be assigned an integer value between 0-5, each of which has a corresponding probability of malignancy as noted, such as based on the following:

0=Enhanced (lower BR 4B, <=25% POM)

1=Normal (upper BR 4B, >25% POM)

2=Mixed normal and enhanced (upper BR 4B, >25% POM)

3=Mixed enhanced and partial or weak shadowing (lower BR 4C, <=75% POM)

4=Mixed normal and partial or weak shadowing (lower BR 4C, <=75% POM)

5=Complete and strong shadowing (upper BR 4C, >75% POM)

Figure 4G:
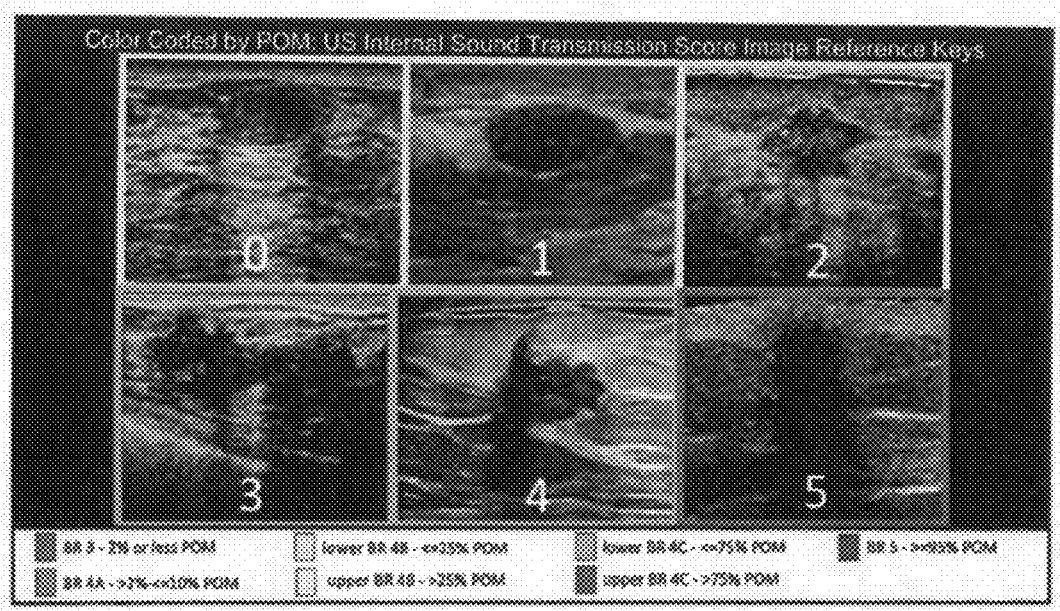
FIG. 4G illustrates an example of an image key for images with different internal zone sound transmissions that warrant corresponding different internal zone feature scores.

FIG. 4G illustrates an example of an image key for images with different internal zone sound transmissions that warrant corresponding different internal zone feature scores 0-5. The lower margin of FIG. 4G illustrates corresponding probabilities of malignancy associated with the internal zone sound transmission feature scores (assuming no other feature scoring information). Partial and weak shadowing effect only part of a breadth of a mass. Complete and weak shadowing effects and entire breadth of the mass. Weak shadowing means that the posterior margin of the mass is not completely obscured by the shadowing. Partial and strong shadowing affect only part of the breadth of the mass, while complete and strong shadowing affect the entire breadth of the mass. Strong shadowing means that the posterior margin of the mass is completely obscured by the shadowing. Complete and strong shadowing obscures entire posterior margins of the mass. Strong shadowing completely obscures at least part of the posterior margin of the mass, while partial shadowing effects only part of a lesion and can be strong or weak. Weak shadowing does not completely obscure posterior margins in the area of shadowing.

Figure 4H:
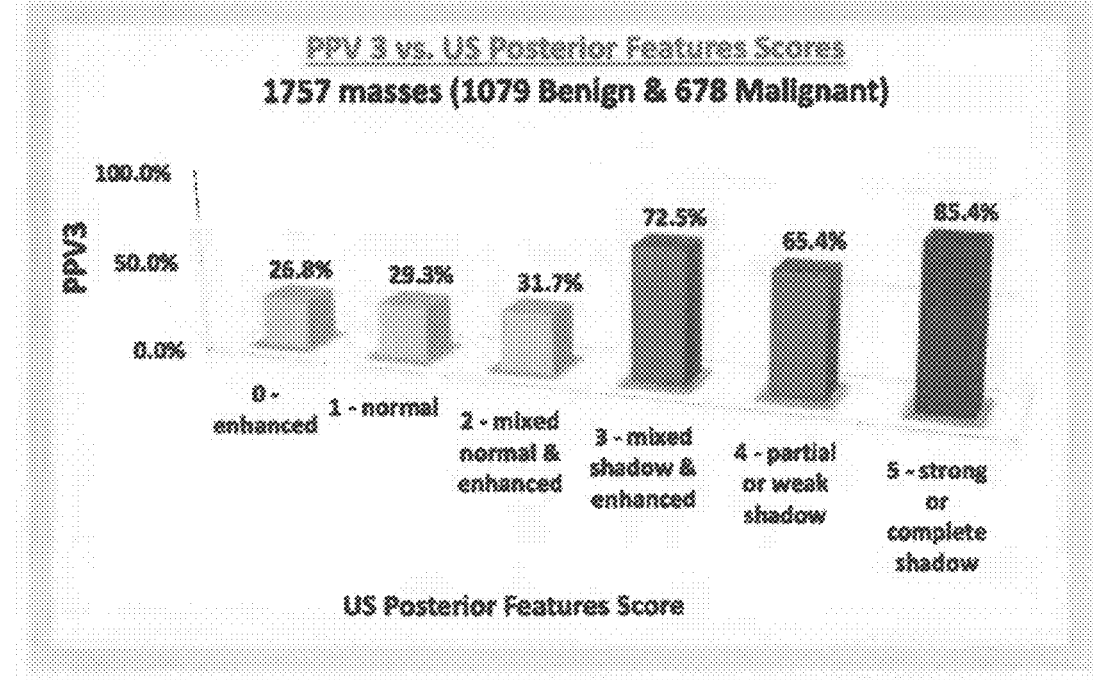
FIG. 4H illustrates an example of a relation between positive predictive values and sound transmission feature scores.

FIG. 4H illustrates an example of a relation between positive predictive values and sound transmission feature scores. The PPV rises continuously with increasing feature score. In accordance with new and unique aspects herein, it is recognized that a single feature score cannot provide both a good positive predictor and a good negative predictor. From FIG. 4H, it can be seen that complete or partial shadowing is a good positive predictor of cancer (e.g. BI-RADS 4C). Enhanced and normal sound transmission are poured negative predictors of an absence of cancer. Thus, while shadowing is suspicious, normal or enhanced sound transmission is not necessarily reassuring. Acoustic shadowing is a good positive predictor of malignancy. A relatively large percentage of cancers may have normal sound transmission or have enhanced sound transmission. Thus, in accordance with new and unique aspects herein, it can be predicted that sound transmission will be a relatively poor negative predictor and that a probability of malignancy will be higher at low scores than for other US characteristics and feature scores. However, embodiments herein can use the good positive predictions based on the sound transmission feature score without suffering from the weaker negative predictions.

US Boundary Zone Feature Score

In the BI-RADS $5^{th}$ edition rating system, a margin category was utilized, and ratings were assigned based on whether the margin area was circumscribed or not circumscribed. When the margin area was not circumscribed, the BI-RADS $5^{th}$ edition rating system considered whether the margin area was indistinct, angular, microlobulated or spiculated. However, the BI-RADS $5^{th}$ edition rating system, did not provide any subcategories or further breakdown when the margin area was circumscribed, simply the margin area either was or was not circumscribed. In the BI-RADS $5^{th}$ edition rating system, the margin was defined generally as:

the edge or border of the lesion; the descriptors of the margin, like the descriptors of the shape, are important predictors of whether a mass is benign or malignant; a circumscribed margin is one that is well-defined with an abrupt transition between the lesion and the surrounding tissue; for ultrasound, to describe the mass as circumscribed, its entire margin must be sharply defined; most circumscribed lesions have round or oval shapes.

In the BI-RADS $5^{th}$ edition rating system, there is no mention, in connection with the margin, of the thin hyperechoic capsule. In accordance with new and unique aspects herein, a US boundary zone feature score has been identified that includes the circumscribed characteristic and that breaks the circumscribed characteristic into four subcategories, namely 0) complete thin hyperechoic capsule, 1) partial thin hyperechoic capsule, 2) complete thin hyper or isoechoic capsule, and 3) circumscribed without visible discrete capsule. At the high end of the boundary zone scoring system are 5) the thick echogenic rim and 6) frank short boundary zone spiculations. The middle of the spectrum includes two scores in which a hyperechoic transition layer cannot be identified: 3) circumscribed without an identifiable thin capsule and indistinct, but without a thick hyperechoic rim or spiculations being identifiable. Thus, the boundary zone system includes identification of variable completeness and thickness of a capsule and the low end, various descriptions of a thick ill-defined rim at the upper end, and lack of a hyperechoic thin rim or thick halo in the middle of the spectrum of scores. In accordance with new and unique aspects herein, a separate feature score is no longer assigned based on the margin area, but instead one or more feature scores are assigned based on a larger boundary zone. The boundary zone described herein does not correspond to the margin area in the prior BI-RADS rating system. The boundary zone is substantially larger than the margin area considered in the prior BI-RADS rating system. The boundary zone is the zone of transition between the margin and the peripheral zone.

Among other things, as noted above, new and unique aspects herein remove the angular and microlobulated characteristics as subcategories from the margin area (and from the boundaries own), and instead use the angular and microlobulated characteristics to the determination of the value it assigned for the internal zone shape feature score. Also, the angular and microlobulated characteristics were redefined for use in the internal zone shape feature score. The angular characteristic refers to irregular shapes with angles, while the microlobulated characteristic refers to irregular shapes without angles, both of which are factors in assigning the internal zone shape feature score. In BI-RADS $5^{th}$ edition, a mass could paradoxically be classified being as either oval-shaped with a microlobulated margin or oval-shaped with an angular margin. The problem with such a system is the presence of a microlobulated margin or and angular margin, by definition meant that the mass was not oval-shaped. By ACR BI-RADS $5^{th}$ edition definition, there are only 3 shapes: oval, round, and irregular. In ACR BI-RADS $5^{th}$ edition, everything that is not oval or round is irregular. Since an oval-shaped mass with microlobulated or angular margins is no longer oval in shape, it cannot be classified as oval-shaped, The only solution to this unique paradox within the BI-RADS $5^{th}$ edition was to move microlobulation and angular margins out of the margin category and into the shape category, where they would necessarily be mutually exclusive with the oval shape category. Thus, in the boundary zone scoring system, microlobulations are included in the "irregular shape without angles, parallel orientation category and angles were moved into the irregular shape with angles category. Note that the irregular shape with angles carries a much higher risk of malignancy (81.4%) than does the irregular shape without angles, parallel orientation category (26.6%), verifying the validity of this reclassification of microlobulation and angles into the shape category.

In accordance with new and unique aspects herein, the US boundary zone is assigned an indistinct characteristic that is broken into two subcategories, namely 1) indistinct and 2) ill defined, thick echogenic rim (e.g. a halo). In accordance with new and unique aspects herein, the spiculated characteristic is considered as a characteristic for the boundary zone and for the peripheral zone. One or both of the boundary zone and peripheral zone may be spiculated. The spiculated characteristic may appear as short spiculated hypoechoic and/or hyperechoic regions in the boundary zone. Also, the spiculated characteristic may appear as long hyperechoic regions in the peripheral zone.

In accordance with new and unique aspects herein, it has been determined that showing a thin hyperechoic capsular around benign masses, in many instances, is very important to achieving a probability of malignancy of less than or equal to 2%. Further, consideration must be afforded for masses in which the thin hyperechoc capsule cannot be seen. In connection there with, new and unique aspects herein overcome the conventional ideas 1) that the hypoechoic central nidus of the mass represents the entire lesion, and 2) that only hypoechoic elements of a mass matter. The conventional approach substantially over emphasizes the hypoechoic elements.

In accordance with new and unique aspects herein, characteristics of the hyperechoic boundary zone and peripheral zone are analyzed to achieve the desired sensitivity of 98% or better with grayscale US or OA images. By looking at the boundary zone and peripheral zone, embodiments herein are able to accurately analyze masses that do not include a thin capsule. The boundary and peripheral zones, including but not limited to sides of the mass within the coronal plane, are analyzed for, among other things, indistinct margins, thick echogenic halo, hyperechoic spicules, and hyperechoic thickened and/or retracted Coopers ligaments.

By way of example, the US boundary zone feature score may be assigned an integer value between 0-5, each of which has a corresponding probability of malignancy as noted, such as based on the following:
  0=Well circumscribed with complete thin hyperechoic capsule (BR 4A, >2%—<=10% POM)
  1=Well-circumscribed with partial thin hyperechoic capsule (BR 4A, >2%—<=10% POM)
  2=Thick well-defined capsule (lower BR 4B, <=25% POM)
  3=Circumscribed, but without thin hyperechoic capsule (lower BR 4B, <=25% POM)
  4=Indistinct margin (upper BR 4B, >25% POM)
  5=Thick ill-defined echogenic rim (halo) in boundary zone (lower BR 4C, <=75% POM)
  6=Frank short hypoechoic and/or hyperechoic spiculations within boundary zone. (Upper BR 4C, >75% POM)

Figure 4I:
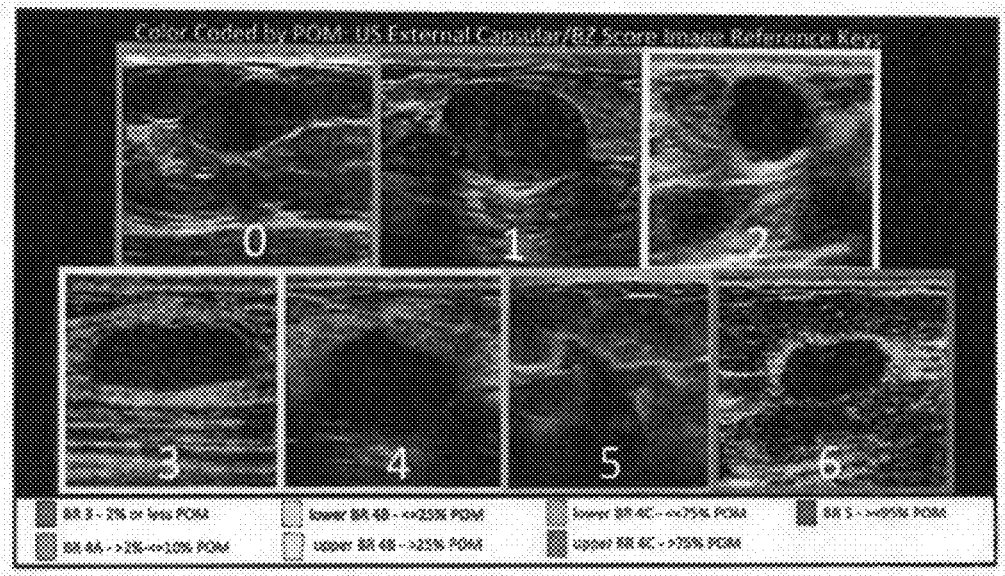
FIG. 4I illustrates an example of an image key for images with different boundary zones that warrant corresponding different external capsular/boundary zone feature scores.

FIG. 4I illustrates an example of an image key for images with different boundary zones that warrant corresponding different external capsular/boundary zone feature scores 0-6. The lower margin of FIG. 4I illustrates corresponding probabilities of malignancy associated with the different external capsular/boundary zone feature scores (assuming no other feature scoring information).

Figure 4J:
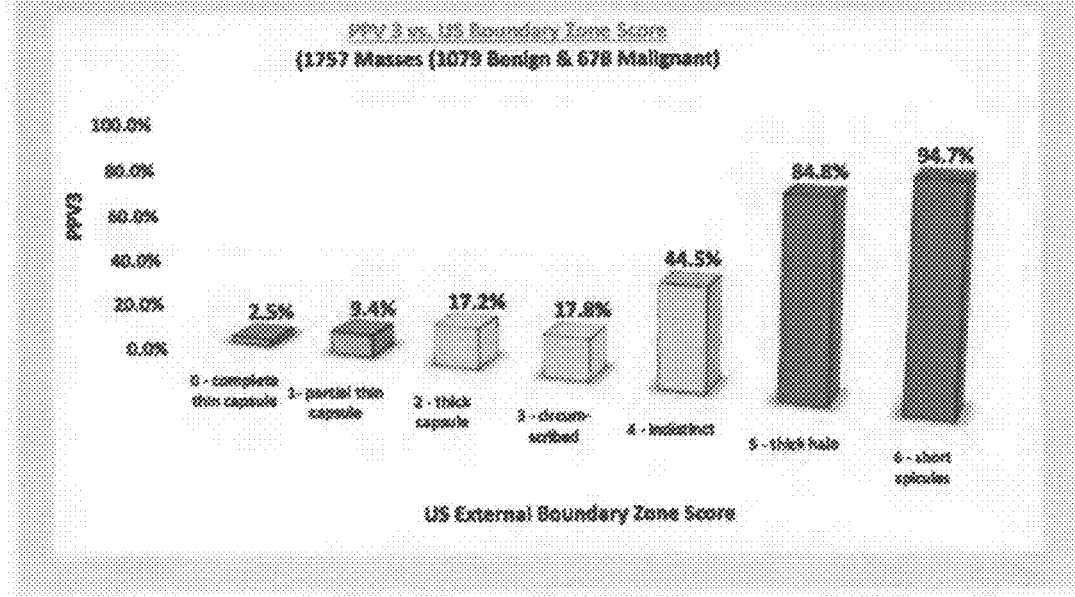
FIG. 4J illustrates an example of a relation between positive predictive values and boundary feature scores.

FIG. 4J illustrates an example of a relation between positive predictive values and boundary feature scores. The PPV rises continuously with increasing feature score. In accordance with new and unique aspects herein, it is recognized that a single feature score cannot provide both a good positive predictor and a good negative predictor. However, the boundary zone feature score may come the closest to any feature that could stand alone as a positive predictor of malignancy. The boundary zone exhibits a false negative ratio at the zero score of 2.5%, which is only slightly above the cut off between BI-RADS 3 and 4A. the positive predictive value at a score of six is 94.7% which is very close to the 95.7% associated with a BI-RADS 5 rating.

The scores of 0-2 correspond to masses with boundary zones that exhibit well-defined capsules that are identified to various degrees and variable thicknesses. The scores 3-4 correspond to masses with boundary zones that do not exhibit to a well-defined capsule, nor a thick rim. The scores 5-6 correspond to masses with a boundary zone that exhibits an ill-defined rim or spiculates.

In the BI-RADS 5$^{th}$ edition rating system, the boundary zone was discarded and only the margin area was considered and rated. In accordance with new and unique aspects herein, it is recognized that the boundary zone feature score represents a very valuable feature score. The boundary zone feature score offers a very good PPV slope versus score. As compared to other feature scores, the boundary zone feature score exhibits the steepest and most uniform PPV slope, offers the lowest FNR at the feature score 0, and exhibits almost the highest PPV at the feature score of 6. As compared to other feature scores, the boundary zone feature score affords very good, if not the best, visual separation of scoring distribution curves between benign and malignant masses. As compared to other feature scores, the boundary zone feature score offers a very wide, if not the widest, separation of means and 99% CIs. As compared to other feature scores, the boundary zone feature score offers a very wide, if not the widest, separation of medians and interquartile ranges, as well as the greatest AUC under ROC curve.

The boundary zone feature score accounts for a thin hyperechoic pseudo-capsule of compressed tissue around a benign mass. The hyperechoic capsule is difficult to demonstrate on the coronal ends of masses on single freeze-frame images because of poor angles of incidence with the ultrasound beam and the resulting critical angle phenomena. Furthermore, apart from angle of incidence issues, demonstration of the thin hyperechoic capsule on the sides of the mass must be done with the lesser lateral resolution of the ultrasound beam (about 300-500 microns). On the other hand, the thin hyperechoic capsule on the anterior and posterior surfaces of the mass are scanned at more optimal angles of incidence that do not suffer from critical angle phenomena and are visualized with the better axial resolution of the ultrasound beam (about 100 microns at 12-14 MHz).

Various techniques may be implemented to better demonstrate the thin hyperechoic capsule surrounding a benign mass. For example, video sweeps may be stored through the long axis of the mass in orthogonal planes. Heel-and-toe compression may be applied manually with a probe to improve angles of incidence on coronal ends of the mass. Spatial compounding may be utilized, to implement, in effect, an electronic form of heel and toe compression. A scan may also be implemented with lighter compression to allow surrounding hyperechoic fibrous tissue to separate away from the equally hyperechoic capsule.

Spiculations are another characteristic of the boundary zone feature score. A mass may exhibit alternating hypoechoic and hyperechoic spicules. Hypoechoic elements represent either fingers of invasive tumors or in situ tumors. Hyperechoic elements represent the interface between the tumor and tissue. A variant of spiculation represents a thick echogenic halo which is thicker along edges and less apparent anteriorly and posteriorly. The spiculation variant may arise due to spicules that extend in a direction parallel to a transmit/receive beam on anterior and posterior surfaces, thereby making poor specular reflections, while they are perpendicular to beams located along either sides of the mass and make strong specular reflections. The spiculation variant may also arise due to the fact that the coronal plane may represent the path of lowest resistance to invasion and spicules most commonly formed in the coronal plane on sides of the mass.

In short, the boundary zone is a very complex etiology that is substantially caused by infiltration of surrounding tissues (e.g. mainly fat). The infiltration may arise from edema (e.g. leaking from abnormally leaky tumor neovessels), cancer cells infiltrating between fat cells, lymphocytes infiltrating between fat cells, desmoplasia between fat cells (e.g. a cursor to spicules), unresolved micro-spicules and tumor neovessels. The boundary zone is complex and includes one or more of active by active tumor cell growth, immune cell response, high cellularity, high neovessel density, desmoplasia, tumor associated macrophages, tumor associated fibroblast, edema and proteinaceous debris.

US Peripheral Zone Feature Score

In accordance with new and unique aspects herein, an additional US feature score has been defined for the peripheral zone. The peripheral zone feature score accounts for calcifications, associated features and spiculation outside of the boundary zone. The calcifications are located outside of a mass and may include intraductal calcifications outside of the mass. The associated features may include architectural distortion and/or duct changes outside of the boundary zone. The peripheral zone feature score is also assigned based on spiculations outside of the boundary zone. The peripheral zone feature score combines duct changes and calcifications outside of a mass into 2 characteristics, namely 1) enlarged ducts outside of a mass (without internal microcalcifications) and 2) enlarged ducts outside of a mass that contain microcalcifications. The architectural distortion and associated features were divided into two characteristics, namely 1) hyperechoic spiculations (or interrupted tissue planes) and 2) thickened Coopers ligaments and/or skin (moved from the associated features).

By way of example, the US peripheral zone feature score may be assigned an integer value between 0-5, each of which has a corresponding probability of malignancy as noted, such as based on the following:

0=Normal tissue (lower BR 4B, <=25% POM)
1=Critical angle phenomena=(shadowing from adjacent structures) (upper BR 4B, >25% POM)
2=Enlarged surrounding ducts not containing microcalcifications (duct extension or branch pattern) (upper BR 4B, >25% POM)
3=Enlarged Surrounding ducts containing microcalcifications (upper BR 4C, >75% POM)
4=Peripheral long hyperechoic spicules (or interrupted tissue plane) (upper BR 4C, >75% POM)
5=Thickened spicules and/or Coopers ligaments and/or retracted or thick skin (BR 5, >=95% POM)

Figure 4K:
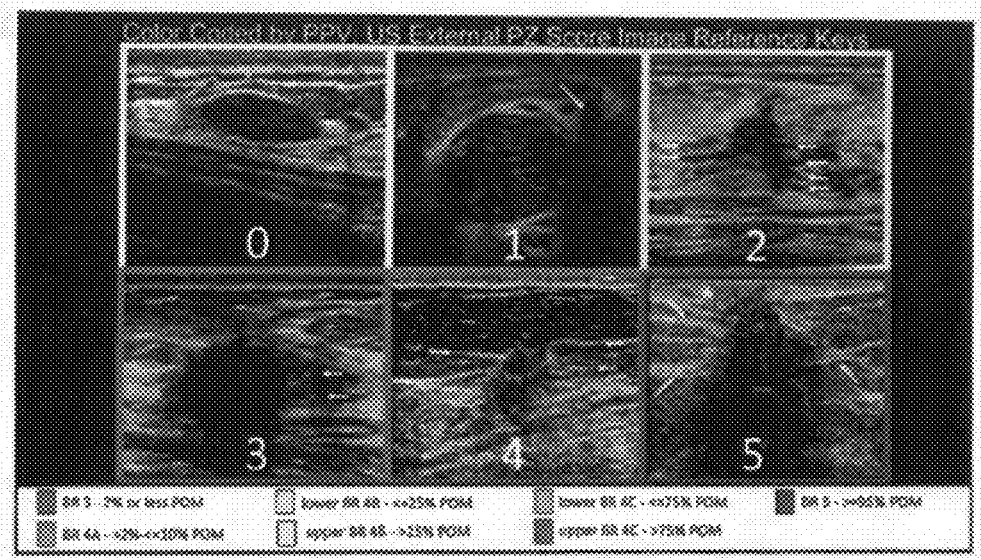
FIG. 4K illustrates an example of an image key for images with different peripheral zones that warrant corresponding different peripheral zone feature scores.
Figure 4L:
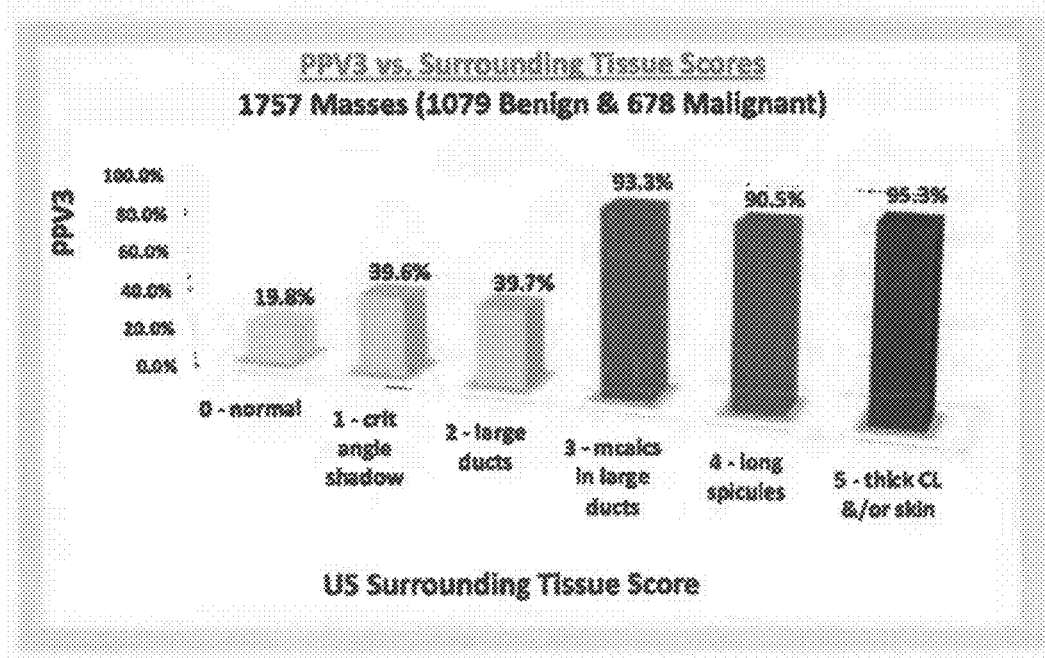
FIG. 4L illustrates an example of a relation between positive predictive values and peripheral zone feature scores. The PPV rises continuously with increasing feature score.

FIG. 4K illustrates an example of an image key for images with different peripheral zones that warrant corresponding different peripheral zone feature scores 0-5. The lower margin of FIG. 4K illustrates corresponding probabilities of malignancy associated with the different peripheral zone feature scores (assuming no other feature scoring information). FIG. 4L illustrates an example of a relation between positive predictive values and peripheral zone feature scores. The PPV rises continuously with increasing feature score. The peripheral feature score exhibits a great positive predictor of cancer with scores of 3, 4 and 5 having PPVs over 90%. However, the peripheral feature score exhibits a poor negative predictor in the absence of CA because some cancers are not spiculated. The peripheral zone may exhibit an interrupted tissue plane. The interrupted tissue plane may be considered in the same manner as thin peripheral zone spicules. For example, a peripheral zone that exhibits an interrupted tissue plane may be assigned a PZ score of 4.

In accordance with new and unique aspects herein, it has been recognized that peripheral zone spicules are always hyperechoic to fat but can to be hypoechoic relative to hyperechoic interlobular stromal fibrous tissue. Interrupted tissue planes should be scored in the same manner as hyperechoic spicules, by assigning a score of 4. Peripheral zone spicules can extend greater than or equal to 2 cm into surrounding tissues on each side of a mass. Peripheral zone spicules and interrupted tissue planes may occur only on one side of a mass. Peripheral zone spicules can be oriented parallel to each other, but often diverge in a butterfly or bowtie fashion. Diverging hyperechoic spicule lines have a higher probability of malignancy than do parallel spicule lines. Peripheral zone spicules are most common on sides of a mass in the coronal plane. Peripheral zone spicules often appear on an SAX sweep across a mass and appear to retract in toward the mass in a bowtie or butterfly pattern.

A single frame of a video sweep or a still image can show either no spicules or only a single spicule in one side of the mass. The video sweep across the short axis of the mass, on the other hand usually shows more numerous spicules that are more widely distributed around the mass. To facilitate recognition of hyperechoic spicules, the following points should be considered. The analysis should analyze images in the coronal plane along the sides of the mass, as the path of lowest resistance for invasion and for formation of spicules is within the coronal plane. While 3-D images with coronal plane imaging facilitate demonstration of spicules, short axis video sweeps may represent a more widely available type of 3-D imaging. In connection with 2-D imaging, spicules in the coronal plane are readily seen in the video SAX sweep where spicules can be seen "pulling in" and "pushing out" in a bowtie or butterfly fashion from the central nidus as the 2-D probe is swept back and forth through the lesion. Hyperechoic lines diverging in a bowtie or butterfly fashion are an indicator of a very high POM and exhibit fewer false positives. Parallel hyperechoic lines, on the other hand, sometimes merely represent compressed tissue planes or septi within the breast and will have lower POMs and exhibit more false positives.

In accordance with new and unique aspects herein, it has been recognized that enlarged surrounding ducts within the peripheral zone are a good characteristic of interest when assigning a peripheral zone feature score. Certain items can be derived from the fact that the greatest ductal or acinar enlargement requires four components. The OA/US imaging can see 3 CIS because it grossly enlarges ducts and the viewer can readily distinguish them from normal docs (e.g. 4-20 times larger than a normal docs size, up to 2-3 mm). Also, the OA/US imaging can see some grade 2 CIS because some grade 2 CIS enlarge ducts enough to enable distinction of the ducts from normal docs (e.g. 2-4 times a normal duct size). The OA/US imaging may not notably illustrate grade 1 CIS because it does not enlarge the ducts enough to distinguish effected ducts from normal docs. Grade 1 CIS are generally only visible on OA/US images when the region is intracystic, grossly enlarges a single TDLU, or develops into a pre-existing papilloma or radial scar.

High peripheral zone feature scores exhibit one of the highest (or the highest) PPV as compared to any other internal or boundary zone feature score, whether based on US only, OA only, or a combination thereof. Recognizing the presence of characteristics of interest within the peripheral zone will always create a BI-RADS 4C or greater classification. Not recognizing the existence of a characteristic of interest in the peripheral zone could lead to under classification of masses to the downgrade of a BI-RADS 4A category. Trying to downgrade BI-RADS 4C or 5 masses that are under classified as BI-RADS 4A will contribute to false negatives and could cause a significant loss of US or OA sensitivity.

OA Feature Scores

Next, the discussion turns to OA feature scores and the use of OA feature scoring as a biomarker in general, as well as for molecular subtyping of tumors. The OA feature scoring may be utilized in various manners. For example, OA feature scoring may be utilized as a qualitative diagnostic biomarker, such as to assist in making a binary decision (e.g. biopsy versus no biopsy). Additionally or alternatively, the qualitative diagnostic biomarker may be utilized to identify a BI-RADS 3 or less versus BI-RADS 4A or higher. The OA feature scores may also be utilized as quantitative predictive biomarkers, such as to help objectively assign a POM and BI-RADS category when a risk of malignancy is above 2%. The OA feature scores may also be utilized as a prognostic biomarker, such as when correlating particular OA feature scores with primary biomarkers and molecular subtypes. For example, the primary biomarkers may represent histologic grade, size and positive LN rates. The secondary biomarkers represent ER, PR, HDR to status, and KI-67 proliferative index. The secondary biomarkers may be utilized as a surrogate for genetic assays to identify molecular subtypes.

FIG. 5A illustrates an example of a set of images that may be co-displayed while medical personnel are assigning the various US feature scores and/or OA feature scores. The six co-registered two-dimensional images comprise a grayscale ultrasound image, and OA short wavelength image, and OA long wavelength image, a total hemoglobin image, a relative up to acoustic image and a combined up to acoustic image, all of which are described in more detail in the 893 patent as well as other publications referenced herein.

The six images are co-registered and include interior and exterior outlines separating the internal zone, boundary zone and peripheral zone. Three internal zone feature scores and to external zone feature scores, as well as various combinations thereof, are assigned in connection with one or more masses in the region of interest. The internal OA features represent a vessel feature score (usually in the OA combined map), deoxygenation blush score (in the OA relative map) and total hemoglobin score (in the OA total map). The external feature scores include the boundary zone vessels and the peripheral zone vessels. The boundary zone vessels may be scored based on capsular vessels (usually the OA combined map, sometimes the OA relative map or OA total map), and boundary zone deoxygenated blood (the OA relative map). The peripheral zone vessels are scored based on peripheral zone radiating vessels (the OA total hemoglobin map, and any other map except the OA relative map).

By way of example, the scores may range between 0-5 or 0-6 with a zero representing a benign condition and a 5/6 representing a feature that is highly suspicious for malignancy. In accordance with embodiments herein, the medical personnel may be directed to assign the corresponding feature scores in a particular order, such as to score the peripheral zone first, followed by the boundary zone, followed by the three feature scores for the internal zone. Optionally, when a subset of the feature scores are utilized, the order in which features are scored may vary. For example, they peripheral zone may be omitted, in which case the boundary zone would be scored first, followed by one or more of the internal zone features. Optionally, one or more of the internal zone features may be omitted, in which case the peripheral zone would be scored first, followed by the boundary zone and then the remaining (if any) internal zone feature scores. Optionally, only the peripheral and boundary zones may be scored, without scoring any internal zone features. As a further option, the boundary zone may be scored first, followed by one or more of the internal zone features, followed by the peripheral zone. Optionally, the boundary zone may be scored first, followed by the peripheral zone, and then followed by one or more of the internal zone features. As a further option, the order in which the internal zone features may be interposed between the boundary and peripheral zone features.

Various combinations of the images in FIG. 5A may be utilized in connection with scoring different features. For example, the OA combining image/map may be utilized to score internal zone features, such as the internal vessels and their degree of oxygenation. The OA combined image/map may also be used, occasionally, for scoring the boundary zone and/or the peripheral zone. The OA grayscale short wavelength image/map may be utilized as a confirmation for internal deoxygenated blush, and as a confirmation of peripheral radiating vessels. The OA total image/map may be utilized for scoring internal vessels and for scoring the internal total hemoglobin. The OA total image/map may also be utilized in connection with scoring the boundary zone and identifying radiating vessels in the peripheral zone. The OA relative image/map may be utilized to score the internal the oxygenation blush and boundary zone blush. The OA relative image/map may also be utilized to identify high pretest probabilities or under colorization, to determine when the background is too noisy for peripheral vessel evaluation, to determine whether a high pretest probability exists and to determine when there is a relative under colorization. The OA grayscale long wavelength image/map may be utilized as a confirmation of radiating vessel patterns in the peripheral region and is a confirmation for interference lines.

In accordance with new and unique aspects herein, it has been recognized that scores aside from the OA images/maps may be overweighted in different manners in connection with scoring. For example, the OA total image/map and the OA combined image/map (which represent the quietest maps) may be overweighted when 1) a mass has already been assigned a POM of 10% or less through analysis with another modality, such as US only, MM, CT, etc. and prior to OA imaging, 2) there is no relative under colorization and 3) downgrading is a primary goal of the analysis. As another example, the OA relative image/map may be overweighted (which represents the most sensitive map) when 1) a pre-OA POM is 20% or more, 2) there is relative under colorization and 3) upgrading or confirming high index of suspicion is a main goal. As another example, the OA short wavelength image/map may be utilized as a supplement to confirm radiating red vessels in the boundary zone or peripheral zone and to confirm red gel standoff or nipple artifacts. As another example, the OA long wavelength image/map may be utilized as a supplement to confirm green radiating vessels in the boundary zone or peripheral zone and to confirm green interference lines.

While certain aspects herein utilize all five OA maps, it is recognized that certain maps have different relative strengths. The OA total and OA combined maps represent the quietest maps and may be utilized as the primary maps in connection with downgrading BI-RADS classifications. The OA relative map may be overweighted as the main map in connection with upgrading BI-RADS classifications and as the main map to confirm high pretest suspicion of malignancy. The OA relative map may be overweighted when there is relative under colorization. The OA short wavelength map may be utilized to confirm certain colors, particularly in the peripheral zone. The OA long wavelength map may be utilized to confirm certain colors, particularly in interference artifacts.

OA Internal Vessel Score

By way of example, the OA internal vessel feature score may be assigned an integer value between 0-5, each of which has a corresponding probability of malignancy as noted, such as based on the following:

0=No internal vessels (lower BR 4B, <=25% POM)
    1=Normal internal vessel(s) without branches, green or red (lower BR 4B, <=25% POM)
    2=Normal internal vessel(s) with branches, green or red (upper BR 4B, >25% POM)
    3=Internal speckle—green ≥red in amount and red <background red (upper BR 4B, >25% POM)
    4=Internal speckle—red >green and IZ red >red in background (lower BR 4C, <=75% POM)
    5=Multiple internal red (deoxygenated) polymorphic vessels (lower BR 4C, <=75% POM)

Figure 6A:
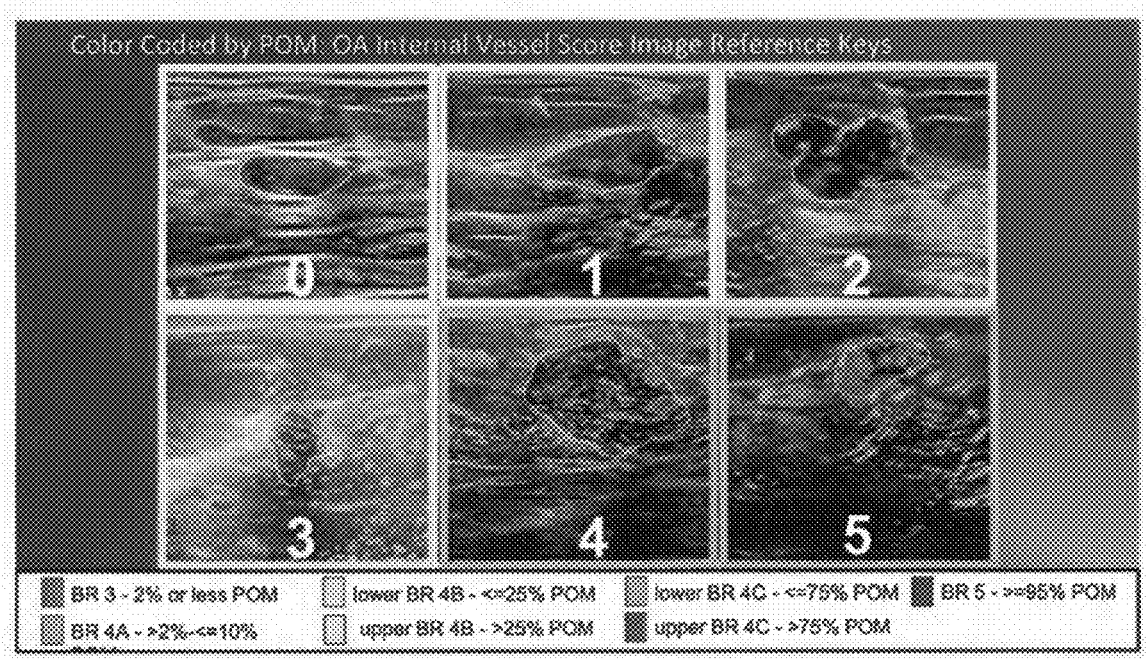
FIG. 6A illustrates an example of an image key for images with different OA internal zones that warrant corresponding different OA internal vessel feature scores.

FIG. 6A illustrates an example of an image key for images with different OA internal zones that warrant corresponding different OA internal vessel feature scores 0-5. The lower margin of FIG. 6A illustrates corresponding probabilities of malignancy associated with the different OA internal vessel feature scores (assuming no other feature scoring information).

Figure 6B:
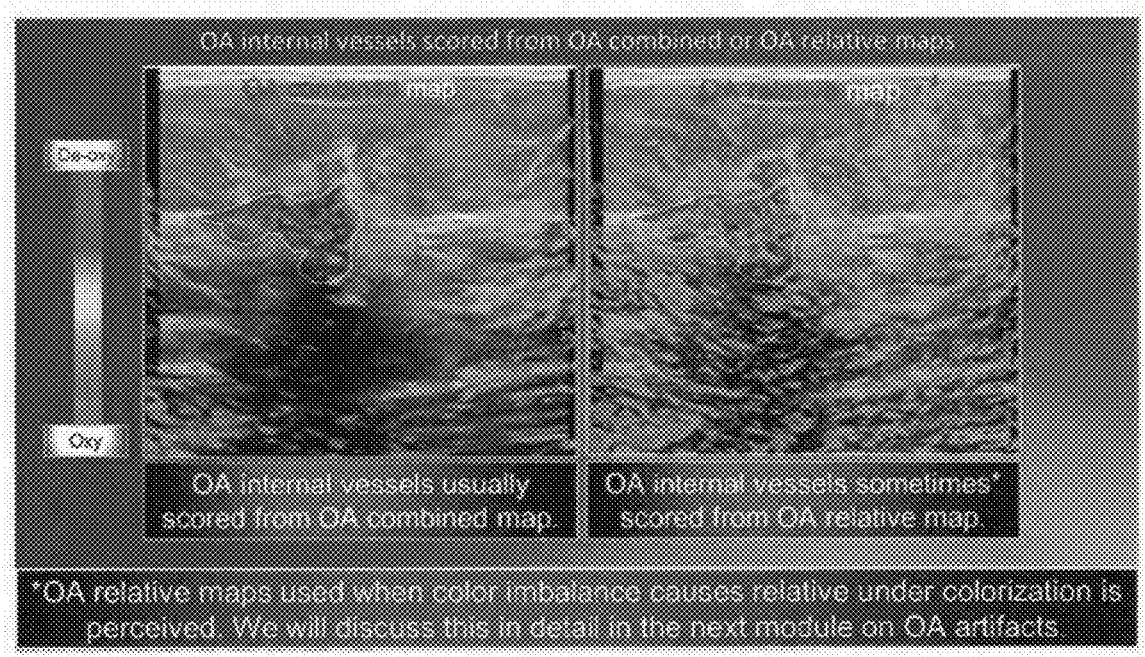
FIG. 6B illustrates an example of and OA combined map and OA relative map with interior and exterior outlines drawn to separate the internal, boundary and peripheral zones.

FIG. 6B illustrates an example of and OA combined map and OA relative map with interior and exterior outlines drawn to separate the internal, boundary and peripheral zones. The OA relative map may be utilized in connection with scoring the OA internal vessels, such as when a color imbalance causes relative under colorization. FIG. 6C illustrates an example of a relation between positive predictive values and OA internal vessel feature scores. The PPV rises continuously with increasing feature score. The graph of FIG. 6C illustrates that the OA internal vessel score is a good positive predictor of malignancy but, taken alone, is not necessarily a good negative predictor of the absence of malignancy. Instead, the OA internal vessel score should be combined with one or more other feature scores that have lower POMs at scores of zero and one in order to exclude cancers.

A false negative low OA internal vessel score may be caused by acoustic shadowing which tends to contribute to significant OA shadowing, thereby diminishing the internal OA signals. Also, the OA internal vessel score, when taken alone, may indicate false negatives in connection with central fibrous in grade I and II and lumen A invasive breast cancers. As another example, the OA internal vessel score, when taken alone, may indicate false negatives in connection with central necrosis in grade III and triple negative invasive breast cancers.

OA Internal Total Hemoglobin Score

By way of example, the OA internal total hemoglobin feature score may be assigned an integer value between 0-5, each of which has a corresponding probability of malignancy as noted, such as based on the following:

0=No internal hemoglobin (lower BR 4B, <=25% POM)
    1=Minimal internal hemoglobin <background (lower BR 4B, <=25% POM)
    2=Minimal # internal discrete vessels <=background (upper BR 4B, >25% POM)
    3=Moderate # internal discrete vessels=background (lower BR 4C, <=75% POM)
    4=Many large polymorphic internal vessels >background (lower BR 4C, <=75% POM)
    5=Many large polymorphic vessels almost fill lesion (lower BR 4C, <=75% POM)

Figure 6D:
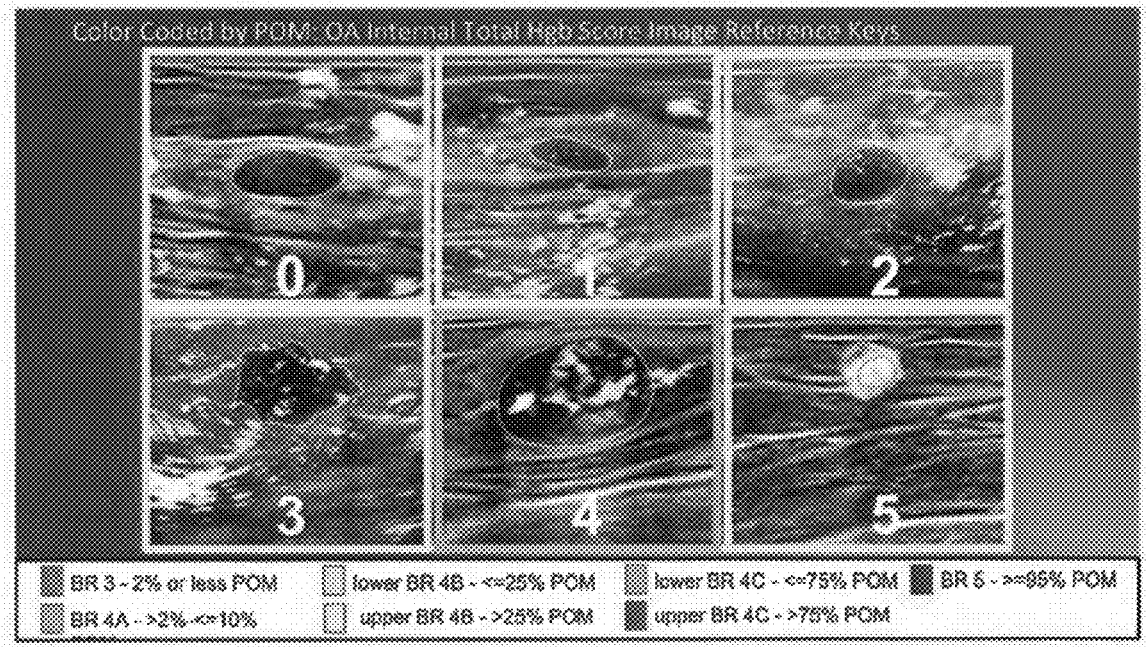
FIG. 6D illustrates an example of an image key for images with different OA internal zones that warrant corresponding different OA internal total hemoglobin feature scores 0-5.
Figure 6E:
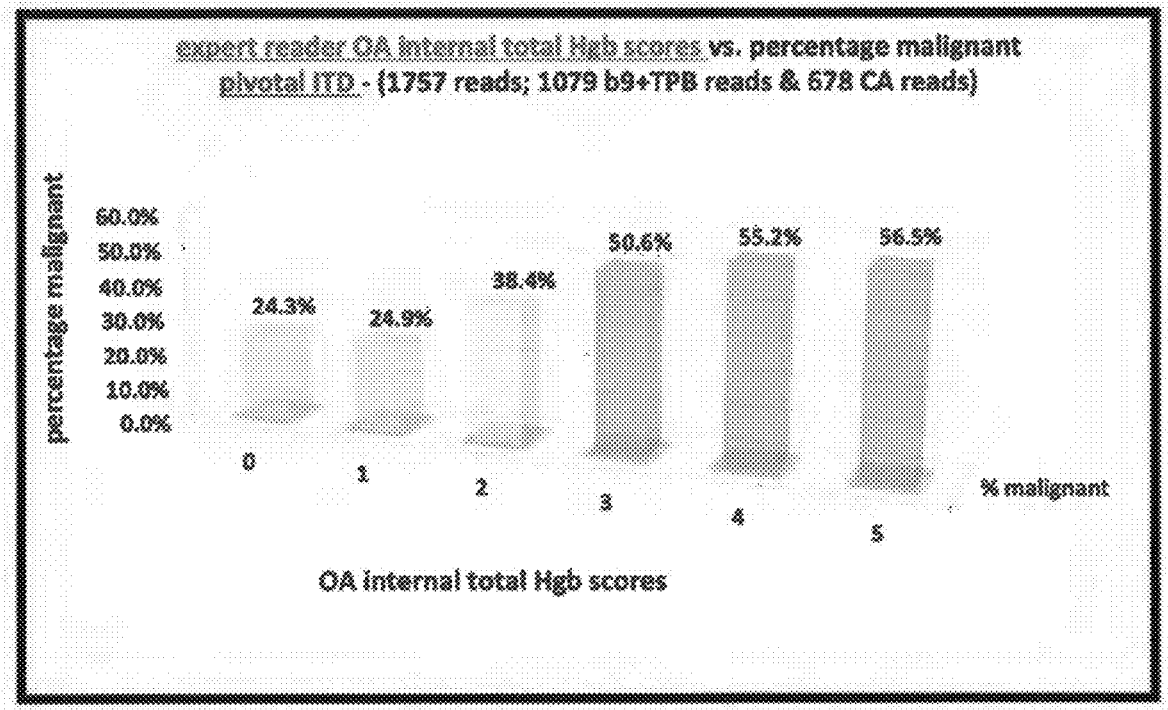
FIG. 6E illustrates an example of a relation between positive predictive values and OA internal total hemoglobin feature scores.

FIG. 6D illustrates an example of an image key for images with different OA internal zones that warrant corresponding different OA internal total hemoglobin feature scores 0 5. The lower margin of FIG. 6D illustrates corresponding probabilities of malignancy associated with the different OA internal total hemoglobin feature scores (assuming no other feature scoring information). FIG. 6E illustrates an example of a relation between positive predictive values and OA internal total hemoglobin feature scores. As shown in FIG. 6D, the OA internal total hemoglobin scores are a good positive predictor of malignancy, but when taken alone, is not a good negative predictor of the absence of malignancy. The OA internal total hemoglobin score should be considered in combination with one or more other feature scores that have lower POMs at scores of zero and one in order to exclude malignancies.

OA Internal deoxygenated blush Score

By way of example, the OA internal deoxygenated blush feature score may be assigned an integer value between 0-5, each of which has a corresponding probability of malignancy as noted, such as based on the following:

0=No internal vessels (lower BR 4B, <=25% POM)
    1=Minimal internal speckle, all or mostly green (lower BR 4B, <=25% POM)
    2=Mild internal speckle; red <green and red <background red (upper BR 4B, >25% POM)
    3=Mild internal speckle; red ≥green, but red <bkgd red (lower BR 4C, <=75% POM)
    4=Moderate internal speckle—red >green and red also >background red (lower BR 4C, <=75% POM)
    5=Internal red blush almost fills lesion (lower BR 4C, <=75% POM)

Figure 6F:
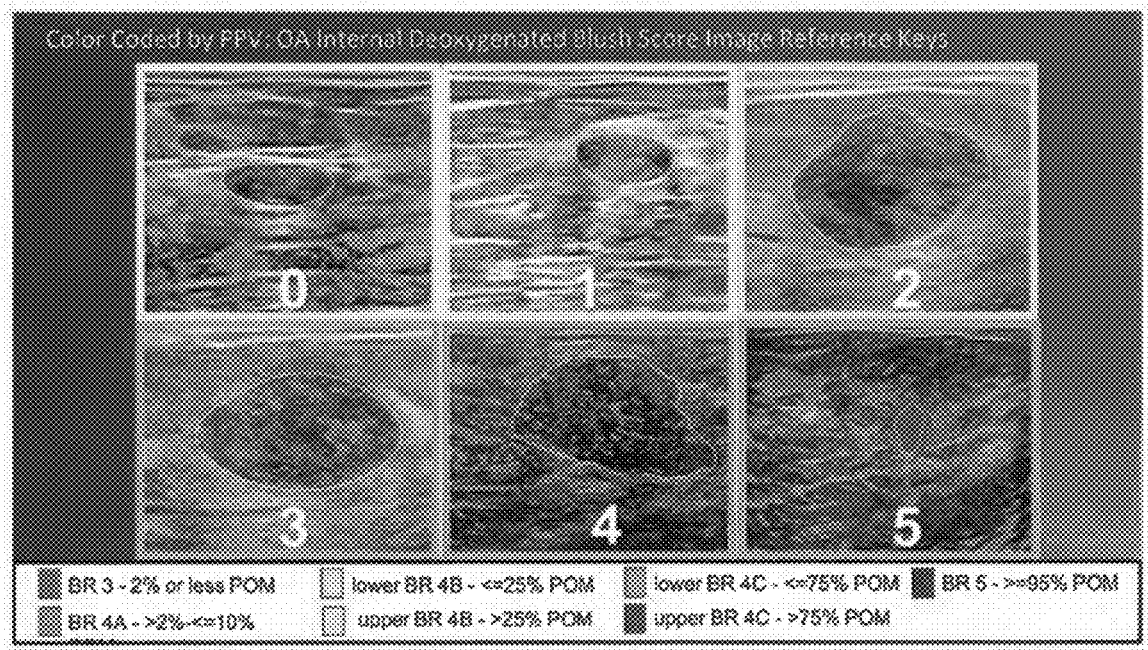
FIG. 6F illustrates an example of an image key for images with different OA internal zones that warrant corresponding different OA internal deoxygenated blush feature scores 0-5.
Figure 6G:
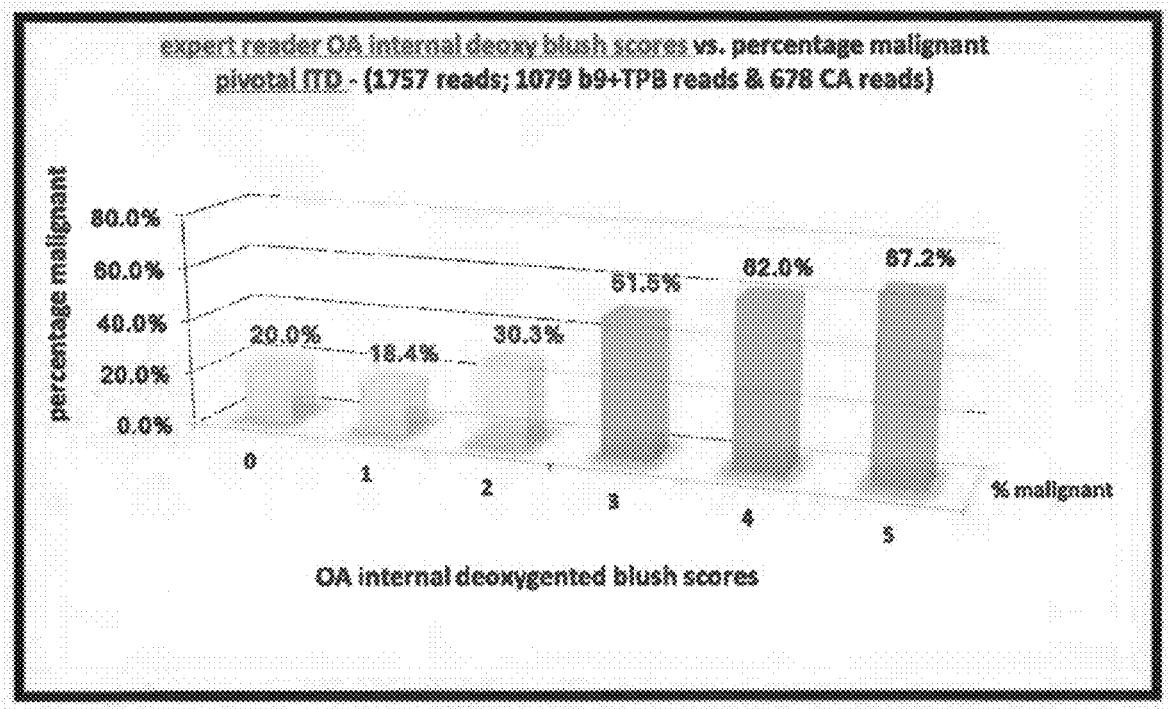
FIG. 6G illustrates an example of a relation between positive predictive values and OA internal deoxygenated blush feature scores.
Figure 6H:
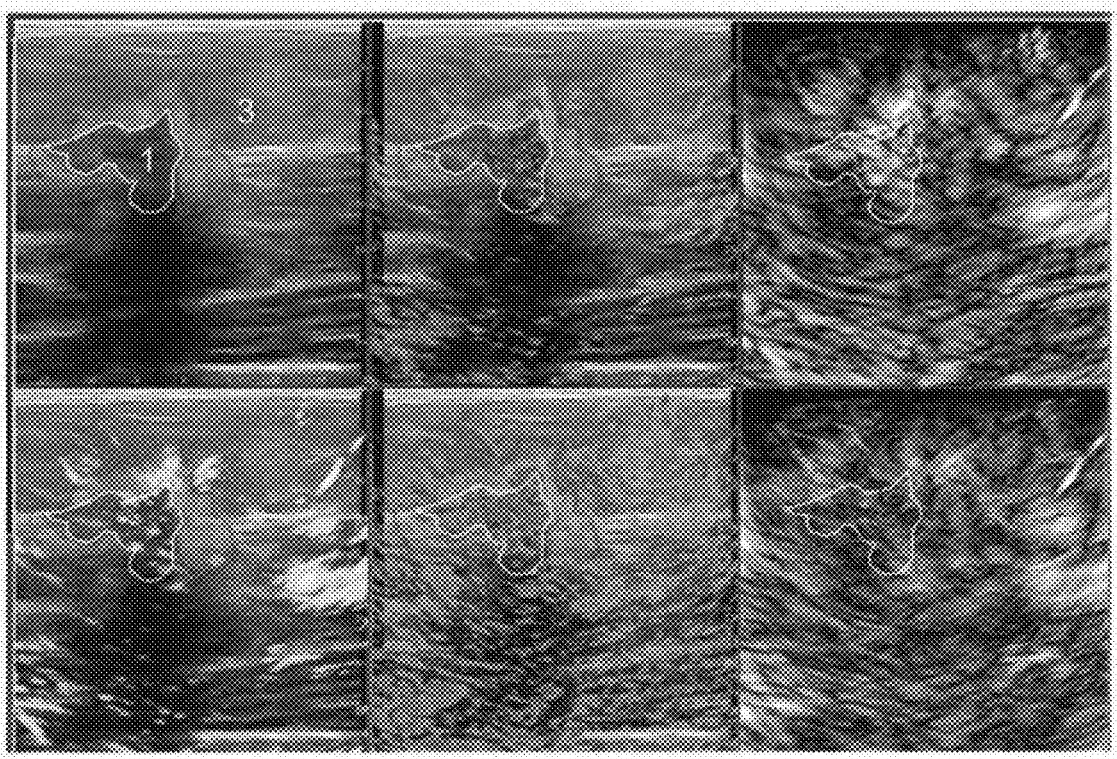
FIG. 6H illustrates an example of a set of six co-registered UL/OA images illustrating the internal zone "1", the boundary zone "2", and the peripheral zone "3".
Figure 6I:
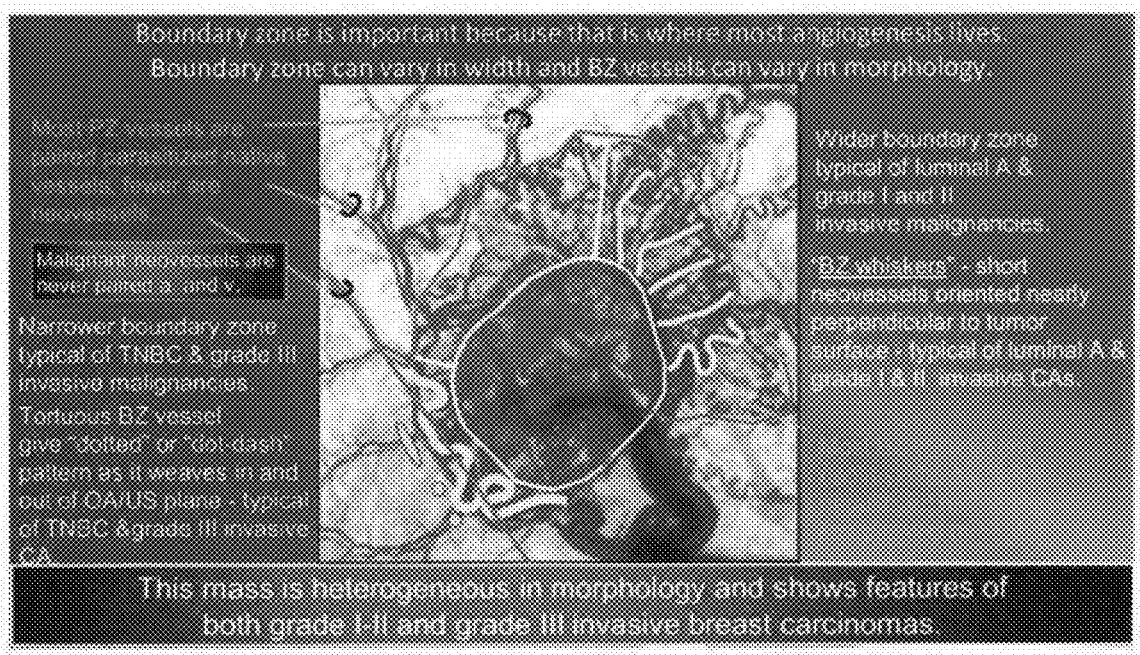
FIG. 6I illustrates an example of the boundary zone where angiogenesis lives.

FIG. 6F illustrates an example of an image key for images with different OA internal zones that warrant corresponding different OA internal deoxygenated blush feature scores 0-5. The lower margin of FIG. 6D illustrates corresponding probabilities of malignancy associated with the different OA internal deoxygenated blush feature scores (assuming no other feature scoring information). FIG. 6G illustrates an example of a relation between positive predictive values and OA internal deoxygenated blush feature scores. As shown in FIG. 6G, the OA internal deoxygenated blush scores are a good positive predictor of malignancy, but when taken alone, is not a good negative predictor of the absence of malignancy. The OA internal deoxygenated blush score should be considered in combination with one or more other feature scores that have lower POMs at scores of zero and one in order to exclude malignancies. FIG. 6H illustrates an example of a set of six co-registered UL/OA images illustrating the internal zone "1", the boundary zone "2", and the peripheral zone "3". FIG. 6I illustrates an example of the boundary zone where angiogenesis lives. FIG. 6J illustrates an example of the boundary zone where angiogenesis lives.

In accordance with new and unique aspects herein it has been recognized that the OA internal feature scores provide certain key information. All living tissues, including benign and malignant masses, have blood flow and use oxygen. All masses, benign and malignant will have some red and some green vessels (associated with responsiveness to Long wavelength and short wavelength OA transmissions). Distinguishing benign versus malignant vessels is not simply based on distinguishing between vessel responsiveness to long and short wavelength OA energy. A morphology of the vessels is important in distinguishing between benign and malignant vessels. Malignant internal vessels are polymorphic, which is evident from immediately adjacent vessels at similar depths that vary in size, shape and orientation. Benign internal vessels are monomorphic, which is evident from adjacent vessels at similar depths within a mass having similar size, shape and orientation.

OA Capsular/Boundary Zone Vessel Score

In accordance with new and unique aspects herein, and OA capsular/boundary zone vessel feature score is defined that provides a mechanism to robustly distinguish between benign and malignant masses. A surprising and unexpected result resulted from the recognition that the OA BZ vessel feature score is unaffected by shadowing, unaffected by central fibrosis, unaffected by central new grosses, is present in all three histologic grades of invasive breast cancer and is present in all molecular subtypes of invasive breast cancer. A surprising and unexpected result resulted from the recognition that the OA BZ vessel feature score is indicative of the growing most active portion of a tumor and corresponds to the region in which the immune system most actively attacks/helps the tumor.

Figure 7A:
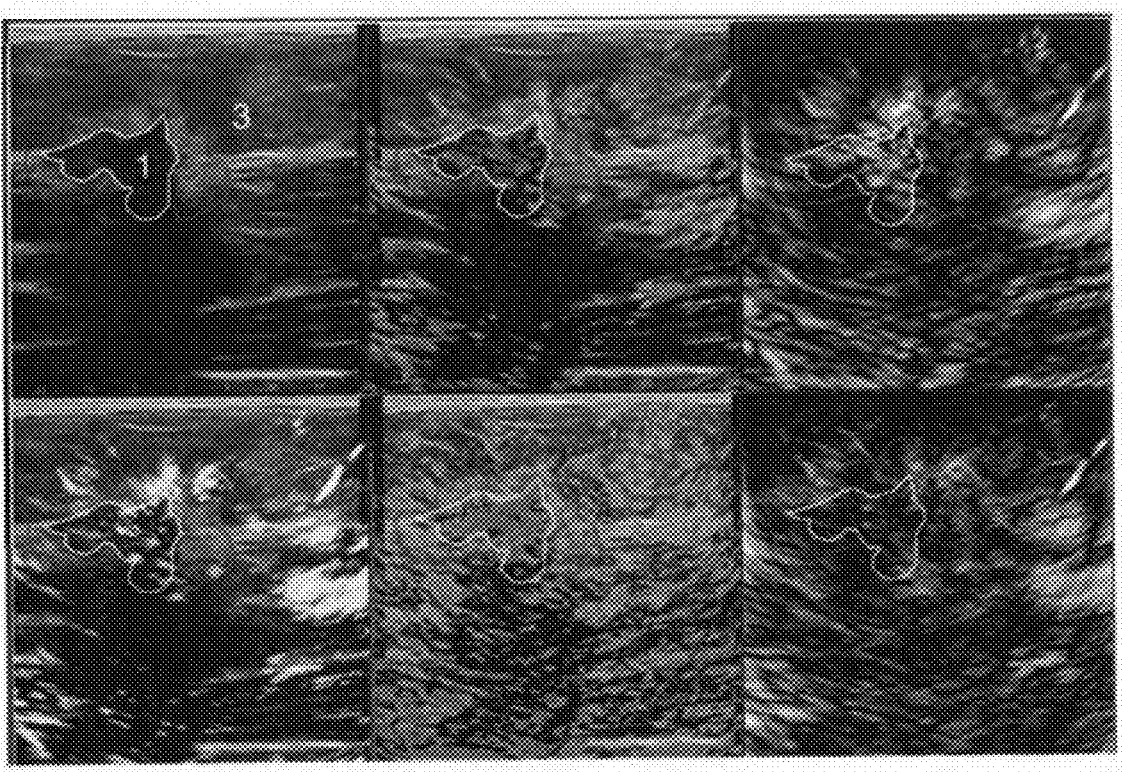
FIG. 7A illustrates an example of a set of six co-registered UL/OA images illustrating the internal zone "1", the boundary zone "2", and the peripheral zone "3".

FIG. 7A illustrates an example of a set of six co-registered UL/OA images illustrating the internal zone "1", the boundary zone "2", and the peripheral zone "3". The boundary zone includes the thick echogenic halo in invasive masses and then hyperechoic Sold in benign masses. The peripheral zone lies outside the exterior outline (aqua colored line) and is outside of the thick echogenic halo.

Figure 7B:
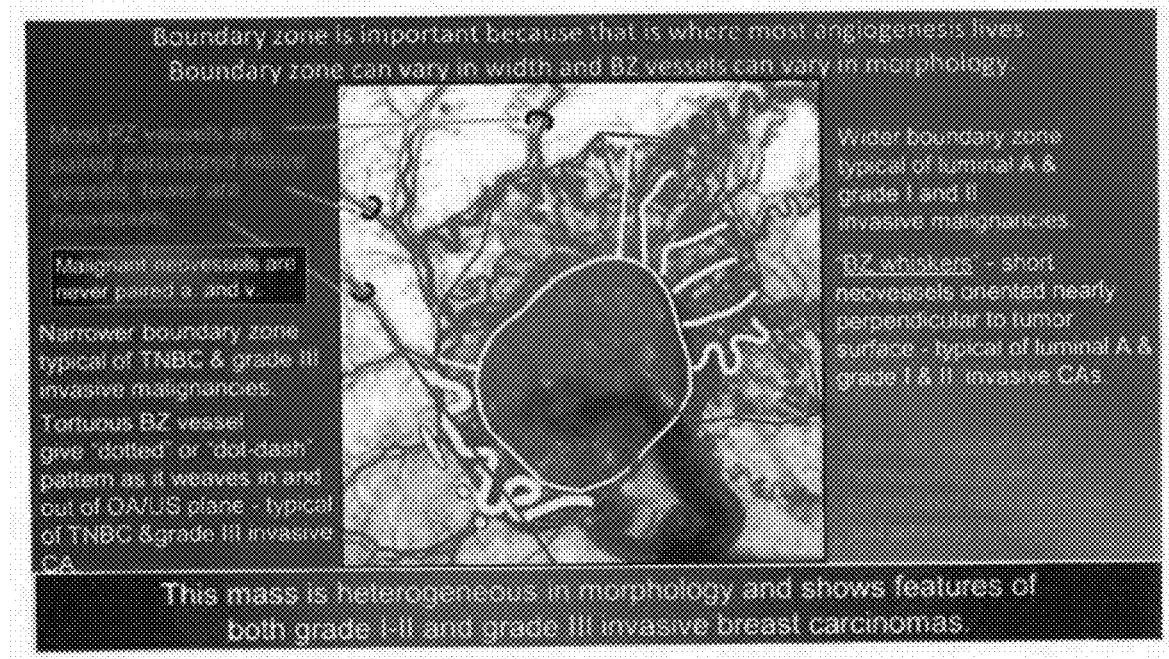
FIG. 7B illustrates an expanded graphical image of the internal, boundary and peripheral zones.

FIG. 7B illustrates an expanded graphical image of the internal, boundary and peripheral zones. The example in FIG. 7B illustrates a mass that is heterogeneous and morphology and shows features of both grade I-II and grade III invasive breast carcinomas. The boundary zone includes a regent in which most angiogenesis lives. The boundary zone can vary in width and boundary zone vessels can vary in morphology. FIG. 7B illustrates a region (upper left corner of the panel in the peripheral zone) in which most of the peripheral zone vessels are paired parasitized native vessels, while fewer vessels are neo-vessels. Malignant neo-vessels are not paired a. and v. The boundary zone is typically narrow in molecular subtype TNBC and grade III invasive malignancies. A tortious boundary zone vessels give a "dotted" or "dot - " pattern as it weaves in and out of the OA/UL plane, which is typical of TNBC and grade III invasive carcinomas. The boundary zone is typically wider in molecular subtype luminal A and grade I and II invasive malignancies. The boundary zone may include "whiskers", which represent short neo-vessels oriented nearly perpendicular to the tumor surface in connection with the luminal A molecular subtype and grade I and II invasive carcinomas. FIG. 7B illustrates a regent (middle right side of the panel in the boundary zone) where the majority of the boundary zone vessels are neo-vessels, while fewer of the vessels are parasitized native vessels.

Figure 7C:
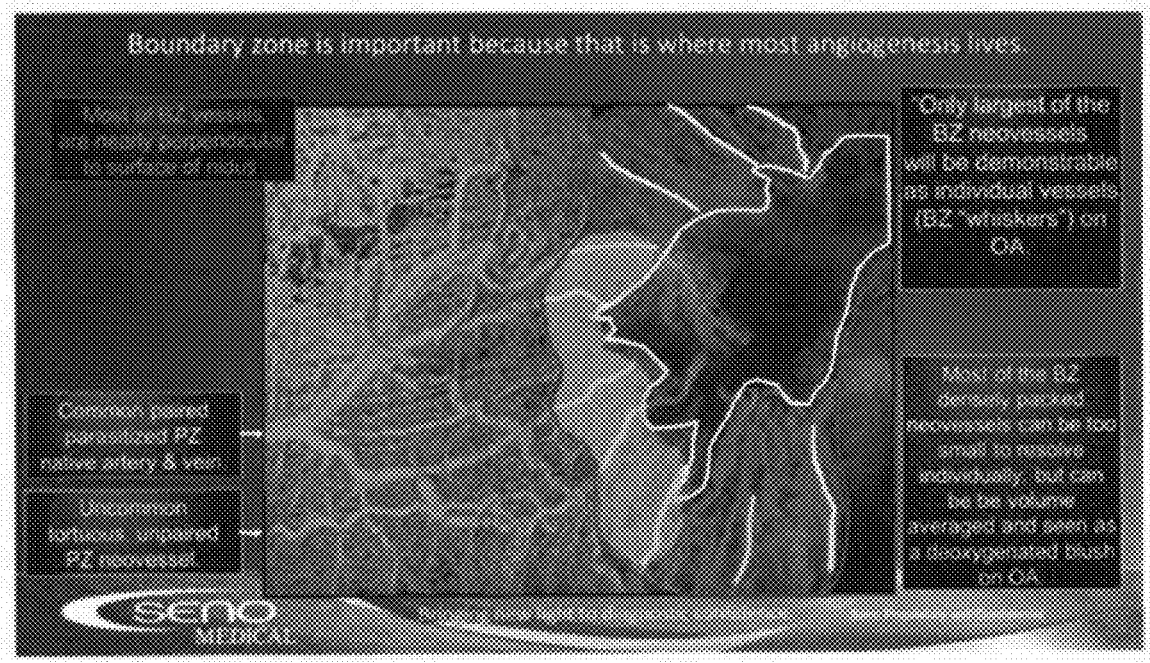
FIG. 7C illustrates an enlarged view of another example of vessels.
Figure 7D:
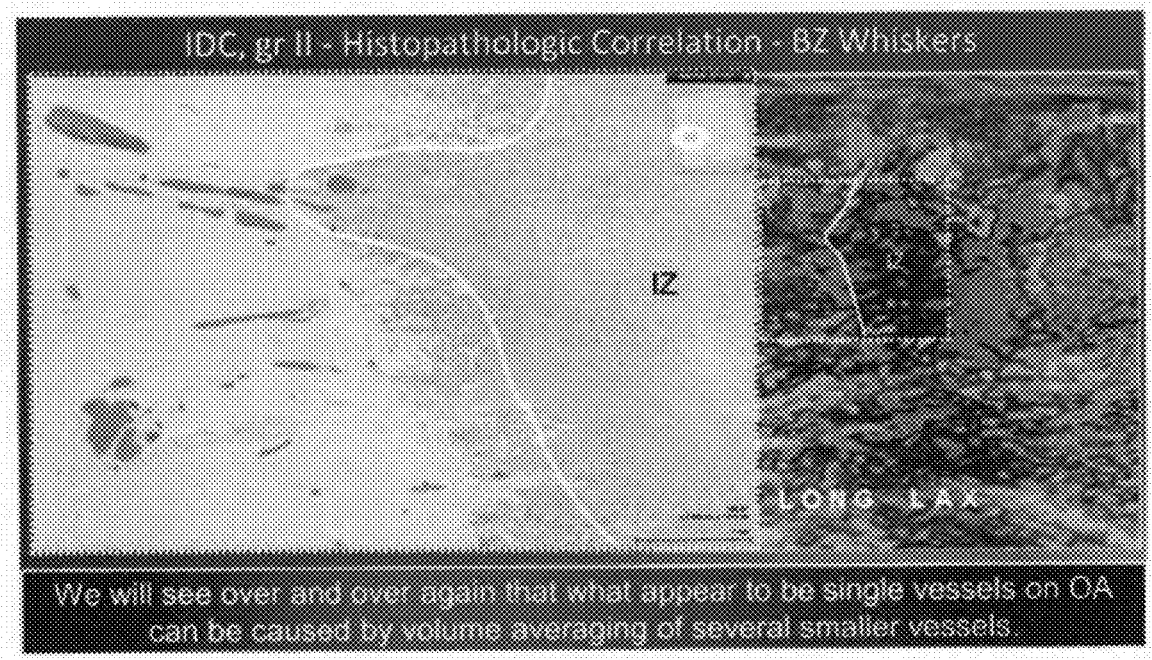
FIG. 7D illustrate an examples of vessel characteristics that may appear in the boundary zone and/or peripheral zone in connection with benign tumors and different types of malignancy molecular subtypes.
Figure 7G:
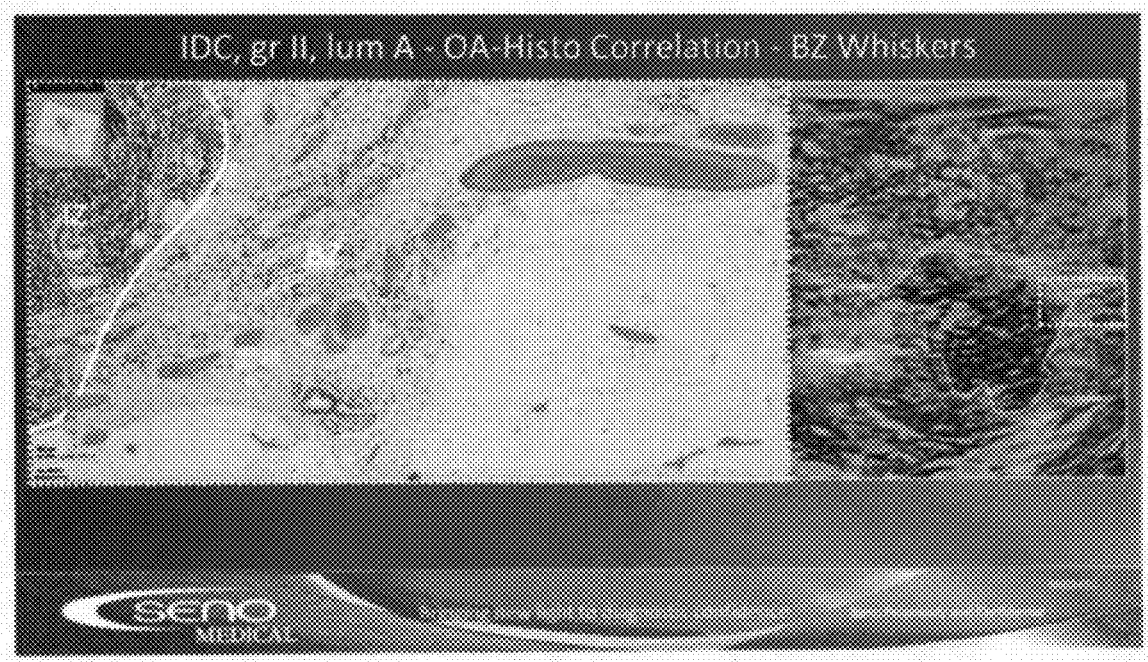
FIG. 7G illustrate an examples of vessel characteristics that may appear in the boundary zone and/or peripheral zone in connection with benign tumors and different types of malignancy molecular subtypes.
Figure 7H:
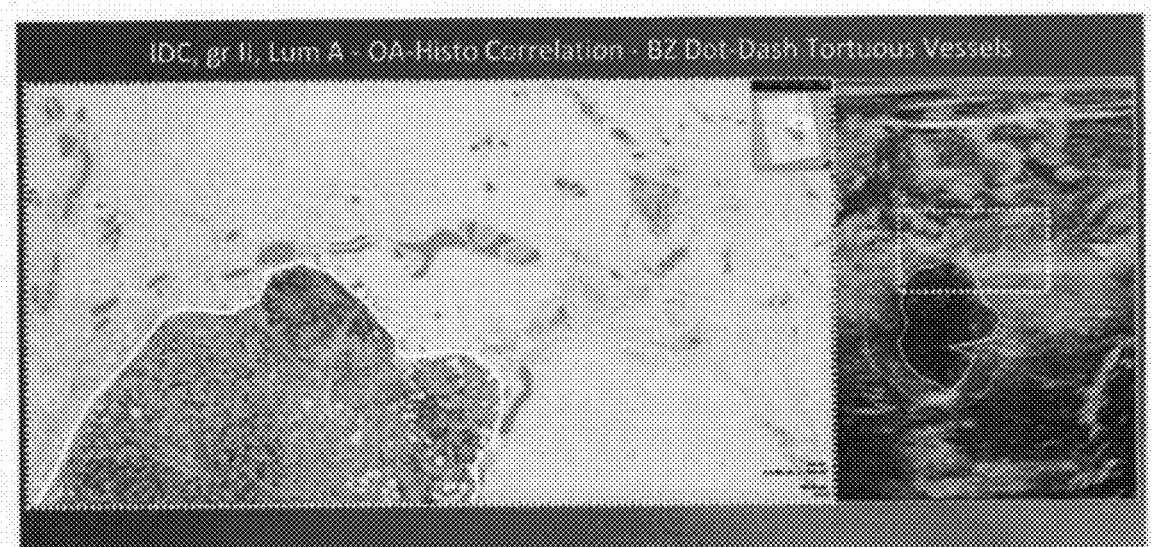
FIG. 7H illustrate an examples of vessel characteristics that may appear in the boundary zone and/or peripheral zone in connection with benign tumors and different types of malignancy molecular subtypes.
Figure 7I:
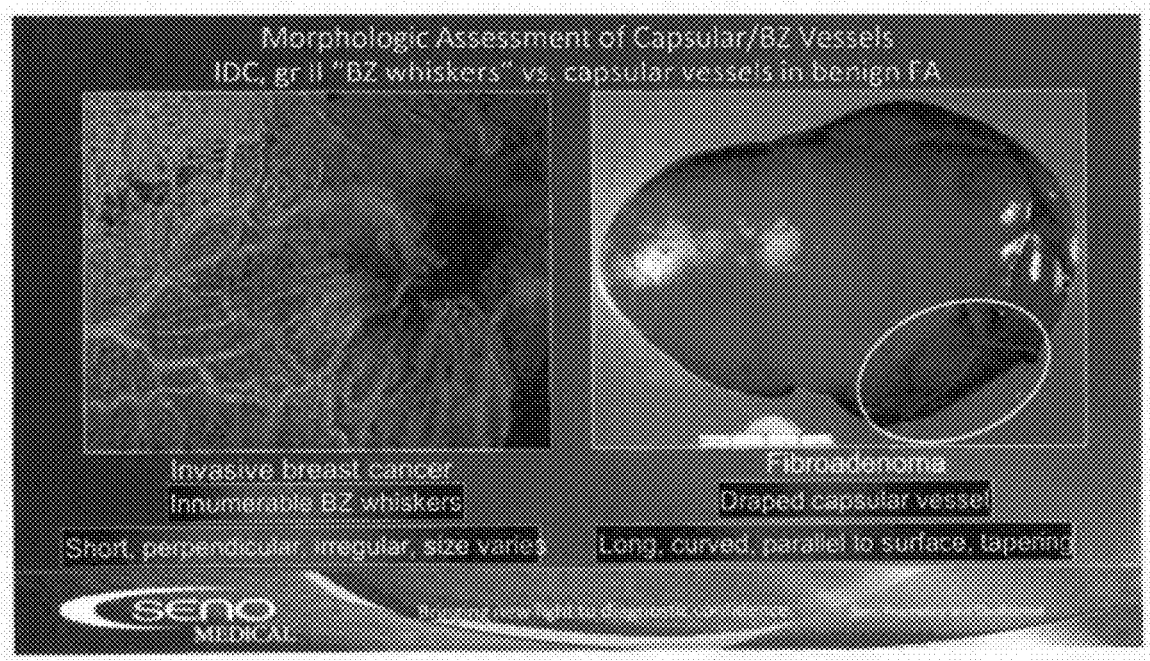
FIG. 7I illustrate an examples of vessel characteristics that may appear in the boundary zone and/or peripheral zone in connection with benign tumors and different types of malignancy molecular subtypes.
Figure 7J:
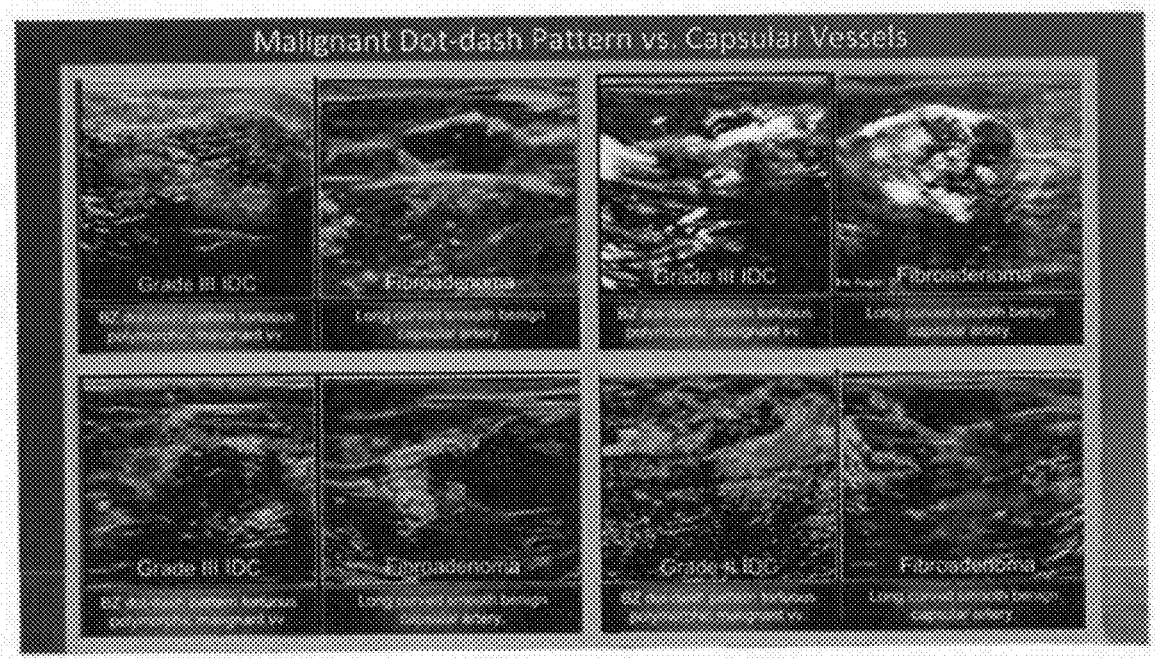
FIG. 7J illustrate an examples of vessel characteristics that may appear in the boundary zone and/or peripheral zone in connection with benign tumors and different types of malignancy molecular subtypes.

FIG. 7C illustrates an enlarged view of another example of vessels. In general, most boundary zone vessels will be generally perpendicular to the surface of the central nidus. Only the largest boundary zone neo-vessels may be demonstrable as individual vessels (e.g. BZ whiskers) in an OA image. When neo-vessels are present in the boundary zone, the neo-vessels may be densely packed and may be too small to be resolved individually (depending upon a level of resolution available). However, the densely packed vessels can be volume averaged and seen as a deoxygenated blush in the OA (to be factored into the deoxygenated blush feature score). The peripheral zone vessels will be generally arranged in parasitized PZ native artery and vein common pairs. Neo-vessels in the peripheral zone may appear tortious and unpaired.

FIGS. 7D-7J illustrate examples of vessel characteristics that may appear in the boundary zone and/or peripheral zone in connection with benign tumors and different types of malignancy molecular subtypes. The vessel characteristics from FIGS. 7D-7J or considered in connection with the OA capsular/boundary zone vessel feature score.

By way of example, the OA capsular/boundary zone vessel feature score may be assigned an integer value between 0-6, each of which has a corresponding probability of malignancy as noted, such as based on the following:

0=No capsular vessels (BR 4A, >2%-<=10% POM)
1=Normal capsular vessels without branches, parallel to capsule, not perpendicular, long, gently curved, and gradually tapered (green &/or red) (BR 4A, >2%-<=10% POM)
2=Normal capsular vessels with normal tapering acutely angled branches, (green &/or red) (BR 4A, >2%-<=10% POM)
3=Boundary zone speckle—green >red in amount and red <background red (upper BR 4B, >25% POM)
4=Boundary zone speckle—red >green and red >background red (upper BR 4B, >25% POM)
5=Multiple boundary zone neovessels—short red and/or green perpendicular "whiskers" or red enlarged tortuous vessels in "dot-dash" pattern) (lower BR 4C, <=75% POM)
6=Boundary zone deoxygenated blush (partial or complete) (lower BR 4C, <=75% POM).

The OA capsular/BZ vessel score can be obtained from one or more of the OA combined map, OA total map and OA relative map.

Figure 7K:
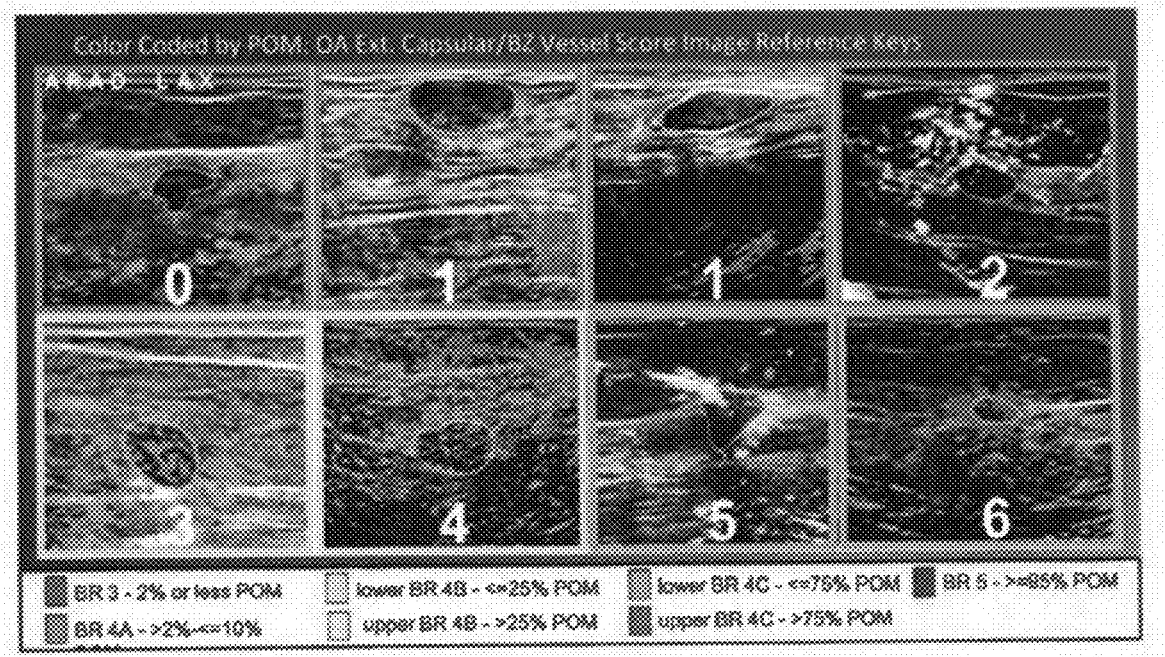
FIG. 7K illustrates an example of an image key for images with different OA boundary zones that warrant corresponding different OA capsular/BZ vessel feature scores 0-6.
Figure 7L:
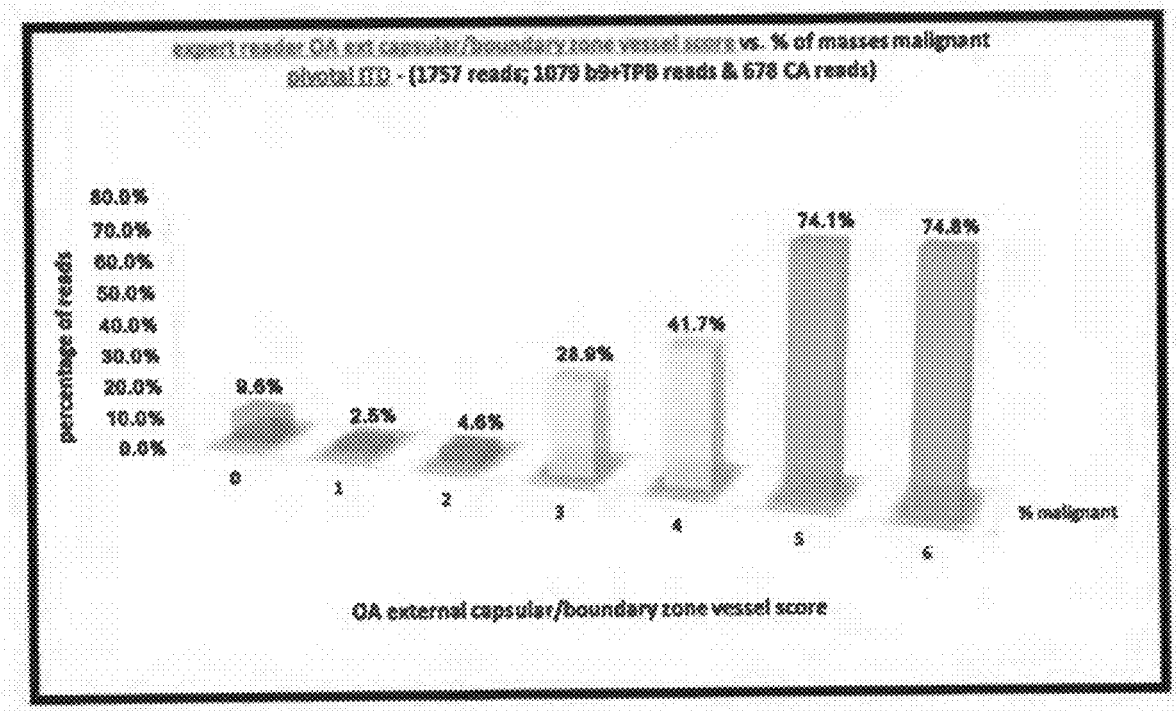
FIG. 7L illustrates an example of a relation between positive predictive values and OA capsular/BZ vessel feature scores.

FIG. 7K illustrates an example of an image key for images with different OA boundary zones that warrant corresponding different OA capsular/BZ vessel feature scores 0-6. The lower margin of FIG. 7K illustrates corresponding probabilities of malignancy associated with the different OA capsular/BZ vessel feature scores. FIG. 7L illustrates an example of a relation between positive predictive values and OA capsular/BZ vessel feature scores. As shown in FIG. 7L, the OA capsular/BZ vessel scores are a good positive predictor of malignancy. In addition, in accordance with new and unique aspects herein, it was found that the OA capsular/BZ vessel score, when taken by itself, also affords a good negative predictor of the absence of malignancy. The OA capsular/BZ vessel score should still be combined with other feature scores that have low POMs at scores of 0 and 1 in order to exclude cancer.

In accordance with new and unique aspects herein, it was found that a capsular/BZ vessel feature score of 5 should be assigned when a dotted or dashed pattern of tortious morphologic vessels is present in the boundary zone. It was also found that vessels exhibiting a whisker pattern in the boundary zone are typically present in histologic grade I and II invasive breast cancers and in luminal A molecular subtype invasive breast cancers. It was also found that vessels exhibiting the dotted or dashed pattern in the boundary zone or more typical in histologic grade III invasive breast cancers and triple-negative molecular subtype invasive breast cancers.

Further, in accordance with new and unique aspects herein, it was found that the OA capsular/BZ vessel feature score represents a very robust (if not the most robust) score of the OA feature scores described herein for distinguishing benign from malignant masses and assessing the POM of the mass. Between benign and malignant masses, the capsular/BZ vessel feature score exhibits a very good (e.g. if not the best) visual separation of scoring distributions, a very wide (if not the widest) separation of means, 99% CIs, medians and interquartile ranges, and a very steep (if not the steepest)

PPV slope with the second highest PPV for high scores and the lowest PPV for low scores (relative to the other OA features described herein).

In the event that changes are mistakenly assigned to the internal zone, where such changes should have been assigned to the boundary zone, they miss assignment may lead to an underestimation of the POM. Accordingly, an accurate distinction between the internal and boundary zones should be drawn with the interior outline of the ROI. Histologic correlation from various exams show that the interior outline separating the internal and boundary zone should typically be drawn 0.5-1.0 mm inside of the border between the hyperechoic central nidus and the boundary zone (thick echogenic rim—Halo).

Figure 7M:
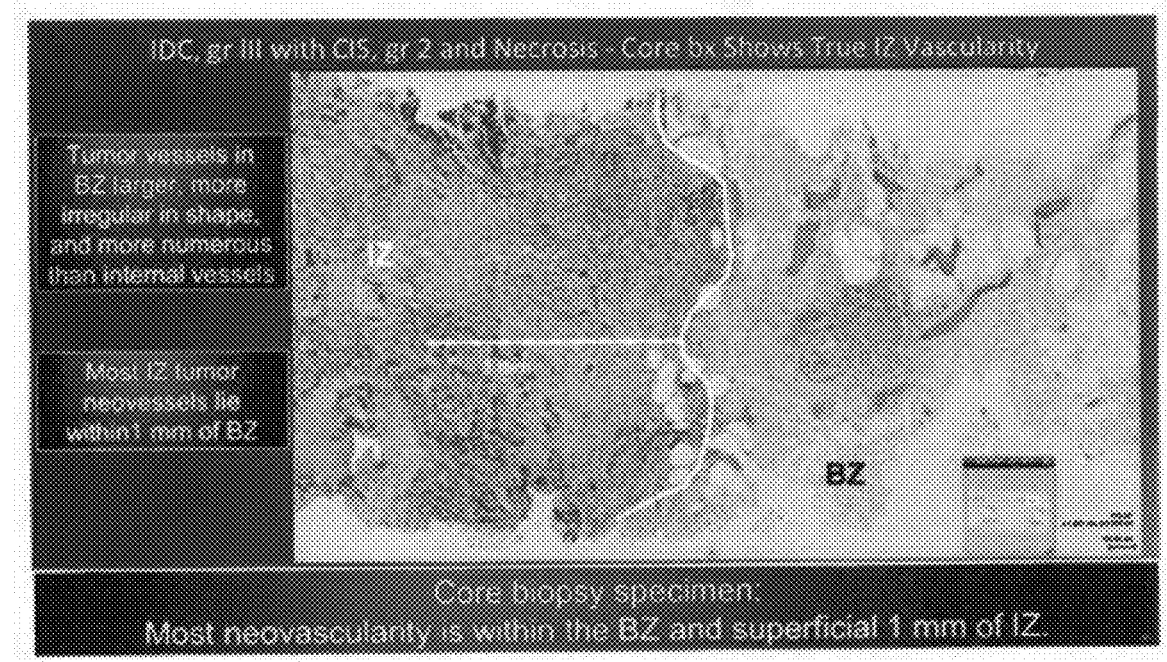
FIG. 7M illustrates an example of how to draw the interior outline between the internal zone and the boundary zone.
Figure 7N:
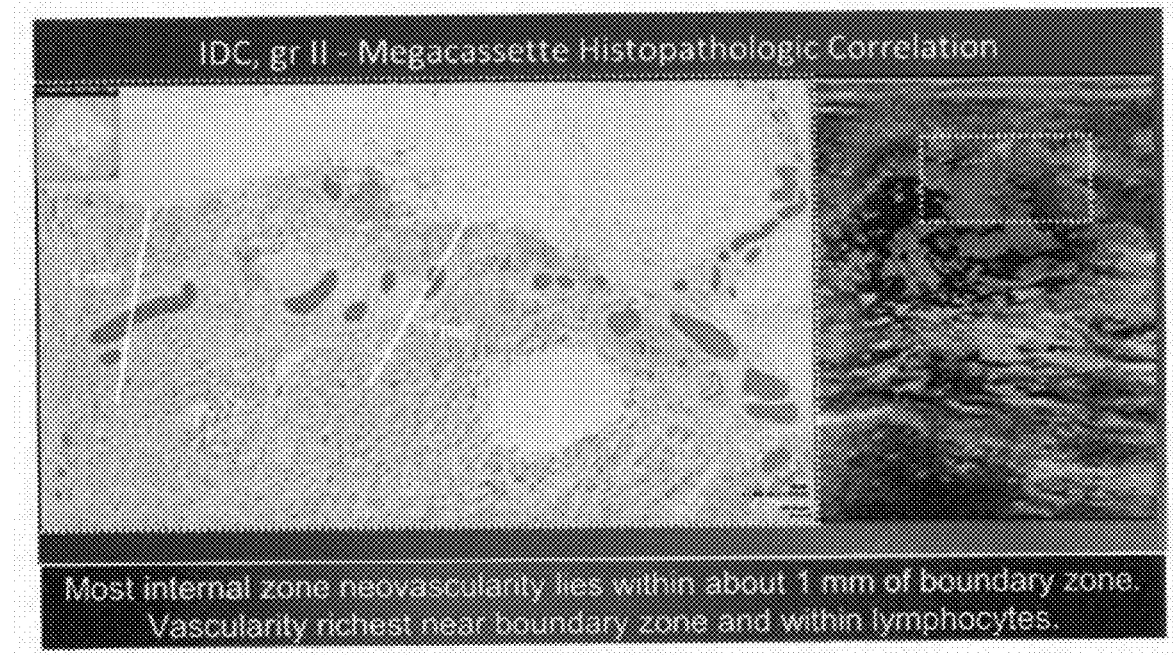
FIG. 7N illustrates a further example of how the neovascularity lies within about 1 mm of the interior outline separating the internal zone from the boundary zone.

FIGS. 7M and 7N illustrate examples of how to draw the interior outline between the internal zone and the boundary zone. As shown in FIG. 7M, tumor vessels in the BZ are larger, more irregular in shape and more numerous than vessels within the internal zone. Eyes E tumor Neil vessels lie within 1 mm of the boundary zone. In accordance with embodiments herein, it has been found that a majority of the neo-vascularity is within the BZ and superficial exterior 1 mm of the IZ. FIG. 7N illustrates a further example of how the neovascularity lies within about 1 mm of the interior outline separating the internal zone from the boundary zone. The vascularity is the richest near the boundary zone and within lymphocytes.

In accordance with new and unique aspects herein, it is been found that boundary zone changes may affect part of the boundary zone. For example, in shadowing masses, only the boundary zone findings that lie anterior to the acoustic shadowing may be present. In circumscribed cancers, the path of lowest resistance to invasion is along the sides of the mass within the coronal plane. The side portion of the mass in the coronal plane is where the thick halo forms and wear short boundary zone spicules form. The side portion of the mass in the coronal plane is where malignant neovessels tend to form within or run parallel immediately beside spicules.

In accordance with new and unique aspects herein, it is been found that boundary zone changes that affect only part of the boundary zone (e.g. more than 20%) should be considered to affect the entire boundary zone. For example, a boundary zone blush that is visible only anterior to a shadowing mass should be considered the same as a complete boundary zone blush score of 6. As another example, boundary zone vessels in a whisker pattern that are only seen on one or both sides of the mass (within the coronal plane) should be considered a positive characteristic for boundary zone vessels having a whisker pattern and afforded a score of 5.

Figure 7O:
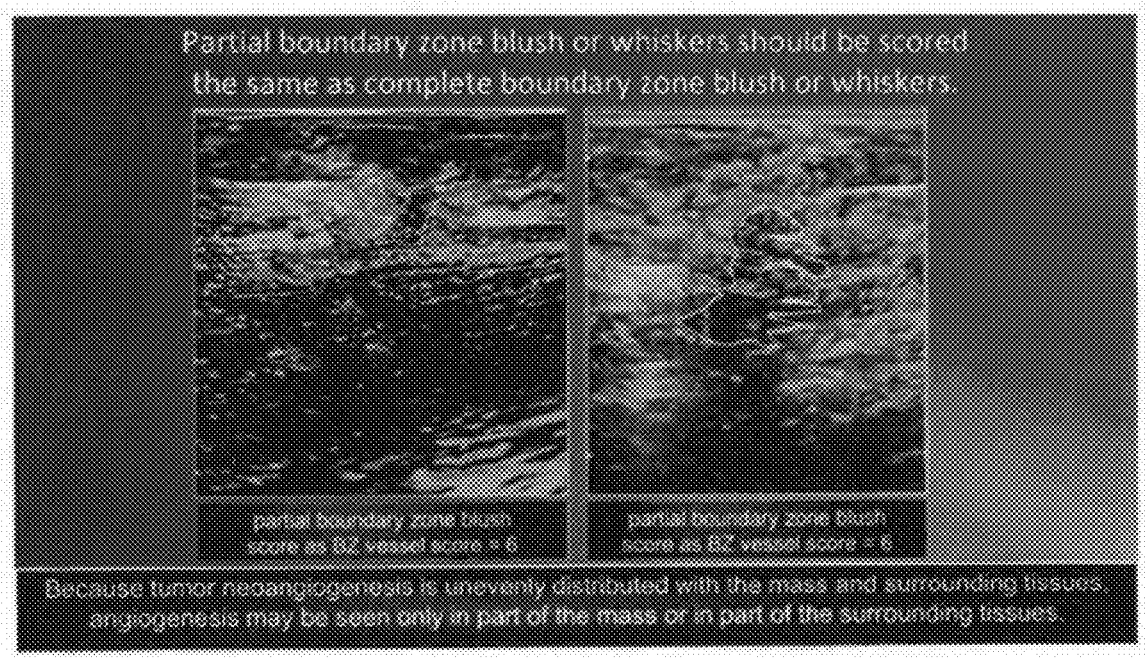
FIG. 7O illustrates example images of partials boundary zone blush or whiskers that should be scored the same as complete boundary zone blush or whiskers.
Figure 7P:
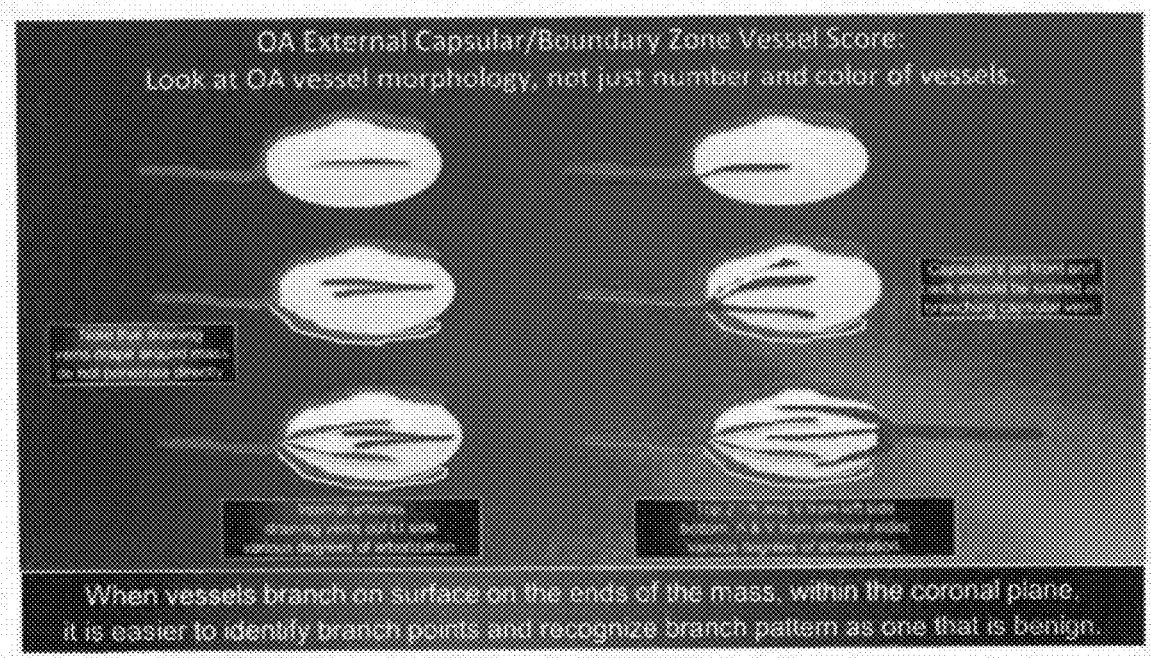
FIG. 7P illustrates examples of vessel morphology characteristics to be considered in connection with assigning a score for the capsular/BZ vessel feature.
Figure 7Q:
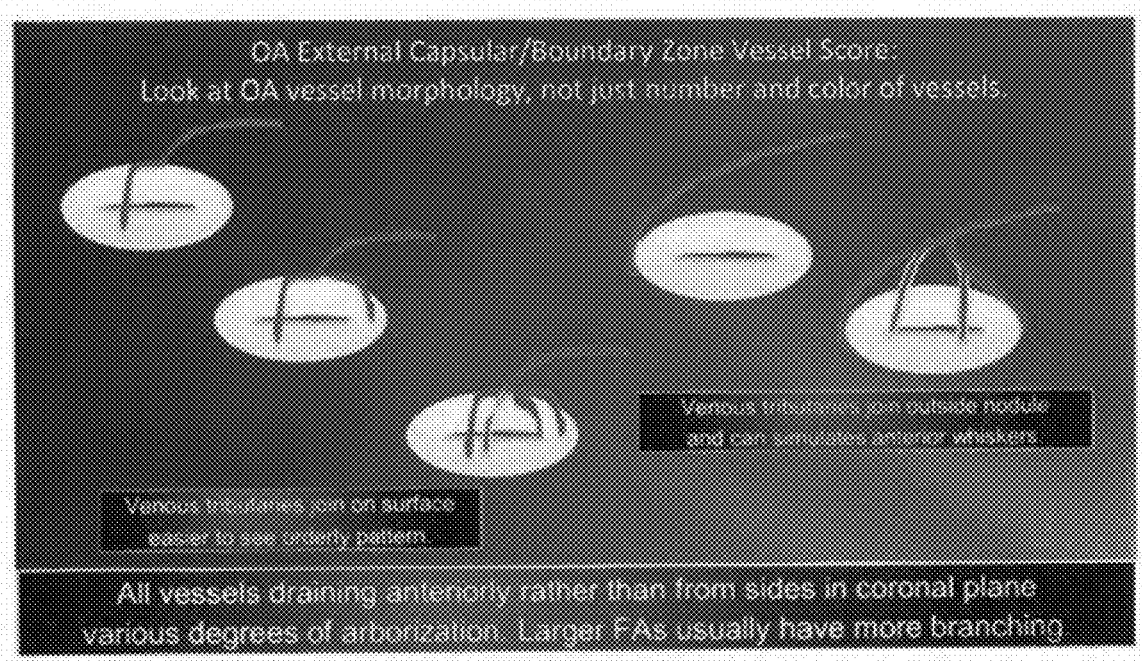
FIG. 7Q illustrates an example of vessel morphology characteristics to be considered in connection with assigning a score for the capsular/BZ vessel feature.
Figure 7R:
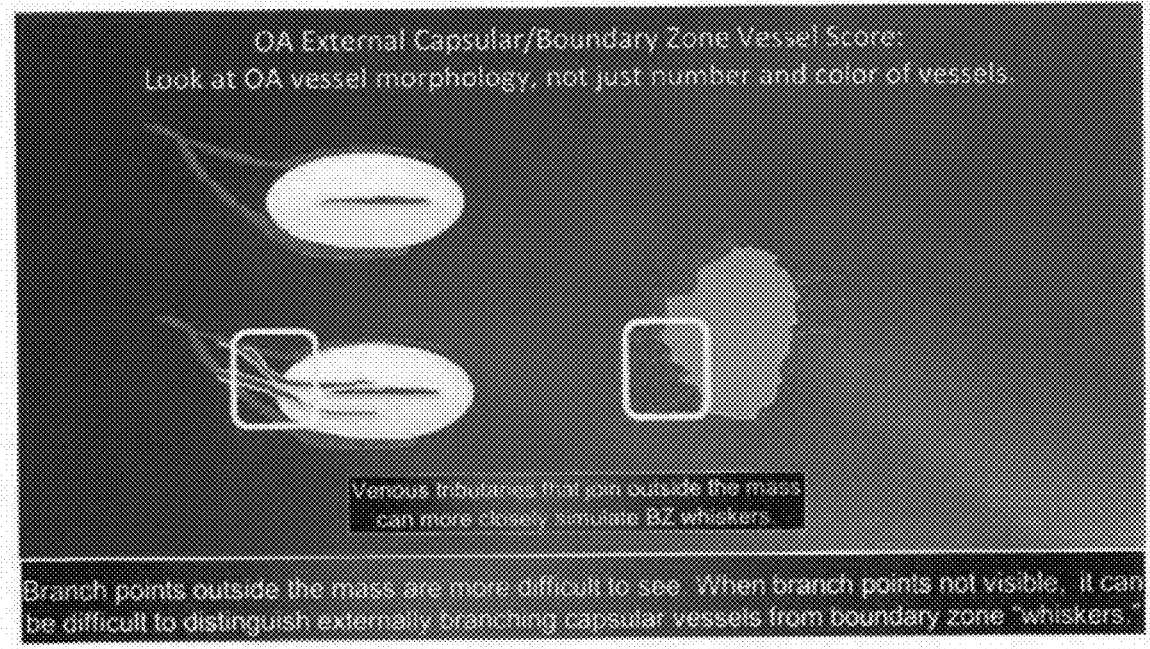
FIG. 7R illustrates examples of vessel morphology characteristics to be considered in connection with assigning a score for the capsular/BZ vessel feature.

FIG. 7O illustrates example images of partials boundary zone blush or whiskers that should be scored the same as complete boundary zone blush or whiskers. Treating a partial boundary zone change as if the change affected the entire boundary zone accounts for the fact that tumor neoangiogenesis is un-evenly distributed within a mass and surrounding tissue and thus angiogenesis may be seen only in part of the mass or in part of the surrounding tissue.

In accordance with new and unique aspects herein, it has been found that most boundary zone vessels and malignant masses are neovessels, but some are parasitized native vessels. Boundary zone neovessels are usually, but not always, relatively deoxygenated, although a very strong red signal (indicating deoxygenated blood) elsewhere in the image could cause the vessels to be mis-color to green (incorrectly indicating oxygenated blood). Boundary parasitized native vessels can be either arteries or veins, and thus, can be relatively oxygenated (appearing in green color) or relatively deoxygenated (appearing in red color). Thus, the boundary zone vessels having a whisker pattern can be relatively deoxygenated (red) in most cases, relatively oxygenated (green) in most cases, or mixed red and green.

In accordance with new and unique aspects herein, it has been determined what extent of the boundary zone vessels should exhibit the whisker pattern to be classified as exhibiting a vessel whisker characteristic. The more vessels that exhibit the whisker pattern, the more confident the characterization. The amount of vessels exhibiting a whisker pattern necessary to classify a vessel whisker characteristic may be proportional to the background tissue OA signal. In images with a high background OA tissue signal present, it is preferable to have a larger amount of vessels exhibiting the whisker pattern. In images with a low the background signal and good colorization, it may be acceptable to have a smaller amount of vessels exhibit the whisker pattern.

The whisker pattern in the background zone vessels should be distinguished from interference lines. More perpendicular BZ signals have better PPV than fewer perpendicular OA easy signals. More red (deoxygenated) perpendicular BZ signals have better PPV than green (oxygenated) perpendicular OA BZ signals. If three or fewer perpendicular OA BZ signals are present, radiating perpendicular signals have better PPV as compared to parallel concave anterior OA BZ signals (which are more likely interference lines). While a mixture of OA functional information (relative oxygenation/ED oxygenation) and also morphology are used for all OA feature scores, vessel morphology is generally more important than oxygenation/D oxygenation in the external capsular/boundary zone.

FIGS. 7P-7S illustrate examples of vessel morphology characteristics to be considered in connection with assigning a score for the capsular/BZ vessel feature.

OA Capsular/Boundary Zone Vessel Score

In accordance with new and unique aspects herein, an OA peripheral zone vessel feature score is defined that provides a mechanism to robustly distinguish between benign and malignant masses. By way of example, the OA peripheral zone vessel feature score may be assigned an integer value between 0-5, each of which has a corresponding probability of malignancy as noted, such as based on the following:

0=No PZ vessels (lower BR 4B, <=25% POM)
1=Normal non-branching or branching non-radiating vessels in surrounding tissues (lower BR 4B, <=25% POM)
2=Cluster of enlarged, tortuous non-radiating vessels in PZ on one side of mass. (Upper BR 4B, >25% POM)
3=One or two radiating PZ vessels on one side of mass (lower BR 4C, <=75% POM)
4=More than two radiating vessels on one side of mass (upper BR 4C, >75% POM)
5=3 or more radiating vessels on more than one side of mass (i.e., 2 on 1 side, and 1 on another side) (upper BR 4C, >75% POM)

Figure 8A:
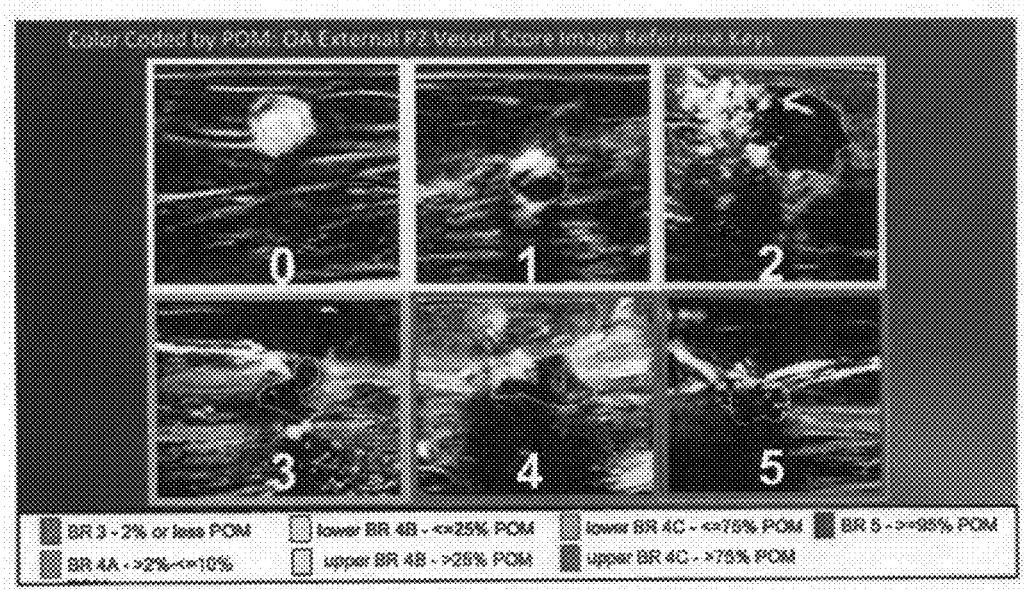
FIG. 8A illustrates an example of an image key for images with different OA peripheral zones that warrant corresponding different OA peripheral zone vessel feature scores 0-5.
Figure 8B:
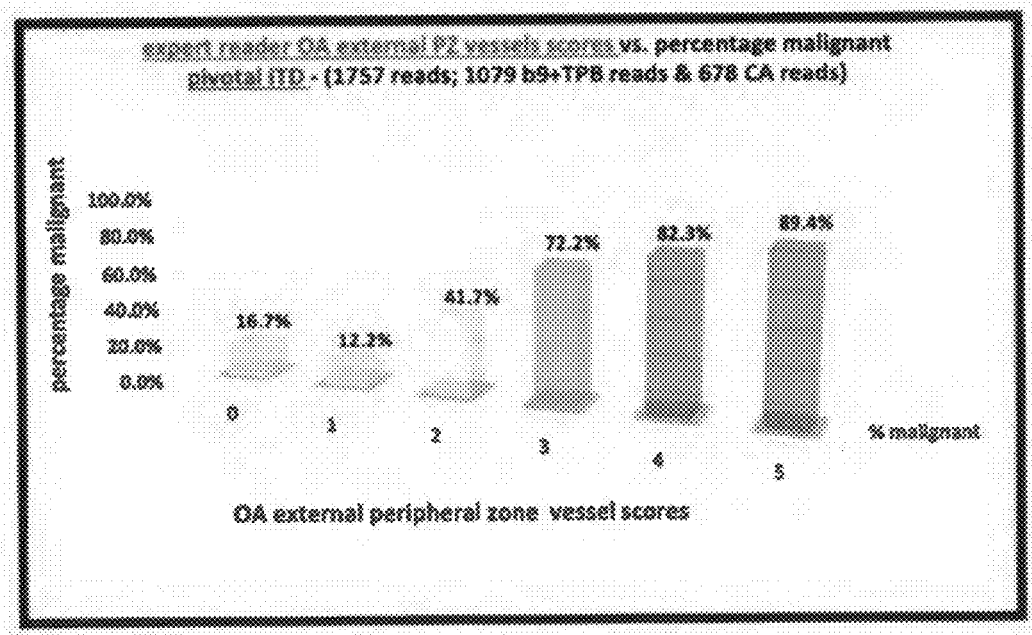
FIG. 8B illustrates an example of a relation between positive predictive values and OA peripheral zone vessel feature scores.

The peripheral zone vessel feature score may be best determined from the OA total map, but optionally may be determined from one or more other maps. In determining the peripheral zone vessel score, care should be taken to distinguish between PC radiating vessels as compared to interference lines. FIG. 8A illustrates an example of an image key for images with different OA peripheral zones that warrant corresponding different OA peripheral zone vessel feature scores 0-5. The lower margin of FIG. 8A illustrates corresponding probabilities of malignancy associated with the different OA peripheral zone vessel feature scores. FIG. 8B illustrates an example of a relation between positive predictive values and OA peripheral zone vessel feature scores. As shown in FIG. 8B, the OA peripheral zone vessel scores are a good positive predictor of malignancy, and potentially the best PPV as compared to other OA features described herein. However, the peripheral zone feature score may not be a good negative predictor of an absence of malignancy when taken alone, but instead should be combined with one or more other OA feature scores that have lower POMs at scores of 0 and 1 in order to exclude cancers.

In accordance with new and unique aspects herein, it has been recognized that an OA PZ vessel feature score may be applied in a manner similar to the BZ feature scoring and relies more heavily upon vessel morphology then on relative degrees of oxygenation/deoxygenation. In malignant masses, most vessels within the internal zone are relatively deoxygenated neovessels. In the peripheral zone, most vessels or a mixture of oxygenated parasitized native arteries and parasitized deoxygenated native veins. Therefore, in the peripheral zone there will be a mixture of red (deoxygenated) and green (oxygenated) vessels. A more important characteristic of the vessels in the peripheral zone is whether the vessels are radiating or not.

It has been recognized that the OA peripheral zone vessel features are generally most visible on the OA total hemoglobin map. Visibility on the OA total hemoglobin map is due in part to the peripheral zone radiating vessels around invasive malignant masses having mixed oxygenated and deoxygenated vessels which appear as red and green vessels. Is more difficult to appreciate the number of radiating vessels when the vessels are different in color as they are in the OA relative map and/or the OA combined map. In contrast, it is easier to appreciate the number of radiating vessels when they are a single color, such as when the vessels appear in yellow in the OA total hemoglobin map or all appear white as in the OA short wavelength map or OA long wavelength map. The OA total map is subjected to a threshold and us has less interfering background OA noise that surrounds the PZ radiating vessels as compared to the background OA signals in the OA relative map. Parallel adjacent parasitized radiating arteries and veins that appear in the same foxhole can cancel out one another on the OA relative and OA combined maps. However, parallel adjacent parasitized radiating arteries and veins, that appear in the same voxel, can add to each other in the total hemoglobin map.

Figure 8C:
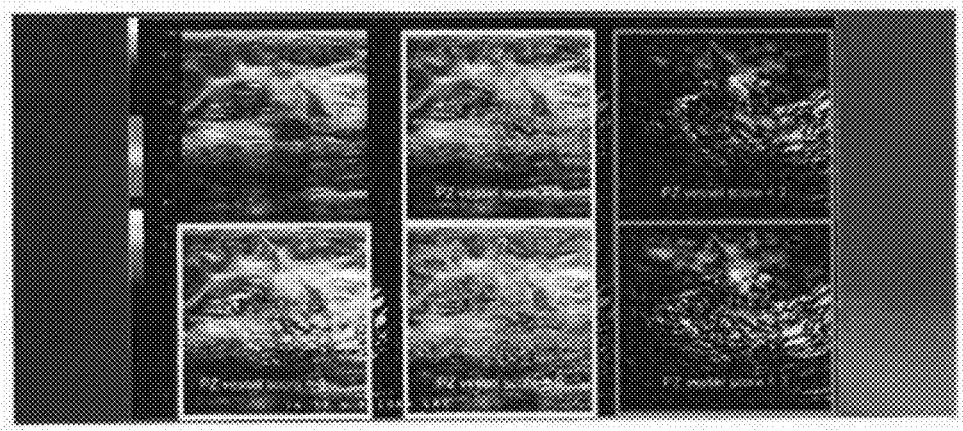
FIG. 8C illustrates examples of radiating vessels in the peripheral zone that can be seen on the OA total map, but not necessarily on the other OA maps.
Figure 8D:
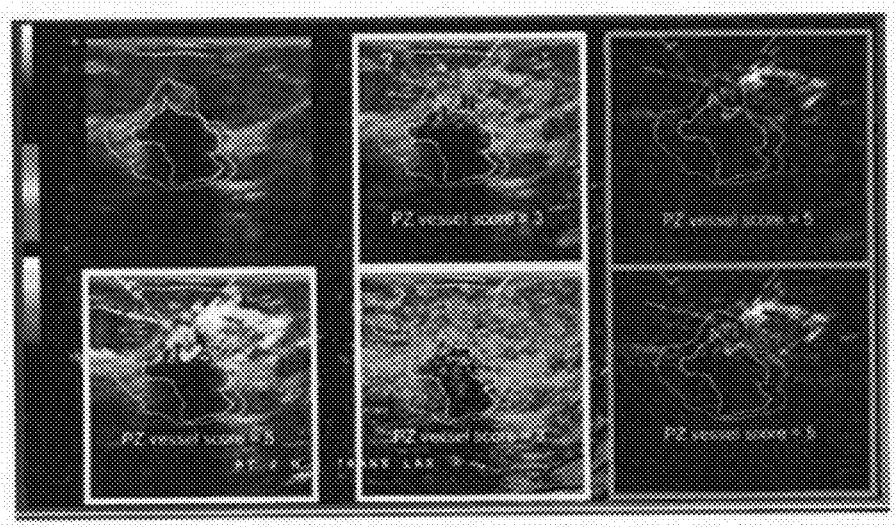
FIG. 8D illustrates two adjacent voxels, with the upper row corresponding to an artery and vein in separate adjacent image voxels, and with the lower row corresponding to an artery and vein in a single voxel of an image.
Figure 8E:
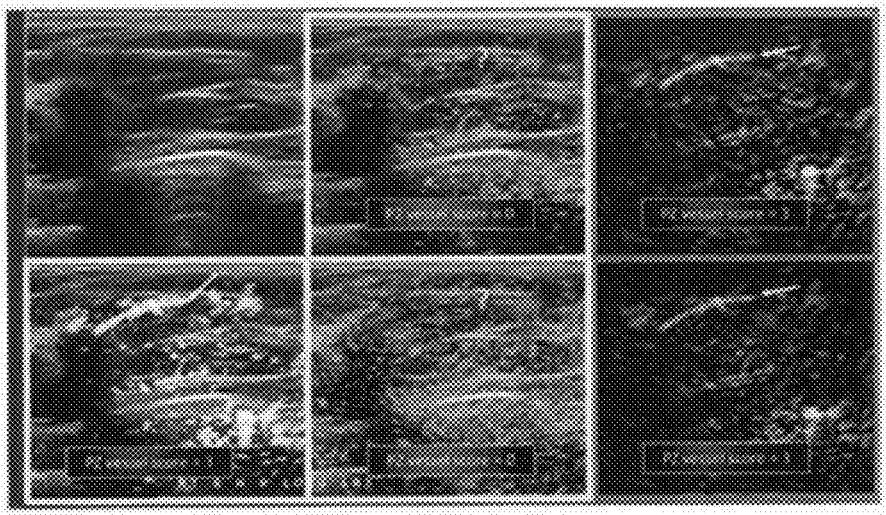
FIG. 8E illustrates examples of radiating vessels in the peripheral zone that can be seen on the OA total map, but not necessarily on the other OA maps.
Figure 8F:
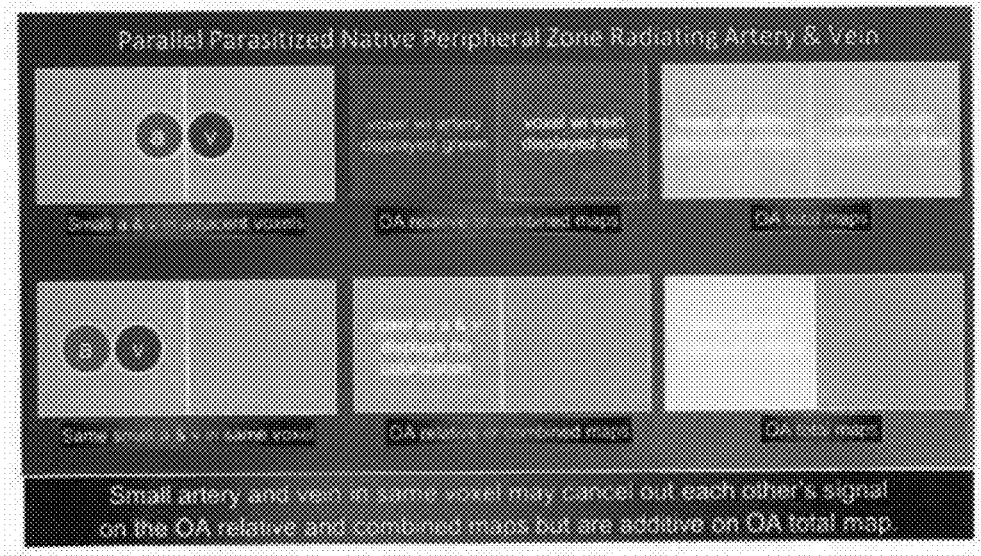
FIG. 8F illustrates how parallel parasitized native peripheral zone radiating arteries and veins are imaged when appearing in a single voxel or adjacent voxels of an image.

FIGS. 8C-8E illustrate examples of radiating vessels in the peripheral zone that can be seen on the OA total map, but not necessarily on the other OA maps. As a confirmation, the OA short wavelength map and OA long wavelength map may be analyzed to determine whether the same PC radiating vessels are present. FIG. 8F illustrates how parallel parasitized native peripheral zone radiating arteries and veins are imaged when appearing in a single voxel or adjacent voxels of an image. FIG. 8D illustrates two adjacent voxels, with the upper row corresponding to an artery and vein in separate adjacent image voxels, and with the lower row corresponding to an artery and vein in a single voxel of an image. When the artery and vein are in separate adjacent voxels (upper row of FIG. 8D), in the OA relative and combined maps, the left voxel will display green, while the right voxel will display red. In the OA total map, both voxels will display yellow (for the artery and for the vein). When the artery and vein are in the same voxel (lower row of FIG. 8D), in the OA relative and OA combined maps, no colorization is displayed. In the OA total map, the corresponding voxel is displayed in yellow.

In accordance with new and unique aspects herein, it has been recognized that the OA long wavelength and OA short wavelength maps can be very useful in confirming the presence of peripheral zone radiating vessels. The peripheral zone reading vessels on the grade OA long wavelength and short wavelength maps are the OA counterpart of architectural distortion and mammography. Radiologists are used to looking for architectural distortion on a grayscale background mammography image. The OA short wavelength and long wavelength maps often show longer segments of the peripheral zone radiating vessels then do any of the three color maps (OA total hemoglobin map, OA relative map and OA combined map).

The number of peripheral radiating vessels in various sides of the mass can be determined from the summation of frames in a complete short axis sweep across a mass. The number of peripheral zone radiating vessels should not be determined from the still OA images or from a single frame of a complete video sweep. In a certain percentage (e.g. 15-20%) of invasive malignant masses, all or most tumor vessels are located in a cluster anteriorly between the mass and the skin. When the foregoing condition is present, the mass should be scored to in the OA PZ vessel features score as "a cluster of enlarged and tortious PZ vessels on the side of the mass". A pattern of a cluster of tumor vessels within the anterior boundary zone and peripheral zone of the tumor is relatively common in the subgroup of DCIS that represents a mammographic soft tissue density or palpable mass. The cluster pattern may also be seen in some invasive cancers. While the PPV of a tumor vessel cluster pattern is less than the PPV of peripheral zone radiating vessels, it does have a mild BI-RADS 4B PPV of about 40%.

OA Interfering Artifact Feature Score

In accordance with new and unique aspects herein, an OA interfering artifact feature score is defined that provides a mechanism to robustly distinguish between benign and malignant masses. By way of example, the OA interfering artifact feature score may be assigned an integer value between 0-5, such as based on the following:

0=No significant artifact
1=Minimal artifact, does not interfere with interpretation
2=Moderate artifact, does not interfere with interpretation
3=Moderate artifact, interferes with interpretation
4=Severe artifact, interferes with interpretation
5=Severe artifact, makes OA images uninterpretable.

Figure 9:
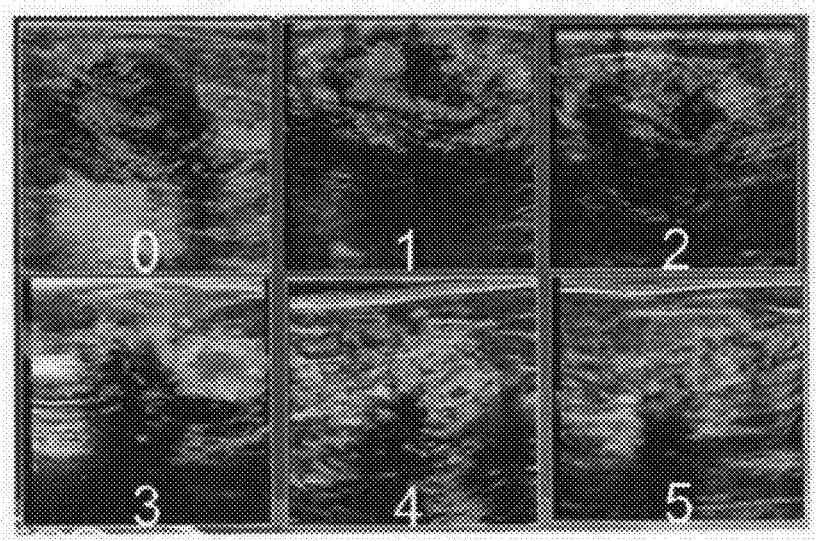
FIG. 9 illustrates an example of an image key for images that warrant corresponding different OA interference artifact feature scores 0-5.

The OA interfering artifact feature score may be derived from any of the OA maps, usually the worst of the maps or views. FIG. 9 illustrates an example of an image key for images that warrant corresponding different OA interference artifact feature scores 0-5. The OA interfering artifact scores are not necessarily used when estimating a POM. Instead, I know a artifact score suggests reliability of the OA data, such as whether or not to upgrade or downgrade a rating and how aggressive to be when upgrading or downgrading. For example, artifact scores of 0-3 generally imply reliable data and facilitate aggressive upgrading or downgrading (e.g. including to BI-RADS 2). As another example artifact scores of 4 imply somewhat less reliable data, allowing a very careful upgrade or downgrade of 1 Bio-Rad category in some cases, but never a downgrade to BI-RADS 2 or of 2 steps. And artifact score of 5 indicates that the OA data is too unreliable to interpret and suggest that the MG, CDU, and/or US POM and BI-RADS category should be left unchanged.

Feature to Sub-Type Modeling

In accordance with embodiments herein, one or more models are built that described relationships between OA/US feature score levels and molecular subtypes of cancers of interest, as well as histologic grades for different breast cancers. The methods and systems to build the models from various types of inputs. For example, the models receive, as inputs, pathology characteristics of interest (COI), such as tumor hormone receptor (ER and PR), and HER-2neu status, and available ki-67(%) index, all of which may be derived from pathology reports (eg case studies). As a further example, the methods and systems build the models by analyzing individual OA/US feature scores and corresponding tumor molecular subtypes (e.g., Luminal A (LumA), Luminal B (LumB), Triple-negative (TNBC) and HER2 amplified (HER2+)) such as using analysis of variance (ANOVA). The ANOVA results are used to build relations within the models between OA/US feature scores and pathology sub-types. The models build a high level of correlation between the OA/US features and individual sub-types of a particular pathology (e.g., cancer). For example, a ratio of total internal to total external OA/US feature scores (RInt/Ext) can represent an indicator of a certain pathology sub-type.

By way of example, the models derived in accordance with embodiments herein may show that statistical significance can be derived between certain molecular sub-types (e.g., ER+ cancers) and levels for certain OA/US features. For example, a high OA-EXT feature score (e.g, 4, 5, 6) may have a very high or low statistical correlation/significance as an indicator of a first subtype of breast cancer (e.g., LumA, LumB, TNBC and HER2+). As another example, a low OA-INT feature score (e.g., 0, 1, 2) may have a high or low statistical correlation/significance as an indicator of the same or a different subtype of cancer. The models may be derived based on statistical hypothesis testing, where a p-value (probability value or asymptotic significance) is the probability for a given statistical model that, when the null hypothesis is true, the statistical summary (such as the sample mean difference between two compared groups) would be the same as or of greater magnitude than the actual observed results. In the present embodiment, a statistical model may show that the ER+ cancer sub-type exhibits a p-value of high probability when the ROI is assigned a higher OA-EXT feature score. Alternatively or additionally, the statistical model may show that the ER+ cancer sub-type exhibits a lower probability p-value when the ROI is assigned a lower OA-INT feature score.

The methods and systems described herein utilize the models and feature scores to identify various pathology subtypes. Among other things, the methods and systems utilize OA/US to differentiate Luminal A and TNBC from other molecular subtypes and serve as a potential prognostic biomarker. By way of example, OA/US features of Luminal A cancers are significantly different from triple-negative and HER2 amplified cancers. These differences can be identified by the methods and systems herein and utilized to supplement gray-scale findings in connection with non-invasively predicting breast cancer subtype and help guide management decisions. As further examples, models may indicate that high external OA/US feature scores are associated with Luminal A molecular subtype, while high external scores are associated with triple-negative cancers. The OA/US imaging may be utilized as a biomarker of breast cancer prognosis. Correlating OA/US features of breast cancers with molecular markers can help monitor response to therapy and guide treatment decisions.

Molecular Subtypes

Cancers may be divided into molecular subtypes that differ genetically and epigenetically in ways that can affect treatment decisions. By diagnosing molecular subtypes, medical oncologist can better decide how to treat a patient with neoadjuvant adjuvant therapy, a form of precision medicine or personalized medicine. In an ideal situation, molecular subtypes are diagnosed by obtaining a biopsy from a suspicious mass and performing multi-gene assays to the suspicious mass. However, multi-gene analyses are expensive, often not approved for re-imbursement by $3^{rd}$ party payers, and therefore, have not routinely been ordered by physicians. Instead, physicians have routinely used surrogate receptor information (ER, PR, HER2, and Ki67) for molecular subtyping. The OA and US data have been correlated with molecular subtypes established with surrogate receptor data rather than directly with multi-gene analyses.

In accordance with new and unique aspects herein, it has been recognized that a surrogate for the multigene assay may implemented to identify an estrogen receptor status, progesterone receptor status, HER-2 receptor status and a presence/extent of KI-67 protein. In accordance with new and unique aspects herein, it has been shown that OA/US images may be analyzed and scored, based on feature scores described herein, to identify a presence or extent of the ER status, PR status, HER-2 receptor status and KI-67. Further, it has been determined how to identify molecular subtypes of cancer based on the presence/extent of the receptors and proteins of interest.

The molecular subtypes considered herein include luminal A, luminal B, HER-2 and triple-negative molecular subtypes. Traits of the luminal A subtype include: ER and/or ER positive and HER2 negative; Ki-67<14. Traits of the luminal B subtype include: ER and/or PR positive and HER2 negative, but Ki-67≥14, or ER and/or PR positive and HER2 positive. Traits of the HER-2 subtype include: ER and PR negative and HER2 positive (e.g. HER2 IHC test 3+ or HER2 IHC test 2+ and HER2 FISH is amplified). Characteristics of the Triple negative (TNBC) subtype include: ER and PR and HER2 all negative. By way of example, approximately 70% of breast cancers may have a luminal molecular subtype, from which approximately 55% are luminal A and 15% are luminal B. Of the remaining 30%, approximately 15% are basal-like, while 15% are approximately HER-2 enriched.

The luminal A molecular subtype is the most common, is thought to arise from luminal epithelial cells of ducts, is generally unifocal (e.g. 72.7%) versus multifocal (e.g. 27.3%). The ER status is very positive, the PR status is very positive, while the HER-2 status is negative. The lumen A molecular subtype exhibits low KI-67 (e.g. less than 14%), response to tamoxifen, aromatase inhibitors. The survival rate is greater than 80% at five years, with a risk of recurrence after 10 years higher than other molecular subtypes. There is a tendency toward bone metastasis and a typical path report may indicate grade I (irregular shape, spiculated) ER=100%, PR=100%, HER-2=negative and KI-67=5.

The lumen B molecular subtype occurs in approximately 15% of all breast cancers, and is thought to arise from luminal epithelial cells of duct. The luminal B subtype is multifocal or multicentric in approximately 53.3% of cases. The ER status and PR status are more weakly positive (relative to luminal A), while the HER-2 status is negative in approximately 70% of cases and positive in approximately 30% of cases. The luminal B subtype exhibits high KI-67 (e.g. greater than 14) and a high P53 gene mutation rate (e.g. 32% for luminal B versus 12% for luminal A). The luminal B subtype response to tamoxifen and aromatase inhibitors, but also needs chemotherapy. There is a lower survival rate (e.g. about 40% after five years), with a tendency towards bone metastasis and a typical path report may indicate grade II-III (irregular shape, indistinct margins) ER=30%, PR=10%, HER-2=+1 and KI-67=25.

The HER-2 molecular subtype occurs in 15% of all breast cancers and is thought to arise from luminal epithelial cells of duct. The HER-2 subtype is multifocal or multicentric in a proximally 65% of cases, and exhibits the highest percentage of positive L ends. Approximately 30-40% of cases may have some ER/PR progression, with 60% of the cases exhibiting an over express HER-2 status, and a high KI-67 greater than 14. A higher p53 gene mutation rate (e.g. 75%) is present, and a higher percentage of cases exhibit extensive DCIS components. The HER-2 molecular subtype response to trastuzumab/pertuzamab, targeted anti-HER2 drugs, exhibits approximately a 31% survival at five years and a high recurrence rate. The HER-2 subtype has a tendency toward brain, liver and lung metastases. A typical path report may indicate grade II-III (irregular shape, indistinct margins) ER=negative, PR=negative, HER-2=3+ and KI-67=69.

The TNBC (basal-like) molecular subtype occurs in 15% of all breast cancers and is thought to arise from myoepthiali (basal) cells of duct (56-85% are TNBC). The TNBC molecular subtype is usually unifocal, exhibits more common BRCA1 mutations, more common in individuals with African American heritage, exhibits a high P53 gene mutation rate (e.g., 82%), a lower rate of LN mets (e.g., spreads hematogenously early), exhibits more chance of presenting as interval cancer, less associated with DCIS, a high recurrence rate in years 1-4, and a tendency toward brain, liver and lung metastases. A typical path report may indicate grade II-III (irregular shape, indistinct margins) ER=negative, PR=negative, HER-2=negative and KI-67=70.

In accordance with new and unique aspects herein, it has been recognized that OA/US feature scores are a strong prognostic indicator or biomarker for molecular subtypes. In accordance with new and unique aspects herein, it has been recognized that certain characteristics of sound transmissions exhibit a predictable relation to certain molecular subtypes. The feature scoring processes described herein distinguish TNBC from other molecular subtypes (e.g., $p=1.164\times10^{-13}$), distinguish Luminal A from other molecular subtypes (e.g., $p=4.2103\times10^{14}$), and distinguishes HER2 from other molecular subtypes (e.g., $p=0.003$). Three primary clinical and pathologic prognostic indicators for breast cancer include size, histologic grade and lymph node (LN) status. Sound transmission represents a very powerful biomarker for ER, PR, HER-2 and KI-67. For example, in connection with cases analyzed herein, the following correlation to sound transmission was found:

- Correlates with ER Status. ($p=9.8713\times10-16$)
- Correlates with PR Status. ($p=3.6206\times10-15$)
- Distinguishes ER+/PR+ from ER+/PR− ($p=0.003$)
- Correlates with HER2 Status ($p=0.008$)
- Correlates with continuous Ki-67. ($p=5.1302\times10-13$)
- Helps distinguish negative axillary LNs from positive axillary LNs. ($p=0.013$)

FIGS. 11 A-11E illustrate examples of correlation between sound transmission and particular molecular subtypes. FIG. 11A illustrates a correlation between the shadowing and enhanced sound transmission characteristic versus ER status. The left panel shows that, when a US image exhibits enhanced sound transmission, the mass is 3.8 times more likely to be ER negative, as compared to ER positive. The right panel shows that, when the US image exhibits partial or complete shadowing, the mass is 3.6 times more likely to be ER positive than ER negative. FIG. 11B illustrates a correlation between the shadowing and enhanced sound transmission characteristic versus PR status. The left panel shows that, when a US image exhibits enhanced sound transmission, the mass is 3.8 times more likely to be PR negative, as compared to PR positive. The right panel shows that, when the US image exhibits partial or complete shadowing, the mass is 2.3 times more likely to be PR positive than PR negative. FIG. 11C illustrates a correlation between the shadowing and enhanced sound transmission characteristic versus EP and PR status. The left panel shows that, when a US image exhibits enhanced sound transmission, the mass is 2.7 times more likely to be ER positive and PR negative, as compared to ER positive and PR positive. The right panel shows that, when the US image exhibits partial or complete shadowing, the mass is 1.4 times more likely to be ER positive and PR positive as compared to ER positive and PR negative. FIG. 11D illustrates a correlation between the shadowing and enhanced sound transmission characteristic versus HER-2 status. The left panel shows that, when a US image exhibits partial enhanced sound transmission, the mass is 2.0 times more likely to be HER-2 positive as compared to HER-2 negative. The right panel shows that, when the US image exhibits partial or complete shadowing, the mass is 1.8 times more likely to be HER-2 negative as compared to HER-2 positive. FIG. 11E illustrates an example of an image reference key to be utilized in connection with scoring partially enhanced sound transmission. The reference image key in the left panel corresponds to a BI-RADS rating of upper BR 4B, while the reference image key in the right panel corresponds to a BI-RADS rating of lower BR 4C. Partially enhanced sound transmission was a minor feature that was seen primarily in cancers of the HER2 amplified molecular subtype.

Figure 11A:
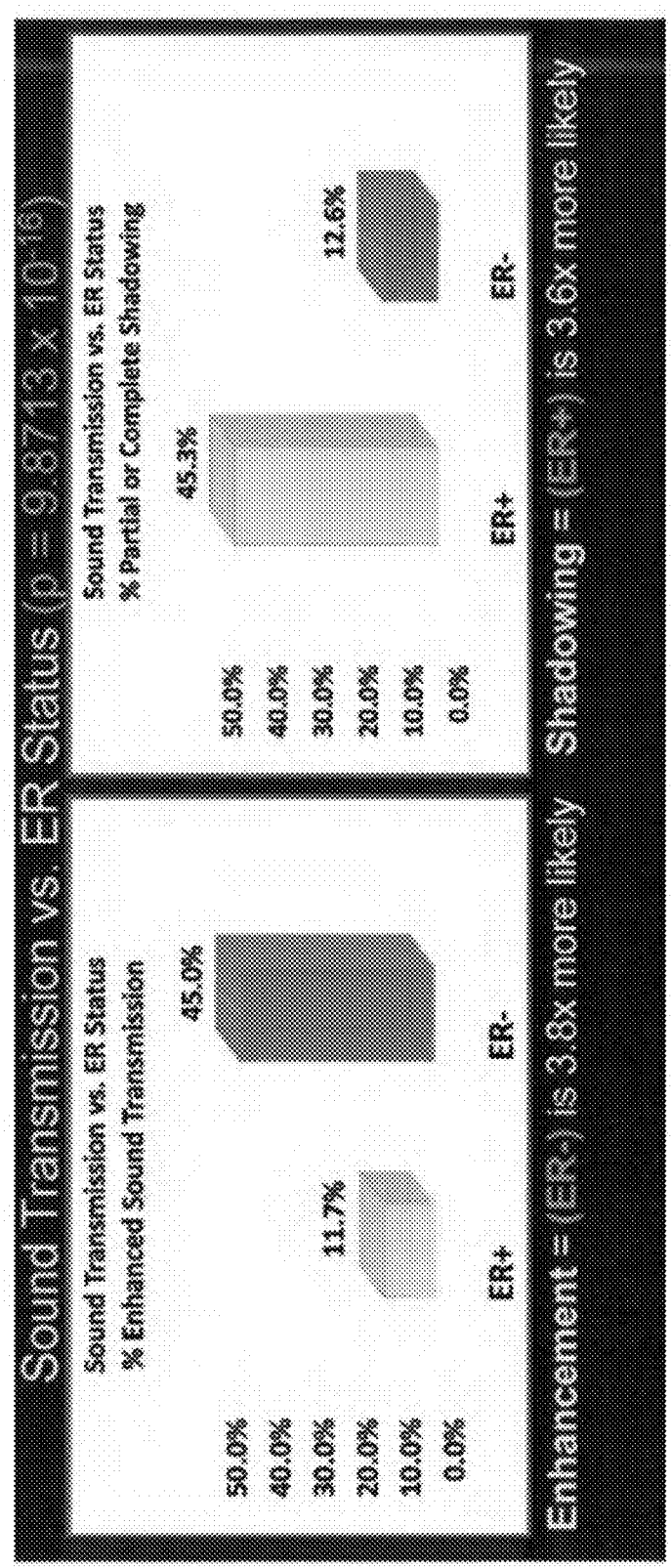
FIG. 11A illustrates a correlation between the shadowing and enhanced sound transmission characteristic versus ER status.
Figure 11B:
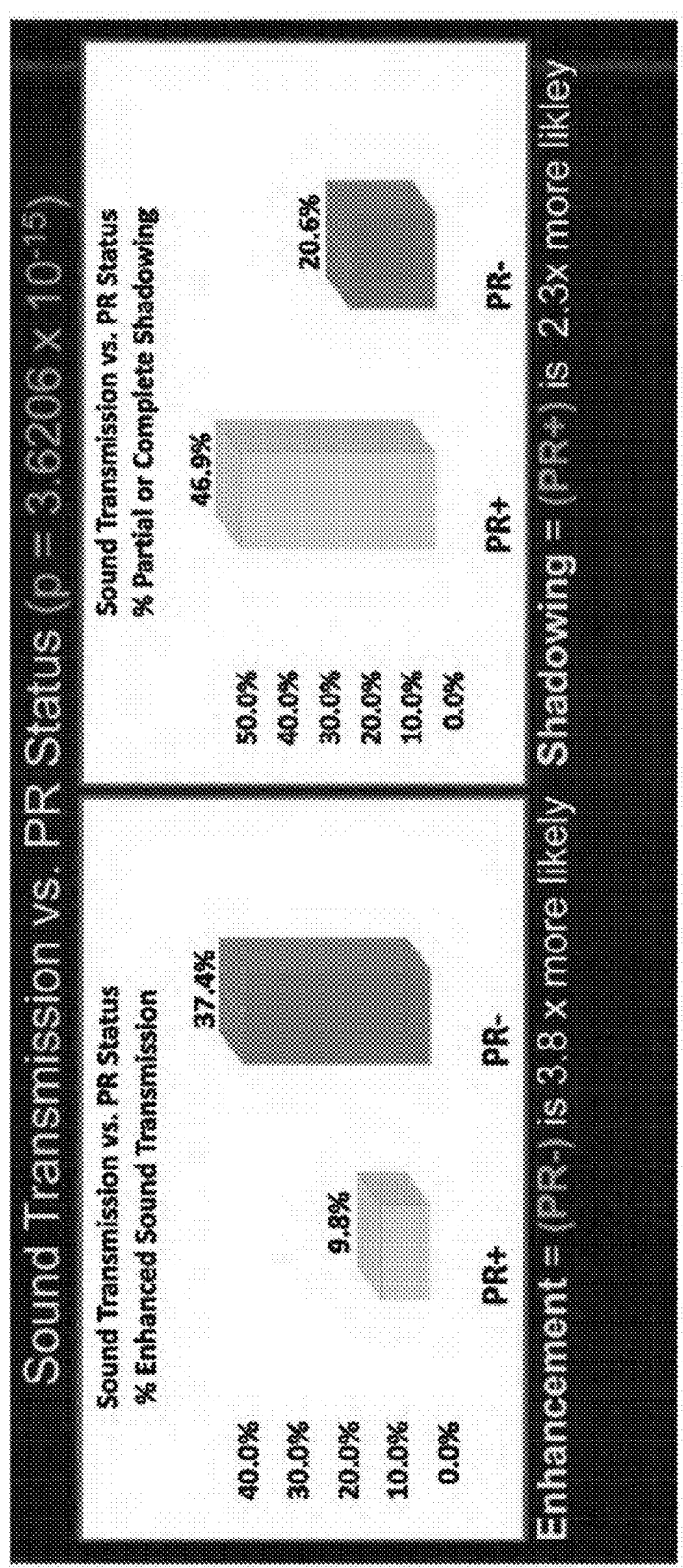
FIG. 11B illustrates a correlation between the shadowing and enhanced sound transmission characteristic versus PR status.
Figure 11C:
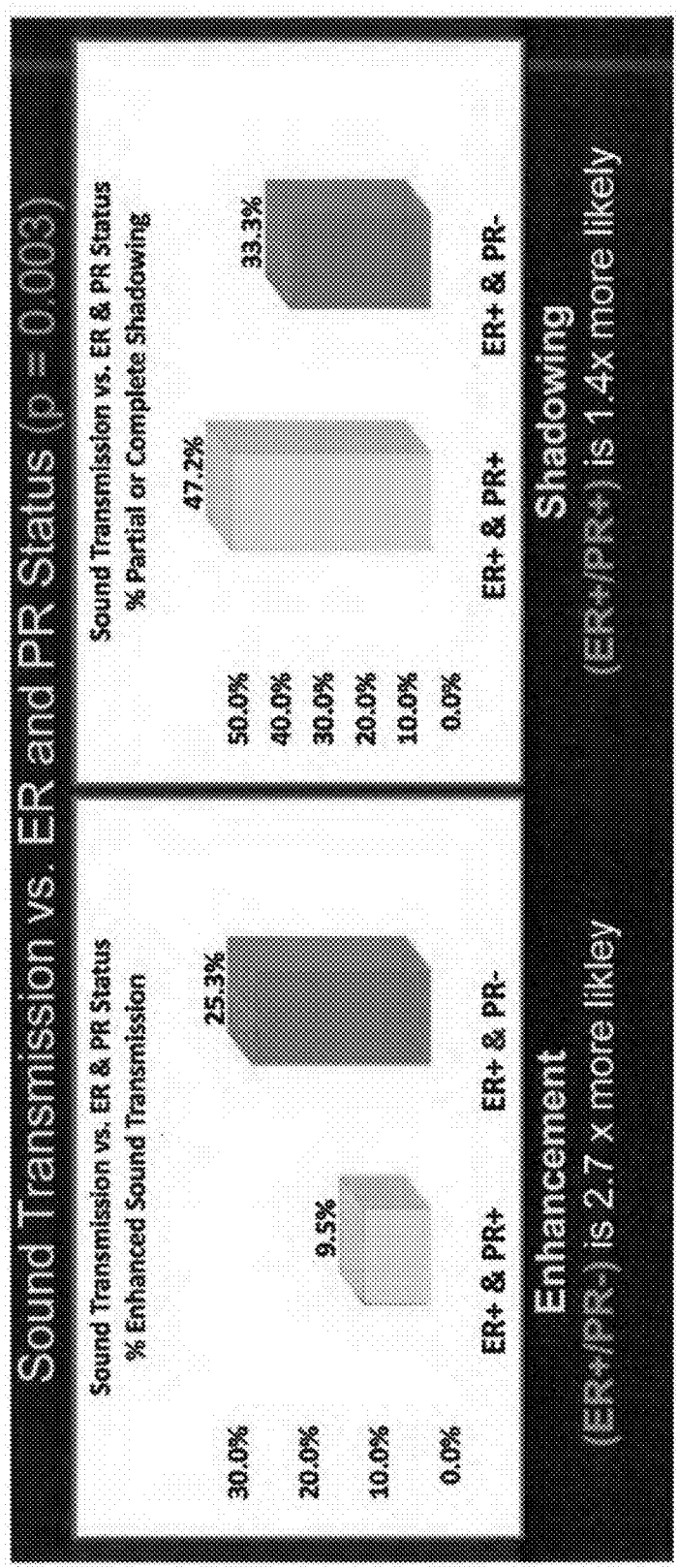
FIG. 11C illustrates a correlation between the shadowing and enhanced sound transmission characteristic versus EP and PR status.
Figure 11D:
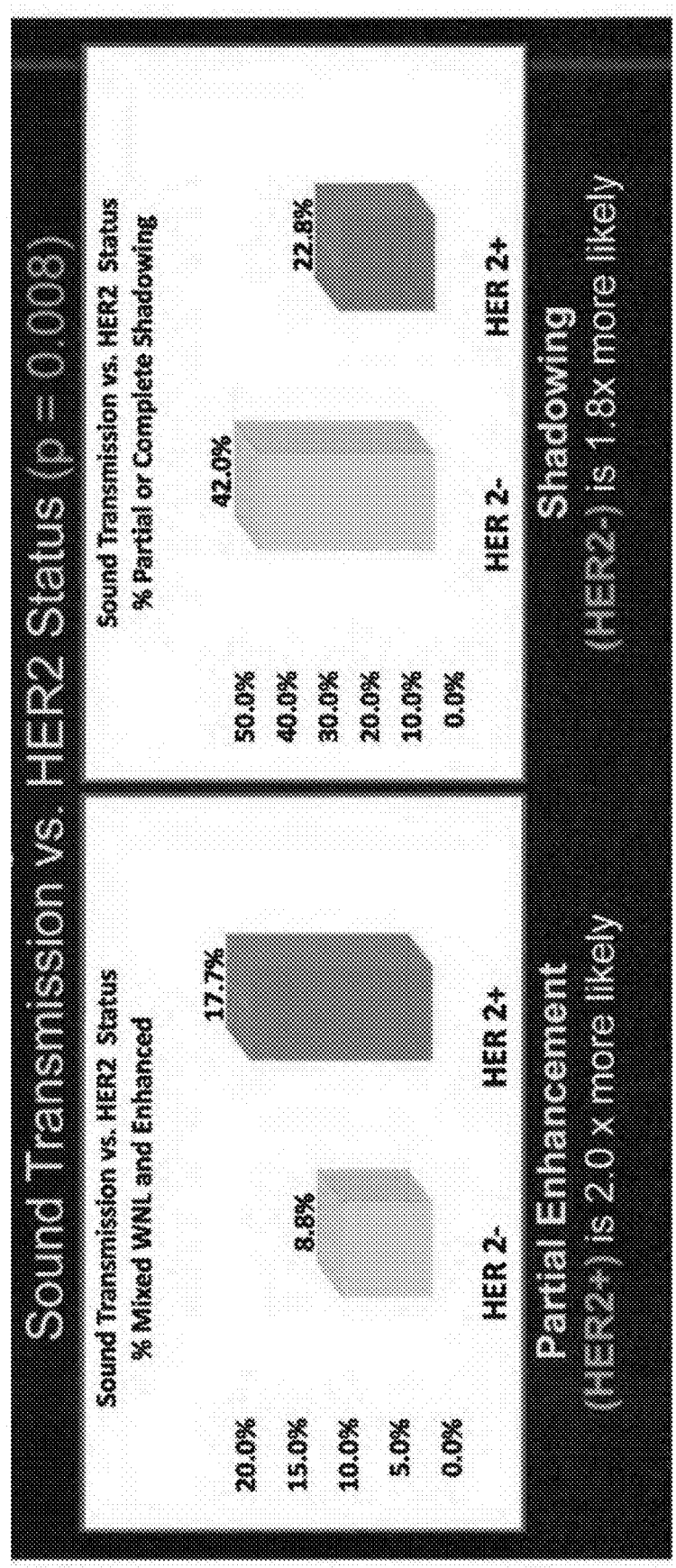
FIG. 11D illustrates a correlation between the shadowing and enhanced sound transmission characteristic versus HER-2 status.
Figure 11E:
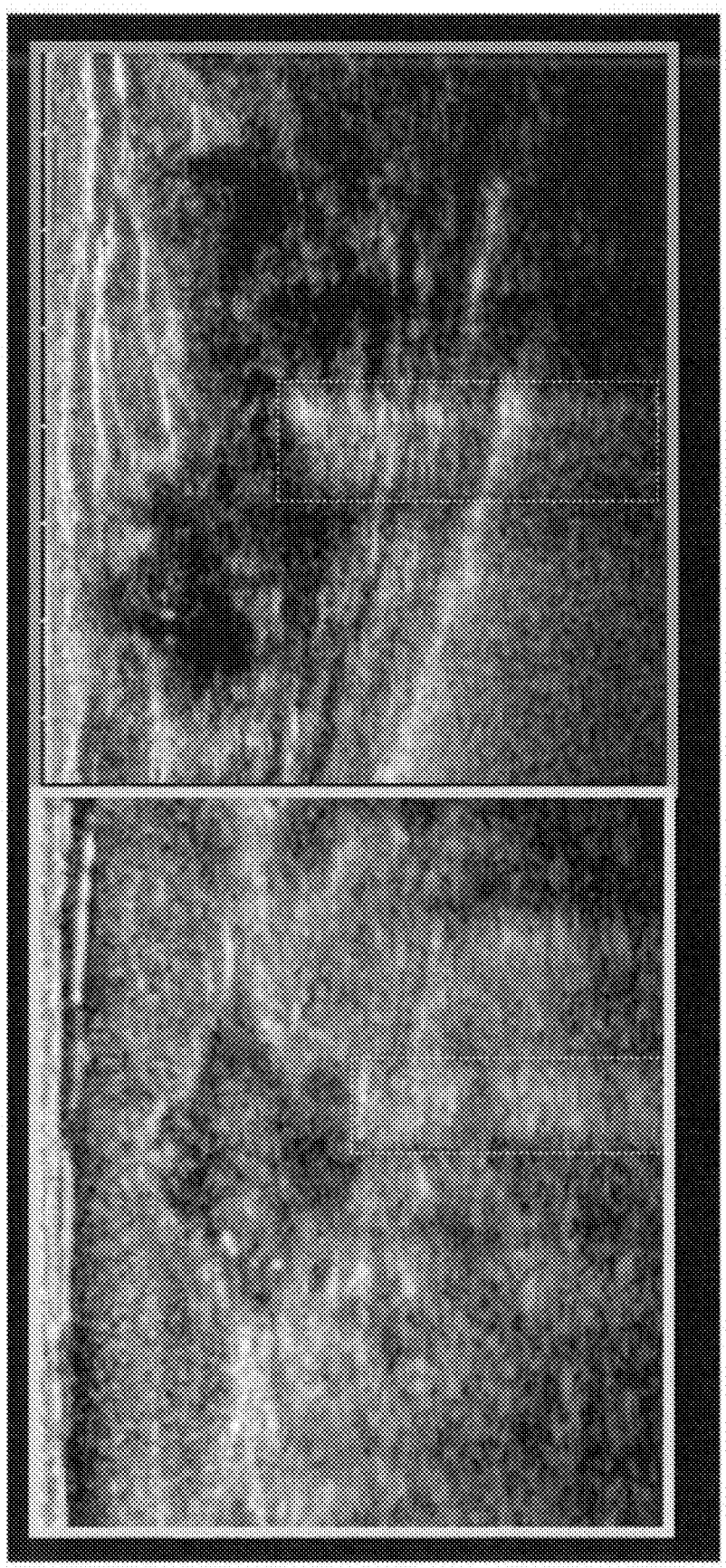
FIG. 11E illustrates an example of an image reference key to be utilized in connection with scoring partially enhanced sound transmission.
Figure 11G:
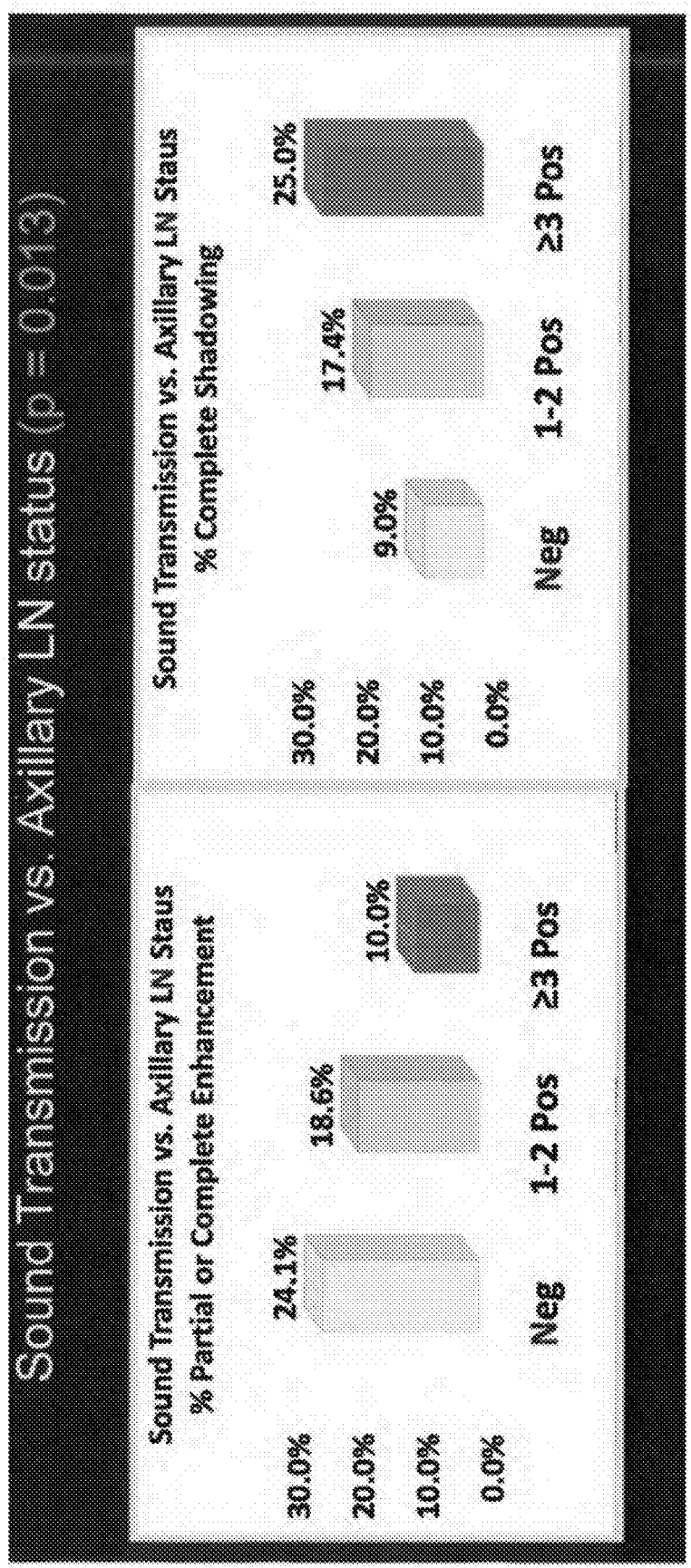
FIG. 11G illustrates a relation between enhanced sound transmission, shadowing and ancillary lymph node status.
Figure 11H:
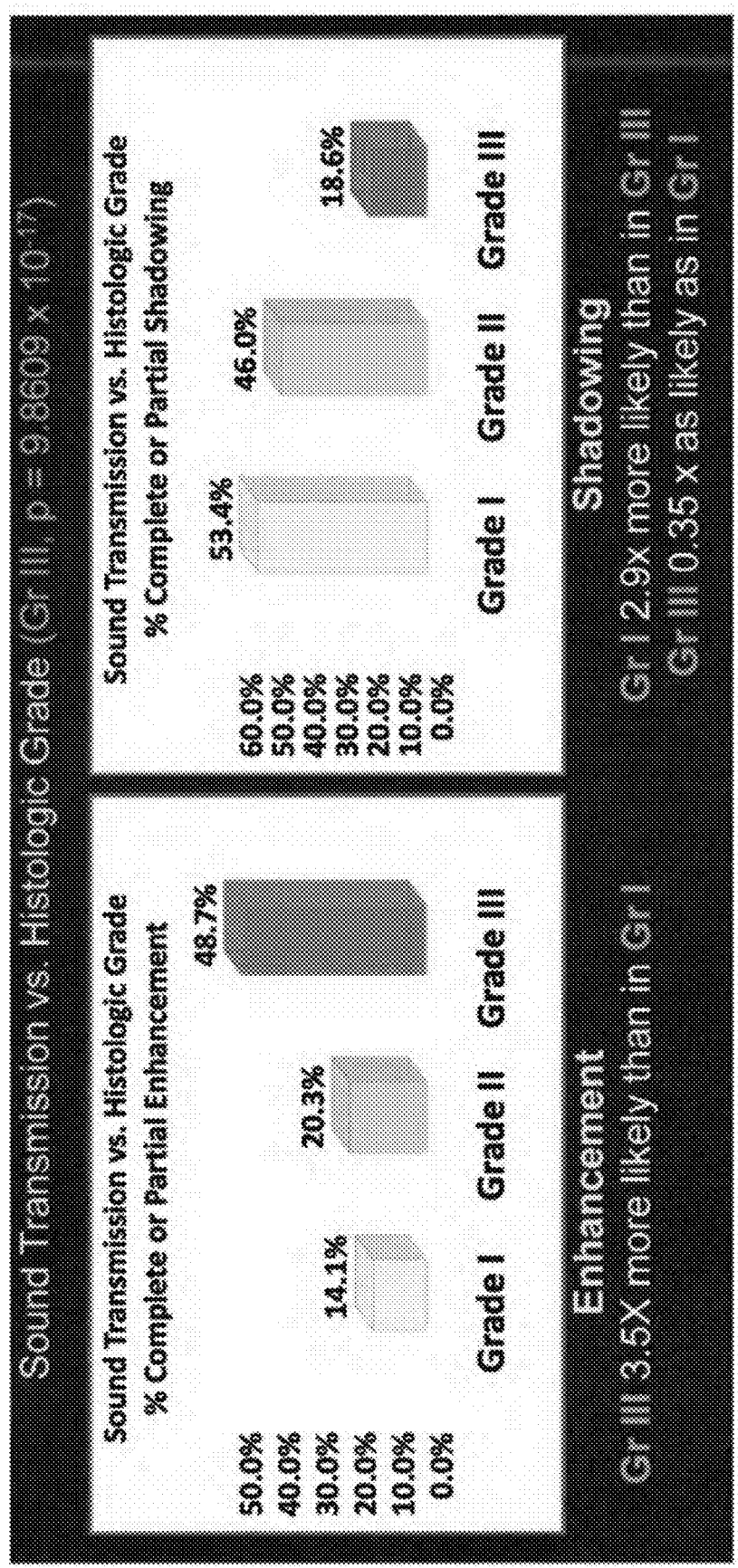
FIG. 11H illustrates a relation between enhanced sound transmission, shadowing and histologic grade.

FIG. 11F illustrates a chart correlating different US feature scores with the Ki-67 molecular subtype, along with a related statistical P value based on a patient population of cases analyzed in connection here with. The Pearson correlation indicates an opposing correlation, meaning that as a US feature score increases, the POM decreases that the malignancy has a high KI-67 proliferation index. The chart also illustrates corresponding P values to indicate a relation between the change in the US feature score and the POM that the malignancy is the KI-67 proliferation index. Note that many features have very strong inverse correlations to Ki-67 proliferation index. FIG. 11G illustrates a relation between enhanced sound transmission, shadowing and ancillary lymph node status. The left panel shows partial or complete enhanced sound transmission versus ancillary lymph node status, while the right panel shows complete shadowing sound transmission versus ancillary left node status. In accordance with new and unique aspects herein, it has been found that sound transmission has a different relation with lymph node metastasis than sound transmission has with other biomarkers. Shadowing appears to indicate an increased risk of lymph node metastasis, while enhanced sound transmission appears to indicate a lowered risk of lymph node metastasis. FIG. 11H illustrates a relation between enhanced sound transmission, shadowing and histologic grade. The left panel shows partial or complete enhanced sound transmission versus histologic grade, while the right panel shows complete shadowing sound transmission versus histologic grade. In accordance with new and unique aspects herein, it is been found that grade III differs more from grade II than grade I differs from grade II. A US image of a malignancy, exhibiting complete or partial enhancement, is 3.5 times more likely to have a grade III, as compared to a grade I. A US image of the malignancy, exhibiting shadowing, is 2.9 times more likely to have a grade I, than a grade III and is 0.35 times more likely to have a grade III than to have a grade I.

Figure 11I:
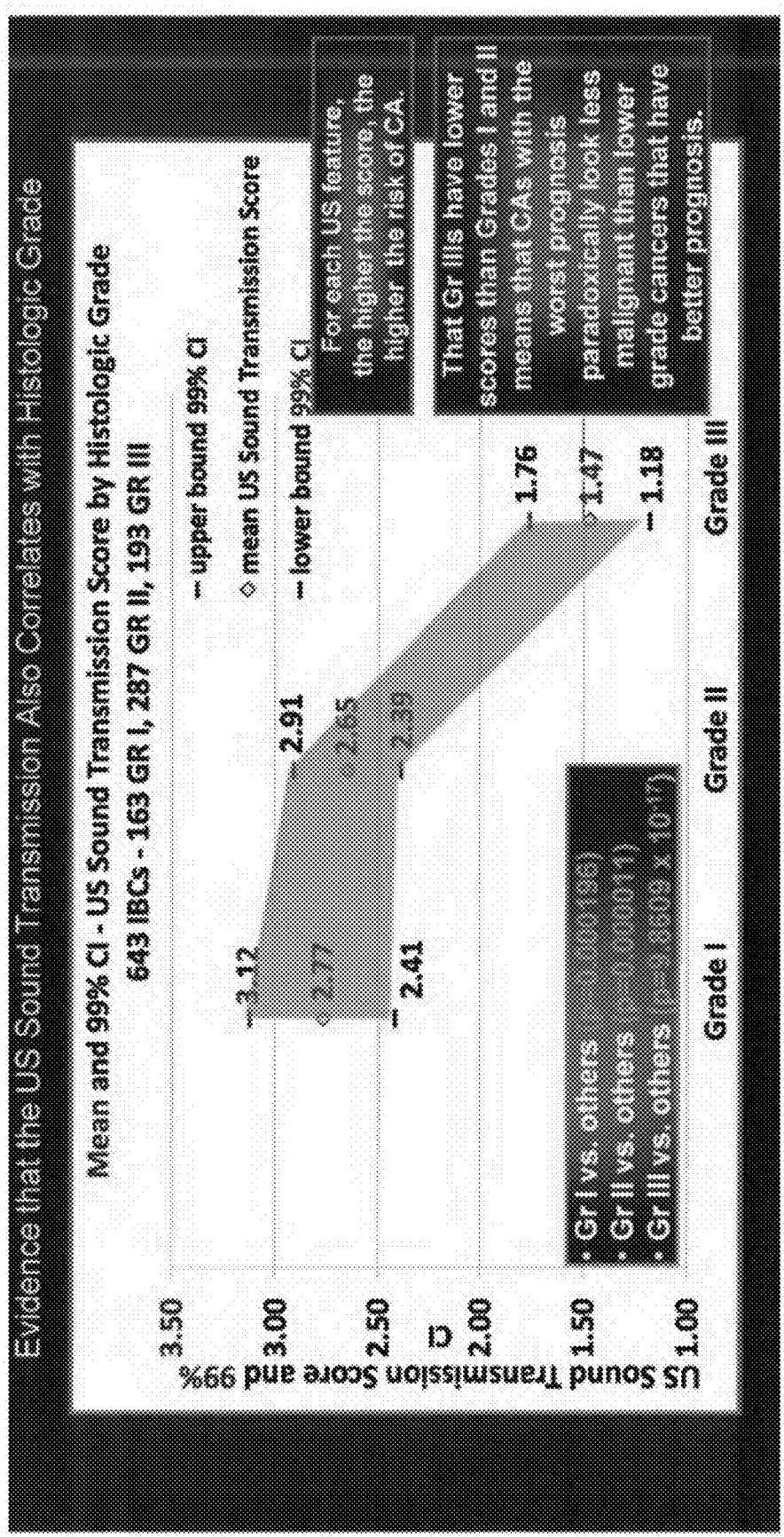
FIG. 11I illustrates an example of US feature scores assigned to the cases in a patient population exhibiting the different histologic grades of carcinoma.
Figure 11J:
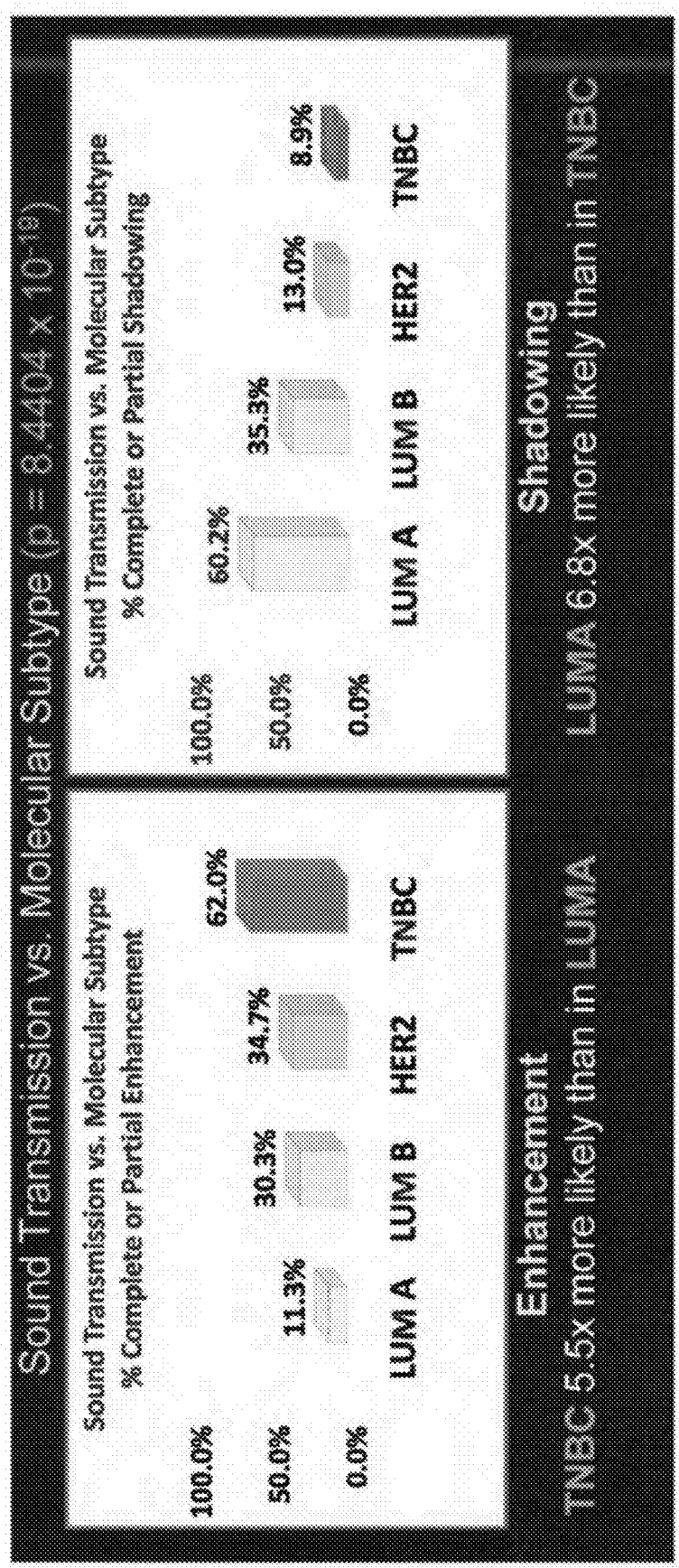
FIG. 11J illustrates a relation between shadowing and enhancement sound transmission characteristics and molecular subtypes

FIG. 11I illustrates an example of US feature scores assigned to the cases in a patient population exhibiting the different histologic grades of carcinoma. In connection with each histologic grade, a mean feature score, and upper and lower feature score boundaries are illustrated. By way of example, the cases having the histologic grade I received a mean US feature score of 2.77, as well as upper and lower boundaries at the 99% CI (confidence index) of 3.12 and 2.41, respectively. The cases having the histologic grade II received a mean US feature score of 2.65, with upper and lower 99% CI boundaries of 2.91 and 2.39, respectively. The cases with the histologic grade III received a mean US feature score of 1.47, with upper and lower 99% CI boundaries of 1.76 and 1.18, respectively. In accordance with new and unique aspects herein, it has been determined that the grade III IBCs look less malignant than grades I and II IBCs, while false-negative US exams or more likely in grade III cases. FIG. 11J illustrates a relation between shadowing and enhancement sound transmission characteristics and molecular subtypes. In FIG. 11J, the left panel considers a group of patients who exhibited one of the 4 molecular subtypes of interest and also exhibited a complete or partial enhancement characteristic in the OA/US images. For example, from the subset of patients who had the TNBC molecular subtype of cancer, 62% of the patients OA/US images exhibited a complete or partial enhancement characteristic. From the subset of patients who had the luminal A, luminal B or HER-2 molecular subtypes of cancer, approximately 11.3%, 30.3% and 34.7%, respectively, of the patients OA/US images exhibited a complete or partial enhancement characteristic. From the foregoing, it has been determined that the TNBC molecular subtype is 5½ times more likely than the luminal A subtype to exhibit an enhancement characteristic within the sound transmission.

In FIG. 11J, the right panel considers the same group of patients who exhibited one of the 4 molecular subtypes of interest and also exhibited a complete or partial shadowing characteristic within the OA/US images. For example, from the subset of patients who had the luminal A molecular subtype of cancer, 60.2% of the patients OA/US images exhibited a complete or partial shadowing characteristic. From the subset of patients who had luminal B, HER-2 or TNBC molecular subtypes of cancer, approximately 35.3%, 13% and 8.9%, respectively, of the patients OA/US images exhibited a complete or partial shadowing characteristic. From the foregoing group of cases, it can be seen that the luminal A subtype is 6.8% more likely than the TNBC subtype to exhibit shadowing within the sound transmission.

Figure 11K:
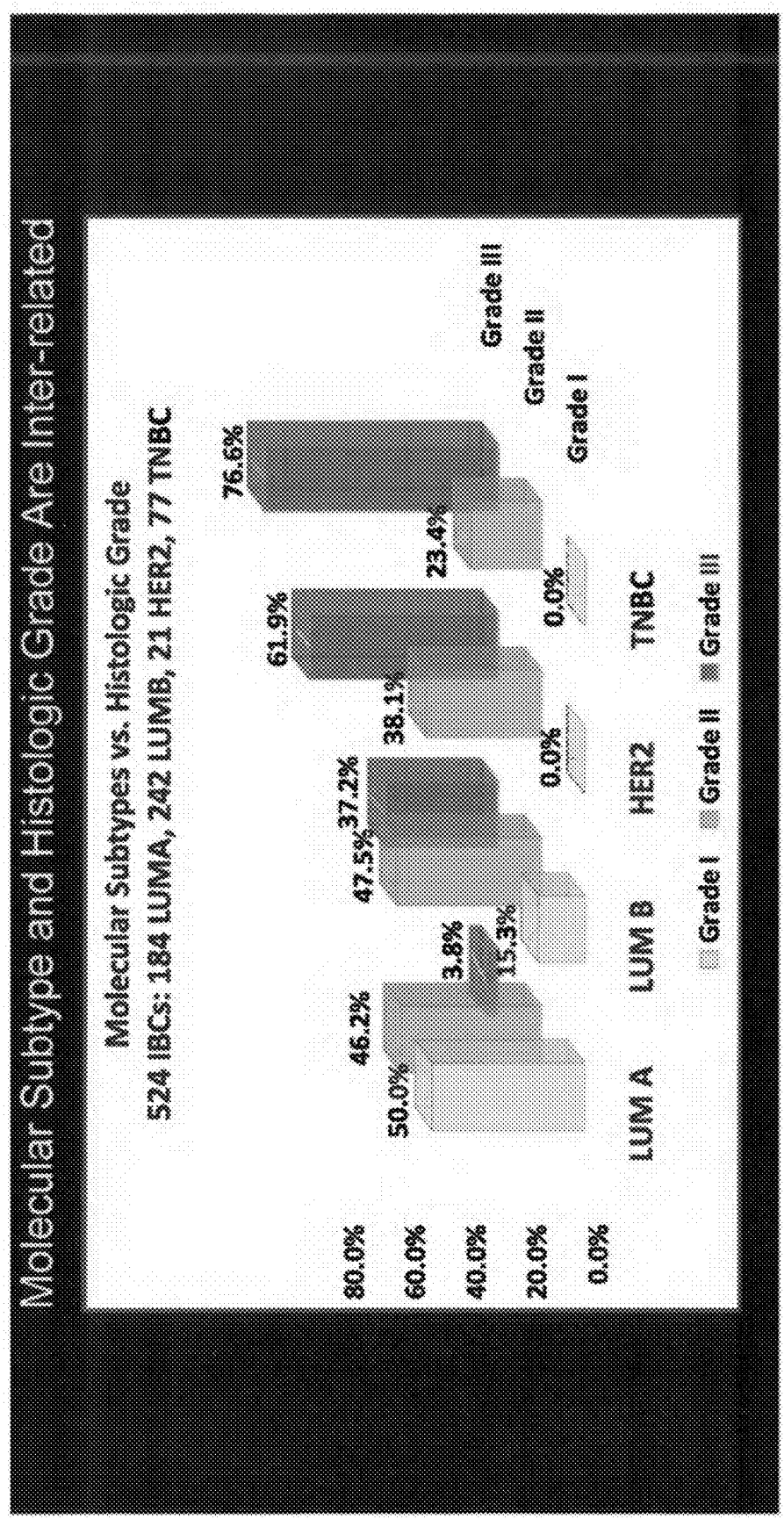
FIG. 11K is presented to illustrate an interrelation, that has been recognized in accordance with new and unique aspects herein, between molecular subtypes and histologic grades I, II, III.

FIG. 11K is presented to illustrate an interrelation, that has been recognized in accordance with new and unique aspects herein, between molecular subtypes and histologic grades I, II, III. FIG. 11K indicates the results of a study of a patient pool for which the corresponding molecular subtypes and histologic grades were designated. In the patient pool, approximately 181 cases exhibited the luminal A subtype, 242 cases exhibited the luminal B subtype, 21 cases exhibited the HER-2 subtype and 77 cases exhibited the TNBC subtype. Within each subtype, the cases were further broken down by grade I, II and III. As is evident from FIG. 11 B, from the TNBC subtype cases, 76.6% exhibited the histologic grade III, while 23.4% exhibited the histologic grade II. Within the luminal A subtype, 50% exhibited the grade I, 46.2% exhibited the grade II, and 3.8% exhibited the grade III. Within the luminal B subtype, 15.3% exhibited the grade I, 47.5% exhibited the grade II, and 37.2% exhibited the grade III. Within the HER-2 subtype, 38.1% exhibited the grade II, while 61.9% exhibited the grade III. Accordingly, it has been found that the molecular subtypes and histologic grades have an interrelation. For example, a substantial majority of the cases having the HER-2 and TNBC subtypes exhibit a histologic grade III, while approximately half of the cases having the luminal A subtype exhibit a histologic grade I. Luminal A and luminal B subtypes exhibit a larger percentage of grade II cases, as compared to the number of grade II cases in the HER-2 and TNBC subtypes.

Figure 11L:
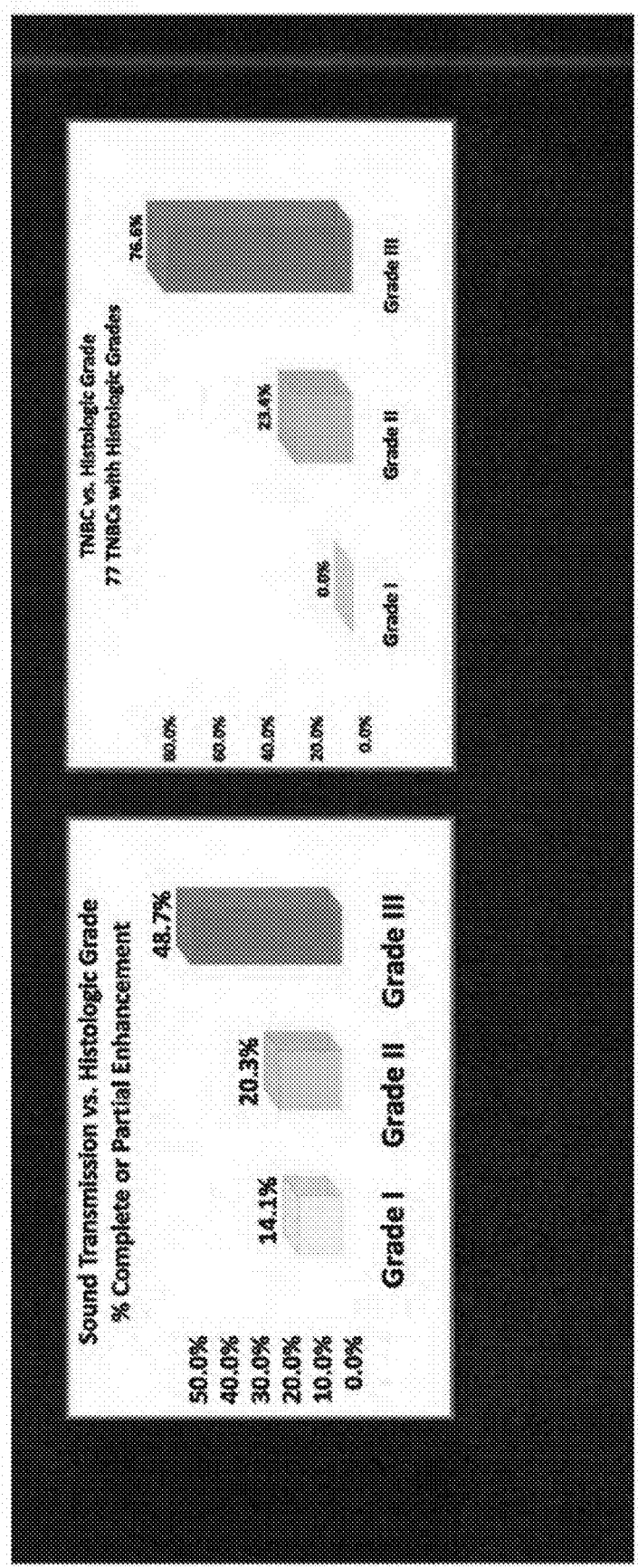
FIG. 11L illustrates a relation identified, in accordance with new and unique aspects herein, between enhanced sound transmission and histologic grade of different molecular subtypes.
Figure 11M:
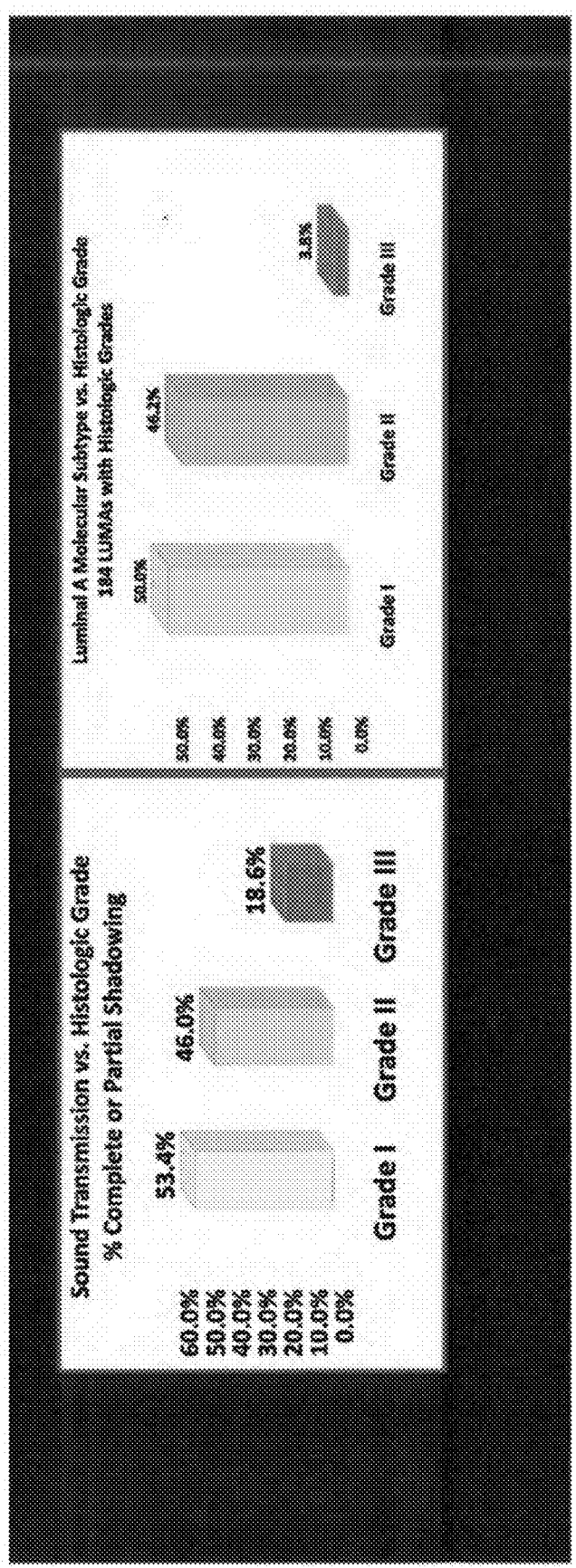
FIG. 11M illustrates a relation identified, in accordance with new and unique aspects herein, between acoustic shadowing and histologic grade of different molecular subtypes.

FIG. 11L illustrates a relation identified, in accordance with new and unique aspects herein, between enhanced sound transmission and histologic grade of different molecular subtypes. The left panel illustrates relation between the number of cases that exhibited enhanced sound transmission as related to the different histologic grades. Approximate 48.7% of the cases exhibiting enhanced sound transmission were histologic grade III, while 20.3% and 14.1% of the cases were histologic grades II and I, respectively. The right panel focuses on cases having TNBC molecular subtype, from which 76.6% of the cases exhibited a histologic grade III, while 23.4% and 0% exhibited grades II and I, respectively. From the foregoing, it has been found that a substantial majority of all TNBC cases, which illustrate a grade III, also illustrate enhanced sound transmission in the OA/US images. FIG. 11M illustrates a relation identified, in accordance with new and unique aspects herein, between acoustic shadowing and histologic grade of different molecular subtypes. The left panel illustrates relation between the number of cases that exhibited acoustic shadowing as related to the different histologic grades. Approximate 53.4% of the cases exhibiting acoustic shadowing were histologic grade I, while 46% and 18.6% of the cases (with acoustic shadowing) were histologic grades II and III, respectively. The right panel focuses on cases having luminal A molecular subtype, from which 50% of the cases exhibited a histologic grade I, while 46.2% and 3.8% were assigned grades II and III, respectively. From the foregoing, it has been found that a substantial majority of all luminal A cases, which illustrate a grade I, also illustrate acoustic shadowing in the OA/US images.

Figure 11N:
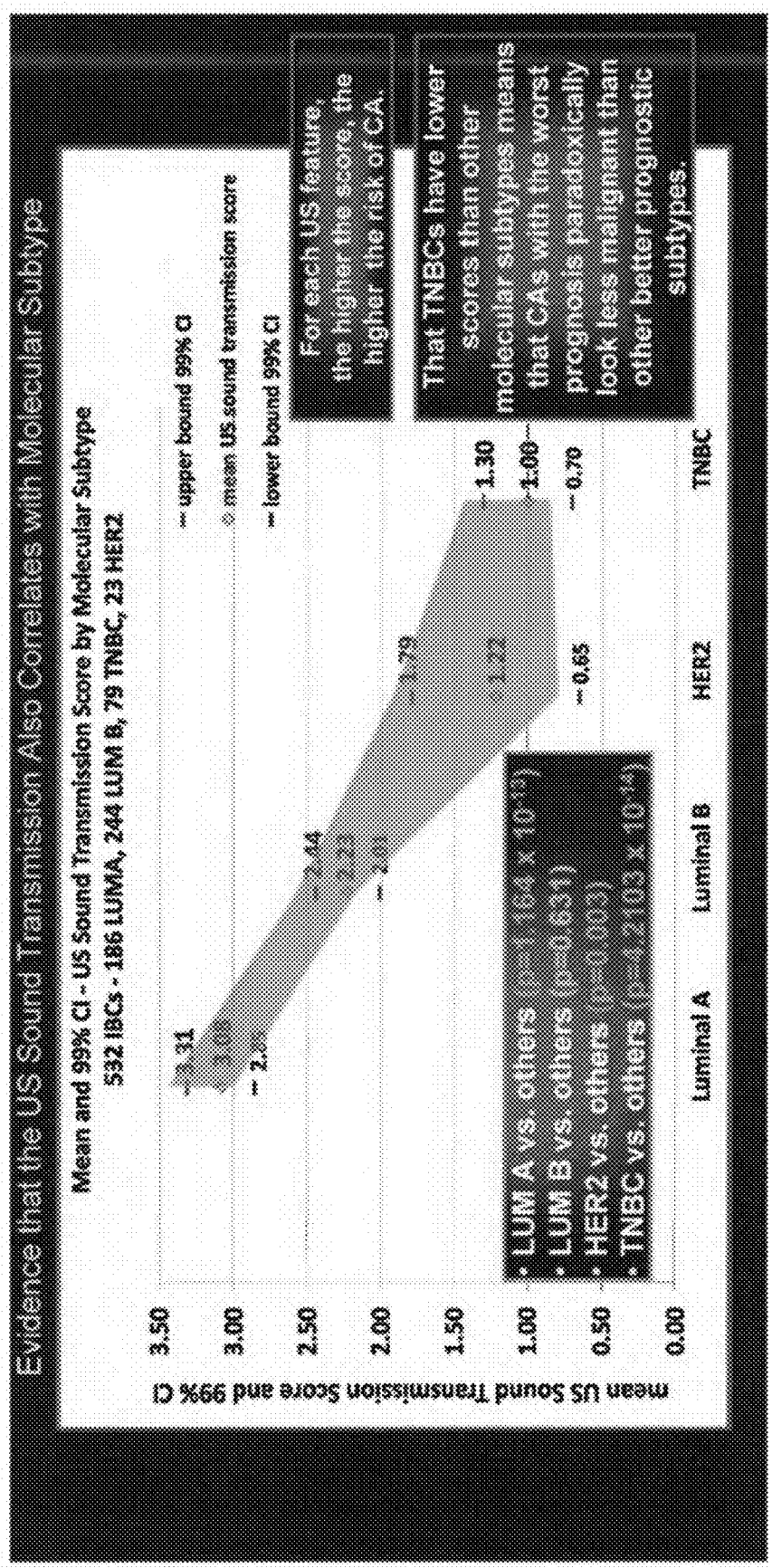
FIG. 11N illustrates an example of US feature scores assigned to the above discussed cases exhibiting the different molecular subtypes.
Figure 110:
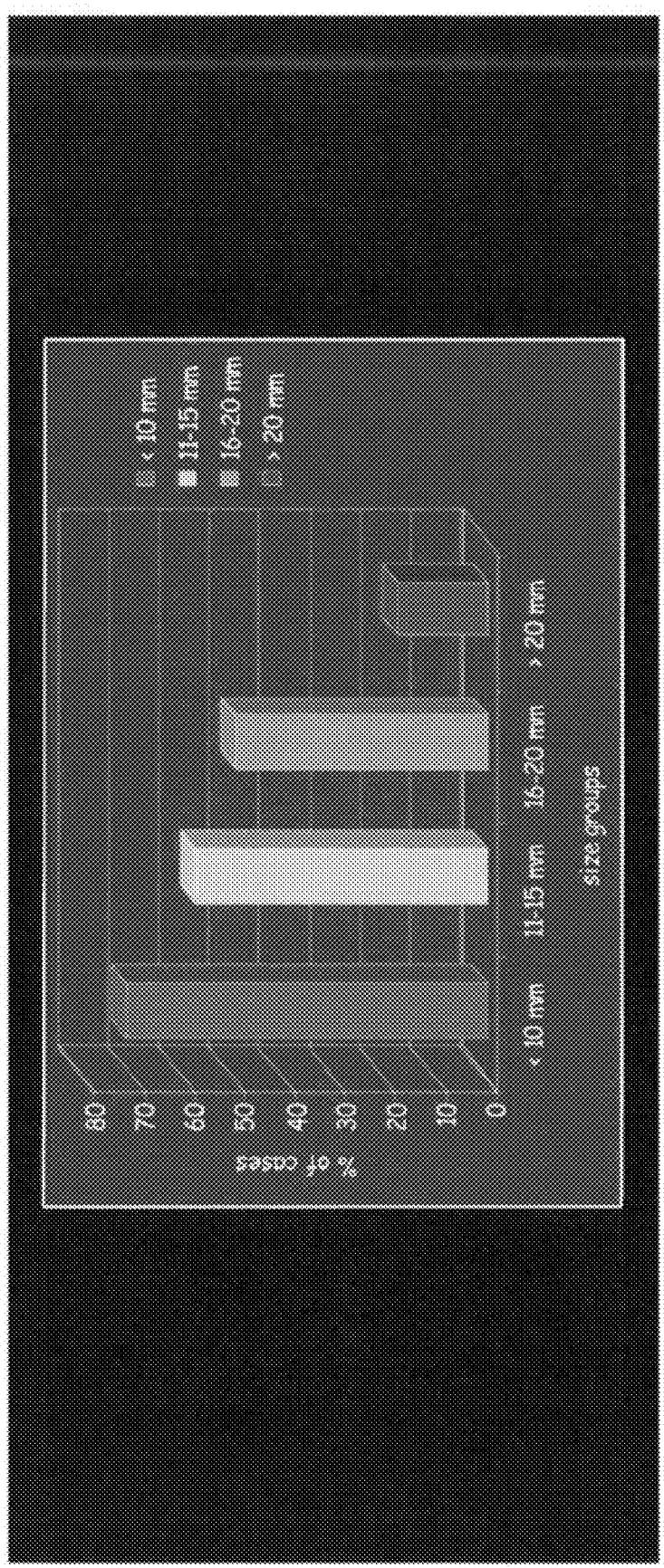

FIG. 11N illustrates an example of US feature scores assigned to the above discussed cases exhibiting the different molecular subtypes. In connection with each molecular subtype, a mean feature score, and upper and lower feature score boundaries are illustrated. By way of example, the cases having the luminal A molecular subtype received a mean US feature score of 3.08, as well as upper and lower boundaries at the 99% CI (confidence index) of 3.31 and 2.85, respectively. The cases having the luminal B molecular subtype received a mean US feature score of 2.23, with upper and lower 99% CI boundaries of 2.44 and 2.01, respectively. The cases with the HER-2 subtype received a mean US feature score of 1.22, and upper and lower 99% CI boundaries of 1.79 and 0.65, respectively. The cases with the TNBC subtype received a mean US feature score of 1.00, with upper and lower 99% CI boundaries of 1.30 and 0.70, respectively. It is also been determined that the TNBC cases may appear less malignant than other molecular subtypes based on US images potentially leading to more false-negative US examinations for the TNBC molecular subtype.

The higher the US feature score, the higher the risk of carcinoma. Interestingly, cases with the TNBC subtype have lower scores than other molecular subtypes, which in part indicates that carcinomas with the worst prognosis paradoxically look less malignant than other subtypes having a better prognosis and could more frequently lead to a false negative classification as BI-RADS 3 with ultrasound alone.

FIG. 11-O illustrates a relation between masses having a nonparallel orientation (e.g. taller than wide) as a prognostic indicator. The horizontal axis plots the size of the masses in millimeters, while the vertical axis plots the number of cases from the study that exhibited a carcinoma. It is recognized that one case may exhibit suspicious areas having different orientations. Approximately 70% of the masses with maximum diameters less than 10 mm in size had a non-parallel orientation. The percentages of non-parallel orientations were 55%, 47% and 15% in the size groups of 11-15 mm, 16-20 mm and greater than 20 mm, respectively. From the foregoing size comparison, it has been recognized that nonparallel orientation correlates with small AAB size, and smaller size is a favorable prognostic indicator, a possibly related to luminal A status. Most AABs are grade I or II, similar to Luminal A molecular subtype cancers.

Small acinar adenocarcinomas of the breast (AAB) that are small enough that they still affect only a single TDLU. Small ABBs of breasts arise from different types of TDLUs. TDLUs are typically found most numerous anterior early within a mammary zone (MZ) and add a periphery of the mammary zone. AAbs arise from TDLUs at the periphery of the MZ, effect that early, and are memo detectable when small. DABs arise from ducts in the center of the MZ, are detected late (calcification occurs late) and often involve whole "sick lobes" at discovery. DABs are often likely to be stem cell carcinomas. Cancers that arise from breast acini have much better prognosis than those arising from mammography ducts. As such, acinar adenocarcinoma of the breast (AAB) and ductal adenocarcinoma of the breast (DAB) provide powerful biomarkers in connection with cumulative survival rates.

In accordance with new and unique aspects herein, it has been recognized that nonparallel orientations of masses indicate a higher likelihood that the mass is grade I or II, luminal A, as compared to other molecular subtypes. While grade III IBCs do have a lower percentage of nonparallel orientations than do grade I and grade II IBCs, the difference is not statistically significant (e.g. p=0.09). Masses exhibiting TNBC have a statistically significant lower percentage of nonparallel orientation than luminal A subtype masses (e.g. with a p-value of 0.002).

Figure 12A:
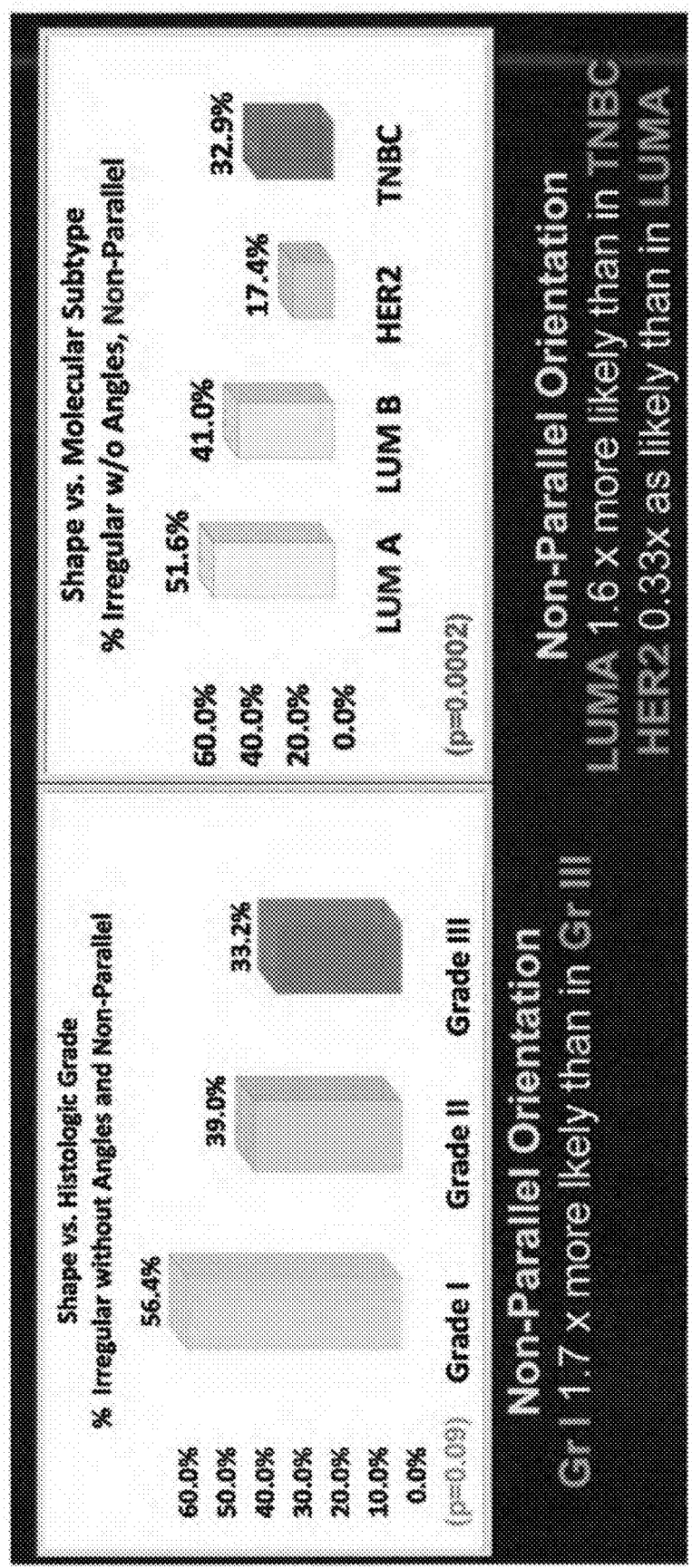
FIG. 12A illustrates a relation between masses having nonparallel orientation, as compared to the histologic grades and the molecular subtypes.

FIG. 12A illustrates a relation between masses having nonparallel orientation, as compared to the histologic grades and the molecular subtypes. The left panel compares the histologic grades to the shape feature of irregularities without angles and that are nonparallel. Masses exhibiting a shape characteristic having a nonparallel orientation are 1.7 times more likely to correspond to a grade I, as compared to a grade III. The right panel compares the molecular subtypes to the shape feature of irregularity without angles and nonparallel. Masses, that exhibit a shape characteristic of irregular without angles and nonparallel, exhibits a 1.6 times greater likelihood to be a luminal A subtype, as compared to a TNBC subtype. Masses, that exhibit the irregular without angles and nonparallel shape characteristic, exhibit a 0.33 times greater likelihood to be a HER-2 subtype as compared to a luminal A subtype. The HER-2 cancer subtype often exhibits large DAB components with ducts that are oriented parallel.

Next, the discussion turns to the relation between grade and acinar or ductal size. Nuclear grade 1 corresponds to virtually all disproportionately enlarged ducts and lobules enough to more easily recognize them as being abnormal (e.g. four, six, eight, 10 times larger than a normal size). Nuclear grade 2 corresponds to ducts and lobules that are sometimes disproportionately enlarged enough for us to recognize an abnormality (e.g. two or four times larger than normal). A nuclear grade 1 frequently does not enlarge the dock and/or lobules enough to be recognized as abnormal compared to be nine ANDIs.

Figure 12B:
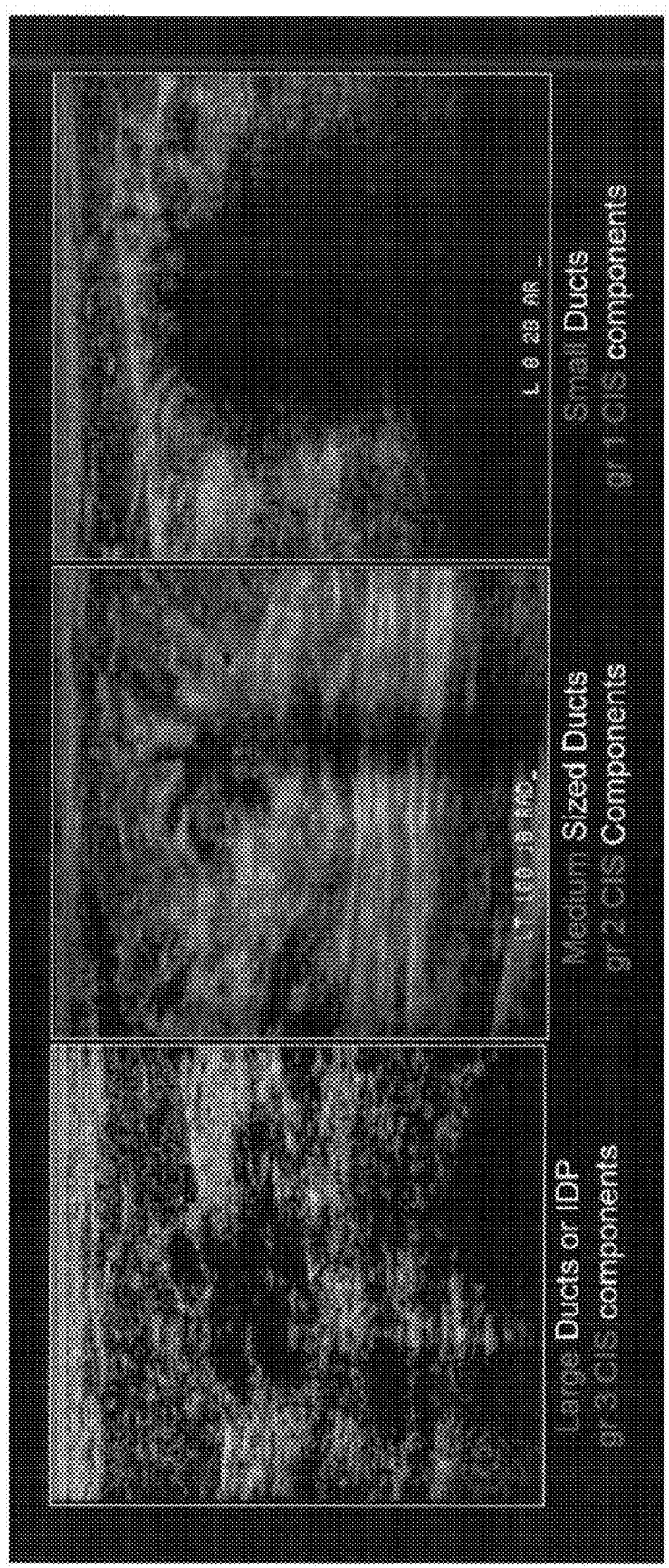
FIG. 12B illustrates examples of images of enlarged ducts, alone or within the tissue surrounding an invasive mass.

FIG. 12B illustrates examples of images of enlarged ducts, alone or within the tissue surrounding an invasive mass. Variable sizes correlate with the CIS nuclear grade. In accordance with new and unique aspects herein, it has been recognized that enlarged ducts in tissue that surrounds a mass is meaningful and distinguishing molecular subtypes and histologic grades from one another. For example, enlarged ducts distinguish the following, where examples of statistical significance are provided:

Distinguishes grade I from other grades. (p=0.001)
Distinguishes Grade III from other grades. (p=0.000 [4.8967 10-7])
Distinguishes Luminal A from other subtypes. (p=0.000006)
Distinguishes TNBC from other subtypes. (p=0.00000'7)
More common in HER2+, but not statistically significant. (p=0.093)

Figure 12C:
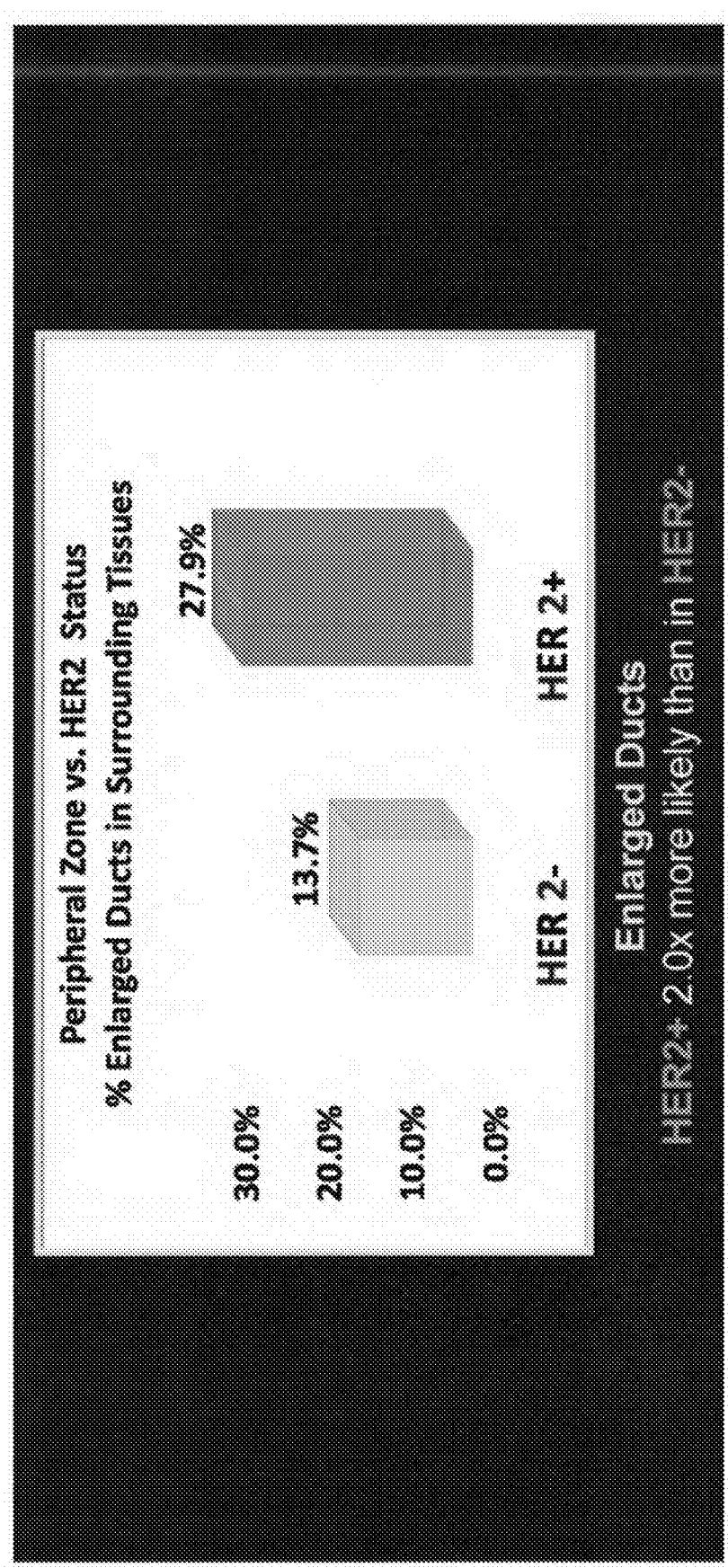
FIG. 12C illustrates a comparison HER-2 negative and HER-2 positive subtypes for a mass that has enlarged ducts in the peripheral zone.
Figure 12D:
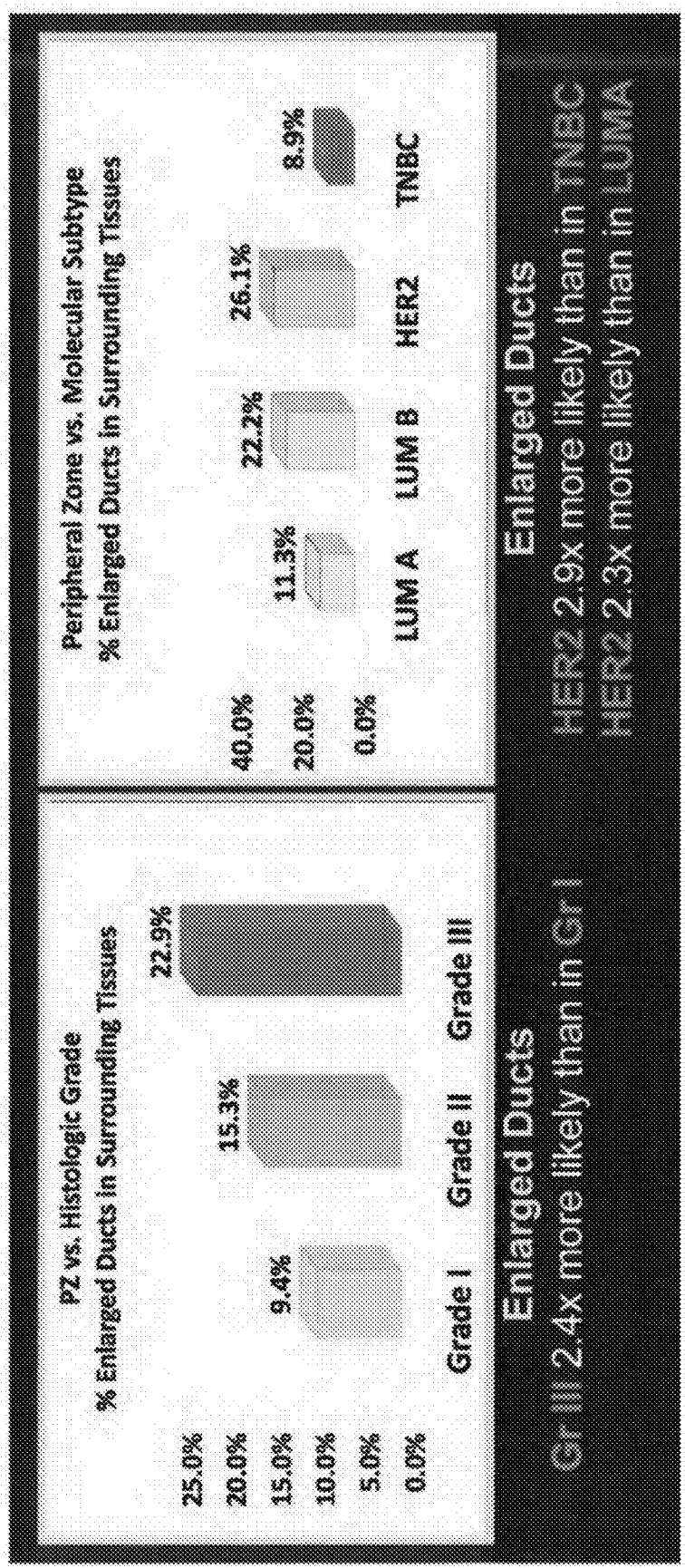
FIG. 12D illustrates a relation between masses having enlarged ducts in the peripheral zone, as compared to the histologic grades and the molecular subtypes.

FIG. 12C illustrates a comparison HER-2 negative and HER-2 positive subtypes for a mass that has enlarged ducts in the peripheral zone. When a mass exhibits enlarged ducts in the peripheral zone, the mass exhibits a 2.0 times greater likelihood that the mass is a HER-2 positive subtype, as compared to a HER-2 negative molecular subtype. FIG. 12D illustrates a relation between masses having enlarged ducts in the peripheral zone, as compared to the histologic grades and the molecular subtypes. The left panel compares the histologic grades to the enlarged ducts in the peripheral zone. Masses exhibiting a enlarged ducts the peripheral zone exhibit a 2.4 times greater likelihood of having a grade III histologic grade as compared to a grade I. The right panel compares the molecular subtypes to the enlarged ducts in the peripheral zone. Masses, that exhibit enlarged ducts in the peripheral zone, exhibits a two-point times greater likelihood to be a HER-2 subtype, as compared to a TNBC subtype. Masses, that exhibit enlarged ducts in the peripheral zone, exhibit a 2.3 times greater likelihood to be a HER-2 subtype as compared to a luminal A subtype. The HER-2 cancer subtype has a large percentage of associated DCIS (DAB), while luminal A and TNBC do not.

Figure 12E:
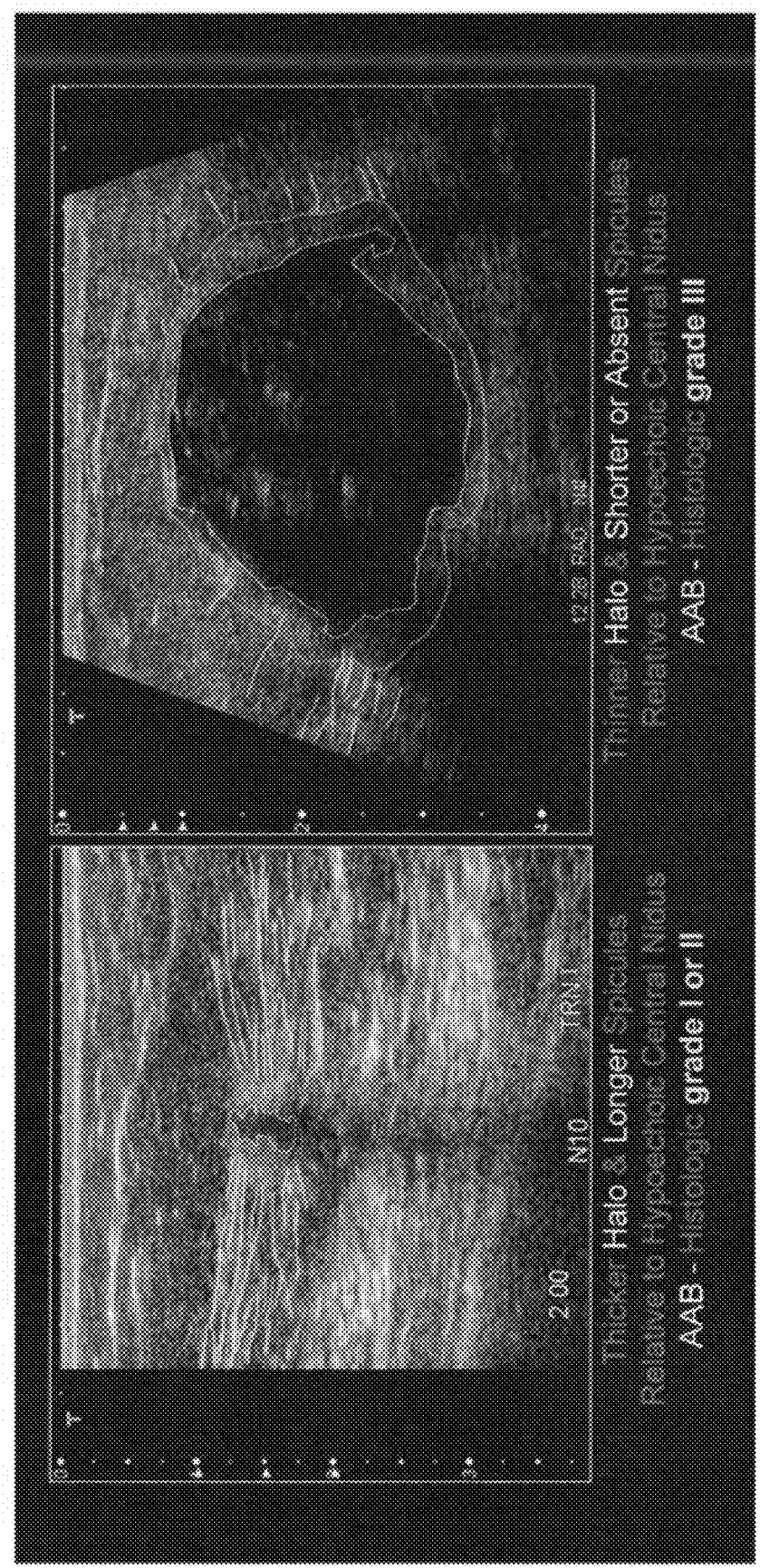
FIG. 12E illustrates examples of images having the variable halo thickness and spicules length.

Next, the discussion turns to the relation between histologic grades, halo thickness and spicules length. Microlobulations have an enlarged acinus and ducts. In accordance with new and unique aspects herein it has been determined that variable halo thickness and spicules length correlate with histologic grade. FIG. 12E illustrates examples of images having the variable halo thickness and spicules length. The left panel illustrates a thicker halo and longer spicules relative to hypoechoic central nidus. The left panel corresponds to a histologic grade I or II. The right panel illustrates a thinner halo and shorter or absent spicules relative to the hypoechoic central nidus. The right panel corresponds to a histologic grade III.

Figure 12F:
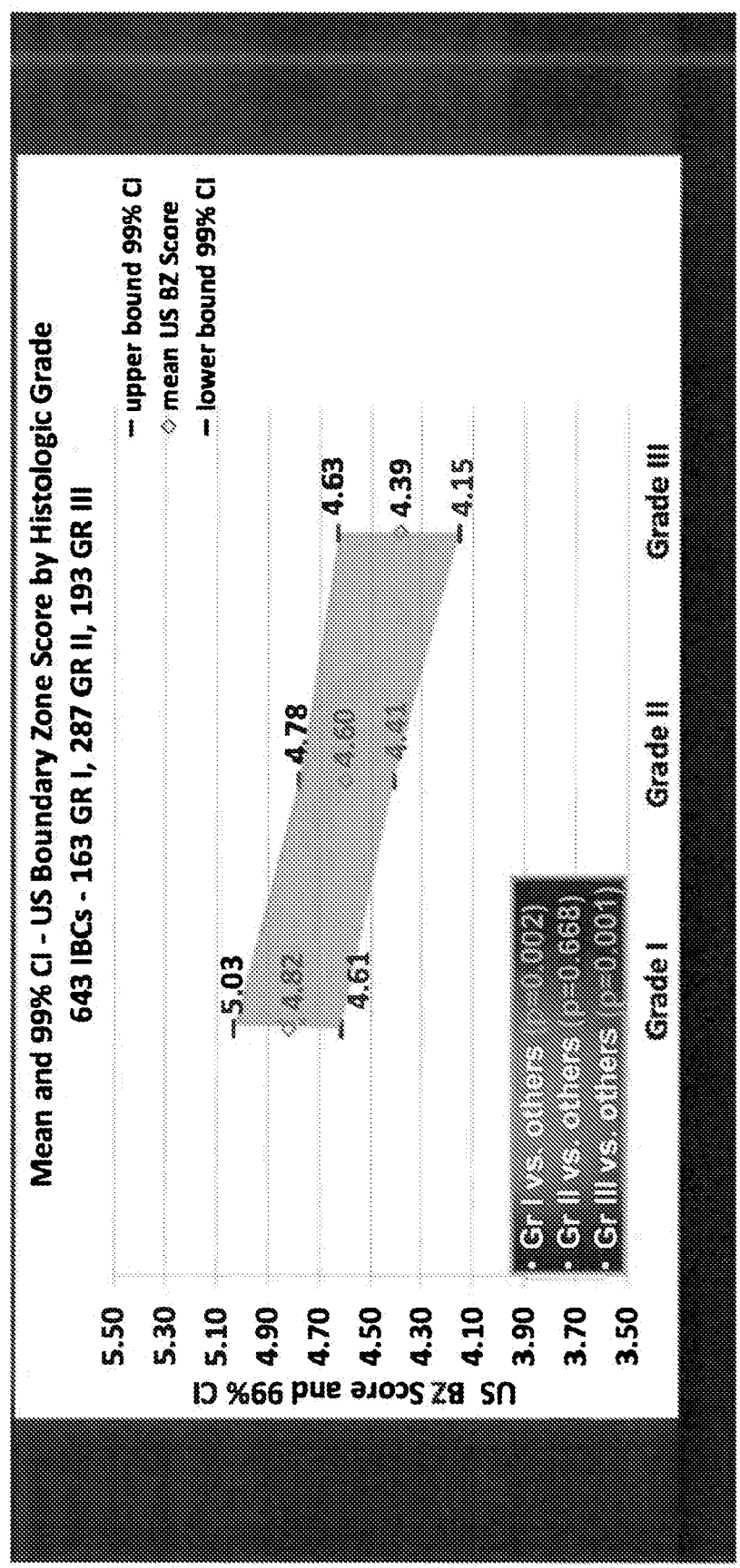
FIG. 12F illustrates a relation between the US boundary zone feature score assigned to the cases in a patient population exhibiting the different histologic grades of carcinoma.

FIG. 12F illustrates a relation between the US boundary zone feature score assigned to the cases in a patient population exhibiting the different histologic grades of carcinoma. In connection with each histologic grade, a mean feature score, and upper and lower feature score boundaries are illustrated. By way of example, the cases having the histologic grade I received a mean US boundary zone feature score of 4.82, as well as upper and lower boundaries at the 99% CI (confidence index) of 5.03 and 4.61, respectively. The cases having the histologic grade II received a mean US boundary zone feature score of 4.60, with upper and lower 99% CI boundaries of 4.78 and 4.41, respectively. The cases with the histologic grade III received a mean US boundary zone feature score of 4.39, with upper and lower 99% CI boundaries of 4.63 and 4.15, respectively. In accordance with new and unique aspects herein, it has been determined that the difference in feature scores between grade III and the other grades is less for the US boundary zone feature score, as compared to the sound transmission scores.

Figure 12G:
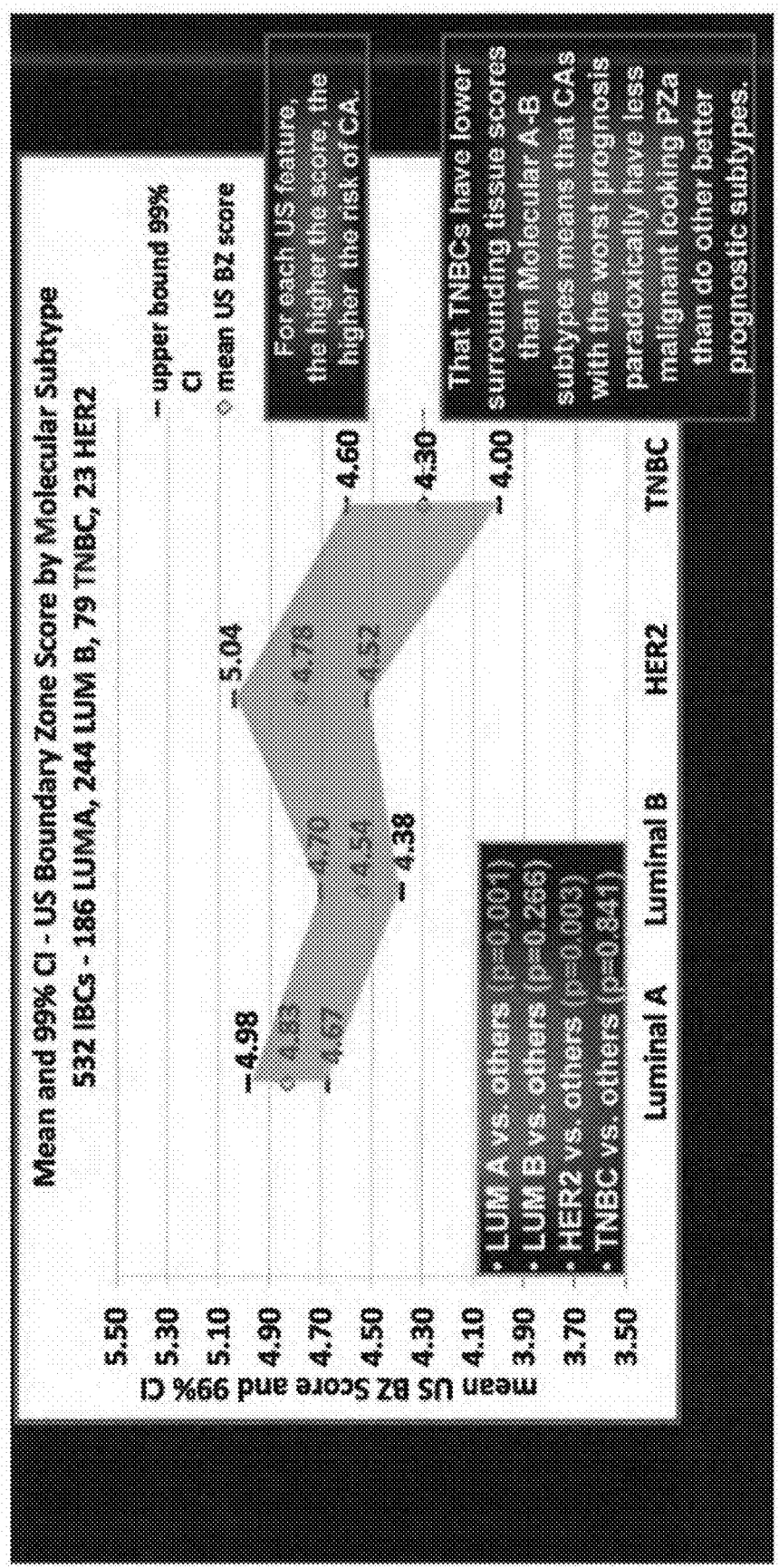
FIG. 12G illustrates a relation between the US boundary zone feature score assigned to the cases exhibiting the different molecular subtypes.

FIG. 12G illustrates a relation between the US boundary zone feature score assigned to the cases exhibiting the different molecular subtypes. In connection with each molecular subtype, a mean feature score, and upper and lower feature score boundaries are illustrated. By way of example, the cases having the luminal A molecular subtype received a mean US boundary zone feature score of 4.83, as well as upper and lower boundaries at the 99% CI (confidence index) of 4.98 and 4.67, respectively. The cases having the luminal B molecular subtype received a mean US boundary zone feature score of 4.54, with upper and lower 99% CI boundaries of 4.70 and 4.38, respectively. The cases with the HER-2 subtype received a mean US boundary zone feature score of 4.78, and upper and lower 99% CI boundaries of 5.04 and 4.52, respectively. The cases with the TNBC subtype received a mean US boundary zone feature score of 4.30, with upper and lower 99% CI boundaries of 4.60 and 4.00, respectively. It is also been determined that the TNBC cases have lower US boundary zone feature scores as compared to the luminal A and luminal B subtypes.

Figure 12H:
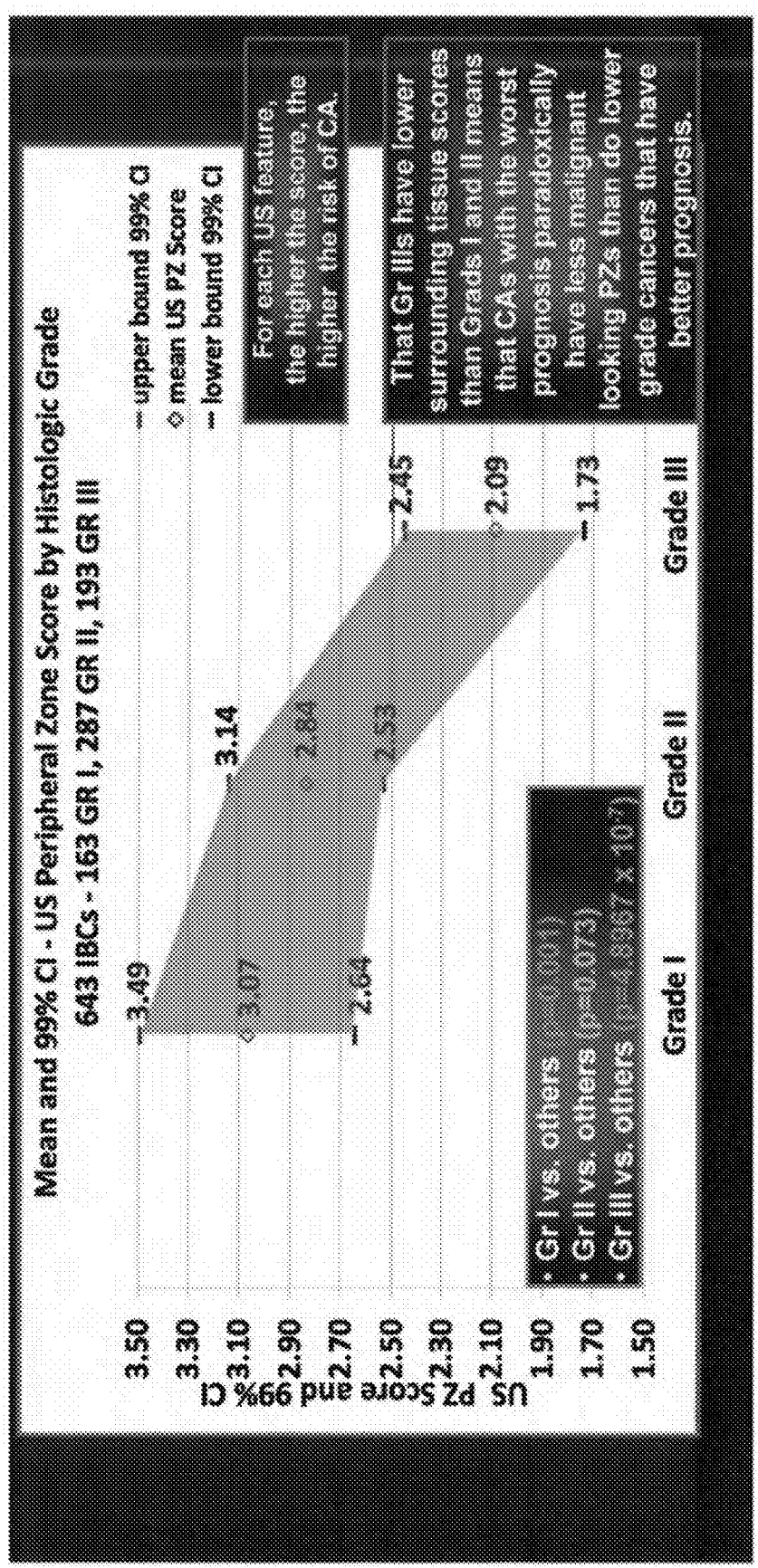
FIG. 12H illustrates a relation between the US peripheral zone feature score assigned to the cases in a patient population exhibiting the different histologic grades of carcinoma.

FIG. 12H illustrates a relation between the US peripheral zone feature score assigned to the cases in a patient population exhibiting the different histologic grades of carcinoma. By way of example, the cases having the histologic grade I received a mean US peripheral zone feature score of 3.07, as well as upper and lower boundaries at the 99% CI (confidence index) of 3.49 and 2.64, respectively. The cases having the histologic grade II received a mean US peripheral zone feature score of 2.84, with upper and lower 99% CI boundaries of 3.14 and 2.53, respectively. The cases with the histologic grade III received a mean US peripheral zone feature score of 2.09, with upper and lower 99% CI boundaries of 2.45 and 1.73, respectively. In accordance with new and unique aspects herein, it has been determined that a substantial difference occurs between the US peripheral zone feature score for masses having grade III as compared to masses having grade I and II. As one example, invasive breast cancers that are grade I and II are far more frequently spiculated then grade III tumors.

Figure 12I:
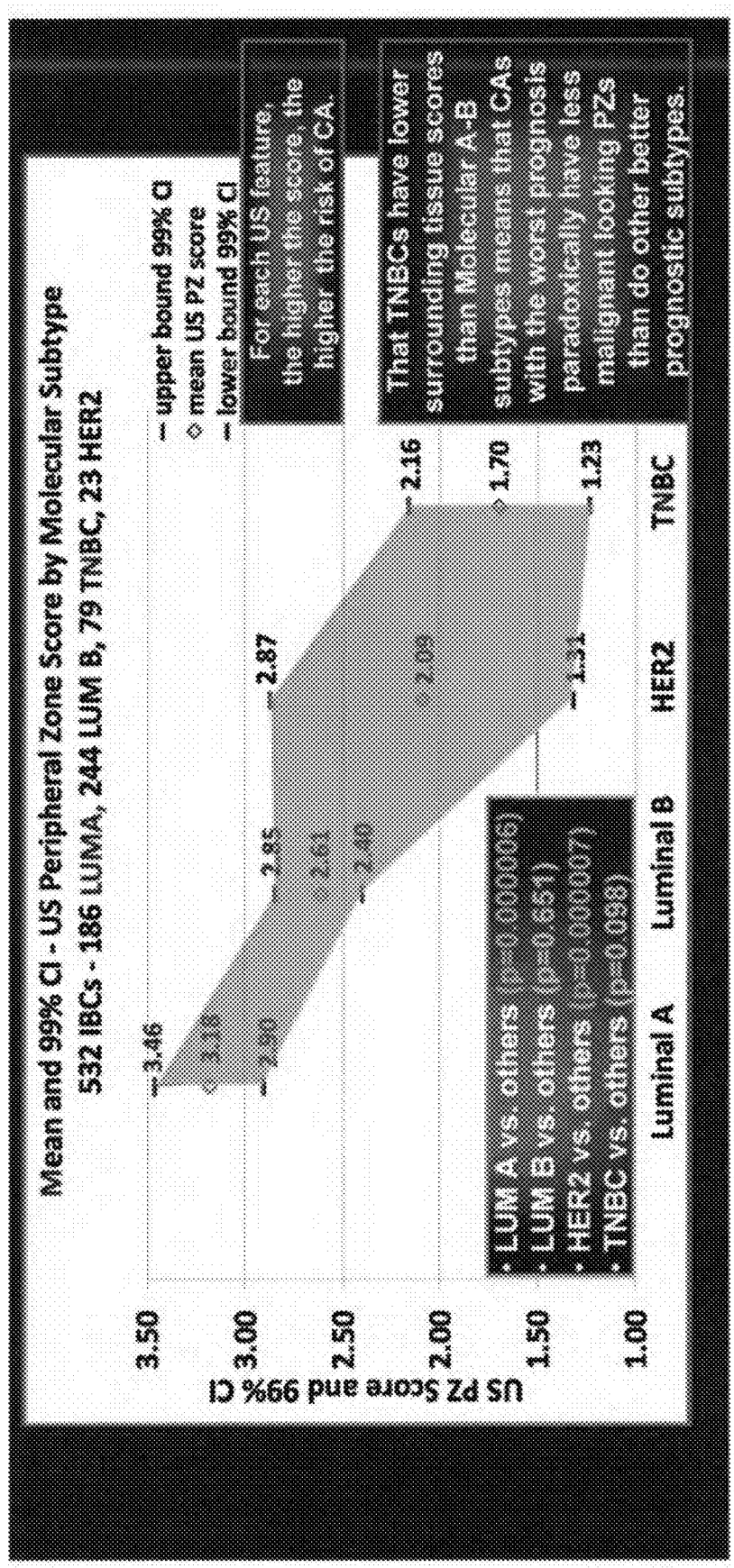
FIG. 12I illustrates a relation between the US peripheral zone feature score assigned to the cases exhibiting the different molecular subtypes.

FIG. 12I illustrates a relation between the US peripheral zone feature score assigned to the cases exhibiting the different molecular subtypes. By way of example, the cases having the luminal A molecular subtype received a mean US boundary zone feature score of 3.18, as well as upper and lower boundaries at the 99% CI (confidence index) of 3.46 and 2.90, respectively. The cases having the luminal B molecular subtype received a mean US peripheral zone feature score of 2.61, with upper and lower 99% CI boundaries of 2.85 and 2.40, respectively. The cases with the HER-2 subtype received a mean US peripheral zone feature score of 2.09, and upper and lower 99% CI boundaries of 2.87 and 1.31, respectively. The cases with the TNBC subtype received a mean US peripheral zone feature score of 1.70, with upper and lower 99% CI boundaries of 2.16 and 1.23, respectively. It is also been determined that the TNBC cases have lower US peripheral zone feature scores as compared to the luminal A and luminal B subtypes.

Predictive Machine Learning Classifier

In accordance with embodiments herein, a feature score to molecular subtype (FSMS) machine learning classifier builds and utilizes classification models in conjunction with US/OA imaging to assist radiologist in predicting molecular subtypes and/or histologic grades, as well as whether lesions belong to a malignancy class or a benign class. The FSMS machine learning classifier builds models that assign probabilities to the molecular subtype and/or histologic grade predictions. One unique aspect herein is the manner in which the PLM classifier builds the models to assign the probabilities to the predictions based on certain types of thresholds and relations between feature scores. In order to provide predictions, the FSMS machine learning classifier combines probability with one or more thresholds. The criteria for where to set the thresholds are separate from building the models. In embodiments herein, the criteria are set based on training labeled data that is collected from numerous individuals and analyzed by readers. The criteria are further set based on the premise that, if certain thresholds were applied to the study data, a molecular subtype and/or histologic grade predictive result would yield a desired level of sensitivity (e.g., 98%).

Embodiments herein provide a FSMS machine learning classifier and classification models which is a software tool used in conjunction with an ultrasound imaging system and/or optoacoustic imaging system to assist radiologists in determining whether a breast lesion has a high enough risk of a particular molecular subtype and/or histologic grade. The input to the classification models includes a set of feature values (e.g., OA and US Feature scores) that are assigned by the radiologist or sonographer and an output that includes an estimated probability of malignancy (POM) for one or more molecular subtypes and/or histologic grades.

Basic Model

At a base level, models may be constructed that include a Prediction for Classification (NPC) model and a Prediction for POM (NPP) model, where POM represents a Probability of Malignancy. The NPC and NPP models utilize various US and OA feature scores and can be trained based on a set of feature scores assigned by a human expert while viewing lesions that are present in a data set of images collected from a group of individuals. While the NPC and NPP models are beneficial, there is an important distinction between an NPP model and an NPC model. The NPC model represents a logistic regression classifier that is trained based on biopsy outcomes (e.g., malignant, benign, molecular subtypes and/or histologic grades). Conversely, the NPP model represents a linear regression equation that is trained based on POM estimates that are assigned by the human expert. Whereas the NPC model predicts the biopsy results, the NPP model predicts the reader's estimate of the POM being associated with a particular molecular subtypes and/or histologic grades. The POM is a continuous value between 0.0 and 1.0, inclusive.

In accordance with embodiments herein, FSMS machine learning classification models have been developed that provide a better predictor of the probability of malignancy for one or more molecular subtypes and/or histologic grades, as compared to the base models discussed above. As the name implies, the classification models are trained using predictive machine learning methods and a supporting software framework.

Figure 14:
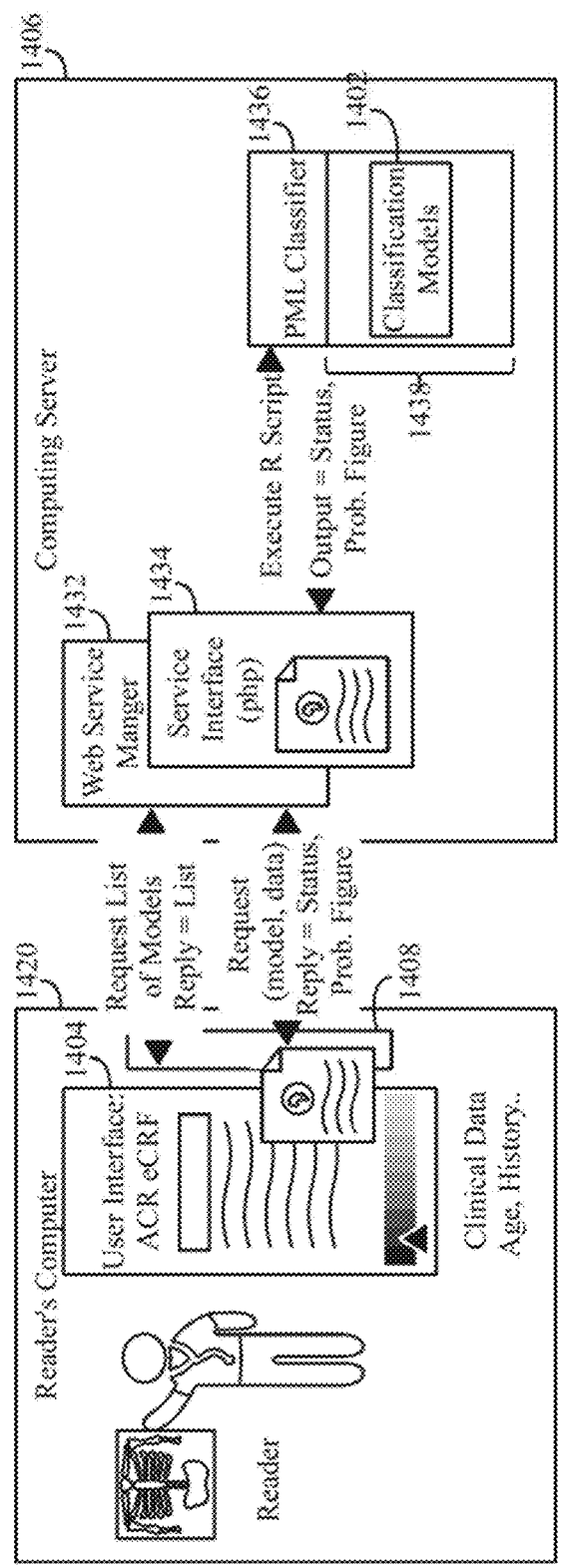
FIG. 14 illustrates a block diagram of the basic components of a classification system in accordance with embodiments herein.

FIG. 14 illustrates a block diagram of the basic components of a classification system in accordance with embodiments herein. The classification system includes one or more computing devices 1420 that represent "reader computers" utilized by clinicians to analyze an individual patient's data set of OA/US images and other medical information related to the individual patient. The computing device 1420 may be implemented as various types of computers, such as a workstation, a laptop computer, a tablet device, a smart phone and the like. The computing device 1420 includes one or more processors executing program instructions stored in memory to provide, among other things, a graphical user interface (GUI) 1404. The GUI 1404 enables radiologists and other experts to enter features scores and view the predictive results for one or more molecular subtypes and/or histologic grades. The GUI 1404 may be developed in any suitable web language, such as HTML and JavaScript. The GUI 1404 may be tailored for different situations, such as feasibility studies, pivotal studies, and commercial use. The GUI 1404 may be implemented on any appropriate platform, including tablets and workstations. The GUI 1404 is independent of the classification models 1402.

The computing device 1420 further includes an application programming interface (API) 1608. The API 1608 presents a protocol that defines the communication between the GUI 1604 and the remote computing server 1606. The API 1608 is a set of rules for communication between the classification models 1602, GUI 1604 and server 1606. The API 1608 decouples the GUI 1604 from the computation software implemented by the server 1606 which simplifies the development and verification of the FSMS machine learning classifier and classification models, and encourages the building of GUIs 1604 for various platforms such as tablets, smart phones and workstations.

The computing devices 1620 communicate with a remote computing server 1606. Nonlimiting examples of entities that may implement the remote computing server 106 include a medical network, a medical facility, a manufacturer of imaging equipment, a third-party data management service, third-party diagnostic image screening services, and the like. The computing server 1606 includes one or more processors executing program instructions, to implement the operations described herein, as well as other operations associated with medical diagnostic imaging, diagnosis, therapy planning, therapy delivery and the like. The server 106 receives requests from the API 1608, computes predictions, and returns the predictive results. The program instructions for the server 1606 may be installed on computers in remote data centers, on a local network, one or more workstations, laptop computers, handheld electronic devices (e.g., tablet device, smart phone), the same physical device as the GUI 1604 and the like.

The remote computing server 1606 includes one or more processors implementing program instructions to provide a web service manager, a network service interface 1634, and a FSMS machine learning classifier 1636. The web service manager 1632 receives request from computing devices 1620 and returns corresponding replies. The network service interface 1634 provides an interface between the web service manager 1632 and the FSMS machine learning classifier 1636. The remote computing server 1606 includes a data storage 1638 that comprises, among other things, classification models 1602. As explained herein, the classification models may be organized in various manners, such as one or more ensembles of classification models 1602. In accordance with certain types of FSMS machine learning classifiers 1636, each classification model 1602 may be built to include one or more decision trees (e.g. 10, 50, 100 decision trees in one classification model).

The classification models 1602 are defined by a mathematical algorithm, independent variables representing features, and parameters determined by training based on one or more labeled data sets for a control group of individuals. The infrastructure of the PML classification system allows for multiple models 1602 to be built in order to better support various feature sets and improvements over time. For example, one ensemble of classification models 1602 may be utilized with US features only, or OA features only, while another ensemble of classification models 1602 may be utilized with a combination of OA and US features. As a further example, one ensemble of classification models 1602 may be utilized in connection with a first molecular subtype of malignancies, while another ensemble of classification models may be utilized in connection with a second molecular subtype of malignancies.

The classification models 1602 may be developed and trained by a FSMS machine learning classifier 1636 that utilizes various languages, such as the R language for statistical computing and graphics (available from https://www.r-project.org). For example, the server 1606 implements the FSMS machine learning classifier 1636 as a set of R scripts that compute classification probabilities from the classification models 1602. The classification models 1602 are not a single model; but rather a collection or ensemble of models that utilize different algorithms, features, and training data sets. The classification models 1602 implement classification through machine learning in which the models are trained based on labeled data for OA images and non-OA images. For example, the classification models 1602 may be built with a master model that is built based on all or substantially all of the available labeled data set and may be built to include one or more bootstrapped models and hold out models. Bootstrapped models represent classification models that are formed from a select subset of the labeled data set. Hold out models represent classification models that are formed utilizing cross validation or another related model evaluation technique. In embodiments herein, the classification is a pattern recognition problem that uses a binary classifiers as a special case in which there are only two outcomes. The classifier may have many classes. For example, a set of animal images can be classified as "cat", "dog", "bird", etc. In mathematical terms, the class label is a categorical variable. When the classifier is applied to an observation, it estimates the probability that the observation belongs to a particular class (e.g. particular molecular subtype and/or histologic grade). The FSMS machine learning classifier and classification models does not decide the class; instead the FSMS machine learning classifier and classification models apply a threshold (or cut point) that results in a prediction. The choice of the threshold may vary.

Each classification model 1602 is defined by three elements: an algorithm, features, and parameters, which are described hereafter in general, along with an explanation for a model "learns" from a training data set. Classification approaches are of two basic types: parametric equations and machine learning algorithms. Parametric equations are more transparent in that the effect of each feature is easy to understand. However equations are limited in what they can model. Machine learning methods can be applied more broadly, but it is often difficult to understand how the model works and what it finds important.

Embodiments herein utilize machine learning algorithms within the FSMS machine learning classifier 1636. Non-limiting examples of machine learning algorithms include classification and regression trees (CART), C4.5 decision trees, K nearest-neighbor, Support Vector Machines (SVM), and Naïve Bayes classifiers. Irrespective of the algorithm, a single model often suffers from either inaccuracy or overfitting. To overcome the potential for inaccuracy or overfitting, embodiments herein train and utilize multiple models to generate multiple predictions for an observation. The collection of the classification models are referred to as an "ensemble" of models. Embodiments herein utilize the random forest algorithm to form an ensemble of decision trees and/or the extreme gradient boosting (XGB) algorithm to form an ensemble that can be used with CART decision trees or with linear classifiers. The XGBOOST algorithm often outperforms other algorithms when properly tuned and can be used on massive data sets.

Figure 15A:
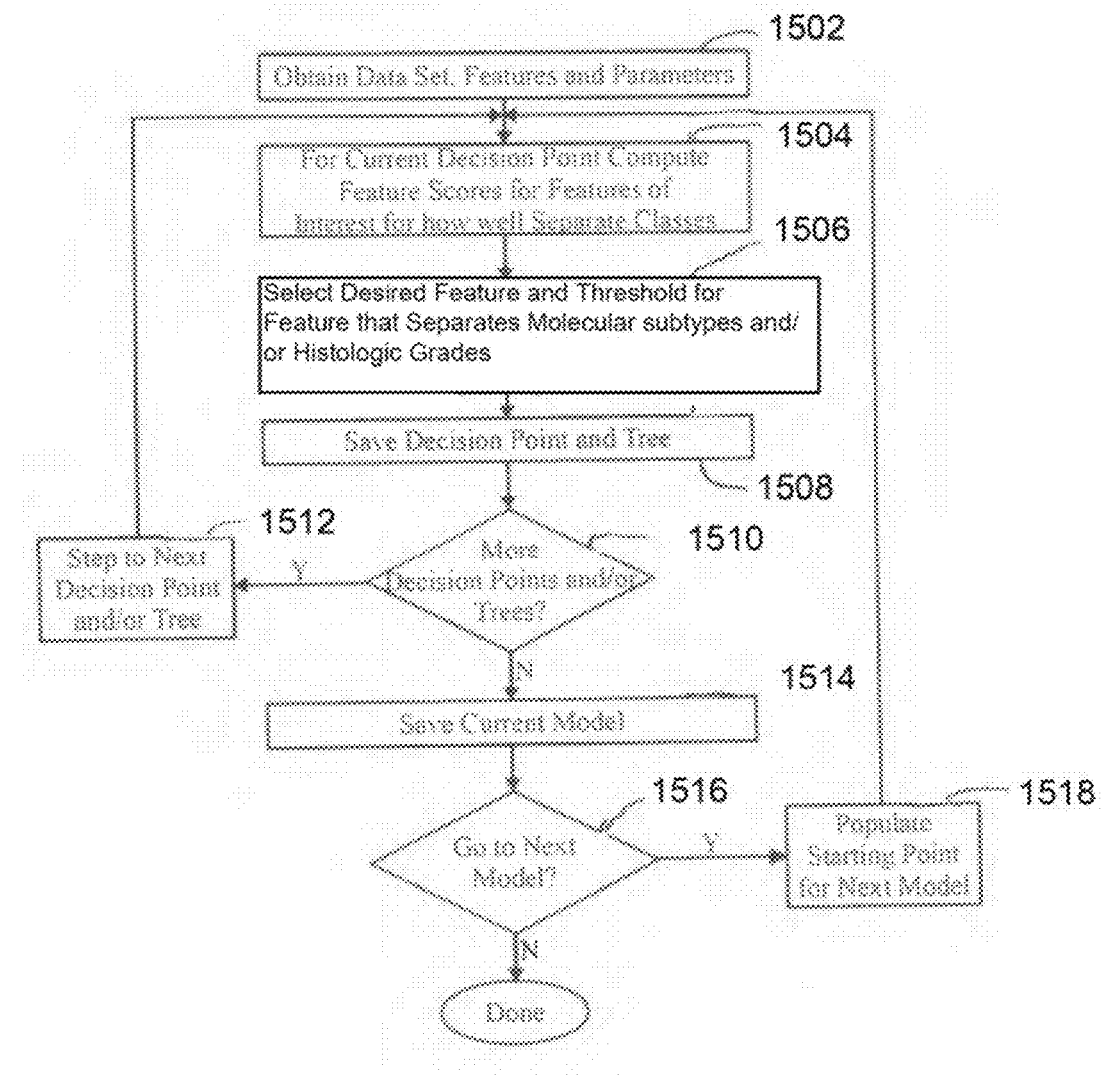
FIG. 15A illustrates a process for building an ensemble of classification models in accordance with embodiments herein.

FIG. 15A illustrates a process for building an ensemble of classification models in accordance with embodiments herein. The operations of FIG. 15A may be implemented by processors at a system located at one location, or server or distributed between multiple remote locations or servers. At 1502, the one or more processors obtain a labeled data set for multiple patients, along with a collection of US/OA features and parameters. The operations at 1504-1518 step through the labeled data set in various manners, based on the type of FSMS machine learning classifier algorithm being utilized to build the ensemble of classification models. It is recognized that the particular branches, decision points and order of operations described in connection with FIG. 15A will vary within embodiments contemplated herein, but still result in an ensemble of classification models as described herein. At 1504, the one or more processors begin analyzing the labeled data set for a current decision point in a current decision tree. The processors compute outcome scores for one or more features of interest. The outcome scores are indicative of how well a particular feature of interest separates the labeled patient data into a particular molecular subtype and/or histologic grade. At 1506, the one or more processors review the outcome scores and select the desired feature, as well as a threshold to be applied to the feature. The feature and threshold selected at 1506 may represent the "best" feature and threshold that separate the labeled data set into one or more molecular subtypes and/or histologic grade classes based on the present point in the decision tree.

Although learning methods vary depending upon the algorithm, the core of the mathematics is an iterative search over the feature space. Iterative searching is computationally intensive, especially when there are a large number of features and/or a large amount of data. Reducing the search space speeds up the process but tends to find a less optimal solution. As before, consider decision trees as an example. Decision trees learn by finding the optimal criteria to split the tree into branches. Each path through the tree ends up at a leaf and the goal is to find the splits, or decision points, such that each leaf contains mostly one class. The feature chosen for a split is found by considering all possible features and their values and selecting the feature that provides a desired result (e.g., the best one). As one example, the selection may be whether to use a boundary score or an internal vessel score as the feature to analyze at the decision point. In addition to selecting the feature to use at each branch, the FSMS machine learning classifier also determines what threshold level to apply to the feature at the decision point. For example, when boundary score is selected as the feature of interest at a particular branch point, then the FSMS machine learning classifier also assigns a boundary threshold, such that when the boundary score is above the boundary threshold, the decision branches in a first direction and when the boundary score is below the boundary threshold, the decision branches in a second direction.

As one example, the operations at 1504,1506 may be performed by computing a score called a "Gini impurity index" which is used to choose a split with the lowest score. Each split considers many features, a tree contains multiple splits, and an ensemble contains many trees. Beyond the feature level parameters, embodiments may utilize machine learning algorithms that have hyper-parameters that are tuned. For example, embodiments that use XGBOOSTtrees have a large set of hyper-parameters, including the number of trees, the maximum tree layer depth, and the learning rate. Hyper-parameters add dimensions to the search space and hence increase the computation effort for training. At 1508, the one or more processors save the decision point within a current decision tree. At 1510, the one or more processors determine whether the analysis should continue for more decision points in the current decision tree and/or whether the analysis should continue for a next the decision tree. If so, flow branches to 1512. Otherwise, flow continues to 1514. At 1512, the one or more processors step to the next decision point in the current decision tree. For example, branching continues until the maximum tree depth, a lesion trait is identified or other criteria are met. The number of branches, the features used at each branch, and values used for separation at each branch are all parameters of the model. In essence, the parameters embody the training data. Good parameters result from a combination of attention to detail in features, data, and algorithm tuning. When a decision tree is finalized, the processors also assign lesion traits (e.g. benign class, malignant class, cancer subtype) to the last layer. The lesion traits may be stored with a classification probability based on the individual corresponding decision tree. Alternatively, when a decision tree is completed at 1510 and a new decision tree is to be started, the operation at 1512 steps to the next decision tree and flow returns to 1504. The operations at 1504-1512 are continuously operated until all of the decision points in a desired number of decision trees are built. At 1514, the one or more processors save, as a current model, the collection of decision trees, each of which is comprised of a set of decision points built from the feature scores, feature selections and threshold selections described above.

At 1516, the one or more processors determine whether another model is to be built from the labeled data set. If so, flow branches to 1518. At 1518, the one or more processors populate starting points within the next model. Otherwise, the process of FIG. 15A ends. In accordance with the operations of FIG. 15A, and/or alternative sequences of operations, embodiments herein fit the model parameters to the labeled data set through a training or learning process. The training/learning process is also referred to as "building" the model.

Next, two examples of predictive machine learning algorithms are described that may be implemented in connection with embodiments herein.

Logistic Regression Models

One example of a predictive machine learning algorithm that may be implemented herein is logistic regression. Logistic regression is a supervised machine learning algorithm because it uses true labels for training. A supervised learning algorithm has input variables (x) and an target variable (Y) when the model is train, as in logistic regression algorithms. Embodiments herein form an ensemble of logistic regression models (e.g., 100), each trained on a subset of the control data set. The prediction is returned as the mean confidence interval (probability of malignancy or LOM) and a confidence interval range (e.g., 90%) of the predictions from the ensemble. The prediction is returned as the Positive Predictive Value (PPV) that corresponds to the classifier probability.

The logistic regression models utilize a training data set that comprises a collection of observations or reads (e.g., 100, 1000, 10000). Each of the observations contains a set of OA images, US images, combinations of OA/US images, OA feature scores, and US feature scores. The OA and US feature scores may be assigned automatically by a computing system that segments and analyzes the OA, US and combined images. Additionally or alternatively, the OA and US feature scores may be assigned by one or more human independent reader. The OA and US scores relate to one or more characteristics of one or more lesions in the OA and US image set for an individual patient. The training data set includes a collection of images for a number of positive cases (malignant) and a number of negative cases (benign).

The logistic regression model utilizes a feature set that includes reader-assigned scores for OA and US features, the patient age and the mammogram (MMG) BI-RADS category assigned by the site radiologist. The MIVIG BI-RADS is not defined for all observations. By way of example, the logistic regression model includes 5 or more OA feature scores, 5 or more US feature scores, age, and MIVIG BI-RADS applied in a heuristic rule. For example, the MIVIG BI-RADS heuristic rule may be defined as {2, 3, 4a, 4b, 4c, 5}. Initially, MMG BI-RADS may not be utilized as a feature in the logistic regression algorithm because too many lesions in the data set may be missing MMG data. However, once a data set collects a sufficient amount of MMG data the logistic regression algorithm can be trained on the subset of data with MIVIG data. Optionally, even while the MIVIG BI-RADS may not be utilizes as a feature, the MIVIG BI-RADS may be applied as a heuristic rule that prohibits a downgrade if the MMG BI-RADS is at a certain level (e.g., 4c or 5). For cases with a MIVIG BI-RADS rating at or above the set level, the SenoGram returns the maximum of the classifier prediction and the benchmark PPV for the category, computed as the midpoint of the range (e.g. 70% for 4c, and 95% for 5). The MMG BI-RADS heuristic rule is not applied if the MMG BI-RADS rating is missing or inconclusive.

The foregoing logistics regression machine learning algorithm was evaluated using repeated K-fold cross-validation with 5 repeats and 10 folds. Metrics were averaged over the 50 test sets to obtain the following approximate results: AUC between 0.92 and 0.96, pAUC between 0.75 and 0.80, sensitivity at or above 97.0%, specificity at or above 52.0%.

Extreme Gradient Boost Trees (XGBTree)

Additionally or alternatively the machine learning algorithm (FSMS machine learning classifier) may be implemented utilizing an Extreme Gradient Boosting Trees (XGBTree) machine learning algorithm. In order to understand the XGBTree, the decision tree should first be understood. Decision trees are a method of splitting the data based on features to either classify or predict some value. Each branch in a decision tree divides the data into one of two (or several, if the tree is not binary) groups. Each leaf node is allocated with a single label (class or predicted value). When predicting using the decision tree, the data is allocated to the appropriate leaf node, and the prediction is the label of that leaf node. Decision trees are flexible and interpretable.

However, a single decision tree is prone to overfitting and is unlikely to generalize well. There are various ways of restricting the flexibility of a decision tree, such as by limiting its depth, but those methods then cause the decision tree to underfit. This is why decision trees are generally not used alone: instead, multiple decision trees are used together. Gradient boosting decision trees are one method (among many) of combining the predictions of multiple decision trees to make predictions that generalize well. Despite their strength, the idea behind XGBTree algorithms is very basic: combine the predictions of multiple decision trees by adding the predictions together. XGBTrees are trained iteratively—i.e. one tree at a time. For instance, the XGBTree algorithm first train a simple, weak decision tree based on the data. The decision tree is trained to minimize an objective function—using a lost term—such as the mean squared error-by recursively splitting the data in a way that maximizes some criterion until some limit-such as the depth of the tree—is met. The criterion is chosen so that the loss function is (approximately) minimized by each split. One commonly used criterion is the classification accuracy which is the fraction of observations that are correctly partitioned by the split.

The training of a decision tree is a recursive processing. The next tree is then trained to minimize the loss function when its outputs are added to the first tree. This is (approximately) achieved by recursively splitting the data according to a new criterion. For example, the criterion can be simply calculated for any split of data based on the gradient statistics (the value of the gradient for each data point). It should be noted that computing the best split requires the model to go through various splits and compute the criterion for each split. There is no analytical solution for determining the best split at each stage.

The XGBTree machine learning algorithm forms an ensemble of XGBTree models, each trained on all or a subset of a data set. As with the logistics regression machine learning algorithm, the prediction is returned as the mean and 90% confidence intervals of the ensemble, with the classification probability mapped to the observed PPV in the training data. The XGBTree machine learning algorithm may utilize the same or different training data as the logistic regression MLA. Additionally, the XGBTree MLA may also utilize individual human expert data. The XGBTree MLA utilizes the same features as for logistic regression MLA, with the possible addition of artifact scores, lesion size and/or lesion orientation. The MMG BI-RADS category may be included as a feature of the XGBTree MLA rather than applied in a heuristic rule, depending upon the amount of missing MMG data.

When growing the XGBTree, both XGBoost and lightGBM use the leaf-wise growth strategy. When training each individual decision tree and splitting the data, there are two strategies that can be employed: level-wise and leaf-wise. The level-wise strategy maintains a balanced tree, whereas the leaf-wise strategy splits the leaf that reduces the loss the most. Level-wise training can be seen as a form of regularized training since leaf-wise training can construct any tree that level-wise training can, whereas the opposite does not hold. Therefore, leaf-wise training is more prone to overfitting but is more flexible. This makes it a better choice for large datasets. Compared to the case of level-wise growth, a tree grown with leaf-wise growth will be deeper when the number of leaves is the same. This means that the same max_depth parameter can result in trees with vastly different levels of complexity depending on the growth strategy.

An important challenge in training the XGBTree is the process of finding the best split for each leaf. When naively done, this step requires the algorithm to go through every feature of every data point. The computational complexity is thus $O(n\_\{data\} \; n\_\{features\})$. Modern datasets tend to be both large in the number of samples and the number of features. For instance, a tf-idf matrix of a million documents with a vocabulary size of 1 million would have a trillion entries. Thus, a naive GBDT would take forever to train on such datasets. There is no method that can find the best split while avoiding going through all features of all data points. Therefore, the various methods that XGBoost and lightGBM present are methods of finding the approximate best split.

Optionally, histogram-based methods (XGBoost and lightGBM) may be utilized. The amount of time it takes to build a tree is proportional to the number of splits that have to be evaluated. Often, small changes in the split don't make much of a difference in the performance of the tree. Histogram-based methods take advantage of this fact by grouping features into a set of bins and perform splitting on the bins instead of the features. This is equivalent to subsampling the number of splits that the model evaluates. Since the features can be binned before building each tree, this method can greatly speed up training, reducing the computational complexity to $O(n\_\{data\} \; n\_\{bins\})$. Though conceptually simple, histogram-based methods present several choices that the user has to make. Firstly the number of bins creates a trade-off between speed and accuracy: the more bins there are, the more accurate the algorithm is, but the slower it is as well. Secondly, how to divide the features into discrete bins is a non-trivial problem: dividing the bins into equal intervals (the most simple method) can often result in an unbalanced allocation of data. XGBoost offers the option tree_method=approx, which computes a new set of bins at each split using the gradient statistics. LightGBM and XGBoost with the tree_method set to histogram will both compute the bins at the beginning of training and reuse the same bins throughout the entire training process.

The operations of FIG. 15A or another model building process may be implemented multiple times utilizing different combinations of the available labeled data set of the control patient population. For example, all or a majority of the label data set for all or majority of the patient population may be utilized to build a master model. In accordance with embodiments herein, the master classification model is then utilized to calculate predictive results and the like. In addition, the labeled data set may be subdivided into folds or subsets, wherein different subsets of the observations in the labeled data set are defined as "hold out" observations. Hold out models are built during cross validation utilizing the portions of the label data set that was not held out. As explained herein, the held out portions of the labeled data set may then be applied to the hold out models in connection with calculating classification probabilities, from which mapping functions are built for positive predictive values, false-negative rates and the like.

Additionally or alternatively, subsets of the observations from the labeled data set may be utilized to build bootstrapped models. For example, the labeled data set may include 100 observations, from which a random sampling of the observations are selected and utilized to build a first bootstrapped model. Multiple bootstrapped models are built based on different combinations of samples of the observations from the labeled data set for the control patient population. Once the classification models are built, when new observations for new patients are obtained, the bootstrapped models are then utilized in connection with calculating predictive results, namely for calculating a prediction interval for the new OA and non-OA feature scores.

Figure 15B:
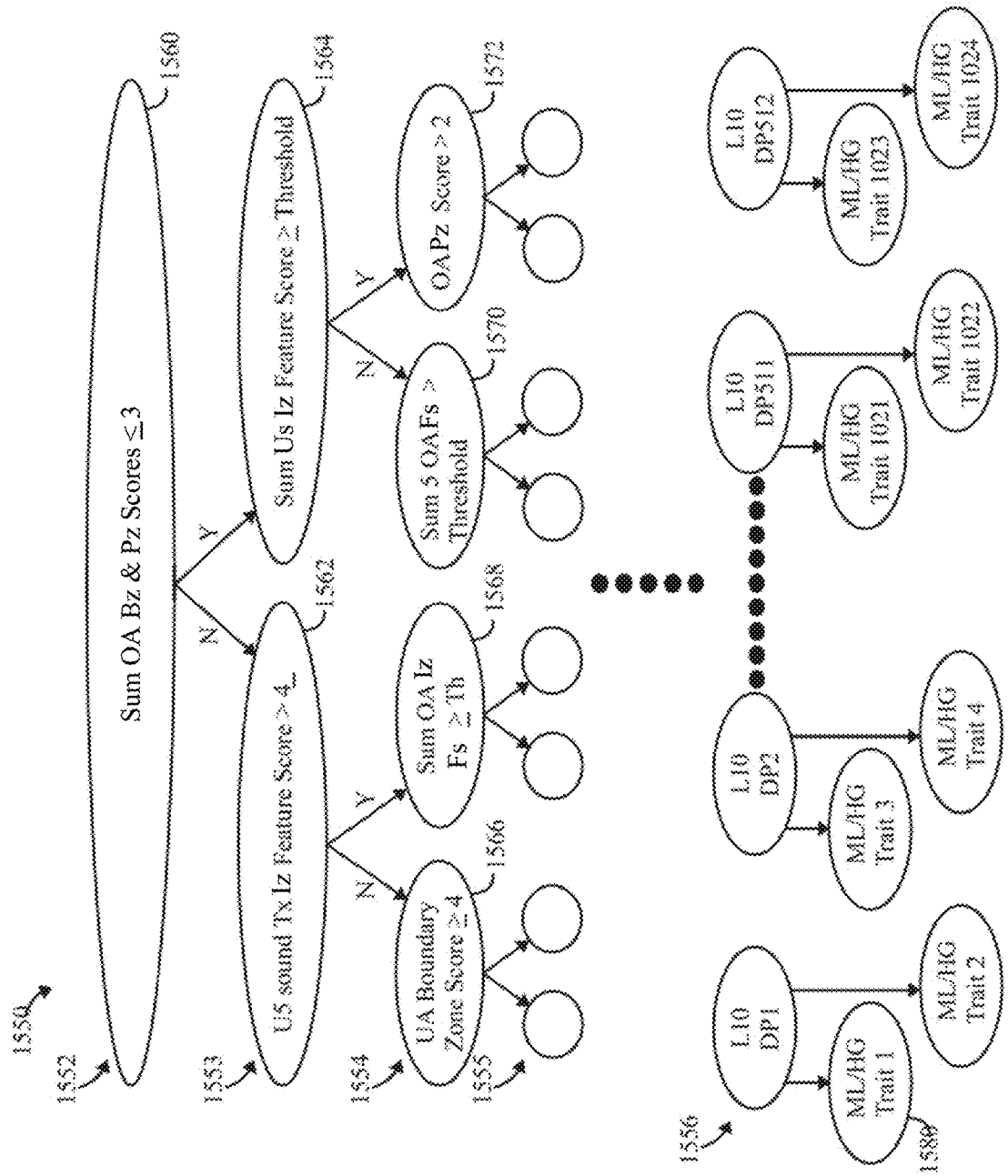
FIG. 15B illustrates an example of a decision tree from a classification model built in accordance with an embodiment herein.

FIG. 15B illustrates an example of a decision tree from a classification model built in accordance with an embodiment herein. For example, the decision tree 1550 may be built by the XGBtree algorithm during one or more iterations through the operations of FIG. 15A. Alternatively, the decision tree 1550 may be built from an XGBtree or other algorithm following operations that differ from FIG. 15A. The decision tree comprises decision points, branches between decision points and lesion traits. Lesion traits are obtained from multiple decision trees and mathematically combined to form a classification probability that a lesion exhibits a particular trait for a corresponding observation (e.g. based on the OA and non-OA feature scores assigned to the OA and non-OA images of the examination). The decision tree 1550 includes multiple layers 1552-1565, including first through tenth layers. The tenth layer 1556 is also denoted by the labels "L10". Each layer 1552-1556 includes a set of decision points (DP). Each decision point tests a feature of interest relative to a threshold. For example, the decision points may test the OA and US features described herein, where each OA and/or US feature score is compared to a threshold.

In the example of FIG. 15B, non-limiting examples of decision points are shown. A first decision point 1560 in the first layer 1552 may test whether the sum of the OA peripheral zone and OA boundary zone feature scores is less than or equal to 3. The OA features are scored manually by a human expert and/or automatically by a machine learning classifier classification. The decision tree branches from DP 1560 to decision points 1562 and 1564 in the second layer 1553. As an example, the decision point 1562 tests whether the US IZ sound transmission feature score is greater than or equal to 4. The decision point 1564 may test whether the sum of the three US internal zone feature scores are greater than or equal to a threshold (e.g. 10). The classification model branches at 1562 or 1564 based on the corresponding decision.

As other examples, the decision points 1566, 1568, 1570, 1572 test various corresponding OA/US feature scores. For example, at 1566, the model determines whether the US boundary zone score is greater than or equal to 4. At 1568, the model determines whether the sum of the OA internal zone feature scores is greater than or equal to a threshold. At 1570, the model determines whether the sum of all five OA feature scores (internal and external) are greater than a threshold. At 1570, the model determines whether the OA peripheral zone feature scores greater than or equal to 2.

The decision tree 1550 continues for multiple layers until reaching a depth limit (e.g., 10 layers) as noted at L10_DP1 to L10_DP512. Each decision point in the $10^{th}$ layer branches to two molecular subtype and/or histologic grade traits (ML/HG trait) 1580 based on the features to be tested and the score thresholds at layer 10. In the example of FIG. 15B, 1024 molecular subtype traits (ML/HG trait 1 to ML/HG trait 1024) are available in a decision tree having 10 layers where each decision point splits into two branches.

While the foregoing example illustrates a combination of US and OA feature scores, it is recognized that the model of FIG. 15B may be implemented based solely on US feature scores. Alternatively, the model of FIG. 15B may be implemented based solely on OA feature scores. Alternatively, the first few layers of the model may analyze only US feature scores, while the later layers of the model analyze only OA feature scores. Optionally, the first few layers of the model may analyze US and OA feature scores for the peripheral and boundary zones, while the later layers of the model analyze US and OA feature scores for the internal boundary zones. Additional and alternative combinations of US and OA feature scores, as well as the corresponding internal, boundary and peripheral zones, may be analyzed in different combinations and orders, and with different thresholds within the layers of the model.

While the foregoing example refers to molecular subtypes, it is recognized that the same decision tree and/or a different decision tree may be utilized to determine histologic grade traits. The molecular subtype traits may correspond to different information, depending upon the nature of the decision tree. For example, the molecular subtype traits may simply represent one of two binary choices regarding a trait of a molecular subtype (e.g. luminal A, luminal B). For example, ML traits 1-10, 20, 32-40 and 100-140 may designate the ML trait to correspond to the luminal A class, while the remaining ML traits designate the lesion to correspond to the TNBC class. Additionally or alternatively, each ML trait may include a classification probability associated therewith. For example, an output of a decision tree may designate a 40% likelihood that a ML trait is in the luminal B class. Optionally, when the decision trees are built to designate cancer molecular subtypes, the ML traits may be representative of more than two binary choices, instead designating a lesion trait to be one of various molecular subtypes and/or histologic grades. Additionally or alternatively, a decision tree may output a classification probability that a type corresponds to a molecular subtype and/or histologic grade. The classification probability provides a level of confidence that the observation (e.g. set of OA and non-OA feature scores for a current patient) is in a particular class, namely either a particular molecular subtype class and/or histologic grade class.

The example of FIG. 15B illustrates a binary type decision tree. Additionally or alternatively, the decision trees may include more than 2 branches from each node, when a test at each decision point includes more than 2 outcomes. The examples of FIG. 15B at decision points show OA feature score tests. It is recognized that many of the decision points will include tests for US feature scores with respect to US feature score thresholds. The FSMS machine learning classifier algorithm builds a master model that comprises multiple decision trees similar to decision tree 1550 based on at least partially different labeled data sets, at least partially different features and/or at least partially different parameters. The feature set and parameters are adjusted as part of a trade-off of a false negative rate vs. probability of malignancy. Although the false negative rate is related to the probability of malignancy, it is a fundamentally different quantity. The difference is important because there is a dichotomy in the use of FNR, or sensitivity, for reporting clinical study results, and the use of PPV, or probability of malignancy, in the BI-RADS lexicon familiar to radiologists. While PPV and probability of malignancy are sometimes used interchangeably, this is not strictly correct, as probability of malignancy refers to the entire population; whereas PPV is an estimate of likelihood based on a sample of the population. The distinction is analogous to the difference between the population mean and the sample mean.

FNR, sensitivity and specificity are at least two of the preferred metrics for diagnostic tests because they are intrinsic to the test and do not rely on prevalence of the disease or condition in the study population. Conversely, PPV does depend upon prevalence; a higher prevalence increases the PPV. When PPV is reported for a study, the prevalence should also be reported.

Figure 16:
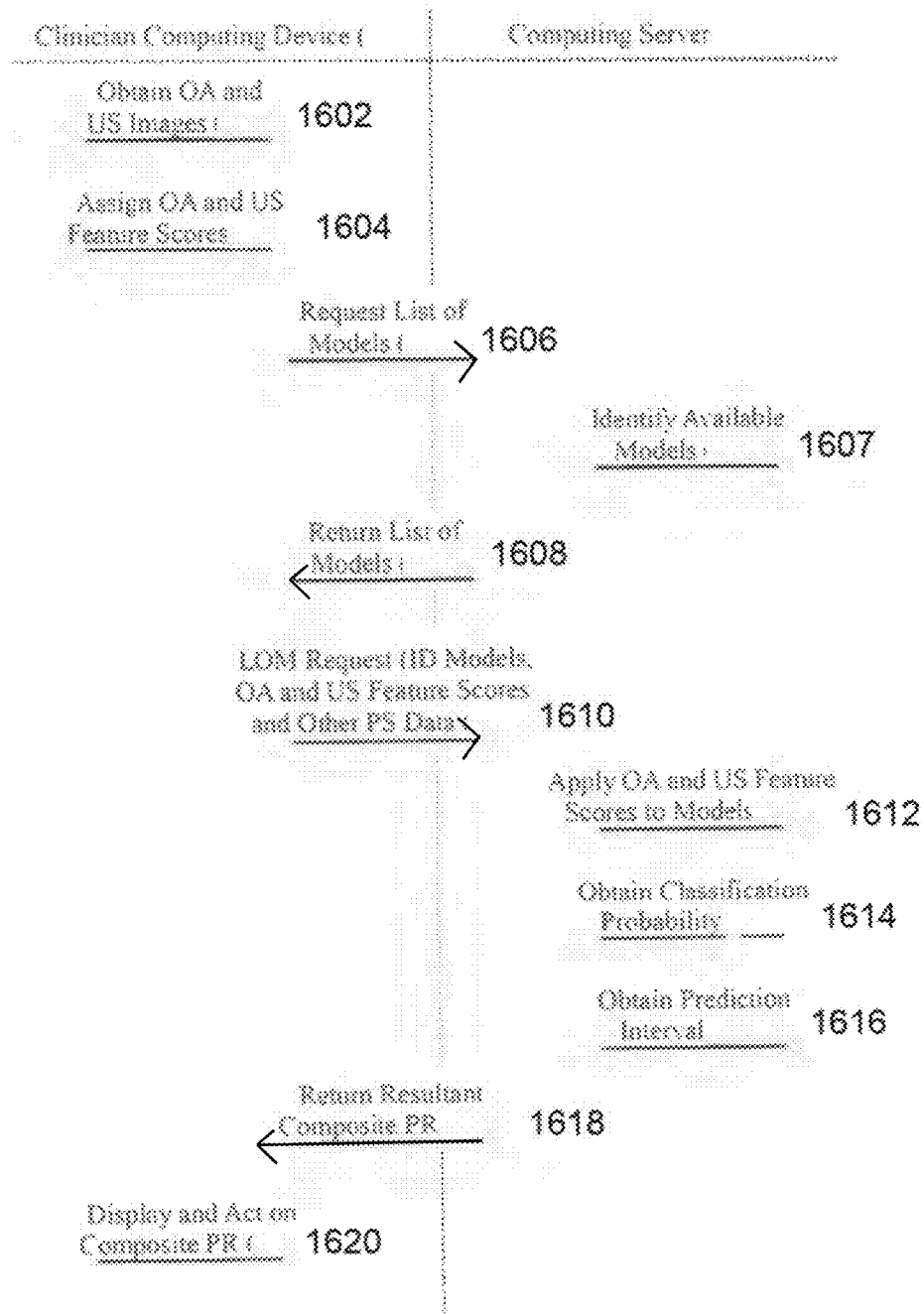
FIG. 16 illustrates a distributed operation diagram to further describe operations performed by a clinician computing device and a computing server in accordance with embodiments herein.

FIG. 16 illustrates a distributed operation diagram to further describe operations performed by a clinician computing device and a computing server in accordance with embodiments herein. The left side of the diagram represents operations performed by the clinician computing device, such as device 1620 in FIG. 16, while the operations on the right side of the diagram are performed by the server, such as server 1606. Beginning at 1802, one or more processors of the computing device 1620 obtain OA and US images. For example, the OA and US images may simply be read from a local or remote memory. Additionally or alternatively, the OA and US images may be obtained in real time, such as when the computing device 1620 is connected to or is formed interval with an optoacoustic imaging system. At 1804, the one or more processors of the computing device 1620 assign OA and US features scores. For example, the OA and US features scores may be assigned by a human expert while viewing the OA and US images. Additionally or alternatively, the OA and US features scores may be automatically assigned by the processors based on automated segmentation and analysis of the OA and US images. The automated assignment of OA in US features may be performed entirely separate from, or in conjunction with, the viewing by the human expert. For example, the OA feature score may relate to one or more of the following OA features: 1) internal vascularity and de-oxygenation, 2) peri-tumoral boundary zone vascularity and deoxygenation, 3) internal deoxygenated blush, 4) internal total blood, 5) external peri-tumoral radiating vessels, and 6) interfering artifact. For example, the non-OA feature score may relate to one or more of the following ultrasound features: 1) US Shape Score, 2) US Internal Texture, 3) US Sound Transmission, 4) US Capsular or Boundary Zone, 5) US Peripheral Zone, 6) Patient Age, 7) Mammogram-BIRADS, 8) Lesion Size, and/or 9) Lesion Posterior Depth.

Next, optional operations at 1806-1808 are described. At 1806, the computing device 1620 generates a request for a list of available models that may be utilized. The request to be generated automatically, without user input, by the computing device 1620. Optionally, the request may be generated in response to an instruction from the clinician through the GUI. The processors of the server 106 receive the request for the list of models and based thereon, identify the available models at 1807. At 1808, the processors of the server 1606 return the list of available models to the computing device 1620. The available models may be determined in various manners. For example, multiple ensembles of models may be stored in connection with one type of FSMS machine learning classifier. For example, the XGBTree FSMS machine learning classifier may generate multiple ensembles of models, where each ensemble of models is based on a different control labeled data set. Additionally or alternatively, each ensemble of models may be generated utilizing a different type of FSMS machine learning classifier. For example, the XGB tree FSMS machine learning classifier may generate a first ensemble of models utilizing a control labeled data set, while a logistic regression FSMS machine learning classifier may generate a second ensemble of models utilizing the same control labeled data set. Ensembles of models may be formed utilizing other types of FSMS machine learning classifiers.

Once the list of models is returned at 1808, the computing device 1620 selects one ensemble of models to be used in connection with the present individual patient. The selection of the ensemble of models may be performed manually by a clinician through the GUI. Additionally or alternatively, the processors of the computing device 1620 may automatically select the ensemble of models based on various criteria. For example, the computing device 120 may automatically selecting ensemble of models based upon the amount of information available for the present individual patient, based upon a nature of the OA and US images and the like. The operations at 506-508 are utilized when multiple ensembles of models are available. Optionally, when only a single ensemble of models is available, the operations at 1806-1808 may be omitted entirely.

At 1810, the computing device 1620 generates and sends a molecular subtype and/or histologic grade POM request (more generally a predictive result request) to the server 1606. The molecular subtype and/or histologic grade POM request (predictive result request) may include, among other things, an identification of the ensemble of models to be utilized, as well as OA and US features scores and other patient specific data (e.g. age, Bi-RAD scores). The server 106 receives the OA and non-OA features scores in connection with OA images and non-OA images collected from a patient examination for a volume of interest, where the volume of interest includes a suspect lesion. At 1812, the processors of the server 1606 apply the OA and non-OA features scores of the present observation to a designated master classification model and bootstrap classification models to obtain a predictive result indicative of a lesion trait (e.g. a likelihood that a lesion is in a malignant class or benign class). At 1814, the processors of the server 1606 obtain the classification probability based on the OA and non-OA features scores of the present observation as applied to the master classification model. Additionally or alternatively, the processors of the server 1606 may obtain a positive predictive value, based on the PPV mapping function and the current classification probability for the present observation. At 1816, the processors of the server 1606 obtain the prediction interval based on the OA and non-OA features scores of the present observation as applied to the bootstrap classification models.

At 1818, the processors of the server return, as a composite predictive result (PR) response the combination of the classification probability and/or PPV, and the reduction interval. As noted herein, the classification probability or the PPV may be utilized as the probability of malignancy. At 1820, the processors of the computing device output the composite PR (e.g. POM and prediction interval for one or more molecular subtypes and/or histologic grades), such as by displaying the composite PR through the GUI. The output of the composite PR may also include storing the composite PR in connection with a patient's records. Additionally or alternatively, the computing device may perform other actions based on the composite PR. For example, the computing device may send a notification to other medical personnel, initiate a report, initiate scheduling of a follow-up procedure and the like. As a further example, when the POM and confidence interval indicate the molecular subtype and/or histologic grade, the computing device may send a notice or report automatically to the patient (e.g. via text message, email or other electronic notification means).

CLOSING STATEMENTS

It is understood that the terms "in accordance with embodiments" and "in accordance with aspects", shall be used to refer to individual structures, functions, operations and the like that are new and unique; however, are not required for each and every implementation.

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

The invention claimed is:

1. A method, comprising: utilizing one or more processors in connection with, receiving Optoacoustic/Ultrasound (OA/US) feature scores in connection with OA/US images collected from a patient examination for a volume of interest; managing scoring of the OA/US feature scores in a predetermined outside-to-inside order, that includes first requiring assignment of one or more OA/US peripheral zone feature scores, second requiring assignment of one or more OA/US boundary zone feature scores, third requiring assignment of one or more OA/US internal zone feature scores; applying the OA/US feature scores to a feature score to molecular subtype (FSMS) model; and determining, from the FSMS model, an indication of at least one of a molecular subtype or histologic grade of a pathology experienced by the patient.

2. The method of claim 1, wherein the pathology represents breast cancer and the molecular subtype represents one or more of Luminal A (LumA), Luminal B (LumB), Triple-negative (TRN) and HER2 amplified (HER2+).

3. A method, comprising: utilizing one or more processors in connection with, receiving Optoacoustic/Ultrasound (OA/US) feature scores in connection with OA/US images collected from a patient examination for a volume of interest; applying the OA/US feature scores to a feature score to molecular subtype (FSMS) model; and determining, from the FSMS model, an indication of at least one of a molecular subtype or histologic grade of a pathology experienced by the patient, wherein the FSMS model distinguishes at least one of the following: A) between Luminal A and Luminal B molecular subtypes based on the OA/US features scores for at least two of: a) US internal zone sound transmission feature score; b) a sum of the US boundary and peripheral zone feature scores; or c) a sum of b), and a US internal zone shape feature score, US internal zone echotexture feature score, and the US internal zone sound transmission feature score; B) between Luminal A and TNBC molecular subtypes based on the OA/US features scores for at least two of: a) US internal zone sound transmission feature score; b) US boundary zone feature score; c) US peripheral zone feature score; d) a sum of US internal zone shape feature score, US internal zone echotexture feature score, and the US internal zone sound transmission feature score; e) a sum of the US boundary and peripheral zone feature scores; or f) a sum of d) and e); C) between Luminal A and HER2 molecular subtypes based on the OA/US features scores for at least two of: a) US internal zone sound transmission feature score; b) a sum of US internal zone shape feature score, US internal zone echotexture feature score, and the US internal zone sound transmission feature score; or c) a sum of b), and a US boundary zone feature score and peripheral zone feature score; or D) between Luminal B and TNBC molecular subtypes based on the ONUS features scores for at least two of: a) US internal zone sound transmission feature score; b) US peripheral zone feature score; c) a sum of US internal zone shape feature score, US internal zone echotexture feature score, and the US internal zone sound transmission feature score; or d) a sum of c), b) and a US boundary zone feature score.

4. The method of claim 1, wherein the OA/US feature scores include at least one of:
   a) multiple US feature scores only, and no OA feature scores;
   b) multiple OA feature scores only and no US feature scores; or
   c) at least one US feature score and at least one OA feature score.

5. The method of claim 1, wherein the FSMS model defines a correlation between one or more of the OA/US feature scores and at least one of one or more molecular subtypes or one or more histologic grades.

6. The method of claim 1, wherein the FSMS model comprises a table associating pairs of molecular subtypes and the OA/US features scores, the table contains a correlation index indicative of an extent to which the corresponding OA/US feature scores differentiate between the corresponding pair of the molecular subtypes.

7. The method of claim 1, wherein the OA/US feature scores include at least one of a US or OA boundary zone and at least one of a US or OA peripheral zone feature score.

8. The method of claim 1, wherein the OA/US feature scores include at least one of a US or OA boundary zone feature score and at least one US/OA internal or peripheral feature score from the following: US internal zone shape feature score, US internal zone echotexture feature score, US internal zone sound transmission feature score, US peripheral zone feature score, OA internal deoxygenated blood feature score, OA internal total hemoglobin feature score, or OA peripheral zone feature score.

9. The method of claim 8, wherein the at least one US or OA boundary zone feature score and the at least one internal or peripheral US/OA feature score are scored applying at least one of a)-j) hereafter:
   a) the US internal zone shape feature score is assigned a value, each of which has a corresponding probability of malignancy, based on the following characteristics: Oval-shaped, parallel orientation, (wider than tall), >=2/1 ratio max width to AP dimension="flat" oval-shaped; Oval-shaped, parallel orientation, (wider than tall)<2/1 ratio width to AP="plump" oval-shaped; Round; Irregular without angles, parallel orientation; Irregular without angles, non-parallel orientation (taller-than-wide); or Irregular with angles, parallel or non-parallel (any angle of ≤90°);
   b) the US internal zone echotexture feature score is assigned a value, each of which has a corresponding probability of malignancy, based on the following characteristics: Homogeneously hyperechoic (as hyperechoic as normal interlobular stromal fibrous tissue); Complex mixed cystic and solid; Homogeneously isoechoic or mildly hypoechoic; Heterogeneous without internal microcalcifications; Heterogeneous with internal microcalcifications; or Severely or markedly hypoechoic (compared to fat);
   c) the US internal zone sound transmission feature score is assigned a value, each of which has a corresponding probability of malignancy, based on the following characteristics: Enhanced; Normal; Mixed normal and enhanced; Mixed enhanced and partial or weak shadowing; Mixed normal and partial or weak shadowing; or Complete and strong shadowing;
   d) the US boundary zone feature score is assigned a value, each of which has a corresponding probability of malignancy, based on the following characteristics: Well circumscribed with complete thin hyperechoic capsule; Well-circumscribed with partial thin hyperechoic capsule; Thick well-defined capsule; Circumscribed, but without thin hyperechoic capsule; Indistinct margin; Thick ill-defined echogenic rim (halo) in boundary zone; or Frank short hypoechoic and/or hyperechoic spiculations within boundary zone;
   e) the US peripheral zone feature score are assigned a value, each of which has a corresponding probability of malignancy, based on the following characteristics: Normal tissue;
   Critical angle phenomena (shadowing from adjacent structures); Enlarged surrounding ducts not containing microcalcifications (duct extension or branch pattern); Enlarged Surrounding ducts containing microcalcifications; Peripheral long hyperechoic spicules (or interrupted tissue plane); or Thickened spicules and/or Coopers ligaments and/or retracted or thick skin;
   f) the OA internal vessel feature score is assigned a value, each of which has a corresponding probability of malignancy, based on the following characteristics: No internal vessels; Normal internal vessel(s) without branches, green or red; Normal internal vessel(s) with branches, green or red; Internal speckle—green ≥red in amount and red <background red; Internal speckle—red >green and IZ red >red in background; or Multiple internal red (deoxygenated) polymorphic vessels;
   g) the OA internal total hemoglobin feature score is assigned a value, each of which has a corresponding probability of malignancy as noted, based on the following characteristics: No internal hemoglobin; Minimal internal hemoglobin <background; Minimal # internal discrete vessels <=background; Moderate # internal discrete vessels=background; Many large polymorphic internal vessels >background; or Many large polymorphic vessels almost fill lesion;
   h) the OA internal deoxygenated blush feature score is assigned a value, corresponding to a probability of malignancy, based on the following characteristics: No internal vessels; Minimal internal speckle, all or mostly green; Mild internal speckle; Mild internal speckle; red ≥green, but red <bkgd red; Moderate internal speckle—red >green and red also >background red; or Internal red blush almost fills lesion;
   i) the OA capsular/boundary zone vessel feature score is assigned a value, each of which has a corresponding probability of malignancy, based on the following characteristics: No capsular vessels; Normal capsular vessels without branches, parallel to capsule, not perpendicular, long, gently curved, and gradually tapered (green &/or red); Normal capsular vessels with normal tapering acutely angled branches, (green &/or red); Boundary zone speckle—green ≥red in amount and red <background red; Boundary zone speckle—red >green and red >background red; Multiple boundary zone neovessels—short red and/or green perpendicular "whiskers" or red enlarged tortuous vessels in "dot-dash" pattern; or Boundary zone deoxygenated blush (partial or complete); and
   j) the OA peripheral zone vessel feature score is assigned a value, each of which has a corresponding probability of malignancy, based on the following characteristics: No PZ vessels; Normal non-branching or branching non-radiating vessels in surrounding tissues; Cluster of enlarged, tortuous non-radiating vessels in PZ on one side of mass; One or two radiating PZ vessels on one side of mass; More than two radiating vessels on one side of mass; or 3 or more radiating vessels on more than one side of the mass.

10. The method of claim 1, further comprising displaying the indication as a collection of predictive results representative of probabilities of malignancy (POM) associated with a collection of the molecular subtypes and/or histologic grades.

11. The method of claim 1, wherein the receiving, applying and determining are performed in connection only with a US data set, US images and US feature scores.

12. The method of claim 1, wherein the receiving, applying and determining are performed in connection only with a OA data set, OA images and OA feature scores.

13. The method of claim 1, wherein the receiving, applying and determining are performed in connection with a combination of a US data set, OA data set, US images, OA images, US feature scores, and OA feature scores.

14. A method, comprising: utilizing one or more processors in connection with, obtaining Optoacoustic/Ultrasound (ONUS) images collected from a patient examination for a region of interest, at least one of the OA/US images having an interior outline for an internal zone for the region of interest, the interior outline separating the internal zone from a boundary zone, wherein the interior outline is drawn between 0.5 and 1.0 mm inside of a margin of a hypoechoic nidus of the region of interest, at least one of the OA/US images having an exterior outline separating the boundary zone from a peripheral zone, receiving OA/US feature scores in connection with OA/US images collected from a patient examination for a region of interest; applying the OA/US feature scores to a feature score to molecular subtype (FSMS) model; and determining, from the FSMS model, an indication of at least one of a molecular subtype or histologic grade of a pathology experienced by the patient.

15. A system, comprising: memory configured to store program instructions and a feature score to molecular subtype (FSMS) model; one or more processors that, when executing the program instructions, or configured to; receive Optoacoustic/Ultrasound (OA/US) feature scores comprises in connection with OA/US images collected from a patient examination for a volume of interest; manage scoring of the OA/US feature scores in a redetermined outside-to-inside order, that includes first requiring assignment of one or more OA/US peripheral zone feature scores, second requiring assignment of one or more OA/US peripheral zone feature scores, second requiring assignment of one or internal zone feature scores; apply the OA/US feature scores to the FSMS model; and determine, from the FSMS model, an indication of at least one of a molecular subtype or histologic grade of a pathology experienced by the patient.

16. The system of claim 15, wherein the pathology represents breast cancer and the memory is configured to store molecular subtype represents one or more of Luminal A (LumA), Luminal B (LumB), Triple-negative (TRN) and HER2 amplified (HER2+).

17. A system, comprising: memory configured to store program instructions and a feature score to molecular subtype (FSMS) model; one or more processors that, when executing the program instructions, or configured to: receive Optoacoustic/Ultrasound (OA/US) feature scores comprises in connection with OA/US images collected from a patient examination to a volume of interest; apply the OA/US feature scores to the FSMS model; and determine, from the FSMS model, an indication of at least one of a molecular subtype or histologic grade of a pathology experienced by the patient, wherein the FSMS model distinguishes at least one of the following: A) between Luminal A and Luminal B molecular subtypes based on the OA/US features scores for at least two of: a) US internal zone sound transmission feature score; b) a sum of the US boundary and peripheral zone feature scores; or c) a sum of b), and a US internal zone shape feature score, US internal zone echotexture feature score, and the US internal zone sound transmission feature score; B) between Luminal A and TNBC molecular subtypes based on the OA/US features scores for at least two of: a) US internal zone sound transmission feature score; b) US boundary zone feature score; c) US peripheral zone feature score; d) a sum of US internal zone shape feature score, US internal zone echotexture feature score, and the US internal zone sound transmission feature score; e) a sum of the US boundary and peripheral zone feature scores; or f) a sum of d) and e); C) between Luminal A and HER2 molecular subtypes based on the OA/US features scores for at least two of: a) US internal zone sound transmission feature score; b) a sum of US internal zone shape feature score, US internal zone echotexture feature score, and the US internal zone sound transmission feature score; or c) a sum of b), and a US boundary zone feature score and peripheral zone feature score; or D) between Luminal B and TNBC molecular subtypes based on the OA/US features scores for at least two of: a) US infernal zone sound transmission feature score; b) US peripheral zone feature score; c) a sum of US internal zone shape feature score, US internal zone echotexture feature score, and the US internal zone sound transmission feature score; or d) a sum of c), b) and a US boundary zone feature score.

18. The system of claim 15, wherein the OA/US feature scores include at least one of:
 a) multiple US feature scores only, and no OA feature scores;
 b) multiple OA feature scores only and no US feature scores; or
 c) at least one US feature score and at least one OA feature score.

19. The system of claim 15, further comprising a display configured to present a probability of malignancy (POM) indicia in a manner and format representative of a collection of probabilities associated with a collection of at least one of the molecular subtypes or histologic grades.

20. The system of claim 19, wherein the display is configured to display the POM indicia to include at least one of a graph, alphanumeric characters, or color-coded scale, the POM indicia noting a central point/mean, and confidence intervals for the corresponding at least one of molecular subtypes or histologic grades.

21. The system of claim 15, wherein the FSMS model comprises a table associating pairs of molecular subtypes and the OA/US features scores, the table contains a correlation index indicative of an extent to which the corresponding OA/US feature scores differentiate between the corresponding pair of the molecular subtypes.

22. The system of claim 15, wherein the OA/US feature scores include at least one of a US or OA boundary zone and at least one of a US or OA peripheral zone feature score.

23. The system of claim 15, wherein the OA/US feature scores include at least one of a US or OA boundary zone feature score and at least one US/OA internal or peripheral feature score from the following: US internal zone shape feature score, US internal zone echotexture feature score, US internal zone sound transmission feature score, US peripheral zone feature score, OA internal deoxygenated blood feature score, OA internal total hemoglobin feature score, or OA peripheral zone feature score.

24. The system of claim 18, further comprising a display configured to present a probability of malignancy (POM)

indicia in a manner and format representative of a collection of probabilities associated with a collection of at least one of the molecular subtypes or histologic grades.

25. The system of claim 24, wherein the display is configured to display the POM indicia to include at least one of a graph, alphanumeric characters, or color-coded scale, the POM indicia noting a central point/mean, and confidence intervals for the corresponding at least one of molecular subtypes or histologic grades.

26. The system of claim 18, wherein the FSMS model comprises a table associating pairs of molecular subtypes and the OA/US features scores, the table contains a correlation index indicative of an extent to which the corresponding OA/US feature scores differentiate between the corresponding pair of the molecular subtypes.

27. The system of claim 18, wherein the OA/US feature scores include at least one of a US or OA boundary zone and at least one of a US or OA peripheral zone feature score.

28. The system of claim 18, wherein the OA/US feature scores include at least one of a US or OA boundary zone feature score and at least one US/OA internal or peripheral feature score from the following: US internal zone shape feature score, US internal zone echotexture feature score, US internal zone sound transmission feature score, US peripheral zone feature score, OA internal deoxygenated blood feature score, OA internal total hemoglobin feature score, or OA peripheral zone feature score.

29. The method of claim 3, wherein the pathology represents breast cancer and the molecular subtype represents one or more of Luminal A (LumA), Luminal B (LumB), Triple-negative (TRN) and HER2 amplified (HER2+).

30. The method of claim 3, wherein the OA/US feature scores include at least one of:
  a) multiple US feature scores only, and no OA feature scores;
  b) multiple OA feature scores only and no US feature scores; or
  c) at least one US feature score and at least one OA feature score.

31. The method of claim 3, wherein the FSMS model defines a correlation between one or more of the OA/US feature scores and at least one of one or more molecular subtypes or one or more histologic grades.

32. The method of claim 3, wherein the FSMS model comprises a table associating pairs of molecular subtypes and the OA/US features scores, the table contains a correlation index indicative of an extent to which the corresponding OA/US feature scores differentiate between the corresponding pair of the molecular subtypes.

33. The method of claim 3, wherein the OA/US feature scores include at least one of a US or OA boundary zone and at least one of a US or OA peripheral zone feature score.

34. The method of claim 3, wherein the OA/US feature scores include at least one of a US or OA boundary zone feature score and at least one US/OA internal or peripheral feature score from the following: US internal zone shape feature score, US internal zone echotexture feature score, US internal zone sound transmission feature score, US peripheral zone feature score, OA internal deoxygenated blood feature score, OA internal total hemoglobin feature score, or OA peripheral zone feature score.

35. The method of claim 34, wherein the at least one US or OA boundary zone feature score and the at least one internal or peripheral US/OA feature score are scored applying at least one of a)-j) hereafter:
  a) the US internal zone shape feature score is assigned a value, each of which has a corresponding probability of malignancy, based on the following characteristics: Oval-shaped, parallel orientation, (wider than tall), >=2/1 ratio max width to AP dimension="flat" oval-shaped; Oval-shaped, parallel orientation, (wider than tall)<2/1 ratio width to AP="plump" oval-shaped; Round; Irregular without angles, parallel orientation; Irregular without angles, non-parallel orientation (taller-than-wide); or Irregular with angles, parallel or non-parallel (any angle of ≤90°);
  b) the US internal zone echotexture feature score is assigned a value, each of which has a corresponding probability of malignancy, based on the following characteristics: Homogeneously hyperechoic (as hyperechoic as normal interlobular stromal fibrous tissue); Complex mixed cystic and solid; Homogeneously isoechoic or mildly hypoechoic; Heterogeneous without internal microcalcifications; Heterogeneous with internal microcalcifications; or Severely or markedly hypoechoic (compared to fat);
  c) the US internal zone sound transmission feature score is assigned a value, each of which has a corresponding probability of malignancy, based on the following characteristics: Enhanced; Normal; Mixed normal and enhanced; Mixed enhanced and partial or weak shadowing; Mixed normal and partial or weak shadowing; or Complete and strong shadowing;
  d) the US boundary zone feature score is assigned a value, each of which has a corresponding probability of malignancy, based on the following characteristics: Well circumscribed with complete thin hyperechoic capsule; Well-circumscribed with partial thin hyperechoic capsule; Thick well-defined capsule; Circumscribed, but without thin hyperechoic capsule; Indistinct margin; Thick ill-defined echogenic rim (halo) in boundary zone; or Frank short hypoechoic and/or hyperechoic spiculations within boundary zone;
  e) the US peripheral zone feature score are assigned a value, each of which has a corresponding probability of malignancy, based on the following characteristics: Normal tissue; Critical angle phenomena (shadowing from adjacent structures); Enlarged surrounding ducts not containing microcalcifications (duct extension or branch pattern); Enlarged Surrounding ducts containing microcalcifications; Peripheral long hyperechoic spicules (or interrupted tissue plane); or Thickened spicules and/or Coopers ligaments and/or retracted or thick skin;
  f) the OA internal vessel feature score is assigned a value, each of which has a corresponding probability of malignancy, based on the following characteristics: No internal vessels; Normal internal vessel(s) without branches, green or red; Normal internal vessel(s) with branches, green or red; Internal speckle—green ≥red in amount and red <background red; Internal speckle—red >green and IZ red >red in background; or Multiple internal red (deoxygenated) polymorphic vessels;
  g) the OA internal total hemoglobin feature score is assigned a value, each of which has a corresponding probability of malignancy as noted, based on the following characteristics: No internal hemoglobin; Minimal internal hemoglobin <background; Minimal # internal discrete vessels <=background; Moderate # internal discrete vessels=background; Many large polymorphic internal vessels >background; or Many large polymorphic vessels almost fill lesion;
  h) the OA internal deoxygenated blush feature score is assigned a value, corresponding to a probability of malignancy, based on the following characteristics: No internal vessels; Minimal internal speckle, all or mostly green; Mild internal speckle; Mild internal speckle; red ≥green, but red <bkgd red; Moderate internal speckle—red >green and red also >background red; or Internal red blush almost fills lesion;

i) the OA capsular/boundary zone vessel feature score is assigned a value, each of which has a corresponding probability of malignancy, based on the following characteristics: No capsular vessels; Normal capsular vessels without branches, parallel to capsule, not perpendicular, long, gently curved, and gradually tapered (green &/or red); Normal capsular vessels with normal tapering acutely angled branches, (green &/or red); Boundary zone speckle—green ≥red in amount and red <background red; Boundary zone speckle—red >green and red >background red; Multiple boundary zone neovessels—short red and/or green perpendicular "whiskers" or red enlarged tortuous vessels in "dot-dash" pattern; or Boundary zone deoxygenated blush (partial or complete); and j) the OA peripheral zone vessel feature score is assigned a value, each of which has a corresponding probability of malignancy, based on the following characteristics: No PZ vessels; Normal non-branching or branching non-radiating vessels in surrounding tissues; Cluster of enlarged, tortuous non-radiating vessels in PZ on one side of mass; One or two radiating PZ vessels on one side of mass; More than two radiating vessels on one side of mass; or 3 or more radiating vessels on more than one side of the mass.

36. The method of claim 3, further comprising displaying the indication as a collection of predictive results representative of probabilities of malignancy (POM) associated with a collection of the molecular subtypes and/or histologic grades.

37. The method of claim 3, wherein the receiving, applying and determining are performed in connection only with a US data set, US images and US feature scores.

38. The method of claim 3, wherein the receiving, applying and determining are performed in connection only with a OA data set, OA images and OA feature scores.

39. The method of claim 3, wherein the receiving, applying and determining are performed in connection with a combination of a US data set, OA data set, US images, OA images, US feature scores, and OA feature scores.

* * * * *